(12) United States Patent
Lyons et al.

(10) Patent No.: US 7,141,376 B2
(45) Date of Patent: Nov. 28, 2006

(54) CARRIER TESTS FOR POLYCYSTIC KIDNEY DISEASE IN THE CAT

(76) Inventors: Leslie A. Lyons, 1355 Tyler Dr., Woodland, CA (US) 95776; Robert A. Grahn, 36 Del Mar, Woodland, CA (US) 95695; Carolyn A. Erdman, 732 Lake Terrance Cir., Davis, CA (US) 95616

( * ) Notice: Subject to any disclaimer, the term of this patent is extended or adjusted under 35 U.S.C. 154(b) by 0 days.

(21) Appl. No.: 10/857,260

(22) Filed: May 28, 2004

(65) Prior Publication Data

US 2006/0110742 A1    May 25, 2006

(51) Int. Cl.
  *C12Q 1/68* (2006.01)
  *C12P 19/34* (2006.01)
  *C12P 21/06* (2006.01)
  *C12N 15/63* (2006.01)
  *C12N 1/21* (2006.01)
  *G01N 33/536* (2006.01)
  *C07K 1/00* (2006.01)
  *C07K 16/00* (2006.01)
  *C07H 21/02* (2006.01)

(52) U.S. Cl. .................. 435/6; 435/69.1; 435/91.2; 435/320.1; 435/252.33; 436/536; 530/350; 530/387.1; 536/23.1

(58) Field of Classification Search .................. 435/6
See application file for complete search history.

(56) References Cited

U.S. PATENT DOCUMENTS

2003/0008288 A1*   1/2003   Germino et al. ............... 435/6

OTHER PUBLICATIONS

Eaton et al. Autosomal dominant polycystic kidney disease in Persian and Persian-cross cats. Vet Pathol. Mar. 1997;34(2):117-26.*
Glücksmann-Kuis et al.; "Polycystic Kidney Disease: The Complete Strcture Of The PKD1 Gene Ands It's Protein"; *Cell*; Apr. 21, 1995; pp. 289-298; vol. 81; Cell Press; U.S. .
Kimberling et al.; Autosomal Dominant Polycystic Kidney Disease: Localization of the Second Gene to Chromosome 4q13-q23, *Genomics*; Aug. 16, 1993; pp. 467-472; vol. 18; Academic Press, Inc.
Peters et al.; "Chromosome 4 Localization Of A Second Gene For Autosomal Dominant Polycystic Kidney Disease"; *Nature Genetics*; Dec. 1993; pp. 359-362; vol. 5; Nature Publishing Group; UK.

* cited by examiner

*Primary Examiner*—Jeffrey Fredman
*Assistant Examiner*—Samuel Woolwine
(74) *Attorney, Agent, or Firm*—Townsend and Townsend and Crew LLP

(57) ABSTRACT

The present invention provides compositions and methods for detecting mutations associated with polycystic kidney disease in the cat.

9 Claims, 8 Drawing Sheets

Figure 2

```
GACGCGGGCTCTGCGGGCGGTTCCGGCGCCTCCTGGTGGCCGAGCTGCAGCGTGGCTTCTTTGACAAGCACACAconsensus
------+---------+---------+---------+---------+---------+---------+
..A...T..G...T..A....A...G....C....T..T....A.A.................... Mmus
..A..C..TTT..C.................G....T............................. Hsap
..G.....C......C....................C.............................. Cfam
..G.............G................................................T. TC Fcat wt
..G.............G................................................T. TC Fcat mut TCTGGCTCTCCATATGGGACCGGCCGCCTTCACTCGCTCCAGCGGGCCACCTGCTGCGTconsensus
------+---------+---------+---------+---------+---------+
............T..T..A.A....A....A..TT.........T...................... Mmus
.................T........A...A.................................... Hsap
........................T.......................A.................A. Cfam
..................C..................................T............. Fcat wt
..................C................................T..A............ Fcat mut CCTCCTCGTCTGCCTCTTCCTGGGCGCCAATGTGTGTGGTACGGGGTCGTGGGAGACGCCGCCTACAG Consensus
------+---------+---------+---------+---------+---------+
T......C...........................A.T..A....A.A................... Mmus
T......A.............CT...........CT.T.C..TT....................... Hsap
...................C..C............................A......C........ Cfam
.................................................................. Fcat wt
.................................................................. Fcat mut
```

Figure 2A. DNA alignment of *PKD1* exon 29 from mouse, human, dog and cat.

```
DAALRRFRRLLVAELQRGFFDKHIWLSIWDRPPRSRFTRVQRATCCVLLVCLFLGANAVWYGVVGDAAY Consensus
------+---------+---------+---------+---------+---------+
E...WQ.Q..........................V....L...A.........R.TT. Mmus
...L..............................I............A..S....... Hsap
E....S..............................I.................T.S Cfam
...V..................L..L................................ Fcat wt
...V..................L..L....................x........... Fcat mut
```

Figure 2B. Protein alignment of *PKD1* exon 29 from mouse, human, dog and cat

Figure 3

Table 1. PCR analysis of *PKD1* in the domestic cat.

| Exon | Exon Size (bp) | Product Size (bp) | Forward Primer 5' - 3' | Reverse Primer 5' - 3' | GenBank No. |
|---|---|---|---|---|---|
| 6 | 183 | 415 | cacctctcctgatctcctc | gccacctacagtattgtgtcttt | No variants |
| 14 | 133 | 271 | cggacaccactcttcactc | actccagcctgctcattgt | No variants |
| 15 | 3619 | 533 | catccccatgtcaaaagt | agcacggggttaggtcat | No variants |
| 23 | 629 | 572 | gaaagacacctgctcaccaa | ggccctcatgtgtatcctc | No variants |
| 24 | 156 | 421 | acctactcccacaggaaacc | ggaacgaggcaacagtga | AY612846 |
| 29 | 210 | 558 | caggtagacgggatagacga | ttcttcctggtcaacgactg | AY612847 |
| 30 | 126 | 376 | tcgtctcgaccttctgcc | cctcgtctgcctcttcct | No variants |
| 37 | 194 | 302 | cagacacggacaggaga | ctcaaggtgagtgggatgtt | AY612848 |
| 38 | 139 | 267 | gacaagatcgagatgggatg | cacactgggattggctga | AY612849 |

Figure 4
Table 2. Sequence analysis of feline *PKD1* to other species.

| Exon/ | Size (bp) | | % sequence identity to species | | | % protein identity to species | | |
|---|---|---|---|---|---|---|---|---|
| Intron | Hsap | Fcat | Cfam | Hsap | Mmus | Cfam | Hsap | Mmus |
| 1 | 424/16096 | na/14150 | na | na | na | na | na | na |
| 2 | 72/121 | 72/109 | 91.7 | 90.3 | 77.8 | 95.7 | 91.3 | 73.9 |
| 3 | 72/268 | 72/280 | 88.9 | 94.4 | 88.9 | 91.3 | 95.7 | 87.0 |
| 4 | 170/213 | 170/na | 88.8 | 82.9 | 72.4 | 87.5 | 87.5 | 69.6 |
| 5 | 672/118 | 672/94 | 86.9 | 79.3 | 74.4 | 83.4 | 74.9 | 67.3 |
| 6 | 184/435 | 184/1093 | 94.0 | 91.8 | 84.8 | 95.0 | 95.0 | 86.7 |
| 7 | 221/188 | 221/413 | 88.2 | 82.4 | 78.4 | 94.5 | 84.9 | 86.1 |
| 8 | 116/410 | 116/413 | 90.5 | 81.9 | 59.5 | 92.1 | 81.6 | 60.5 |
| 9 | 127/366 | 127/314 | 86.6 | 73.2 | 73.2 | 88.1 | 76.2 | 73.8 |
| 10 | 248/452 | 248/434 | 75.0 | 64.9 | 45.3 | 67.1 | 57.3 | 41.0 |
| 11 | 756/877 | 755/806 | 83.0 | 77.6 | 67.3 | 84.8 | 80.8 | 73.2 |
| 12 | 132/197 | 132/194 | 91.7 | 88.6 | 81.8 | 97.7 | 90.9 | 93.2 |
| 13 | 176/314 | 176/195 | 86.4 | 84.7 | 80.7 | 89.7 | 87.9 | 87.9 |
| 14 | 134/468 | 134/548 | 83.2 | 80.6 | 73.1 | 76.7 | 75.0 | 75.0 |
| 15 | 3620/219 | 3620/156 | 76.0 | 80.4 | 71.6 | 87.3 | 79.6 | 75.7 |
| 16 | 150/934 | 150/1026 | 90.7 | 84.7 | 80.0 | 96.0 | 84.0 | 88.0 |
| 17 | 144/127 | 204/108 | 86.8 | 85.4 | 78.5 | 85.4 | 79.2 | 72.9 |
| 18 | 280/93 | 280/75 | 92.9 | 86.4 | 77.9 | 97.8 | 92.5 | 86.0 |
| 19 | 214/66 | 214/72 | 90.2 | 85.5 | 68.7 | 97.1 | 91.4 | 81.4 |
| 20 | 160/390 | 172/336 | 84.3 | 73.8 | 58.1 | 86.0 | 71.7 | 71.7 |
| 21 | 153/679 | 153/691 | 84.3 | 73.9 | 67.3 | 84.3 | 68.6 | 60.0 |
| 22 | 145/602 | 145/99 | 86.9 | 84.8 | 84.1 | 89.6 | 81.2 | 85.4 |
| 23 | 630/295 | 621/306 | 86.6 | 80.7 | 78.1 | 87.3 | 83.4 | 81.0 |
| 24 | 157/180 | 157/247 | 83.4 | 79.0 | 83.4 | 80.4 | 84.3 | 80.4 |
| 25 | 253/124 | 254/109 | 86.6 | 81.8 | 76.7 | 90.5 | 86.9 | 84.5 |
| 26 | 196/1494 | 196/1020 | 88.8 | 81.1 | 80.6 | 92.3 | 78.5 | 86.2 |
| 27 | 171/86 | 171/80 | 95.9 | 88.3 | 78.9 | 100.0 | 87.5 | 89.3 |
| 28 | 144/94 | 144/89 | 93.8 | 88.9 | 89.6 | 95.7 | 93.6 | 95.7 |
| 29 | 211/90 | 211/89 | 91.0 | 85.3 | 80.6 | 90.5 | 83.9 | 78.7 |
| 30 | 127/1659 | 127/766 | 91.3 | 87.4 | 77.2 | 92.9 | 85.7 | 78.6 |
| 31 | 117/87 | 117/103 | 88.0 | 88.0 | 71.9 | 84.6 | 84.6 | 60.5 |
| 32 | 53/224 | 53/158 | 90.6 | 83.0 | 76.0 | 88.2 | 88.2 | 75.0 |
| 33 | 185/77 | 173/106 | 89.6 | 84.4 | 79.2 | 87.7 | 78.9 | 77.2 |
| 34 | 94/2937 | 94/2565 | 79.8 | 71.3 | 70.2 | 63.3 | 50.0 | 46.7 |
| 35 | 119/78 | 119/75 | 78.2 | 80.7 | 68.1 | 59.0 | 66.7 | 46.2 |
| 36 | 203/72 | 203/75 | 88.2 | 85.7 | 82.8 | 86.6 | 86.6 | 85.1 |
| 37 | 195/450 | 195/369 | 91.3 | 87.7 | 86.2 | 98.5 | 96.9 | 95.4 |
| 38 | 140/361 | 140/620 | 87.1 | 84.3 | 85.0 | 95.7 | 87.0 | 89.1 |
| 39 | 113/291 | 113/205 | 91.2 | 90.3 | 83.2 | 94.6 | 91.9 | 91.9 |
| 40 | 142/140 | 148/154 | 79.1 | 76.8 | 76.8 | 68.8 | 54.3 | 58.7 |
| 41 | 126/183 | 126/269 | 94.4 | 89.7 | 83.3 | 97.6 | 85.4 | 85.4 |
| 42 | 175/248 | 175/135 | 90.3 | 88.6 | 77.7 | 93.1 | 87.9 | 93.1 |
| 43 | 291/75 | 291/93 | 86.9 | 82.8 | 71.8 | 87.6 | 81.4 | 69.1 |
| 44 | 135/83 | 136/80 | 84.4 | 77.0 | 77.0 | 80.0 | 80.0 | 77.8 |
| 45 | 306/90 | 306/95 | 86.9 | 82.0 | 70.3 | 95.1 | 83.3 | 78.4 |
| 46 | 1485 | 1466 | 81.2 | 66.7 | 67.8 | 85.5 | 78.7 | 65.4 |

Figure 5

SEQ ID NO:1
AY612847
Exon 29 Variant
c>a transversion at position 307
t>g transversion at position 102
1 bp del after position 105 (●)
g>a transition at position 132
11bp insertion at position 390 (italics)

TTCTTCCTGGTCAACGACTGGCTGTCGGTGGAGACTGAGGCCAATGGCGGCCTCGTGGAGAAGGAGGTGCTGGCA
GCAAGTAAGGGCCTGGGCCCGTCCCTGCCC●GGGCTGGCCGAGGGGTGGCCTGTGCCACTGGCCTCCTGAAGCCA
GCTGTGCCCTTTCTGCAGGCGACGCGGCTGTGCGGCGGTTCCGGCGCCTCCTGGTGGCCGAGCTGCAGCGTGGCT
TTTTTGACAAGCATCTCTGGCTCTCCCTCTGGGACCGGCCTCCTCGGAGCCGCTTCACCCGCGTCCAGCGGGCCA
CCTGTT<u>GAGTC</u>CTCCTCGTCTGCCTCTTCCTGGGCGCCAATGCTGTGTGGTACGGGGTCGTGGGAGACGCCGCCT
ACAGGTGGGTGCCCGA*GGGGGGCCCG*ATGATCTCCTCCTGCCCGACCCCTCCTACCCCCCACAGCCTCTCCCAGC
CCGGGTCTCTCTCCTCTCCTGCCACACAGCGCGGGGCCCGTGTCCGGTCTGATCCCGCTGAGTGCCGACACAGTT
GCCGTCGGCCTGGTGTCCAGTGTGGTCGTCTATCCCGTCTACCTG

SEQ ID NO:5
translation of AY612847 starting at bp 3 of exon 29.

DAAVRRFRRLLVAELQRGFFDKHLWLSLWDRPPRSRFTRVQRATCC●VLLVCLFLGANAVWYGVVGDAAYR

● indicates the stop position

Figure 6

SEQ ID NO:2
AY612846
Exon 24 Variant
257 g>a
5 bp deletion after 347
38 a>g

GGAACGAGGCAACAGTGAGTGCTGCCGGCAACAGAGGGCTCTCCAGCCCCCCAGCCCCAGGCTGCAGGGAGGGCG
CCACAGGGCTCCGGGAGCGTCCCCCAGGGTGTGCGAGCTGCGCGGGGCAGCCGTCCAATGCTGTCCTTGTGCCCC
TAGAACACTACCTGTCCCGGGAGCCCGAGCCCTACCTGGCTGTGTACCTGCACTCGGTGCCGCAGCCCAACGAGC
ACAACTGCTCAGCCAGCAGGAGGATCGGCCCAGAGGCGCTGGCGGGCAGGGACCACAGGCCCTACACCTTCTTCA
TCGCCCCCGGGTGAGCCCACGCCCCGCCCTGGGAGCAGGCCACCGTG●●●●●GACCCACAGTGGGGGCTATGACG
GCTGGCTGGACGCCAGCAGGGTCACTGGGTTTCCTGTGGGAGTAGGT

SEQ ID NO:6
translation of AY612846 starting at position 153 thru 306

EHYLSREPEPYLAVYLHSVPQPNEHNCSASRRIGPEALAGRDHRPYTFFIA

Figure 7

SEQ ID NO:3
AY612848
Exon 37 Variant
c>t transition at position 263 (Bold)

CTCAAGTGAGTGGGATGTTGGGGGGCCGGGCTGCCAGCCCCTGGCGCCTGTGGGCCCCTCTGACGCCTCCCTTGG
CCCAGGTCCTGCTGGAGGCCCTGTACTTCTCCCTGGTGGCCAAGCGGCTGCACCCCGACGAGGATGACACCCTGG
TGGAGAGCCCGGCTGTGACCCCTGTGAGTGAGCGTGTGCCCCGTGTGCGGCCCCCACACGGCTTTGCGCTCTTCC
TGGCGAAGGAAGAGGCCCCGAAAGGTCAAGAAGCTGCATGGGATGCTGAGGGTGAGCCGCTCTCCTGTCCCGTGTC
TG

SEQ ID NO:7
translation of AY612848

QVLLEALYFSLVAKRLHPDEDDTLVESPAVTPVSERVPRVRPPHGFALFLAKEEARKVKKLHGMLR

Figure 8

SEQ ID NO: 4
AY612849
Exon 38 Variant
c>t transition at position 127

CACACTGGGATTGGCTGACCCCAGGGCCGTCCCTGCCCCCAGAGCTTCCTGGTATACATGCTCTTCCTGCTGGTG
ACGCTGCTGGCCAACCATGGGGACGCTTCCTGCCACAGCCACGCCTACCGCTTGCAGAGTGCCATCAAACAGGAG
CTCGGCAGCCAGGCCTTCCTGGCCATCACCCGGTACAGGCACCCCCGTGCTCATGCGCGTGTCCACCTGCCAGGC
CGGGGAGGCATTGATGCCCGCCACATCCCATCTCGATCTTGTC

SEQ ID NO:8
translation of AY612849

LVYMLFLLVTLLANHGDASCHSHAYRLQSAIKQELGSQAFLAITR

SEQUENCE LISTING

```
<160> NUMBER OF SEQ ID NOS: 47

<210> SEQ ID NO 1
<211> LENGTH: 569
<212> TYPE: DNA
<213> ORGANISM: Felis catus
<220> FEATURE:
<223> OTHER INFORMATION: subsequence of polycystic kidney disease type 1
      (PKD1) exon 29 variant

<400> SEQUENCE: 1
ttcttcctgg tcaacgactg gctgtcggtg gagactgagg ccaatggcgg cctcgtggag      60
```

```
aaggaggtgc tggcagcaag taagggcctg ggcccgtccc tgcccgggct ggccgagggg      120
tggcctgtgc cactggcctc ctgaagccag ctgtgcccct tctgcaggcg acgcggctgt      180
gcggcggttc cggcgcctcc tggtggccga gctgcagcgt ggcttttttg acaagcatct      240
ctggctctcc ctctgggacc ggcctcctcg gagccgcttc acccgcgtcc agcgggccac      300
ctgttgagtc ctcctcgtct gcctcttcct gggcgccaat gctgtgtggt acgggtcgt       360 gggagacgcc gcctacaggt gggtgcccga ggggggcccg atgatctcct cctgcccgac      420
ccctcctacc ccccacagcc tctcccagcc cgggtctctc tcctctcctg ccacacagcg      480
cggggcccgt gtccggtctg atcccgctga gtgccgacac agttgccgtc ggcctggtgt      540
ccagtgtggt cgtctatccc gtctacctg                                       569
```

<210> SEQ ID NO 2
<211> LENGTH: 417
<212> TYPE: DNA
<213> ORGANISM: Felis catus
<220> FEATURE:
<223> OTHER INFORMATION: subsequence of polycystic kidney disease type 1
      (PKD1) exon 24 variant

<400> SEQUENCE: 2

```
ggaacgaggc aacagtgagt gctgccggca acagagggct ctccagcccc ccagcccag       60 gctgcaggga gggcgccaca gggctccggg agcgtccccc agggtgtgcg agctgcgcgg      120
ggcagccgtc caatgctgtc cttgtgcccc tagaacacta cctgtcccgg gagcccgagc      180
cctacctggc tgtgtacctg cactcggtgc cgcagcccaa cgagcacaac tgctcagcca      240
gcaggaggat cggcccagag gcgctggcgg cagggacca caggccctac accttcttca      300
tcgcccccgg gtgagcccac gccccgccct gggagcaggc caccgtggac ccacagtggg      360
ggctatgacg gctggctgga cgccagcagg gtcactgggt ttcctgtggg agtaggt        417
```

<210> SEQ ID NO 3
<211> LENGTH: 302
<212> TYPE: DNA
<213> ORGANISM: Felis catus
<220> FEATURE:
<223> OTHER INFORMATION: subsequence of polycystic kidney disease type 1
      (PKD1) exon 37 variant

<400> SEQUENCE: 3

```
ctcaagtgag tgggatgttg gggggccggg ctgccagccc ctggcgcctg tgggcccctc      60
tgacgcctcc cttggcccag gtcctgctgg aggccctgta cttctccctg gtggccaagc      120
ggctgcaccc cgacgaggat gacaccctgg tggagagccc ggctgtgacc cctgtgagtg      180
agcgtgtgcc ccgtgtgcgg cccccacacg gctttgcgct cttcctggcg aaggaagagg      240
cccgaaaggt caagaagctg catgggatgc tgagggtgag ccgctctcct gtcccgtgtc      300
tg                                                                    302
```

<210> SEQ ID NO 4
<211> LENGTH: 268
<212> TYPE: DNA
<213> ORGANISM: Felis catus
<220> FEATURE:
<223> OTHER INFORMATION: subsequence of polycystic kidney disease type 1
      (PKD1) exon 38 variant

<400> SEQUENCE: 4

```
cacactggga ttggctgacc ccagggccgt ccctgccccc agagcttcct ggtatacatg      60
```

```
ctcttcctgc tggtgacgct gctggccaac catggggacg cttcctgcca cagccacgcc    120
taccgcttgc agagtgccat caaacaggag ctcggcagcc aggccttcct ggccatcacc    180
cggtacaggc accccgtgc tcatgcgcgt gtccacctgc caggccgggg aggcattgat     240
gcccgccaca tcccatctcg atcttgtc                                       268
```

```
<210> SEQ ID NO 5
<211> LENGTH: 46
<212> TYPE: PRT
<213> ORGANISM: Felis catus
<220> FEATURE:
<223> OTHER INFORMATION: subsequence of polycystic kidney disease type 1
      (PKD1) exon 29 variant translation starting at bp 3

<400> SEQUENCE: 5

Asp Ala Ala Val Arg Arg Phe Arg Arg Leu Leu Val Ala Glu Leu Gln
 1               5                  10                  15

Arg Gly Phe Phe Asp Lys His Leu Trp Leu Ser Leu Trp Asp Arg Pro
            20                  25                  30

Pro Arg Ser Arg Phe Thr Arg Val Gln Arg Ala Thr Cys Cys
        35                  40                  45

<210> SEQ ID NO 6
<211> LENGTH: 45
<212> TYPE: PRT
<213> ORGANISM: Felis catus
<220> FEATURE:
<223> OTHER INFORMATION: subsequence of polycystic kidney disease type 1
      (PKD1) exon 24 variant translation

<400> SEQUENCE: 6

Glu Pro Glu Pro Tyr Leu Ala Val Tyr Leu His Ser Val Pro Gln Pro
 1               5                  10                  15

Asn Glu His Asn Cys Ser Ala Ser Arg Arg Ile Gly Pro Glu Ala Leu
            20                  25                  30

Ala Gly Arg Asp His Arg Pro Tyr Thr Phe Phe Ile Ala
        35                  40                  45

<210> SEQ ID NO 7
<211> LENGTH: 66
<212> TYPE: PRT
<213> ORGANISM: Felis catus
<220> FEATURE:
<223> OTHER INFORMATION: subsequence of polycystic kidney disease type 1
      (PKD1) exon 37 variant translation

<400> SEQUENCE: 7

Gln Val Leu Leu Glu Ala Leu Tyr Phe Ser Leu Val Ala Lys Arg Leu
 1               5                  10                  15

His Pro Asp Glu Asp Thr Leu Val Glu Ser Pro Ala Val Thr Pro
            20                  25                  30

Val Ser Glu Arg Val Pro Arg Val Arg Pro Pro His Gly Phe Ala Leu
        35                  40                  45

Phe Leu Ala Lys Glu Glu Ala Arg Lys Val Lys Lys Leu His Gly Met
    50                  55                  60

Leu Arg
 65

<210> SEQ ID NO 8
<211> LENGTH: 45
<212> TYPE: PRT
```

<213> ORGANISM: Felis catus
<220> FEATURE:
<223> OTHER INFORMATION: subsequence of polycystic kidney disease type 1
      (PKD1) exon 38 variant translation

<400> SEQUENCE: 8

Leu Val Tyr Met Leu Phe Leu Leu Val Thr Leu Leu Ala Asn His Gly
  1               5                  10                  15

Asp Ala Ser Cys His Ser His Ala Tyr Arg Leu Gln Ser Ala Ile Lys
             20                  25                  30

Gln Glu Leu Gly Ser Gln Ala Phe Leu Ala Ile Thr Arg
         35                  40                  45

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 6 PCR amplification 5' forward primer

<400> SEQUENCE: 9
cacctctcct gatcctcctc                                              20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:domestic cat
      PKD1 exon 6 PCR amplification 3' reverse primer

<400> SEQUENCE: 10
gccacctaca gtattgtgtc ttt                                          23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 14 PCR amplification 5' forward primer

<400> SEQUENCE: 11
cggacaccac tctttcactc                                              20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:domestic cat
      PKD1 exon 14 PCR amplification 3' reverse primer

<400> SEQUENCE: 12
actccagcct gctcattgt                                               19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:domestic cat
      PKD1 exon 15 PCR amplification 5' forward primer

<400> SEQUENCE: 13
catcccccat gtcaaaagt                                              19

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 15 PCR amplification 3' reverse primer

<400> SEQUENCE: 14
agcacggggt taggtcat                                               18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 23 PCR amplification 5' forward primer

<400> SEQUENCE: 15
gaaagacacc tgctcaccaa                                             20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:domestic cat
      PKD1 exon 23 PCR amplification 3' reverse primer

<400> SEQUENCE: 16
ggccctcatg tgtatcctc                                              19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 24 PCR amplification 5' forward primer

<400> SEQUENCE: 17
acctactccc acaggaaacc                                             20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 24 PCR amplification 3' reverse primer

<400> SEQUENCE: 18
ggaacgaggc aacagtga                                               18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 29 PCR amplification 5' forward primer

<400> SEQUENCE: 19
caggtagacg ggatagacga                                             20

-continued

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 29 PCR amplification 3' reverse primer

<400> SEQUENCE: 20
ttcttcctgg tcaacgactg                                           20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 30 PCR amplification 5' forward primer

<400> SEQUENCE: 21
tcgtctcgac cttctgcc                                             18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 30 PCR amplification 3' reverse primer

<400> SEQUENCE: 22
cctcgtctgc ctcttcct                                             18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 37 PCR amplification 5' forward primer

<400> SEQUENCE: 23
cagacacggg acaggaga                                             18

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 37 PCR amplification 3' reverse primer

<400> SEQUENCE: 24
ctcaaggtga gtgggatgtt                                           20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:domestic cat
      PKD1 exon 38 PCR amplification 5' forward primer

<400> SEQUENCE: 25
gacaagatcg agatgggatg                                           20

-continued

```
<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:domestic cat
      PKD1 exon 38 PCR amplification 3' reverse primer

<400> SEQUENCE: 26
cacactggga ttggctga                                                 18

<210> SEQ ID NO 27
<211> LENGTH: 39536
<212> TYPE: DNA
<213> ORGANISM: Felis catus
<220> FEATURE:
<223> OTHER INFORMATION: GenBank Accession No. AC145332.28 genomic DNA
      for PKD1 39536 bp contig

<400> SEQUENCE: 27
atcttcatag ggaattccag agagctctg cagccgacgc cttccggtgc cgcagcatca      60
gtgtgtctga acatgtggtc cgcaggtagt gggcttcttc gggtgggggg ctcagaccct    120
gcagcttggc ccgtgcggcg gcactgcagg cgggagcgcc cgggtggcgg tgcatggggc    180
gcttgcatga cctcgtcgcc tggccggagc tggaggagca ggagacagag gcccgtcctg    240
cccagcccag ccctcggtcc cggggagcct ggtggtgagg ggtgggaagg ttgcattctg    300
tccccgagcc tcgtcccagc acgggctggc tgcaggcctc ctcggaggct ggcctgggag    360
cccaaagcag ggagggcggt agctctgagg aagccaggca cccgtggca gctgcccaca     420 ggcctgtccc cggaggcgag ggggcctctg cgtatgaaag cagcgcccac ggggacagg     480 agggagcgtg ctcctgggat tggctttcgt atcctctcag gtggactttg ttcttgagct    540
ttctcttagt aaaggtccgc tttctggggc ggctgaaagg gcgcggggc tttgagtggg     600 ggcagcgggg gtgggggccg ggctggtgag gtcagaaccc ttgaggggcg tggcctcgct    660
cacttctccc tgctgtgtct gagtgcgggt gtgggcccct gggggtcgct gctcccgccg    720
gcgccggctg tgctaggctg agctgagctg cgggatgggg gtggtctcct ccccaggaag    780
ccccttcggg cccaggagac ccacttccta ggagcctggc ttgggctcca gcctcaggct    840
ggcctctgct gagtgtggtt tgggggggctg ggggtggggc agcgaggctc tccgctcttt   900
tctagcacag tctctatcac aagcagaacg tggcaaaggg gctttgaaaa attggcatca    960
gaattaagcc cacataagcc ccttctggtc acggggtgcg tgcggagctg gggcggcctg   1020
agttcagggt gaagagctgc acacgaagcc cagaccctcc ccgtcatcgg gaggtggctc   1080
cgtgggcaga atgcaatctt tgtgcgtgcg tgtgtgtgtg tgtgtgtgtg tgtgtgtgtg   1140
tgtgtggtct tcgtgtctct gcatgactaa agggctctgc cacaaagccg tccctaact    1200 cctgcgcttc ggtgagggga tgtcggtctc tcgtgtctcc cgtgaggcct tgccctcctc   1260
tctctgggag gatgtgtcag cgcggtctgc cgagccgtgg ctccactggc cgtgcgccct   1320 ggtgggcgt ttgtgggcgc ggccccccag caaatgcatg cctccagctc tggccctgg    1380 ggggagagga ggggccggtc ggcacctgac ctcgctgggc ccctcccttc agcaggatcc   1440
agacgtccct cacgagtgcc agcttgggt ctgcggacga gaactcaatg cccaggctg     1500 acgacaactt gaaaaatctc cacctggagc tcacggagac ttgtctggac atgatggcca   1560
gatacgtgtt ctccaacttc acggcggtcc ccaagaggta caggctggga gggaggcaca   1620
gcaccgcgct ctctttttctg tgactgtaat gggtcaaagt ggcggtggcg ggtgagtcgt   1680
```

```
gcggggctcc ttcctgcagg cggccctcag tgggaggcgc ctttggaacc acgatgcctg    1740
tccagagccc gctgggcaag atgttggccg atgccctct gctttcaggt ccctgtagg     1800 ggagttcctc ttggctggtg gcaggaccaa gacctggctg gttggaaaca agctcgtcac   1860
tgtgacgacg agcgtgggga ccgggacccg gtcactgctg ggcttggact caggagagct   1920
gcagggcagc ccagagctga ggtgaccgca ccttccagcc cctacctatc gggccgtgac   1980
cctggcggtc ccgagcccag gctggggtgg ctcggttgca cgccagcctg gagcctgtga   2040
gacatctcgg tcacgctcgg cacggacctt ccgtcctcag ctctgacccc agtgcgcacg   2100
tgaggcagac aaaggaggcg cctgccaagt tggagtccca ggctgggcag caggtgtgcc   2160
gtggggcccg ggaccgcgtc cgctccatgt ctggtgagcc tgtgcccctc cctgcctcct   2220
cggggcctct gtgggtgcac gcactcgcgg acactgccgg gatgttgttt ccgcgagccc   2280
tcgtcacggg gggtgtggca ggcggtgtgc cttttgcacg actctggccc gcgggccctt   2340
gtcgccgagg gtccgtttct catggcttgt gtttcctgtg aaccctcggc agtccttgtc   2400
ctcagctcag ctcaccctg tagctttctt ttgctgcagc cagaacgagc cacggtccaa   2460 cggtggggc aggtggggca ggtgctgggg ccccttccta ctgccctggg cccaccgagg   2520
tcgacaccca gagagggctg agctgcctct ggttgctggc ctggggctcc gtggccagca   2580
gggccctggg tggaacagcc agttctgagc cggcggctct cgtcgggca ggtgggggtc    2640 accagccctc ctgtcctccc cttcctcagg gggccacggc cttcgtgtcg gtgccttgga   2700
cgctcaagcc acccactgcc caggcgcaca gaccacacca gccagcacgt ccgagagggc   2760
ctcggctgcc gcccagctcc cggcgcagga gaagacgagc ctggcggcct acgtacccct   2820
gctgacccag ggctgggcgg agatcttggt ccggaggccc acgggtactg acgggtctgc   2880
ccttggcacg cctgggcctc ggtcagcaca cacggtggcc gcgggaccat tagccacgag   2940
ggtcttaggt acacaggagg ggcaggcagg ctgggccgag ggagcttctg ctccgtgacg   3000
cccacacggt gagcggtgag ggggatccac agggctgagt ggggagggcc tgcgctagtc   3060
cgctcgggcc tccctgacag agtgccccgg agcgggcagc tccagcaaca gtaaggtatt   3120
tcctcctgct cccggggct gtaagtccca ggtgagggtg ccaaccgggc tgggtcctct    3180
tgaggcctct cttcccgggg tgcacacgcg tgtgtcttcc ctcgtgttct tgcgtggtcg   3240
tccctctgtg cgggtgtgtg tcccctggta aggactctgt ggattaggga ccacccggga   3300
gattcggttt tcccttaccg cggtgctttc cgaggtgctg gaggtgagga cttccacaca   3360
ggaattttgc ggcatacgat tcagcctgta atgggtattt gaggttaaag gaagccaagg   3420 cccgggggcct ggggtccgct tagggagcag tgtggcgagt ggtgactggg gaggacaagg   3480
cgcccggtcc tggggagcct cctgggcagt aaggctgtgg gccctgggtc ctcttgggga   3540
gccggcacgg gggaggccag agactggatg agaaggccca ggaagggccg gaggaggtgg   3600
gtcagggttg agggagatgc tctcaatgtg aggacgctcg gcgtggaggg ccgtgtcgaa   3660
gcgttggccc gtgggccttg tggggagagg gagcccagaa agccccggc tctgccccat    3720 ccaagctttt cggtgatgtc tgttcttcgc ggtgcctctg ccgggcctga cgtgggtgtg   3780
agagctgacc tggggcggag agtggtatga gctgaggccc tcctgtgcgt ccgtgaggcg   3840
ggcgaccacc ggacgggagc tactcctgac ctgggggtct ggcggtgtgg gggtggagcg   3900
tcggggccag ccaggggcct gccttttgcta gagccttccc ccacttcccc atcgctccct   3960
ggttgagcac aggagctctt gcccaccccc ggcatgtgc ccttggggt ggggatggcc     4020
```

```
ggtggccgtg tcgggcccgc ggcctgagag gtgctgcctg cccctccgca gggaacacca    4080
gctggctgat gagcctggag aaccccctca gcccttctc  ctcggacatc aacaacatgc    4140
ccctgcagga gctgtccaac gccctcatgg ccgccgagcg cttcaaggag cgtcgtgaca    4200
cggccctgta caagtcactt tcggtgccgg cggccggctc cgccaagccc cctccgcccc    4260
cacgttctaa cacaggtggg tacccgtccc gcccaacctg gccgtgctgt ctggaggcag    4320
cgtcgctccc ctgcgccgcg ggtcgcgccc acagtggggg tccgagct  ttcctcgccg    4380 ccgccacagc ctgacgtggg agcagggccc attcccacta aaggaccgt cttcccgagg    4440 cgcgcggtag ccgtgcgggg gcgggcacgg cagagccccc gcaaagcctt tgccctgcgc    4500
tctcctcgga gcgcccgtgg ccggggctct aggcggtagc cgcgcttctg ctcgggtgtg    4560
ggtgtggatg cgccgagcac acagtctgca cctgcctgcg ctcgtgcccg tgcccagcct    4620
gctgctgcgg agcttccggg ccaccgtctg gccttccctg tggccgcaga tggcgcttag    4680
cggcccggga cctgtgttgg cgaggaggag ggccgcgctc cccttccaga cgtcggctcc    4740
ggcagcttgg ggagccgggc gccgctggcc cctccgctct ctctctccag gcccgggctc    4800
tgtgcgggac tagtggtgcc tttcctctgc tcgactgtgc atagtctccc cttctgctga    4860
ctggccgctc gcggtttccc ttgcagtggc ctctttctcc tccctgtacc agaccagttg    4920
ccaaggagag ctgcacagga gcatttcctg ggcaggtact cgtgtgtctc tttaagggaa    4980
gcggtgtttg ctccagagcg ccgctctgcc tcgtagatgc tgttctcatc gcccctcatc    5040
cgctcatccc tccgtggtcc tgccagagcc gctccgtgcc ctctgggaga agggccccga    5100
ctcgcatgag gacgtctgtg cagaatgcct gcgctttgct ggcggacccc ctctgctgca    5160
tgcccttcgt ggctgagctc tgtccccacg tcgggcaggc ccttacagcc acatcttcag    5220
gcctcaggag gtgaccttgg gcagctaagc cacagatgct ggcaggggc  agttctttgg    5280 ggcgagcctg gccctgggc  tcagccccac tgacttttcc cgggcttctg gtggtccgat    5340
tggctttgcg aacccacaaa ttgggctgtg tctgcctctc gtcgtgggct ggccagaggc    5400
cctacagacc agcctttggc ccgttgttcc caggccctgg caggggccgg ctctgacctg    5460 catggcccctt gggcacacct gggtgcccac acgtggacag gagccagtta ggaaagggca    5520
gcgtgcagac gggctccggc aggcggctga caggccgtgc gcgtgtgggg ctgcgtgtgt    5580
ggcggccgcg gactgcgcta accccggtt  gcttcccct  ccccgcccc  tgccctgcc    5640 cctgccctg  ccctcacatc ggcacaggaa atgctgcttc agggcatcgt accctcctta    5700
gcattcctca gctcggggtt ggcttgggct ccgatagtgc gcctcggctt tccagaacgg    5760
gcttccgagt ctgtgtgtgc gcacgggtgt ttctccatca ggcttctcct caggtcccat    5820
cacagaggga ctctggcctc tcgtcccggt tcctgggggc cggtgtgggc gcgccactcc    5880
ttctgagctg ggaccccgtc ttgggcgggg gctcctccct ccctcatggg ctcttgggct    5940
cgggtcccgc ccccggccgt ttcccttgct ggagcagcag cggcgggtgc tgtggatcct    6000
gggctgggga ttccaggagc cggatgcccc ccacgtccct acgtccggga gcctgtgttg    6060
gagactcccc gtgtcagggg tcacatccag gcccctgagg gcgcccttct ccagctgact    6120
tgatggggtg tgggcagctt agagccacag gcaaggaagg ccttaggtga ggctctgttg    6180
gggggccgct gtgctctctt gccggggaga ggctggtacc tcaggccacg tgagctcctg    6240
ggggccgggc cagcacctag tagcctcatc tgtgtcctcc cagactccgc ggtggttctg    6300
gaggagggaa gtcccagcga gactgatttg ccaggcgagc ccactgagct ggaggacttt    6360
gaggccaccc tgggcccaga gaggcgctgt cggcgccctg aagcctacag tagggtgagt    6420
```

```
actaggcggg ggagggcgct gtgggaagag gggcggggcc tccgctccag gcttcgtggc    6480
tccggctggc ttgctgtgaa ctcacacgag gtttttcttc ctcttttgtt atctaagaac    6540
tggctagctg tccttccaag ttccttctgc gtggatggcc cggggcttcc cggtggtccc    6600
cgcagggcta gtggttgatt gtcggcatcc tgtggccctt gctgctcagc acgggcagga    6660
gtcgtcctag gggaggggc ggggccgtgg ccatccgctt gctgccgagt ggctcctctg    6720
gccctggctg gggggcaggt ggggcttcat cgcccccgag taggcccctg ggagggttca    6780
ctggtgtctt ccaacgaagg ctctctggac tccttccttt ccagtcgtct tccagctcca    6840
gccaagagga gaagtctttc gccgcagagg aggtggctgc cggagggctc cccatcgggc    6900
gggccgtgtc tgccgaggga gcccggccct ctgcggggct ctccttccag cccgcccagc    6960
ccctcagcaa gtctagctcc tcgccggagc tgcagaccct gcaggataca ctcggggacc    7020
ctggggacaa ggccgacgtt ggccggctga gccccgaggc caaggccgc tcacagtccg    7080 ggactctgga cggggcaggt gccgcctggt caaccccagg tgaagagagt cagggccggg    7140
gccctgcgag gcccgaggt cccttgcctt ctggctgtcc ccgttccccc ggtggcctgc    7200
gtcccagagg ctacaccatt tcggattcgg ccccgtcacg cagaggcaag agggtagagc    7260
gggacgcctt caagagcaga gctgggggcct ccaatactga gaaggtgccg ggcatcaacc    7320
ccaggtgagc cttgccctt cgggctggag ctgccggaca gtccccgtgg ggacacggtg    7380
cctgagcggc ccccgccga acagactggg ctacaggtcg tgtagtctgt gccccgtggc    7440
cggtgggagc cagacaagag ggcagttcct tcggcgatgg ggcggaggtc cgcttctttg    7500
tgcctgggtc gccggtgcca gcagtgacca ggcccggccc ggccctccca tctctgcccc    7560
tgcagcttcg tgttcctgca gctctaccac tctcctttct ttggcgacga gtccaacaag    7620
ccgatccttc tgcctaacga ggtatgtgtg cttttctctcc ggtgcggggt cccccccgga    7680
gcctgggtgg gggacgccgt cggggtgccca cagcccaggc ttgcagagac aaagcctcag    7740
ctccctgtgg cagcctagag cgaccctcc cccagcctgc cccgggcga ggagagccct    7800 ccccggacag gcacctgacg ggctggtggt ggcacgacct ccgcccaagg ctcaggcggg    7860
gctctgtggc tacagtcctt cgagcgctcg gtgcagctcc tcgaccagat cccatcctac    7920
gacacgcaca agatcgcggt cctgtacgtg ggagaaggcc aggtaagggt gctgggggcc    7980
cgagcccagc cggatggcct cctggctgg ggctgggttc agggcccggc ccctcgtcca    8040
ccaccgagct cagtcactgc gtgagctgcc agagcgtcag gtgctcgtgg ggccccgtgc    8100
gggctgctgt tcccgtgccc gggatgcggc gggagtgaca gcggagcgtg tgagcacacg    8160
gtgcccagag ggatgttggg ggctgcagag agggtggtgg gtgcatggac gccacaggtg    8220
tgggcggggc accgctcaca tcagcgaccc gggcacgggg tggctggcgc agtgcccacg    8280
gggcgcacgg ggggccggag gcaggatggg gaagtagagg ggaggcgtgg acggcctcag    8340
ggctgcgtgt tgttcccagg gaggtgggag ggccacgaat ggttctgagc cgagggttgg    8400
aggtaactcg gccccagcct ccggagcatc cttctggctg ccgcacgaag agccggtgga    8460
agcggggcgc ccctcgtccc catgagatga gcaggcctgc ggcgcgggc cgggatgccg    8520 cggaatgcca gcctctgggt gtgttttgg tccgcctgag caaactggct ggtgacccg    8580 tgctctgtgc gagagacggg gtccagatgg cgcccccggg tgcgcgccgg gccccgagg    8640 agccgggcag gggcggtgc cgccgagctc ctctctcccc acagagcagc agcgagctcg    8700
ccatcctgtc caacgagcac ggctcgtacc ggtacacaga gttcctgacg ggcctgggca    8760
```

-continued

```
agctcatcga gctcaaggac tgccagccgg ataaggtgta cctgggcggt ctggacgtgt  8820
gcggggagga cggccagttc acctactgct ggcacgatga catcatgcag ggtatgcgcc  8880
ttccgccggc ccgcactcgg ggctgagggt ggccgagggt ggccgagggc ctgacttccc  8940
ccgacgggga cgggtgtgg gtagcagtgg ggctggcgcc tctgcgtccg gaagctctgc  9000
cctcggggtg aggaggcaag gctgctggcc aggcactgga gggggcggt cccgcaggcc  9060
cgagagcctc tggaggaacc aagaggcgcc ccacgcgggt gctctgcctg ggccatgcc  9120
aggccccgct caacttggcc ccatgcgcct tgcagctgtc ttccatatcg ccaccctgat  9180
gcccaccaag gacgtggaca agcaccgctg tgacaagaag cgccatctgg gcaacgactt  9240
tgtgtccatt gtctataatg attccggcga ggacttcaaa ctgggcacca ttaaagtgag  9300
tgggggccct ggctcgagtc tacacctctg gcaagtgct ctctctggtc tgtgttgagt  9360
gcaggcagca ggcactgtcg gggtcagtac ggcaataaaa ggacctccag tgcctcccgc  9420
cgccagttgg agtaggcacg ttccccccc ccgcccacc cccgagccag tgttctctgt  9480
aatgacaacg acggggacag cggccctcat gggagcccat gagcctagtg gggggccggg  9540
cacagagcag ggatttgtgt gtccctgggt ctcggcgtcc ccctctctga cacctccctc  9600
gtgtcatcac acagcactgg ggtgtgcccc gtggcctcgc cttccctaga tgacgatgct  9660
agggcccaag gccccggtgg ggaggcgggc tccacccagg agacttgggg tgtgaggcat  9720
gtggaaggca gggtcggggg gcaggtcccg aagctcacaa gcgttcagat tctaaaccca  9780
acagcaagcc tcagagggg tcgctgaacg cgaacacgcg gccgctggtg agagtctagt  9840
cgcgggccac ggtgcccgag gggtcgcacg gagctggggt gggtgtgtgt ggtgcacacc  9900
cagagacgca cagggaagcg gtccgcccgt gtaggcgtcc gggctgctct cgggacgaca  9960
gggaggcagc tggcagccag gtggcagcag gagtcacggg tagcacaggc aggcgaggtg  10020
ggggtcatgg gtcatgggtc atgcgcctgt ttagggtcgt gactggacct gaactcgggg  10080
ggattcagtc ggtgggatct ggatgtggag tcggcttta ggagggaagg cggcccgggg  10140
gaggagatga gggttcagcc ctgccccgg gctcggtcgg aagcgggtct acggggctag  10200
tgaccgaaag ggcaggtttg tggagttagg agccgagcga gagagggca aggcccgagg  10260
tgacctctgc ccttgtctgc acagggccag ttcaacttcg tccacgtgat catcaccccc  10320
ctggactacg agtgcaacct ggtgtccctg cagtgcagga agggtgagcc ctggggccgg  10380
gcggggaggc cctcgcggcc ctgagcccct cacgagctct gtgtctcctc agacatggag  10440
ggcctcgtgg acaccagcgt ggccaagatc gtgtctgatc gcaacctgcc cttcgtggcc  10500
cgtcagatgg ctctgcacgc caacgtgagc agagggtcg gccgggggcg gggtgggacg  10560
ggcccagggg tgcggccac aagggcctca gcgctccccg tctcccaccc cagatggcct  10620
cccaggtgca ccatagccgc tccaacccca cggatatcta cccgtccaag tggatcgcca  10680
ggctccgtca catcaagcgg ctgcgccacc gggtagggca ggtgggcctc agaggccttg  10740
gggggagggg ggcgtgcact ggcatccagc tcacggaggg caagtgcccc ccccccgccc  10800
ccgctccttc ctgaaggctc cccgtcccct gcagatccgt gaggaagccc actactccaa  10860
ccccagcctg ccgctgacgc agacgcaccc tccgggccac gccaaggccc cggccgagcc  10920
cacgcccacg tacgagacgg gccagcggaa gcgcctcatc tcctctgtgg atgacttcac  10980
cgagttcgtg tgagccgggt cccgtgcccc gccgttatat gcgcaaatga aataaagcag  11040
tggtgcagcc ccggcctccc catcgtgtca ctcagagcca gacgcggatg cagtcagcca  11100
gctggtttat ttgactttgt cgggtgggga tgggatcaag gctgtagcta tggccacacc  11160
```

```
cacgggggc  caccctgcca  ccacccacgt  gttctccggt  gcacagaccc  tcacctgccc   11220
cagccccggg  agccagcccc  ggggcagggc  tgcttccacc  ctggagttct  ggccccgccc   11280
gcgtcctcct  cctcccccag  acctgacacc  cgcgggtctg  gctctgccc   tcttgctgtc   11340
acagcccagg  cagagagcaa  ggccgtgggg  gtggggaggg  gggtggtgac  aggaagtgcc   11400
gaggcgatgg  ctgggccctt  ccaacaagcc  tcccatccca  gccccaggcc  caacttggat   11460
ccaactctgg  ttaggtgtct  ggggagggag  gccagcgctg  cagccccagc  acccctttccc  11520
acaggagacg  gggggcatgg  agccactgca  gccaccaggt  ccctcggccc  taaggaaaaa   11580
gagagcgacg  tacaaaaata  catttttaac  cccatataaa  ttacgacaga  gacactgcgg   11640
ctgaaggtgc  gtgcactcag  caggggcaag  ggagaggtaa  taacttaggg  ggagacgatg   11700
ggaggtgcag  gttcccctcc  ccgaagcctg  gatccttagc  aaaggggaga  tgtctgccca   11760
ggaggtgggg  ccgggcacag  cccgctgtac  ctgaggactc  cggtaataaa  ttagcatctc   11820
agaggctggg  cactcagccc  aatactgctg  tgtcctccca  cggggagccg  gggagggac   11880
cctgggtcct  ggctgccac   atggcgtctt  taaagtgctg  agaccacag   agagagagac   11940
gactgctccc  tgggggcctt  cgtgcagctc  ttctgcctgg  cccgagaccg  taagggtggc   12000
agaaattaat  actgagcggt  gtctgctctg  gctccctctg  cagaggggac  tgaagccaga   12060
ggaccacccc  agggaagggg  tctgagcccg  gaccccccg   ggactaagtg  ctgccggggt   12120
ggaccttgtt  cttagcccgc  agggaaaccc  tgcaggggcc  cggggccaga  cccacgccac   12180
gactggcccg  gcaagacgg   ccaggcaggg  ccggccgcag  gtctgaggag  gggctgtggg   12240
cacccgtgct  cctgcggcct  tgcaggctct  gaagcctctg  ctccagctgg  tagacatcct   12300
ccgtggcctg  gttgagtcgg  tcgaactggg  tcagaagggc  ctcgaacacg  gcctggagac   12360
gagagggctc  gggctcccca  cgcggcccca  gccggctcag  gccccgccg   ggtgtgtcca   12420
gctggctgga  ggccgtggag  ggccgggagg  cgtctgagcc  cccactgggg  ggggtgcgt   12480
ccggggacga  cttggagccc  ctggaggagc  gcgagggcag  cggttccatc  ccttcaaacc   12540
ggactttgtg  acgaactgg   gggcggcaca  ggggctccgt  cagtccggct  gcaccccggg   12600
ctcccctggg  cccagggtgc  gtccctctcc  cccccactgg  gccgtaccca  cctccttaac   12660
cttactgaag  cccatccaga  ggcgcagccg  gcgcaagaac  agctccacca  tctcgtagtc   12720
ctgcggctcc  caggccggcc  ggtagagctc  cccacgcagc  gcgtggtacc  gccaccgcag   12780
gaggaccgcc  cccagcctca  gggccccca   cagccgcagc  gcccagagcc  cagtgcacag   12840
cagcggggag  aggcgccagg  actcggcagg  gcacgggca   ggaccccag   acccgggaca   12900
cggcaccaag  acgccctca   gggcgctccg  aaacgagtcc  acgcaggaag  cgaccagctg   12960
caaggggaag  gggcgcgcgt  gaggggcgcg  tcccggctg   agcccccccc  tccctaagg   13020
gcctctccgc  cacctaccaa  aatggccagt  tgggcataag  ccaggagag   caccaccggg   13080
cccagggccg  cgcccacgag  ctccggcggg  gccctgtaca  gtgttttgcc  aaaaaaccga   13140
caactggcgc  acgaagcgca  gctgctgggc  ggcctgggg   tgagcggtgt  cggttgaccg   13200
aaccgccccc  ggtttgaccc  ggccccggcc  caggccccgg  ccgaccccg   ccggcccagc   13260
ccttaccttg  actagcagga  gaaagagcag  cgaggcggcc  aggccgcgag  ccgcggagct   13320
tagctgcgcc  acctgctcga  acctggtgaa  gcggcgcggg  cggcggcgca  cgaaacgggt   13380
ccactggcgg  tcggcgacac  ccagctgggc  caggcgcacg  agcgccgcgg  ccgcggttag   13440
ggccaccagc  agccaccgcg  cccaggatcc  ggactgttcg  gcgcgcgtcc  gcccttcctg   13500
```

```
gcgccacaca cgcgcctcgg ccaccgagaa gtacagcgcg aacagcagca ggcttacctg    13560 cggggcggg gcgaggttag gggggagggg cggggcgagg ttagggggg aggggcgggg    13620 cgaaattagg ggggagggc ggggggactt gctcggggc ggggcgacgg ggcgagcgcg    13680
gccggcaccc accgaggtga gcagcggcag cgagaggccg gaactcaggc gtcgcagcgc    13740
gaacgggcgc acgctgactg cggtcacggc gtgcccggcc accggaact cgaggcgcag    13800 cgtgacggcg gcatgtagcc ccacggccgg gctgtagcgc gtgagctcca cgaacaccgc    13860
gcggctccta cacggcgaga ggggcgggca ggtaaagac tgggtgtctt cccagagaaa    13920
ggggcttggg cggcgggtga ctcggggccc ggggaggag tggaggctga gcggtcagtg    13980
aggtgcgtgg ggaaagatgg ggacacggaa aagcggcggg gtgagggagt ggaccgcgga    14040
ggggcagggc cccggaggag ggccgcgtgg ggaccccggt gtgtccgccg gaagcgccgc    14100
agtgcggaga ggcggggaca ggccgagcgc gagcacctgt tgtcgatcca gttgtgcagc    14160
tgcaggaagc ccagctgcgc gcggctctct tccaggctca gccccagctc ctgcacgtag    14220
cccccgctgt cgtacacggc gcagtagccc caggaccaga ccctgccggc gaggggacgg    14280
cgttagagcc aggccccagc cctggaagaa cctgggaggc aaggctggct ggggctaggg    14340
ggcgcccgtg gagaacaacc ccccctcccc gcgtcccggc tcctcccgga tcccggggcc    14400
ctccctctgt gctcacccca gcaggtctgg cgcagagtag gccacatct cggagccgtt    14460 gtgggcagca ctgccccagc cgatgccata gtcgcctgtg ctgaaggagc ctgcggctgc    14520
cgcgcacacg ggcacacccg ggcgagcagg gtctgggcag agtgctgaaa gcaaaggggg    14580
agttcttggc cagctgggct ctacgtgatc ccaccagacc ctccctgcaa cccagaaggc    14640
agaggtcaca gtgtcacaga cggagaaagt aagggatgca cagctaggca gctggaacca    14700
gaatgcagcc aggggtgtct ctttgggaga gagcaaggac gcagtgccag gcctccctcc    14760
acggctcacc ttcctgcagc cgcacctgcc gcagtcgcgg gggccccagc tctgggctgg    14820
actggttccc atggatgtag gggagcaaga cgtgggacat ccacggccaa aactcctcag    14880
acctgctcac acagagtccc gtgttctacc cggcagtgcc ctgcacccct ggggcgggg    14940 gtggtcagag gcccacagag cactgctcct gccgccccag cccagccaac agcaggctgc    15000
cggtgccacg ggacgggacg aggtcaagac ccagaagcct caagctcagc atactgacat    15060
ttggagcagg aagtgttacg gggcggttct gggtactcta agattatttg ttttgagaga    15120
gacacagaca gcatgagcgg ggtaggggta gagaatgagg gagacagaat cccaagtagg    15180
gtccgcaacg tcaggacgca gtctgacgcg gggctttcac ccccgacact gtgggatcgt    15240
gacctgcacc gaaaccaaga ctctgacgct caactgaccg ggcaccccca ggcgccccgg    15300
gacgttttga acggtatctc cagtcccgtg ttgccaacac cacctactcc ggtcctgaca    15360
acccacgaca atccaagacg ctgccccacg tcccctgggg actgggttgc accaaggaca    15420
agatcgagat gggatgtggc gggcatcaat gcctccccgg cctggcaggt ggacacgcgc    15480
atgagcacgg gggtgcctgt accgggtgat ggccaggaag gcctggctgc cgagctcctg    15540
tttgatggca ctctgcaggc ggtaggcgtg gctgtgcag gaagcgtccc catggttggc    15600
cagcagcgtc accagcagga agagcatgta taccaggaag ctctggggc agggacggcc    15660 ctggggtcag ccaatcccag tgtgcccac cgtcacggca ctggcagca aaccgcccgt    15720 ggccaagggg cctggtgccg gtgggggcgg cacagacacc cgccagcatc ccgccagagg    15780
ggcggacagg tggtccctcc aaaggcagag aagatggccc ctaaggcccg cgaggctgcc    15840
catcgagccg ggcacgggaa gaggcacagc agggcacagg caccgggagc tgggggcgag    15900
```

```
gggggcgggg gcggggcgca gagggccaca gggcgcacgc gcgggtctc cgagggagaa    15960 cctgcaagga ggtgcggttt cggccagaca cgggacagga gagcggctca ccctcagcat    16020
cccgtgcagc ttcttgacct ttcgggcctc ttccttcgcc aggaagagcg caaagccgtg    16080
tgggggccgc acacggggca cacgctcact cacagggtc acagccgggc tctccaccag    16140
ggtgtcatcc tcgtcgggt gcagccgctt ggccaccagg gagaagtaca gggcctccag    16200
caggacctgg gccaagggag gcgtcagagg gcccacagg cgccaggggc tggcagcccg    16260
gccccccaac atcccactca ccttgagcgg ctcccagccg aagaaggagg ccaagaagct    16320
ggagctgctc gagaggagcc acatcacacc cacaccaggg gagaagctgg cacccaccca    16380
gccggagacc cctacagcca cagccaccaa gagcaggctg agtccgtggg ccaggggagc    16440
acaccaggct ggcagcagcc gcctccgcag accgtccacc agtcctggga aggaagacag    16500
gtgacgggca gcccacgggg aggggccggg aggggcgtcc tggggacacg agagcacacc    16560
tgtcctggcg ggctttgctg actggggccg ctcccaggtc agacctgggc tgggcagccc    16620
cctgtcccct agcctctgca gcatcagcgt ctccgtcctc tctgcaggag cgctggacct    16680
gaggcacaga aagggggggg gggcgtagcc cacgctcagc tgtcggccca cagcacgacg    16740
tccctgagcc cccgtacccc tgcacccgcc ccccatgtca gccgagagaa gacaatgccc    16800
caaatccagg tagatacagc gctggggctc agaccaccac cggtgactcc gggaagggcc    16860
cccgatgcct gccctgcccc tcaggccgaa aacccacgtc agcctccgct gccgtctccc    16920
cctcgctcgc tgctcctcca cccacggaca gagtcctctc ccatcgtcac cccagcagcg    16980
gtggctcaca gcgtggctga agcggcccca aggccccggg ttcgcgtcgc gaccttccgg    17040
ggcgcacccc gcacacctcg cgtcttcgcc cccaacctcc ccacgcagac ccacgtttca    17100
caaagggacc gcgcgctgac gcagctttgt gacacaagat gcaactcttg aacaaggaaa    17160
cacctttgtc tcaaaattcc gaccgtatct agggttcccg gggccgagag aagcgtgtgt    17220
ggcccacggc gccacaccga cctggccggc tgcacagctg ccccaccaag gtacgggggc    17280
tccgggggcg gggggatgtg aaacaagggt gtgacgggca cttcctgagg gccaagcgcg    17340
cgcctggcgg gggggcctgc acagctgtgc cctgactaca cagaacaggc cccctcccc    17400 cgctcccagc aggtgcctgc catgagctgc gctgaacgcg cctgggtttg tgagccttcg    17460
acagagtaag aagtatcgtt tatgcgggtg ggaaatcagg acagcaagca aacttttttct    17520 tgagatggac tagagaacag gtgctccata tcctcattag gcaggagcag cagcattcct    17580
gttctttcta gggctttctc cggacgccca cgttcatgtt ttacacgtgg atgtggtgtc    17640
agggcaggtg gcatagcgga tatggcctaa aatacacgcg gcttcaccaa acatcaagcc    17700
gcaggagacc aaagcctgcc tgtcacgggc cagcaccccg ggtccccggc cgaggccggc    17760
accgttctgg ccccgagtga aaggagccaa ggccacgcac gctgctgggg ggggagcgt    17820 gcaggcaaga cgcccggagg cagggaggac agagaggagg tccccatcac tacgccctca    17880
tgcatttgca ggcaggaagg ccccagccgg ggagcagcca cgccaagaac ggcaggaagg    17940
agacctgggg ctcttgtctt ggggaggatg cctctaggca gaagggggc agaagacagc    18000 aaagatgaag gcagaaaagg agggaagcgg tcggcggagg cggcagggcc agctcacgca    18060
gctgctggag cgtcgtaagg cgagccgcct ccgagggaca cccccccccc ccccccccg    18120 ccctgccact tccgcgggca aggacacagt gaactgacag ggctgggtca taaaggactc    18180
tgtggttcct gctttgcttg ggccactcgc tctgaggtgt cggccgtcat gccgtgaggg    18240
```

```
cactcaagcc agccacggtg agggccagat ggggacaacc accaacctgc ctgccgtctg   18300
gctcccttga agcacagagt tttgggataa ccggtcacac ggcgacagag ggccggtgcc   18360
ctaggagagc agcggcaggg cctgcctcgg ggagcaggac tccgccgagg ggacgtttc    18420 gacggaggcg caagagcaaa caggagggtc agactcggga ccggaagggc agcggcaggt   18480
gtgcgtgaag agggacgcca agagaggagt cggggtcaa tgaaaacttg tggtggccgg    18540
agcgtgcacc gggccggttc tgagaccggg accggggggg cggggcgcag agtctctgga   18600 gggggcctg ggccctgcgg ggcgggcagc tccgcgcagg ccagtgaacg tccgcggggc    18660
ccgttcgcgc agtcggccca aggcctgaac ctggacttga ggaagggctc tgggctggag   18720
ctatctgggg ctgctgtccc aggatctccc catagtatag accttctgaa tcaatttcca   18780
atttcttcgt aacatgcgat cataccacgg ttatctgtgt ttgtaaacga cccgagagcc   18840 ccccacccc gtcccgttcc ctgtgctcag gacggttcac gtgtgtcatc tgtggtgctt    18900
gaaaacgaca agggttaaaa ggagcagaaa tgcgattatt ggaggaaaaa aaggaagtaa   18960
gagacagttt cacacgaatc gtccatctca gaagttgaga gattcttaaa aacataaaat   19020
tgaaacaatc tcaaaagaaa acaagcagga tgtttggaaa acctggtcct gagcaccca    19080 tcaccccaca cctccgccac ctgtggggaa cgctcgccac cctgtgaggt cctttcaata   19140
ggtaaggggc ccagccccgc acaaggccag tcccaggcgg ggagcgggc ttcttggcct    19200 gggatcccgg ccgccccca accccggga gccagggact tacaggccag cgatcagatc    19260
cgtttctatt tgcgcgtccc gggcaggggc caggctgccg gcccttcag ccacgatccg    19320 ccggatgagg tcctcgtcta gagggaaaac acgtcagcga gggcatggtt tctcccaccc   19380
ccaggttcct cagaaccttc ccggggatcg catgggata ccaccctccc cacccctgct    19440
cacccgaagc tgagaaggac ttggcaggtg aggaggggct gaccagggag agcccgtcct   19500
cctccgggcc caggcggccc cgtgccagcc gctgcaggt gctgcccacg atggatgggt    19560
cactcagcag gtccggccaa ttcagcgtgc cttcactgga cggccagcac accaggctgt   19620
aggtgacaca ggtgaaacaa gggggccca gggggacaca cgtacaacac ggccctaggg    19680
gacaaaacgc acgcagcgca gacacccata atgcaccacg cacgaggtgt ggcagaccca   19740
cgccaaggct cacgctctct ctggggactc tacccttttg caatcatcca aaaataagtc   19800
acttttcatt tgtccggcaa aggcctgttg agaagcacag agaacacctc aggttctgag   19860
ctgctcagag gcagcgggac ccacccagcc tgggcaggaa cccggggggg gtggggggg    19920 acacactcgc ctcagcgcgg agcccggga aggccaggaa ggagctgtcc agcacagacg    19980
agtccaggta gctgtcgatg tccaggaccg gctgccccgc aggggtgggg ctcgggcccc   20040
cagccaccta ggggagaggc aggcattcag cagaggtgtg ccacctccgg agcaggcaga   20100
gcctaggctg gggctgtgct agagaatgtt ctagaatcgg gcacacgttc tgtatctgca   20160
ctgtccatca cggtagccac aggccgttca gggcactgga atgcagctgg cagagctgag   20220
gactccagtt ttatttgtca tcgactcgaa ccagccgtgg tggcggcgga ttatcccatg   20280 ggaccctgg cgcacacacc cccagggtat ggtggtgggt ccctcctgaa ggaagtgctc    20340
tgtccttccc tcatctcatg cagtccccat cagatcgggc gggaagcgcc tgctccttgt   20400
ctctctgagc ctgtgaggca ctggcccttc ggcaggtgca cggagccac cagggaggcc    20460 gtttgggctc ttccttgtca gagggtttaa atcgccactc tggcctcttg ctagagatct   20520
gctcaggttt gcgacatcct tccggtgtctt tccgggaccc tgcccgtctc ccctcagtca   20580
cctgacaggc tggtccacag cggtcacggg aaccccccc ccccaatctg ccctgtgatt    20640
```

```
tccgtggcat cagaagtggg gccccgttgg ttcattcgtg atctggacaa tctgcatctc    20700
tctgtctccc tgggtcagtc gtctcgacct tctgcccctc cctccggcca cccttggcgg    20760
cagcaacgag gcccacgctc cgtcctctgg aagctccccg ggccccagcc caccttgctc    20820
cgggacatcc ggaagagaaa cagaatgacc aggtagacgg gatagacgac cacactggac    20880
accaggccga cggcaactgt gtcggcactc agcgggatca gaccgacac  gggcccgcg     20940 ctgtgtggca ggagaggaga gagacccggg ctgggagagg ctgtgggggg taggaggggt    21000
cgggcaggag gagatcatcg ggcacccacc tgtaggcggc gtctcccacg accccgtacc    21060
acacagcatt ggcgcccagg aagaggcaga cgaggaggac gcaacaggtg gcccgctgga    21120
cgcgggtgaa gcggctccga ggaggccggt cccagaggga gagccagaga tgcttgtcaa    21180
aaaagccacg ctgcagctcg gccaccagga ggcgccggaa ccgccgcaca gccgcgtcgc    21240
ctgcagaaag ggcacagctg gcttcaggag gccagcggca caggccaccc ctcggccagc    21300
ccggggaagg gacgggccca ggcccttact tgctgccagc acctccttct ccacgaggcc    21360
gccattggcc tcagtctcca ccgacagcca gtcgttgacc aggaagaagg tgctgcaggc    21420
ggtctgcagg tcccggacga tgatgtgctg caggaaccag gcggggctga gccctgcagc    21480
ggaggggcgg ggagtcaggc tgaagggcgc cggtgggtg ccggaggggc agccgcgggc    21540
gcccccacag gacctttgtt gtcgtgccac acgcggatct tccgcacgct gcccaggctg    21600
tgcggcgtgg cgatctggaa cacgtccagg ctgttgcggc ggaaggccct gtccccgtcc    21660
aggtgccggt ggccgctgcg gccctcagcc ccgtacagca tgatgcccac gtgtgccgtg    21720
gttcctggag gatggacaga gaggcagcgg ggctgggtac atgaccccgg gcggaccttc    21780
cttcgctcag cagacaggcc gctctgacag gtgccctctc accccctaa  acgtgccaga    21840 cacgcagccg ccaacgacac ggcgcagcag gcggggcgcc agattaaccg agcgactacg    21900
tgagacacag tcgcccccac ctccctgtga taccatatgc acgtgatgtt ttacaaaaac    21960
ggggactggc cggtgagggt aagagcacag cgaggaggag aaaagtggta acgtgggaga    22020
gacgttcaga acaacggtca ccaggcaggt cgacactggc cgaggccacg acaccaaact    22080
cgccaacgta ggcagacagg gaccacgaga gaaagaacaa agatgtcaca gagcaaccca    22140
cgtgagcggt cagaggggtg tcacggagca ggagggccag cgaggacaag tgtgggggg     22200 gggcagggc aagaggacca atgaggacat gccgggggt ggggtcaccg aggagggcca      22260
agcagaacac gcgggggag  ggggagcaa gagcaggagg gccaacgaag gcacgctgag      22320
gggggagcgc aggaagtggc cgaggcatgg agaacacgct cacgcgcgtg gcagctccta    22380
cagccgcacg gccagcactg cccacgctgc tcagcaagtt ttccacaaag aaatcgaacg    22440
cttttgcccc cggcacgtct aacgttcaag tcacactgtc ctcgctccgt cagtccgtct    22500
tcccagtaac ggctcaccac caccccccact gtcgtccgct cgctcacaca ggtgggcccc    22560
gcactccgat gccccgtgtg cccggagagc accgtgaggc ctgatgagct cccgccccac    22620
gcggcaccgg gtgaacggag ccctcgtccc gtcatctact aagatagtcg ctaccagaga    22680
agatagccag agagcacacg caagggcggc cgggaggcct ggaccagaca gccccccgcc    22740
tcacctgagc cccggcccca gccagtcttc accaggatct cgtacttgaa gcggccccc      22800 ttcccacaga aagggatcac gcggacacgg ctgacgtcca gctggtccag cttacgcagg    22860
atcacggcca tgaccacata ggtcaccagg cacacggaac aggtcagcag gacgacgtag    22920
ttcacgcctg aggccggttc ctgggagac  agagccatca ggtccaggag gcacggccct    22980
```

```
cgcctcactt tctcaggacg agagaaaggc tggggcctcc gagcccccca gaaacacggt  23040
gcaactcact ggaaagatga accgcacgtg gctgggaggc acgaagaggc tggccccgaa  23100
ggcagtgagg tggcgggtga ggcagacggc ctggctgggc gacgtctctt ccaaaggcac  23160
aaggccctct gtcctccaca tcatgtcctt ctcgctgaag tactggcaca ggggatgtgt  23220
acaggcccac ggtcacttcc agtgccgacc aacggaagtg gctggtcaag ttcaggtaat  23280
aagtcccgcc tgggtctctg ctcctagaag ttgagcgagt gtcacagcca gaccctgccc  23340
agcccgagtc acggcaggtc ctgctcccag acccctcggc tgcagccacg cccaccacgg  23400
gtggccaggc ctgccgcctc cggtcctcct gccgccagac ctactcccac aggaaaccca  23460
gtgaccctgc tggcgtccag ccagccgtca gagattagcc cccactgtgg gtccacggtg  23520
gcctgctccc agggcgggc gtgggctcac ccggggggcga tgaagaaggt gtagggcctg  23580
tggtccctgc ccgccagcgc ctccgggccg atcctcctgc tggctgagca gttgtgctcg  23640
ttgggctgcg gcaccgagtg caggtacaca gccaggtagg gctcgggctc ccgggacagg  23700
tagtgttcta ggggcacaag gacagcattg gacggctgcc ccgcgcagct cgcacaccct  23760
gggggacgct cccggagccc tgtggcgccc tccctgcagc ctggggctgg ggggctggag  23820
agctctctgt tgccggcagc actcactgtt gcctcgttcc ccgctgccct ggggccaggc  23880 cccgccagc ctatgaagca ggaggcagac tttcctaaag gccacgagtc gggggggggt  23940
gggggggggc acgaaagaca cctgctcacc aagggtcccc cacacaggct gggccgaggc  24000
ccgcagcacc caccgctaag caccgagtag gtgagctgta ggtgcaaccc ggcgtcaggg  24060
ttgttgtcct cggggacgac cacaacgccg accgaggcct gcggctggac gacggcagag  24120
ccggcagggg tgcggcagcc ccgtgcagcc tggtctgagt tgttgggtac tttcacggtg  24180
atggcacgct ccgaggccag acggccaatg gggatctggg ccccggcctg tgtctggaag  24240
gccatggacg ccaccttggt ggagacagta tagttgctga tgtagccgaa ggggaagggg  24300
ttggagtcga cgaggatgat gagctgtacc acatcactga ggttggacag ggccccgctg  24360
aaggcctcag ggatggagaa gtggcagcca ggaaccgagg cgtcgccctg acagagcagg  24420
ctcagcgggt ctgagcgctt gccctgcgcc acgatctcct cgccggccag cgtcaggggc  24480
tcctcgttga gcacgcggga gcgcatgagg atacacatga gggccgacga caggtggtag  24540
gccctggatg ccaccatcag ggacggcggc tctgcaccca gctctgaggg ctgcgggccc  24600
tgcacgtccg cgctggccaa gtggatgagg tcacctgtgg gagaggtggg aggagaggtg  24660
gcggggaggg ctcagagggg gggcaagcgg ggaggggggg tggggcacg cgcctgcctg  24720 ggccccggccg cacctgtgat gttgagaatg ctgtcggcaa tggccgtggg cgtgccggtg  24780
ccctcggcgg tctcggcctg caggatgtgc atcatgccct cgagcttgtg cagcgtcttc  24840
ttcagacacg aacggcacac gagctccctg ctggacacct gcaggaggc cagacgccgt  24900 aggcagccct cctccggcct ggctgagcag ggccggcacc ccccgtgacc cctcaaccca  24960
cttcagttcc gtcacaccgg ccacgtggcc caggcctttc ccaacgcccc ttcacgccgc  25020
gactggagaa accaccccaa gcgtgggttc cagccatgtg cctccctgcc gagagctctt  25080
ctgtggtttc tccccacccg cgggcgagga aggtccaagg taacgcggtc ctgccgctcg  25140
ccctaatcca tgtgcctggc catgagagcc acgtgtcaca ggtgacctct cccgcctggg  25200
aaggttctct gcttccttct ctgctgaaag ctgtgcagca atttcccacc acgcagaggc  25260
acagcgtgcc cccgccccg tcaagactgt gctcagctca gccgagcctg gttctcgagt  25320
cctgggcgac agtggtggct aactgcttgg ggctgcagaa gccagatcag gtgtgaccgt  25380
```

```
gggctgagtg ggagggcacc ggaacagcct cttcacgtgt gctctcctta gagccaagcc    25440
gctccttacc cgtaggccac cctgcacagt cgcacctgca gctcacatgc taaatggcca    25500
aggacaggca cacggccagg gagacttggc caggacaggg gctgccatgg ggcccgaggc    25560
ccaccctacc gtgcactggg ccagcgccgc ggcaatctgc cggatgtcat ccacggtgtt    25620
gacccgcagg gagaccagaa tctctgtgac gttttttgcgt atctgggctt gcagctgccg    25680
cctggggtcc gactctgctg acgaggccag tgcctgctcg tgctgagggc agtgagcaca    25740
ggggagccct cagggcaatg gcagcttca ctggtagcga cacaagttgt ctcagccact    25800
agaaaactcg ggcagtggct caaaccctgt ttcttcaggg acaaaggggg cttaggggg    25860 ctttcccagg acttctcatg ggggtgtgga gggctggcat caggggaagg gtccacaggc    25920
tgggactgtg gagaagagga gttatttcaa ggagacgagt caggggggcca actgcttgcg    25980 aggcagcgaa gactggcccg ggcccaccct ccccaccgag ggcagatgag aggagggact    26040
cctcacccct gcgctggcct cgttgagcac agtgatgagg gccagagagt actcgatgac    26100
gtgctggggg tcagcctgtc tcagtagtct gggaagcatg ctctccgtga ggctgtgcag    26160
ccaagtcgtg aggtccaggg ggccacctgg caggtcgcta gggagttcgg gcagagtgat    26220
ggccagagac ctgcgtgcag aagctcttgg tgaacaagtg gcagtccccg ctcccacctg    26280
cccagatccc gcccgggctc acctattgag agcaaccaca cggcgccta gctggtcctg    26340 cacgaccacg gccaagtcca cctggaagtg tggtgcaaaa ccaggcggca acacggctcc    26400
gtaggcagag aggctgcccc tgtagacgca gaactcttcg cagtggccct ggcgacagcg    26460
ccgcagcaac agggcgtaca cgagtggggc gcctgcgtct tccgcatcct gccagcctgc    26520
gggcccctca gtgtcagcgg cgccccagac tccctgcgcc gcgcctccct gtcacctgca    26580
gctgtactca cctgtgcact cgaaatgcac cttggtggtg agggcgcgca cggcgtccag    26640
cgggaagagg cggcaagagc ctccgcgcgg gggccggttg gcggagaggc ggatggaggc    26700
gcagccctct tcctccccg agcggcccag caccgtgagc gtgaacgtgt aaccctcgcc    26760
gtcccgcagc acgccgcgcc gtaccaccag ccgcatgcct gagctgcctg tcgacgtggt    26820
cgtctcgtcc agcaccagcg tctcattgct gaaagtacgc gccgcccagc gctgccgagc    26880
caggggacag agaccaaggt gctgaggacc gggagcagcc ccgccccgcc ccgccccgcc    26940
gaggccccgc cccgcccccc cagtcctaca ttcgctcacc cctcgctggg agccccgct    27000 acagttgtca cagcggccct ctaggtacac ataggagata cggctcaatg cgtacagcgg    27060
cctgcgcctt gcaggacaca cactccaagg acacaagggg cacccgaccc ctacggatca    27120
acacctggag acaagaaaag aagccacgac ctgagccagg gcctccactc ctggggccca    27180
caccctgagt ctgcacaggg cagtcagccc cagccaggct ccccagggga gctgggcctc    27240
tggcctctac cctgatgctg ttctcctggc tgggaagcct cctctctggg ccctgccagc    27300
acctagttaa cccggagtcc aacttcccaa ggctccgtgg gctcagccct cctcaagaac    27360
attcgttcag ttttttgatgt ctcccagtct ggaggatggt ggtggacacc caagagggca    27420
gagtccacct cgtgcttatt ttccgtagca cccaaagccc agcttgggcc tagcacacac    27480
gaagcactca ggtactcacc tgtgaacaag atggatggac ggacggacgt acccgtggag    27540
gagaaacaga acgaacgcac gtgtggggtg aaggcggccg tgctcactac acagcccat    27600 ctgaggtcgg tcccacctca gccaatccag gctggacccc gctccgagct ccccgtcccc    27660
cacacagccc gtcccaggca ccagcagcac ctcgcgcacc tgccgccatc ggcaggccgc    27720
```

```
agcagcgccg gccccagggg ccgctggcac ctcggtcctg acctgcctgg agggtgcagg   27780
gggcagcaat gttgaacacg tgtccaccca gggctgagaa caggctcttc ctgttcaaaa   27840
acgaggacac ccatgctctg ggaagggggc cggtttcctc actgcctttg gtgctgctgg   27900 aacccccttac ttctcactaa taaataccta gagcacccag gacccctcta agctccagaa  27960
ggccgcagcg cttccggaag gaaacaaaac tgaagcaaaa cgttttgtta aagagaatct   28020
gtatcaatca gacgtagtaa ctcacagtaa gaaccaatag cttccagaac accaaaacac   28080
aggaaacctt caccaagagt gtttggcatg aatggccctg tgcgctcagc cctccctggc   28140
tgcacctcag ccacgccagg gcccagaact ccgccttgct gggctaagga ctgggcccct   28200
ggcacctacc gtctggtttg tggcctcctc cttccggcct gccttccaca cggtcaggtt   28260
gaaggtgtac tccacgccag cttgcaggcg ctcccggggg acgtgaccca cgctgctccc   28320
ccggggccca aaggccagag tgcacccgcc agtctcactc tgtagccaca agggaagggg   28380
tcgtgaggcc ctgacggct tcaaagcaga gcccagcccc gggcacattt ggaagacccc    28440
ctgcccctcc gaggctcatc cgcacgaacg accaagggag ccagaggga cctcacgccc    28500 cctggtgcac cggacctgcg ttgaggccac acaggcccag tggaagctga gtggcgtctg   28560
gtcgccgtcc tccaggttgg gatcgtagga cttgctccca tccaacacca gatcctgagt   28620
gtccgaccac acccggtacg agcctccctc gatgatgggc accaggcgct cagggaccac   28680
tgtcacgttg gcttggatgc tccgtgccag cggggtgtcc ccaaatgaca ccaggaacac   28740
aaagcagtag tggcccacag gcagcgccag ccgtggcacc accagctggg gccggctcat   28800
gtccacgctg ggcagagcca cggggggccat gcgcaccggc cgatggcagc cagcggcacg   28860
gtacacctcc caccggtact ccgtctggta ggtgacgcag tcacggaggt tgacgtgggc   28920
ttccaggtag ttgcgctggg agcgccgcat cagcacctgc gggggcaggg ccacgtccac   28980
ctcgggctcc ctacaggcca gcacgtggac ggtgacccgt ggcctgggcc cacaaagaag   29040
ctcaccaggg ttggaagcgt tcacctccac gcggtagtcc ccaggccgca ggtaggagtg   29100
ttcagcccag ggctcctccg tgtcctccgc cggggcccca tccccgaagt cccagcgata   29160
ggccacacgc cgggggctag ggctcgtggc ggcctcgaac cgggccgaac ggttggtaaa   29220
gcagcggccg ctgcgcagca ccacgtgctg gatggtgtcc tggacctcga ccacgagggt   29280
gcggttcacg ccacccagct cgttgaaggc gcgcacgtgg atttccagca gccccgcggc   29340 cacggggtg taggtgacgt cgcggcctga cagaatgacc agcgagtccc cctggacctt    29400
ttgcaaggag aagtaccacg cgtaggccac gcgggacccc cgctgcacgc gggccgtgaa   29460
gttcctctcc atgcccgtgg ggatgcctgg ctcacagcag ttgggcacct ggagcccacc   29520
caccgcctct agcaccaaga tgcgcacctg cgcctgggcc cggctcacgt ggttttccgc   29580
ctgcacgctc agcgtgtagt ccccggcccg ggggaaactg cgggagaagc ggggcccggg   29640
cagggcctcc gggcggccc cgccgacctg caggtagaag ctgacggcag agccagcggc    29700
cagcaggacc tgcaggtgga ccggctgccc gggcgccacc accttgctgc tggcccacag   29760
cacgaggccc gcgacgggct cctccaccgt gagctcacgt gtggccaggc ccagctgac    29820 ggcattggag gcgttgagcc gaacggagaa ggcgccggcg tcacggaaga ccacagaaac   29880
gtgctggccg tgcctgctgc cacccggcac ctcccagcac cagctcacgt cggtgcctga   29940
gtccagctgc ccccagaagg gcacggcgga acccgccgcc acgaagctgc cgcccagctc   30000
gccggccctg atgctgaggc cgcttacggg cacctgcaca gccacctcag tggtggcgtt   30060
ggccgacccc agctggttcc tagccgtgac cgtgaccagg tacaggccgg gggtggggaa   30120
```

```
ggtgtgggtc gtggacggct ctggggtctc ccagctcagt cctccctcca gagaccagct    30180
ataaatgacg ccgctgcccc cagccagctt ggcacagagg gtgacgctgg catcgacggc    30240
ggccgggttc ggggaggcag ctgcggccag ccacccaca ggctccacaa agtccaccgt    30300
gcggttggcc agggcgctgc ccagcatgtt ggcggcccgc agctggatgc ggtaagtgcc    30360
ggcctcgagc acagtgagcg agaaggctct gccgctgccg gccagcgccg ggccgccgtc    30420
ccgctgggcg gtccagctgt aggagatgtt ggtgccgtcc cggaccacgg cctgcagctg    30480
cagcgtgcgg ttggtgggaa agcagcagcc gcctccgccc ccaccacct gcagcccctc    30540 gatgtgctgc aggacataga caaagatgct gtcctgggcg gcgcccacct cgttctcggc    30600
cgtgacgatg atgttgaagg tgcccacgga gcggaaggtg taggagatgg tggggccccc    30660
ggggatgggc gtgcagcggt cgcagagcac ccaggagtag cgcacgtcgc tgccggcctc    30720
cagggaggtg gtaaagctga cgctgccgtt gaggggcacc accgtgcggc tggcgttgac    30780
gctgagcccc cgcgcacgct cccgcaccgt gacgttcagc cgagcctcgc cacggctcac    30840
ctcgttccac ccggtcacgc ggacggtgaa gtgcccgtg ctgttgtagg cgtgggtgac    30900
cgcggagccc tcgaggagcc cgccgtcccc cagctcccac aggtaggtgg cggggcaccc    30960
gcggcccacg gcggagaaca ggtatggctg ctgcagctcc agcacgcgag aaccgttgac    31020
ccggacgccc gtgagctcca cgggctcctg cacctccacg agcgcggagt cgttggcagc    31080
cgagatgttg ttggatacgg caaccgtcac caggtaggag ccagaggccg ggtaggcaaa    31140
cgtggcctcg ggcccccga cgcgggcagg atcctcagtg ccaaagtccc aggtgtaacg    31200
gtagaggaac gggggccagg cacgagccac ccaccgggcc tcgtccccga gccgcacgaa    31260
ctgcctctcg ggccacaggg tcacgttgcc cagctcgggc tccacgcaga cgctggtgaa    31320
gtaatgggcc ttgttcacgt ggctcgagag gaccagcgtc aaggggaacg tgccgctccg    31380
tgtgaagttg tgcgtcaccg tcgggtcccc cgagacggtg gtgttggagg agccatcccc    31440
gaacgtccag tcaaagatgt agtgggtggg gtccccagtg acgtgggccg tgagccgggc    31500
gaggggctgc acaggatgc aggccgcagg ctcgatccgc agcacctcca ggacaaaacac    31560 ctgcaggggc aggctcagcg ccaggcggcc cgcggggctg gacgctccca cagtcaccgt    31620
gcagttccgt gcccgcaggt acacgtgctc caccgtggcc tcggggcccg tgagcaccgt    31680
gccatccccc atgtcaaaag tccacgtgac gttgtctccc gactccaggg tggcactgac    31740
ggtcacaggc gcgcccctgct ccacggacgg gctgaggctc acgctcaggc ccgaagctc    31800 ctcaaagaca cggatgccga cacatgccgt cacgctgcta accgtgttgt tgacctccag    31860
acggacgcgg tactcgcccc ctgagctgta tgtgtggttg acctccggcc ggtgctgcgt    31920
cacagctgga gagccatctc cgaagtccca cgtgtacagg atgcccccag gtgagggcag    31980
tgggcgtggg gcaaaggtga cagactggcc agccaccagg acacggcttc ccacggccac    32040
agccacggca ggcagggtgg cacgcacgct cacagacact tgccgcgtca ggttctcgaa    32100
ggcgttggac accagcaggg tcaggttgta ctcacctggg ggacaggcct gagtgagaac    32160
agggccaggg ccacctccac cacctgcttg gcgaagtcat gacctaaccc cgtgctgctg    32220
cgcgccaggg cccctcggga agatagaaca ggccctcggt caaaatgtca atggagaatg    32280
cccttgggcc ctgtcccggg aggtcctcgc aatgggccca gtaccgggtg ccacaagcag    32340
agggcaagac gcggggctgg ggcataaaag agatgggagc agaccctccc ctggtgaaca    32400
gacagggtcg gtgcagggca agggtggtgg ggtcaccaat gatcactgtg cattctgcgt    32460
```

-continued

```
gtgaaacttc tggaatttta aaaataaaag gtaactccct tctgagccaa aagtgggtct    32520
gagtaggagc caggaaggtc cagtttctgc ccaagagatt tgaatcacgg ggctcagtgg    32580
cccggacacc actctttcac tctattaagc gccccaggcc accaacccag actgggcaga    32640 aggggctgt ccccacggca gggtggcggg ccccagcgct cacctgggat ggcgtaggcg     32700
tgtgtgacat tgtgctccac cagcacttgg gcgaccgcag ggtctggcac ccgaaaggac    32760
tcactgtacg gaggcttgaa ctggccaatc acctggtccc cgtccccaaa ggtccacctg    32820
ccgggccaca ggcagacaat gagcaggctg gagtgggagc acgctggccc ggctgcagcc    32880
gctcccctct cccagggtcc catgtacccg ccacctcctg gcaggtgagg aggggcgggc    32940
tgggggagag ccgggcctca gccccacaag ggctcagctg gctccactgc ccgccagacc    33000
aggagcactc acagaaaagc cacctccaca gccgagtcca ccagcacgtg ggcagccagt    33060
gccagcgtgg cattgggggg caacacgggt ggcactgcag acacccagag gcccctcatc    33120
ctgttcatcc gctccacggt gacgttatag ttcacggtga cattgctcac atggttggag    33180
gccgtcagct gtggggacag gtagcagtgt gtgggctgcc ggcgggtggc gaggaggccc    33240
aaagcagcgc aggcagaacc ccaccctgca ctcaccgcg gccagccgag gggtcctcgg     33300
gaagcaaagc ggaacagaag gccaagatga gcacggcagt cccggccccg ccccgcccc    33360 gcccccgccc ccgcccaccc accgagagct gaagaccgc agcgctctgg tagatgacgt     33420
tgaagaccac attgtggaag gtaagggact gcttgtcgtc tatagtccag cggaagacca    33480
cgtctgagcc ggcctccacc atggggctgt acctctgcag ggagggcaca gtgtgggcgg    33540
cgctggggct ttggagaccc aattctgccc taagcagaat tccaccacct agacacgcct    33600
ccccaggggg tttcccaggc caagacttca gacaccacga ggaggtggag ggcaggggga    33660 gggggtggg gggcctaggg gggccacgtg tcataggact atgggctgac acgcccttg     33720 acgtttcagt tcctccggct tcctgtctgg aaagtgatct agcaccaggg acagaaagag    33780
cccaccatct gagtctccgt gcaccctgtc cctgggctcc tgctcgggcc cacagtctca    33840
gcacaggctg cttaggaagg cacgggagtc tcaagaggcc tcgtggttct gggtgtttac    33900
ccgagtcagc tgacagaaca ggtgtgagga gagagctgag gtcagagacg gcccttctga    33960
cagcccgtgt gcaggccgta gagctggtgg ctgacctgtg cgtgtgtggg agggcgtggg    34020
gggacacccc gagcagcagg tatggcactg acagcagcag ggtgacatga ggaccacccc    34080
cccccccccc ccagcaaaag cactccctto agcatgatgg gaacacagca gcggccttga    34140
agacactcag gctccgtgag ggtagagctg ctcaggggcc gtgggagaga ccgcagatgc    34200
tcagagctgc tgtttgacag gtggttcctc actaactcgg gaactaccac cggtctgagg    34260
agcccaagaa cagaacctgc ccagaaacca accccgggcc gccttccccg cctcactcac    34320
caccaggacg ccttgcagca cccgggcttc ggggctgggt gtggcccgga ggccgcagat    34380
gggctcctcg gccttcacct gcaggctgag gttggcctgg ccggcgctat tctccaccac    34440
cacctccacc gtgtgctcgc cctcacggag gccgggcagg gccagcaccg agaacagggt    34500
ggtgttggcc tcgagagcac agctgggtac caggcagcc accggggcag ggcaggcggc    34560
ctcaaagggt gcgctgacat tgccccagg ccagtgggcc gtggccgtgg cgttggtgcc    34620
cgagtctacc cggagcacca agaccgagcc gttggtgggc acatagaggc ggccatcgtg    34680
gggggtggga tgggccacac gcaggccagc caccggggag agcacatcaa agtcgcagga    34740
caggttgtgc atgacacgc tgttgccac cgtggcccgg acctcatagt gcccaggccg      34800
ccgcagcccc gggttgggcc tcaggccgag cagagggtg aggcgctctg tggcggcgag     34860
```

```
cagccgcagg gcgcaggcgg ggccagtcgg ggccacctcc agctgggcgg gcaggtgggc   34920
cagccaggcc gaggccacgg cggacaagta cggcgcctca gggccagggg tccgagcgcc   34980
ggcgagcagt gcaggagggc acctggtcca gcgtcgtgct gcaaggtgac aaggtcaccg   35040
gggagcaggg ggccgtcctg gccctggaag gggacctgca ggaaggagac aggctgtgtc   35100
gggtcctcac ggtgggacgc tgcagggcgg ggggctacaa gggagcacag gaccaggggc   35160
tccagcaggc aggtgggatc cacctgggat aatctagact cacacccaca gggggcccgg   35220
ctctcgggca ctcactcact cactcactca ctccccagg ccctcatgga ggggctgac    35280 agacaggctc agagggtgg gccgtgtgca gggcagaggg ccaggatgcg ggccaggcag   35340
gggcaggaca gcagaaggg cccggtggc agcttctcgt gctgggggc gagcaaggac     35400 aaggacaaag cctgagaaag gcagggcct ggtgcgtcaa gcggaagagt gtactgtctg    35460
tgcttcaggg agagacccag gcctcaggca gcagggccag cacacgtact gagtagtggg   35520
tgggagggcc tgccggcacg gagaacagaa actccttcca gagcacacag gaggtcccag   35580
ggggccctgg ccctgacgtg gacgtgttgg cacaggcccg gggccggcag agggtgtccg   35640
gtgacagggg gataccagtt tgggggcacc agcgtccctc tggggtgcac gcgggcaccg   35700
gccgagcctg gctctccagg gacgcactct caggctcccc gccatgtcct ggggcccctg   35760
caaggagagg agggtgtca gggacccccg cttgctaatg gccccagtc agggacaccc    35820 cacccccagg gagacacgag gtcttgccag gccgcacgcc aaccccacc cccaccatcc    35880 ctcctccatt cctcctgaca ccaggccagc tgaccgactc aggcgagtcc cggcgacacc   35940
gagcaggagt cggtttctct acagaccca ctctgtgcat ctcaaggctg gagaccagtc    36000
caatagccaa ggagccacta cacgtgatgg cacagacagg tccccactgc cccaacggga   36060
cggagcccca cctgctcctc cctcgggccg gaacacctgc agccgcagct gggcgggtcg   36120
gtggagctcc tgagtgccga actcggcagc gatgaggaag gcttctctac tcaggcccag   36180
gctggggaac accatcacct ggggaaaggg ggactgctca gctccacaga ccccagcccc   36240
cgccacccca cccccccagc acccactggg tcagagggga aggagcccc agacagggct    36300 tcacattgtg gctaacggtc actcgagaca aaaaatcagg tcaaaaccat ctgtgggcag   36360
caggaccctg accttgtttt ttaaaaatcc acaaacaccc agagaaaaca ctgaggagca   36420
ctcagagctc tctgagctgc ccgggcgggt gcctctcccc tgtgcacggc agtgggcttc   36480
ctacgcgtct ctcctcggca ggtaggacgt taaaggtcca gaaaaaagag cttgttttc    36540 agagacactc aaaagccagg ccaaggctaa gtctccagat caggtcgtgg agggtcctgg   36600
ggtcagccta cctcgacggg ctcctggggg gctgacaggg cctcctgctg tgccagggga   36660
ctcaagggtc cctgcaggtc tccaggggc gctcccacga ggaagttctc cgcatcccac    36720
acaggacctg ggacagcgcg tgtacagtaa ggtgctggtc gcgggccaag gaagagggtg   36780
tccgcgggcc ccaggcaggg ccagacccag gactgagcca cttgtcggta gccccagcc    36840 ccctcccct ctgactgctt catctggtgc aggctcaggt tgggacaaca ggtgctcagc    36900
aaacaccaaa ccgacactga gcagctagga aggagcctgg gtgagagacg ggactgtcct   36960
ggggcagccg ggaaacactg cgtggttggg ggctgggggg ggggcgggg ggcggggggc    37020 gggacagcca tgcggaggag ctcccagggc ggccaggaga cctttcatcg tttagggagg   37080
cagctgtcct ggtccaggac acaaggtgcc ccctagcccc tccggtagcc ccaagcgcac   37140
ctccaggccg gagttcacag acgtagctgt ggggcaccga gcacaggtcc gtgttgcact   37200
```

```
gccccgcggg cccaagccgc acacagcgct cagccgtggc agggtgcggc tccccaggca    37260
gccagttctg gcagctctcc aggctgaagg cctcaccccg cacggcaggg cccgcctcag    37320
cccccctccac agccgagaag ccaatccaca cgtccaggct cctgcaggca gatggtgggg   37380
ggagagggca ctcggggggg gggctctcca aagacacccc tccatctgcc ctgtctctct    37440
gggagcttct tcctcgttcc ctacagcagc ccctcaggtg agaccttgtc cctccccccc    37500
gctttcgaga cgaggaaaaa cgaggctcag aaaaaggacc tggcaagcaa ggcggcggca    37560
atgtccaccc ccacctgccc atggggccag gggcccagct gagggctcct tgccgggaga    37620
ggcctcaatg tggccaaagg ctgcacacac ccacgcttat tccgtgagaa ggctccaggt    37680
gttgcatttg gggagcaaga cgcctgaaca tcagcccccc aaacgctact cctcacagct    37740
ctgacaaggt aggagggccc tcctggagac tgggctgata cacaaggt caggaacggg      37800
gcaaacaatg gcacacggag aggagtgagg tactacagtc agagccaggc actggggccc    37860
ggctaccgcc agttaaccga gtgacccctgg gcaagggccc agaccattct gggcctcgag   37920
ttcctctggt ggacactgag gatgtccagg gtgcgatcca cactgcaatc gacacctccc    37980
caaacaggga ctctgggaga agcaggcgtc cagcccccat tcccttccca gccctggcag    38040
gtgctgagag cagaggcagg ggcgaggcct gctataggag agcacatttc ctcgcgggcc    38100
tgggggacg aaggcatcca agaggttcct tgtgcgtggg tggcctccat ggtcacacca    38160
gaactgtccc tgcccctgcc aggagggggct cggcagggga cagcaggggg tgggcagcac   38220
gtgggacctg tgatgcatcc cctaccctac ccgtacctcc acatctgtgt ctgaaacgct    38280
gatgagatgg tgtcggatga gcagggctcc caggcccac tcaggccggc cggccggcct     38340
tggcccctcc aagcaccccc acctctcctg atcctcctca agacttaggc tctgtctccg    38400
acccagcatt cggggatccc acctcgcagc ctgtctgggg gtgggggcag gtacctggtg   38460
acctgggaga ccaggaagcg ctggacggcg ggactgtcca ccatggccag ggcggccccg    38520
gcccaggcct ggcactgctc ctgtgcctgc agccaggcgg ccttctcggc caccaggcgg    38580
tagcagtgcc cattaccggg gaagatcacg gtgtccgagg ggcagagcgg atgcaccact    38640
ggggagtcag caggcaggga tgggggcatc agtgtgggcc cagccaggac tgccccaccc    38700
attccagccc ctgggggcga gaaggcaccc acctcgacct ggctcctcgc ccaaagacac    38760
aatactgtag gtggcttcca ggccggagcc accacgattt cggacgccaa gcttgagggt    38820
ctcatcactg agtaccgaga ctggacactc gagctccagg gcagcagggg ccgcctccac    38880
ttgcaccttg gccctagct gggccgagcc agccccagg gccagcacgg ctgtcacctg       38940
gtagtggccg gcagggaat agcggtgagt ggtggcagga ccagcaacat ccaccttagg     39000
ggagccgtca ccaaagtccc agtgtgtgga gctgacgggt agggaggcag tgacatggaa    39060
ggctgctggc tggccagagg ccaggggtcc tggaggcccc accagggcgg cccctgggga    39120
ggcagggaag acgttctcaa ggagggtggg gcccccgcag gcagggcga ggggcagcgg    39180
ggggctggag cacaagggta ggcaagccga ggaggcgttg gggggctggg ccgccccgca    39240
caggcaccag ccctggtccg agaggcccc gaggcccag ccagccgcaa agcagaaggc      39300
gccgcaggcc tcgggtgcca gcgggccctc gtgggcagtg agaaggcca ccggcaccac     39360
ggcaccggag ctgttgtccg ggaggcaggc gatgtactcc tcacctggac agagcagaca   39420
gcctggtcct tgtcgggccc cgccttgct gcaccctgc cccagccta ggctggtccc       39480
caggcaggcc ccacccctac ggtgtctgtg cccatccta gacccagat cagtcg          39536
```

-continued

```
<210> SEQ ID NO 28
<211> LENGTH: 16009
<212> TYPE: DNA
<213> ORGANISM: Felis catus
<220> FEATURE:
<223> OTHER INFORMATION: GenBank Accession No. AC145332.28 genomic DNA
      for PKD1 16009 bp contig
<220> FEATURE:
<221> NAME/KEY: modified_base
<222> LOCATION: (1)..(16009)
<223> OTHER INFORMATION: n = g, a, c or t

<400> SEQUENCE: 28
```

| | | | | |
|---|---|---|---|---|
| cctgcccac | cccccctac | acccgcctcc | cagcaccacc | ctcccgcccc | aagagaccca | 60 |
| ccaaggtccc | cccanacgcc | acacccacct | gagcgggatt | gtccccgccc | ctgacccagc | 120 |
| gncacaaacc | cccggcccca | aaagggcccc | agggcccccc | ccaccccccc | ccaaaaaaaa | 180 |
| aaggaccacg | ggacctcggg | ganaaccggg | ccccttgggg | ccctgggag | gggcnncggg | 240 |
| gaccccggc | ccccggggnnn | nttttttggg | ggggccggga | gtaatcctta | cctggaaaga | 300 |
| gcaaaaaacc | tggttctttt | tgggcccccc | cccttttgca | ccctgcccc | caacctaggg | 360 |
| tggttcccag | ggaggcccca | cccctaaggg | ggttggggcc | ccatcctaga | acccagatta | 420 |
| agttggcagc | acccccccc | ccccgcctgg | cactcaccac | cctcccctcc | tcccacctgc | 480 |
| actgctccct | tgaccccga | cctggtctgt | ctcagcagcc | acaattgctg | cccaggtgcc | 540 |
| tctgttccca | gagtcccacc | tgccaccacc | ccccaggccg | gtgaccctgg | aacacctacg | 600 |
| gggtcctagc | cgacagagaa | ggaccgagcg | ggtcacattc | agccatactc | accacagccg | 660 |
| ctgtctgaca | atgggacgcc | gagcaggggc | cggccagcta | gggggccggg | cccggcacac | 720 |
| gtggccgcct | cgggccgaac | cacgcgaacc | tgctgctctt | ccacccagcg | aggcagccac | 780 |
| gccagaccac | aatcacactc | cagtgggttt | ccgctcaggt | ttctgcagga | ggcgcagggc | 840 |
| cgggcgctca | ggagtcggca | gggcagatga | ggggccctcg | aggaagtctg | cactggcctc | 900 |
| gccccaggga | gtggggccg | gggcgtccc | accacccta | tggcagcccg | ccgggccctc | 960 |
| ggagggctcc | agcaggcgag | caaacagccc | tcggggcctg | gtctcaaatg | ggagtgggcc | 1020 |
| cggaggccag | ggcaggacgg | cagggagggt | tactggggc | ctcggggttg | gctaccaaca | 1080 |
| cccaccaaaa | accacaactt | acatttcact | taaattaaat | aaattagcaa | ataatccttc | 1140 |
| ttctaaagta | gaaatcttgt | tgttacttat | gtccctggaa | gaaaggggg | attcagcagt | 1200 |
| gtctgacggg | agccccata | accgaaacgt | tgacaggtag | ccaccacctg | accccccccc | 1260 |
| cccccccgag | agggacact | cacagctctg | tcagtgcgga | gaggttcgcc | aggagcccag | 1320 |
| cgtccagtgc | ccggagcagg | ttgtgggaca | catctctaag | gagcagagcg | gccacaaatc | 1380 |
| agcgccagag | ccccggacag | gatgcgagca | ggtgcaggcc | caggcccagg | cccaccccca | 1440 |
| gaggcttcct | cacagccaca | acttgcagcc | tcccaccccc | cactcactac | acttggggcc | 1500 |
| agggtatggg | atccaaacaa | aggagcagga | gaaggctggg | agcctgagt | gcgccatcca | 1560 |
| caccctgccc | ccaccagtcc | cctgcccct | ggcccagcat | ggcagcccaa | gggtctccag | 1620 |
| ggccaggggc | ctagctgttg | ccggctccag | gaaggagatg | gtctcaaaat | gccctgagac | 1680 |
| acagtggggc | gcaaagaccg | ataaaaggag | gagaccctgg | tggacaaccc | cacagcacag | 1740 |
| caatgccgat | ggaacgcagc | caagcccaag | gctaacagga | ccccagtaag | aacacggtag | 1800 |
| tacacaggtt | caacgggaag | catcactggg | taagaatcac | cacgcaacgt | aggtttatgc | 1860 |
| tatgttacgc | cgagctgcgt | gtgctgggcc | ctccggagac | atattgaccc | tgcaagagtc | 1920 |
| cactcaagga | cacaagatta | acacagacaa | cactagccac | caggagtgag | agactgacct | 1980 |

```
caataaaccc caggaggttc aaaatcaaag gtgacagggg aacgtctcag cagtgaggaa      2040
aaacaaaagc caaaaccaag acccaaagtt aaaggtgaca ctcttctaga accgaacaga      2100
ctgaaagaat acaggaggac gcgacagact cttcacagca cgaaaggaca ggcagaaaaa      2160
acatccacgc cagatgatcc aactacagaa aaacatgcaa cctccacaca gaatatcact      2220
aagatcagaa aacgagctga gaagggcgct agcaacttag acaagggacc aaaggccctg      2280
ctgcccttttg cacacacact gctaatcaac ggtgaggact acagggggaaa aaagacttaa     2340
agaacatgaa atcagtgaga gaaacacaga ggtcagacgg acggaaaaac cgttcccggt      2400
gggtaacaac tggagacacc ccaatggaaa cagcacgata gacttttatc caagttgtga      2460
atgttttcag aaccgtgacc cctggcgctg gcgacgccgg ccccactcct ccaggagagt      2520
caaagccttt caggcaacac gctctgtagc caaagattcc tggctggcct ggggggtggag     2580
gccatggcgg cccctgccca tccacttctt gggacagaga cccacggacc accctgacct      2640
ggtgaacacc tctggtcacc tgctccactg ctcccctcac ccttcttca ggctcacaca       2700
tgtctaagta gaccccggtc acagccttca aagtgatgac acctgggcct cccacccgca      2760
gagcctctgc ccttccagat gtcacctccc gccctctgag gtccccagaa cacctctcac      2820
cagcccctacc cctgccccca gtgacaaccc agttgtgcag aggccaggga tccattgatg     2880
cctcctctca gcctaaccat tcctaggtcc tgccaaccca gctcttaaaa cactcaagac      2940
tcccgcctac cccagccaca gcccagtcca gacaccccat ccccggacac ctgcctggcc     3000
cccacccagc tcgcaatagt caccctctga acgggtcct gctctgcccg gcctgctcca       3060
aatacagcag gaccttagtc agaacacgct ggtgtgaaat caaggtcctc ccaggagccg      3120
aggcactgag tggcagctga gaccaggcct ccatacaaac aggccccccaa aaacacagag    3180
aaagggggaga gtcccgggac cttgcaggct gggatgcctg gagcagtacc cctgcctggc    3240
ttgcaatgcc aggaaccaca tctggaacca ggctgaggaa atgaccccca ccatggcccc     3300
tgacagctgc ttcaccgtgg agacccgctg gccacacagc atctcatggc aaccaacaag    3360
gacctaggaa agggcaggac cagctggagc cctctcacag ggcagcactg ccgcccccccc   3420
cccccaggag ccaggggagc cacagagccc ctcctgtcac ctgtgggggca aaccaggctt   3480
tacagtcaga gagcctggag ccgccaggcg ggggcagccc cctcagggggc aagaaaaatc   3540
caggcgcaaa atgcagcccc tctctctgca actggacaaa cggagatcta aggaagggc    3600
cggaaagggg tgcacagtaa caactcggtc ttttttaagt ttatttattc atcgagagag    3660
agaaagagag acagagaaag aaggggacag agaatcccaa gcaggctctg cgctgtcggc   3720
acagagcccg atgcggaact cgatcccacc aaccatgcga tcatgacctg agctgaatga    3780
agtcaagagg cgggagctta acccgaccgc gctacccaga tgccctggtt aacgtctcaa    3840
tcttgggagc aggcaagtcc ccctaccccc cccccgtttt cccatactca ttctgccctt    3900
gacagacaag aaacggggtg tggagacttc cgtgcagaaa aggacagact gcccaacggg    3960
acctgggatg ggggcttcag aggggagcag acacaagggc gggtggcatg ggggggccagg  4020
agccccaccg aagagcaggt tgggtcacca aggcctcctc caccctgagg aggtgtactg    4080
tgactgacaa tgggctcaag gccagagccc tgccgtccc agcaaggtgc cccagatgag     4140
gcactggcct tagcgagcct ctcggtttcc cacgggccgg aggagaaaac tccgtgtgtg    4200
cacgggcgcg cgcgcacacg cgcacgcatg catgcatgcg cgcgcgcgcg cgcgcgcaca    4260
cgcacacgcg cgcacacaca cacacacaca cacacacaca cacacacaca cacacacaca    4320
```

```
cacacacctg ctcgtgtagg tcccaggaac tccaagactg gagaggcctg accctgccag    4380
gtggttccca ggatgggctg ggcaggctgg gaggccaggg agacacagcc ggcctcacac    4440
ccactgctca actacgacgt cctgcagtgg caatggctgt gccatgagaa acttccgtga    4500
gacctacgga cggaccccg  gatgtctgga ctgaggctgg caggggggcct gggcctctga   4560 gggacaatca ggctgccgcg gcatgagaac caacagtccc aggagagaga cgatccagac    4620
agatgcgacc tagggatggt ggtgcacggg gtgagagtcc caggagagct tcccagcttg    4680
ggtctcaagc acaagaggaa agaaagaagg aaaatcccta aaatgttttt ccacatcccg    4740
ttttctggaa aatccatcat gagtggcagc tgctgggagc cgcctgtggt gcctgagaaa    4800
ccagggcagc gggtgggagg ggcaggtcga gccccgggcc caggccactc agccagcacc    4860
caccctggcc tgtcagggca ccactgtccc tggcctcatt ggcctgtggc tccaggccat    4920
cctcggccca gttaagtcct ccatccagct ctgcctggcc tagcgcgccc cactgaggct    4980
cccttccccc acatgcggaa ggccccaccg tcatggtcac acagtcacgg gcactggcca    5040
cgtgctcctt gccttccagg ccccagctga gccccttccc ccacccccagc actcacctgg   5100 gccgagcctg gccacagtg  cacagaaaac accagcagtc tcccccggga ccctgctggc    5160
caaggtccca taccctaagg gcagaaccag gacaggagcc aggtgccaca ccaaaggtcc    5220
tgagccccag cccccagcct gcccagatgt gggagcatct gcgtggggca ggccacaatg    5280
accgtatgca ctggcaggga tgggaagagc agaagggacc ctgaggggga gccctggggg    5340
gacgccagaa ggaggaaact gaaggaacc  cacagaccca aggtcccaaa cagccacttg    5400
tccacatttc catctgttct tgccatcact gctctggggg aacaccaagg aggcctcaca    5460
ccagccctgc tccaaccccc cagccgctag gacttccgct gcagccccca ggtgacatca    5520
tcacagtctg acaccctgcc cctacaccgg ggtcctgcaa tgcaaggggg agacacagca    5580
cgcccaggga gcctctgccg caggggccca gcacagccaa gcacagcagt gtccggcccc    5640
tcctgggagg agggccagta gcctggccgg acagcaccct taagaggtcc tggggcaaag    5700
agggcccacc ctctgggcca gctagacact ccccggcccc tccgaggccc acacaaacaa    5760
cctccaggga ccccaaggcc caggctgcag gggtcaggcc agcttaggga ggaggtgggt    5820
gacctgggga cacacacacc accaggggggc aggcacacat ccgtgacagc acaagacaca   5880
tttcacctcc ccaggcacca gggatcaggc cgggaggctg gccttccttc tcctccccca    5940
aagtcaccca gcagtcaccg gggagcccag tctgtccccc tgtgccgggg tggtcctgac    6000
tccccccgct ttccagacca acattctct  cgggccttgg ggttcaggca tccaaccgca    6060
tgtccctgta tgtctggggtc tgatctttcc tgctcaaagc agaagcctag tggagggatc   6120
cctgcttcga ctacggagct ggaagtgccg gcaaacgctg ttgaaggacc ccatcccatg    6180
agccccggca gctcccctgt gccgtctgca cacaaggctc agcacttacg acccgcccct    6240
gctcacatcc caggccgggg agggcaggc  ggggcaggga gagatcagaa ggggctgcac    6300
tggtaaagtg gagtgggtca gggtgtgtga aggtggaagc ctgaggatag gatggccaca    6360
gtcagcacgt cctgagagtt cctgagtctg ggggtctcc  cagagcagtc cccttctaga    6420
gtggaggagc cagaggcccg ggataagctg ggaccctgtc ccacagccct gagcagcctc    6480
agtttcctcc tctgccaaag agaggagtgg ccctgtgcc  cgctcccag tccagatgct     6540 gggcggggtc tggggccag  ccggagcccc caaggaaaca tctgcacatt ccagacgcat    6600
gtggtcagcg gcggggtga  gtgccaggcc ccagcctgtc accccaccc  ctgcgctggc    6660 cgccgcactg gaaacagggc ttggggggggg gggggggaa  tgagctctgg agggggcctct  6720
```

```
gcagaggtta tgtaacccac tccttgcgag ccagcagctg cctcctccct ctggcaggac    6780
aggacggcct tgctggaggg ggagaaggta ccccactccc catccaacgc ccagggtcc     6840 gtgctcctcc ctccatccct cacaggcctc tggaaacat agcctgggct ggcctgtcct    6900
ctccccggag gccccacagg tctcatcagc ccagcaagga agaacccgc atgccccct     6960 cccgccctca ggagccaggc ccaggcacaa ggggagaggc cagagtgctg acctgggcc    7020 cccccgccc cccccccc cgcctcacta gcagcattgg gggcaggcgg ctgggagccc      7080
agcacccgag ccagtttgag tgtaataacc tcattctgtt ttcattccat ctatttatgg   7140
tgagcaaggc tggcttccag gaccggaaat gatgatgttt aaattaatga attcaagttt   7200
aggaaggagc ggatttgaag acaaacatgc cgagtgggcc cgcgggggag gggcaggagc   7260
aggctctccg gggagaaggg acaggaggg cccctccggc ccagggcat cagcaagggg     7320 ctatctcagc caccaaggtg aggaggaaag gcctgccgag ggaaccttcc agatccagga   7380
agtggcccac atttctcagc atcttttggg gcccctcac ccaggctctg cctcccaca    7440 agtggaccct caccaggaca ggacacgggt atctggggtg gtgatgctgc tggcctagga   7500
agccctggga ccacaggctg ggctggggca tgggggcggg ggcggggggg gcctctgacc   7560
tgcagaaagg agatgaaggt atgggtgtc ccccacacta ggagggaaag acatcctctg    7620
gaggagaggt gttccaagtt caattcacca gaggtagcca ccttcagggg attaacaagg   7680
cagggctgcg caggagaggg tccagcttgc cctccaccc acagctggga atttgggcaa    7740
ggggaggaaa ggaccagtaa agtgggggggg gggggcagc cttcctccag atctggcacc   7800
gtgcctgggt accacatcca gacctgtcac agccagccag gagcacacac catcccctcc   7860
cgcaggtggt agtgctgggg ctctggagg ccaccctcct caccatcacg cccaccatca    7920
cctcccagag tcggaagacc ggacaagaac agccaggctc ctccccattc tggctgggga   7980
gctggcatgt ggcctctggc cttccaggga cacagacatc acccactcgg ctcctgggca   8040
cagacgaccg tgccaaccag cctgacagca gggttacaga gcagtgcgaa ggcaccagaa   8100
cctggaggct gccagcgctg ttagccttgc cctgagcact ggccctcgtc ccctgcttaa   8160
accagcagga aaagctggct tctggccctg cctcaggaca aagccccttc cagggtggcc   8220
cccagcaccc tggagcgagc tccgtgcctt cagggcccgg ggggctgcta aagccggagc   8280
caccacactt gtccaggccg ggcccacag cacctcaggg agagaaagag ccctgcccac    8340
cttggccaca gatgcagccc cctccctggc acgggcggct gggcaccacc gggccccttg   8400
gcggagacgg ctgccaagcc acagagaacg aggtgttccg ggaaaaaagg acgtgagctg   8460
cattttccag ctgcgttttg ttcggcagca agactgcagg cacgctcggc cggcgccccc   8520
gctgcacgcg gcccaccccg tggacacagc cccgccttgg ccggctggag acacacaggc   8580
acccaactcg gagggccagg ccccagtgtg cccggggcca gacggccgcc gcaccccag    8640 acagcggcag gacacacggg gtgttttcat tccagagtgc tcagcgggct ggaccgtcct   8700
gggttcccac tgctggcgct ggccactgca gagtgttccg gaaaggaaaa tgtgcatctc   8760
catccaaaat ggcttcctta ctcgacacca aagcccagcc agggtctccc tcgagagcca   8820
gggtctcaag agccgtgggg gaaacacaag tggtgggaga agtaccccc ccccagtccc    8880 aggggtagcc cgtgggggca ggacccacgt cccgcagggc cacccagcca gctgtgatag   8940
gacagtggcc agagactcac tgctcaggc caaggcagag cgagagagag aggaggagga    9000 ggaggccct acaggagacg acactctggt ctcggggggag aatcacaaga tgagcctgca   9060
```

```
gggaagcagg aaagggaacc cgagtctcac caacaccggg cacctacact gctagcccaa    9120
gggagatcac aaggctgtgc catgtgcgtg accacaggca agcagcagga gggtgccaag    9180
cggctctcgt ggccctggat ctcaatggcg ccacatcatc ccaggtcaca gaacaaggtg    9240
accacgagaa ttcacacatt ctgtttatac ctccaagctt ccaagtgtca cgaatctgta    9300
ctcgaatgca tcaaaaacac aaacgcataa aactgagatc cacacaccag aggagtgcac    9360
caggcctcac gaatccacgc acaccaggcg tccctgcggt gggtgctgag ggtgtgcaag    9420
ggtgcgcctg ctggggctcc cttgtgcctg cctcatcggc cgtggggtct gagcaatgtg    9480
ctcagatctg agtcaccagc acatgtgctc cgggggtcct ctcctcgggc ttttgtctgt    9540
cagcgggcgg gtcccaagga cccactttcc ggcagccagt gcttgaggac aaagtaacag    9600
gctccaagaa catgggggaa tagaacccag ggccacttgg gcaacagtta cgatcactgt    9660
ggcctcagca ccgagccttg tggacgagcc cacaacccca ggagggcatc cattcaaggt    9720
gcctgccttg caggtgtgga cactacagct caggaaggct gagtgactca gccaaggtca    9780
cgcagaaaat gggggagctg gggggcgcct gggtggctta gtcggttaag cgtccgactt    9840
cagctcaggt catgatctcg cggtctgtga attcaagccc cacatcgggc tcggtgctga    9900
cagctcagag cctggagcct ggagcctgtt ttggattctg tgtctccctc tctctctctg    9960
accctccccc gttcatgttc tctctctgtc tcaaaaataa ataaatgtta aaaaaaagaa   10020
aatgggggag ctgggacatg acccaggtct gacttagggc cagagtcccg actcctgggt   10080
ccccacgctt ccctcctaga accaggcagg aagttagcgg gaagaaccac agtgtggatg   10140
gccaagtgaa gtccaaggag ggagttgggc ccaagggctg cgcagggcag ggccgagcag   10200
gcagctgagc ccagatccca cccagtccct ctcaatccca ctcaaagatg tccccactgc   10260
cacctcgtcg aaccaggccc ccgtgcgcag ctccagggct ctgctccaga acgtgctgac   10320
aaaatcactt ctctgccaca actccccagc catgtgacct gaggaagtga ctccacctcg   10380
ggaagcctca gtttcccagt ctgtgaaacg catcaagtgt ggttccaacc ccacagcact   10440
atggcaaggc actgagagat caaggacaga aaaggcttag caaggagccc agaacatggc   10500
aacacagagg gagaggacga gacagtggtg gggagtgggg gtgacacccc ccccccgctc   10560
ttttcttcag agatttgttt tttaattcgg atgtaattca catgctctga ggttcaccgt   10620
tgtgaagtat acaattcagt ggttttttagc atcttctcag ggttgtgcaa ccatcaccac   10680
tgtgtgattc cacaacattc tcatcacccc aaacagaaac cccacgctcc ttggccgtca   10740
tctccaaacc ccatccccca ccccagctgg agaaaacact aatctgcttt ctggctccgt   10800
ggatttgcct gttctggaca tttcctaccg gtgaaatcat tcaacacggg gcctctagtc   10860
tggcttcctt caccgaacat gttttcaagg cgcatccagg atgttgcagg tgccagcgct   10920
ttgttccttt tgatggccga gtggtactcc accgtgtgga cggaccacat tccgtggatc   10980
tgctcgtctg ctgccagaca ctggggctgt tccacgtctc tgctaccgt gggtagttta    11040 tgggtagaca cgggtttcag ttctcttgaa cagacaccca ggagcagaaa agctggctcc   11100
taccgtggct ccacatttaa tctttccagg agctggcaga tggctctccg atgtgccgct   11160
ccgttttacg cccgcccgtg gtgcgtgagg gttccagttt ctgcacgtcc tcaccaacac   11220
gtgctatgac ccgtctttgg tgatagacct ctcactgcag tttgatctgg gttcccttga   11280
aagccggatg ctgagcatct tttcacatgc tcactggtca cccgcgtctt tattggagac   11340
aacgtctgtt cagatccttc acccatttc acttgggccg tgtatctcgt cagcatcgac   11400
cgtgtgtaag acgcccttcg tttacgttct ggccgcaggc gcccatcaca gaaacggcct   11460
```

-continued

```
gcacatgctc gcccctgcag gtgggcccat cccccgccct cacggctccc gggcgccgct    11520
gggctcccga gggttggctg ctggcgctgt gggcgtgccg gtgtcggtcc cttctcgtac    11580
ccaagtgtgc acacgcagcc aaggcctccc cactcgccct cccgcccggt tgggggccaa    11640
ccgcacccag aagctgacag gtgccctcct gtccacagct ctggcaactc agccttccgt    11700
gtcccactgg gaaaccaccg ctacacgtgc gtttctctct gatttccaag tgcaggccgg    11760
acacaccgtg cagctcgggg atcgtgaggg gagagcagct gggcacgcgg gaggcgccaa    11820
tcctcccgag acccatctcc acgcagcagc cagtgttccc tgccacttct atccgggacc    11880
tttcaatgcc accctccccg cctgcttctc ccatgcctcc gtcacctcga gcctcagaga    11940
cccctccagg ctgtcccccgt ctggcacgca ctccctcaga ccttgcagcg tcacctacgc    12000
cgggggtccg tccaggcagc gcctccaaag cagcccactc cccgcatctg tgtcttcagt    12060
ttaacatgga cttgaccgta ataaccgagc ctcacagact ctaggcacgg ggcgcagcac    12120
acagcagcca ggctctccgt ctgatgacga gggctcaggg aggggaccct ctgtggccag    12180
gccagtcctc aaggcagcaa cacacgcggc acgtacagcc ggacacgtta cgcacacaac    12240
gggcccaacg gccacagatg ccacctcccc tcacgcccgt gtgccacgca gatgctgggg    12300
gcccagcctc cccggtctcc ctcgctccct cctgtcattt aggggcgagg ccctaagtac    12360
ccccaggtga caaaagaccc taaggtcctg atatttccct ccacgaacca agtccccacc    12420
gagttcctgc tccaaaccta gtcctacaga ccaccgacgg aaaccaacag cacacatccc    12480
gagaaggggg tggccgacaa cagccaggca cacgtgacac tgatcgacag accacagctg    12540
gaggagcacc atcacatcca gacctctctc ctgtgaccaa cattctacct ccgtgctgtc    12600
ctgtgccacg cagtagccac tggccacaag ggcctccagg gtacctgaaa catggcttgc    12660
cacacaacac agctctggac tgtcaaacta caggaaacgg agggcagcgg gacaaaccag    12720
atgtcgccat ggtgacggca gaggtgcagt tcaagcccag accccagtcg gggccgcttt    12780
caacaagcag catgaggaag gaaagagatg tgggaaaacg gatacctcgt cagaagacag    12840
agcacagtaa ttgcactgtg tggaccgtat ctggatccta attcaaagta ctcaaaaaac    12900
agagacaatc caaaacctaa acacactgga cacatactga gatcagggaa tcacccactg    12960
tcttagggga gaccacggtg tggccatcca ctccaaaatg cttatacatc aaagaacgag    13020
agagctggaa tttggttcaa aaacggaggt gggagtgtgg agggcagggc agagggcaac    13080
aggtccatga ggttcagcac aaaactttgc ctacttctgt gcatgttcca atggtacacg    13140
atgaagcttt aaaaacagca gcccttttgct agtgacgtca tctctctcag gccacctaac    13200
cagcagcacc atctcaccca ggaaaggctc agtttcagaa gcccaggcca tcctgcatgc    13260
tgaggccccg agtcccctgt gggccagcct tggtccctat acccgtctgg ccctggggca    13320
cctcaagcta tacgaggagt ctcatggagg ggtggccacg ggactgatga cacaggtacc    13380
aggcctgaac cgctggcggc acccagaaag cagggctgct ggggcccctg gcaacgcac    13440
acccttaccc agcaggctcc ctgccctctc tgagcttggt ccctctccct tggagaggag    13500
aagactccat ctccctctcc ctgagcacag ggcttgcagg gttgacaggc tgctggggca    13560
gccgacagag cccagatggt ggtctgggga accagtgggg agcccgatct ccctcagttc    13620
ctggccccca gcctccagaa atctcccaga ggcagcttcg gggtgtaaag acagtgtgg    13680
ggtatcctct gatccccatc tacctacttc tcagggtccc atcgcaagct cagcgggtcc    13740
agcaacctgg gaatcctgtc ctgtcaggct gggccagccc gccagttccc aagaccagag    13800
```

```
cctaagggga cacacacgaa gcaacagtcc tgggctccat cactgtgctc aagaggctcc    13860
agagcctgcg ccccgctgca ggccccccag tgacccacct ctacagttga tttcctgcac    13920
agctcctgga ggccagctca gcaccaggtg ctggggaagc aggggaacca gagaagagcc    13980
agaaggagcc aggcctgacc tcagcagctc ccagccaacc agagatgggt aacttcactc    14040
acagcatcca gaagcaggtg gggtgcatcg gaagcgatta tacagggggct ggtgcaggcg    14100 acacgcccat ctcccacctc agagacagct gggatggcaa cttaggctta agtgatcagg    14160
tggctgagcg acaggctccc acctgacccct ggagaacccc caattccacc cgacaaagcc    14220
ccaaggacat ccagaccacc caggagaagt accctacttc acccacctac ccaccaacat    14280
ccaaactcat ctcaacactg gccacgggtc cctaattaa aggggcccac acactggagg    14340
cgcccaggga atgttacaga accaaattcc aggacccatc cccggggtgg gatggtctga    14400
ggacactaaa tgctccccag aggattccag catgtggcca aagacagaca ggactcccag    14460
ctcaggtgcc tgaaagtgcc caagaaatcc acacagggcc acaggaatgc ggatcagcag    14520
gccccgaacc tgtcccctag ccagggaaca acggtctgca aatcctggtc ccctgcaccc    14580
tccccattcc aactctgggt ccggagcacc tcaggcaaac tgggccctgc catgtgctgg    14640
ccgctacttg ttcttgggca aatcacacca tccgagtcca agtggaaacc tgacaatagc    14700
tcttcagcat tttaaaccag tcctggcaac tccacctacc cattgtcccc aggataacat    14760
cggagcccta gacgcgaagg gcataaggcc cattaagagc gcagcccacc tctcgtcctg    14820
ccccactctc tcaaaatgcc cctgcagttg ccacagtggg gtgtaccccta cacccacaca    14880 tggccaaatg cagcctccaa gccttgcaca caccgctccc tcctcccgc ctcccgcagc    14940 ctccagactc ctccttcagc atcaggccaa ttcttacaca tccttcaaat ctctgtccag    15000
acacctcttc caggaagcct ggcccgccat cccagacaga gctctctccc tcccggtttc    15060
ctgctgcaga ggtcccaggt gcagagcgtt ccccccaggc tgccttctat tagcctctaa    15120
ttagcgtcta acagtttgcg ggttcccttc agacgcctcc cacgcagccc ccgcgcgctg    15180
ccgcgggttc cccccttaact cgcgattgcg gagccccacc aggtgggata cttctgcttt    15240
cagagaaacc gggatgtttc tgctgcgccc tggcccaggc caggggggct gaggaccggc    15300
cgcggtcccg ggtactcctt atttagtcgg gccgacctca ctgcgtttgg agcctcgccc    15360
tgggagaggc ctgcccgca ctgcgtttcc ccttcagagg ccggggacgc gcccacgccc    15420
tgcgaggccc gccaggccgg cggcctgccc ggccccggcct ctccccggag ccgagggtgc    15480
aggcgcgccg gggccgcccc acgccccggg cgccccgat tccggcgcc cgccggcgc    15540 catggcaacc gccggcccg cggcgcaggg cggctgatta ctcacagcgc ggtggcgtcg    15600 gggggatgc gcagcgcggg tccgagcgtc cgtagtccgc ggccggagca gttaacgcgg    15660
caggcggcgc cgggcgccgg gccgaagagg cagggcgggg cgcacggccc gaagccgcgc    15720
ccggggcccc ccgccagcgc cccgagccag aggcccaggc caggacgag cgccaggcgg    15780 gcgggcgcgg cgggcgtcat catcagggca gcgcgctcat ggccccggcc cggccccgaa    15840
gccccgaccc cgcccggggn cnggggggccg tgtctcaggc ggggcccgta tactgaatgg    15900
cggggcgcgg tgacaatatc cgacgggcgc catgttctgt tttgcttcca cgaccccgt    15960 tcggggcctg ggccccggcc attattctag gttcaggggc gggggttc                 16009
```

<210> SEQ ID NO 29
<211> LENGTH: 9973
<212> TYPE: DNA
<213> ORGANISM: Felis catus

```
<220> FEATURE:
<223> OTHER INFORMATION: GenBank Accession No. AC145332.28 genomic DNA
      for PKD1 9973 bp contig
<220> FEATURE:
<221> NAME/KEY: modified_base
<222> LOCATION: (1)..(9973)
<223> OTHER INFORMATION: n = g, a, c or t

<400> SEQUENCE: 29
cggcatcgtc agggcagcgc gcgcatggcc ccggcccggc cccgagcccc cgagcccgcc      60
cggcgccggc ggccgcggct caggcggggc ccgcggactg catggcgggg cgcggggcgg     120
gatccgacgg cggccacggc ctgtctgcct gcgcgacgcc cgctcggcgc tcgggcccgg     180
ccgcactcta cgtccacggc cggccggtcg cgcgctcgcg ctgcagtgcg ggcccgccgc     240
cgctcctcct ccagctcctg gcgcggcgcg gggcgggcgg gggcggggcg tcctcaggcc     300
ccgcccttcg ctctgcaggg cggccgcgcg ctcggagggt aggcggggcg tggcgcggcc     360
gcgcgcactc ctccctcggg agcggcgcgg gtggggcttc ggcacggctg ccctcgcgtg     420
ccctccagcc tcggttcccc gcctccgggg cgcccgcag  ccttcgcgg tggcgagcgt      480 cgccgcagta cgaacaccag cggtggtaac ccccgcggcc cgcgaccttt gagcgcccgc     540
tgcgtgcgct cgcccactcc cagcgcctct gtccctttcc gtctcggccg tattccgagc     600
tcctggcccg gggtagggc ccagtaaata cgcaccgcgt cctctcttgg cgctcctcca     660
gagggccggc gacgtgtggc ggctagtccc cgctgtcaca gaggtgacgc cccaggtggg     720
cctcagctgg gcgggggagg cgcagcgtcc cagccgccgc ccgccgggcg gagggcagga     780
ggcctcgctc tgcagccggg ggcacccgcg tcctaccaaa tctaaaagaa aagtggattt     840
gtggctctcg gggctgggga gcctggaatg gggagtgact gctcatgggt gtggggtttc     900
ctcctgggat gaggaggacg ttctctggaa ttaggtagtg gcgatggttg cacagccttg     960
taaacacact aaaaatcact gaattgtgct cttaaaagga tggattttac gttgtctcaa    1020 cttttcagtga agaagtaata aaattgttcc accatcgggc catcgtgggt ccctgactgt    1080
aggtagcaga gcggtcacag ggagaagtcc ccagaccctc acatgggcga ggtccctgtc    1140
ccactatcct gagaccaggt ggcagactgc atcccaaggc ttccggactt cctgtcctct    1200 gtcccctgc tgaaaatagc tggaaacctc aaccagatcc acaagtctgg gtctatgtcc     1260
tgctacctgt cactggaaga gcccaagcaa ggtcaccatg gggcgcactg cagctctgct    1320
tcccctcccc cccagcatga cgtggcatcc aaacccctca ctctcctcat ctgtgtaatg    1380
gaaatagcat ttagggctgt ttcagggctg ggggaagatc acatccagcc cagagccagc    1440
tctcaggaaa gatcccaggg tgaacaggtg gggaccccat gaggcagagg ccagggatga    1500
acagggaaca ggtagtctgc catgtcctgg aggtcacatg actcaggaac aggcagagga    1560
tctccaggtg tccagggtgg aggaaggcgg ccgatagtcc agctctggca gctgtggccc    1620
gttctcaggg ctcaactctc caatttggag cctcttggac caattcccta cagggtacgg    1680
agaaggactt aagttagaca ggaggggaa tagggaggga ctgttgagcc cgcgagcctc     1740
ttgggcctca cgaacacttt tatacagagt cacagaggga gtgcttggga acccagtttg    1800
gaaaacactg atatgagggt ctaagccaag gtagggttga tggggtgacg caggagccct    1860
ggggagggaa ggagaggct cagatggtac cttatctggg gctgggatg ggtgggcatg     1920 acctcaggga ggagggatgt ggagggaaag gtgaggagta ggttctggac acgtggtgcc    1980
ctaggccact ggagaaggtg cccagagtgc aacttaaagg gggggggtga gactgggagg    2040
ggagggtgag cagacctggg gcagatgaaa atccccagat gtggggagcc ccaccctaga    2100
```

```
ggaggagggg aaagaaggtt tggagggagt ctgacgagaa tgccccagag aagtagtgga    2160
aaacaggtac ggtgtatgga agttgaggga aaggctacag ggaggaagcc agcagggggct   2220 cgggttgcag aacagagca agggcttggg ggtggtgcag ccacgcatgc ccccttggcc     2280
cacccacact gcacagaacc acatgtaccc cccccttgg ggcttccagc actgtctaca    2340
gcctcccgcc tcttagccct tccccacgtt gttccctttg cccgcagtgc ttttccatcc    2400
cacctccacg attacttacg ctcgcagaat cagcagaggt acctcctcta agaagcttcc   2460
tcggccccta tgtcatgtgc caattggcat cacgcactcg ggggacgcgt atttatgagc   2520
tacctattgc gggcagatat ctattgcgga cagcacagag cctgcttggg attctctctc    2580
cccctctttc tctgccccctc ccctgctcat gctctctctc tcaaaataaa taataaaac    2640 ttaaaatgat ttttttaatt aaaaagaaa ggtatggggc gcctgggtgg cgcagtcggt    2700
taagcgtccg acttcagcca ggtcacgatc tcgcggtccg tgagttcgag ccccgcgtcg   2760
ggctctgggc tgatggctcg gagcctggag cctgtttccg attctgtgtc tccctctctc    2820
tctgcccctc ccccgttcat gctctgtctc tctctgtccc aaaataaat aaacgttgaa    2880 aaaaaaaaaa aagctttaaa aaaagaaagg taaatgtaga agcgacagat tccttctttg   2940
tattaattgc agtcatggtt ccatgggtgt atacatatgt aaaaacttac gaaattgtac   3000
attttctttt tcaaggttta tttatttaca taatctcgac acccaaggtg gggctcgaac    3060
tcacagccct gagactgagt cgcgtgctct actggctgag ccagccaggt gccctaagag    3120
tacaaattac cttagaagaa agagtagaat ggatcaataa acaaacaga gctattttta   3180 atgtataaag ccactgagat ttttaaaaag agtctgctgg caagtgtgac tgcaagagag   3240
ataaaaacaa aatacagagc attaaggtta agaacacagg attattcaca gaaatagaag    3300
taaaaattat aaaagaaata tatgtgcaat tgctcataaa cttttgaaat ctcgatagga    3360
tcattatatg ctagaacaag acaaacgatt aaaactgact caagaagaaa taaaaagttc   3420
aaatagacca atcataaagg aagaaatcga aaatgtagca gagccatggg gtaggggagg   3480
ggagaagacg cttaatccag atctgtttat gggaagattc catcaaatgt ggacagatca   3540
gatatgcgat ctgatgtgat tttttttta aatttttttt tcagtgtttt ttatttattt    3600
ttgggacaga gagagacaga gcatgaacgg ggagggggca gagagagagg gagacacaga   3660
atcggaaaca ggctccaggc tccgagccat cagcccagag cccgacgcgg ggctcgaact    3720 cacgaccgc gagatcgtga cctggctgaa gtcggacgct taaccgactg cgccacccag   3780
gcgccccgcg atctgatgtg attttatgtg tactcttaga ggacgtgggc acatcccaat   3840
aaatttaatg catattatg tgtaatgcaa cgtattcggt atagcataat ttgtatgcct    3900
aaacaaactg gattaagata gtacagaaaa aggaatccgt tgtccggtga ttttcagctc   3960
tgtgtcaacc acagaaccct tgtttcacac aaagccgcaa actacaaaac gtggacggtg   4020
ctgagggagc tgagcagtgg atcccagaga gatgcgggtc ctggtgctca gagcctgtga    4080
acggggcctc acctggcaaa agagaccctcg aagctgtgct tgagttaagg gtcttaagat    4140
gaagggttgt cctggattag ccagagggg cctaaatgtg atcacaacgg tccctgtgat   4200
gggagatttg atggcagtag gaaggccggg cggctctggg aaggggagct ggaagaaggt    4260
ggccacgagc caaggagagc gagctgaaga ggcaaggatc ctccccagaa gaacccagac   4320
ttgctttagc tccctgagcc ccgtcagctt cggatctcca ttcaccgtgg cctcccaagc    4380
agaatataac aaatttgagc tgttttgtgg tggtaccacg tttccctgct atagatcttt    4440
```

```
gttacctctc ctacattttt gtgggagact gataggggtcg ccactgccag acctaataac    4500
ggtttgggga gaacgagcac tttttattct tttttttttt tccttaattt tttaatgtta    4560
attttttttat agagacagag cgtgaacggg ggaggggcag agagagaggg agacacagaa   4620
tacgaagcag gctccagggt ctgagctggc agcacagagc ccgacgcggg gctcgaactc    4680
acggaccgcg agatcatgac ccgagccgaa gtgggacagc caaccaactg agccacccgg    4740
gcgctccaag cacttttatt tctcgtgggc ggaagtcaca gatcactttc ataattaagg    4800
agaaaaggag agacaaggcg agtgcatcac tggcccacac caggcgcagc cggtgctcgg    4860
actgctgccg ttgtcaaggc tacacaggta tccgttttat tcctttatac ctctgcctcc    4920
gagcacagca ctcaaaggtt gcccggagag cctggagtgg ggggctgtcc tgtgctcctc    4980
cagacagagg tctcaccggc ccggggcctg agtgcagagt cggaccgagc agcagcccgc    5040
ggggctcagg cccatttttgc atcctgagac ggaccgccaa gagcactcag gtctgagtac    5100
ctgagccacg gggggaaggg atggcagagg gcagtcaggc ttgcagggag accgcccact    5160
gctccagccc tcacacaata gtccctgccc caacgggcgg acacccaccc cttaccacct    5220
gtcctgtccg ggagggcctg ggtgcaaccc aggtgagagc cgagtgccgc aggcggggtg    5280
tctcctctca gcctcgcggg agcaggaggg agcagggggct cagcgtggcc cctgtgcacc    5340
ttggcactgg ggggagggggg cgagcacacc tctgacatca gccgcttcct ggggtgactc    5400
tctcttctgt cttctgggg gagctgctac agttcctctc tgccgtctcc atggcaacac      5460
tcacgtggat ttcatagagc ataaggtgtt tgagctggaa gggacctcag agatcagctc     5520
ctctcgcccc ctcattccag gcagagggggc gcaggttcag gacaccacgt gccccggggc    5580
ccgcagccag ccagggatcc gggggcctctg ccttctggca ccatcccag ccagggtccc     5640
ctccctgaga tcacaggcag ctcagttccc taggactcac ttctggggag gggctctggg    5700
gacatgagac ttggggagtg ctgcgactcc tccccccccc ccccccact gaatacaaga     5760
cccctgaggt ccagtccagc cctgtcctgc tcagtcacag acctgttcat tgagtgcttg    5820
gtggagacag gacgggtgcc gtcctcagga agctcagagg ctggtgcgga ggccctgcag    5880
cctcctgagg gacccgtggg gagcaaatgt gtgtccacag cgtgtctgta gagcaaggag    5940
tgggggtggg aggagcctgg aaggctgcct gcctggagga gggggctcca agcagtgcct    6000
ggaaggacga ggaagactgc ctggctccag gaccatggcc ccgtgggtca gcagaatgtg    6060
tcggtaaggc tggccggctt ggaaaatggg gctccagaga gggatcgcct caggccgtag    6120
gtcccagaga gttgttgtgt ctgggtactc atggcacacg tcactccatg acagagggtc    6180
tgtcatggc aagtcagagg gcagcatgcc cggagctgga ggcccaggca caagaaggca    6240
tcaggaaccc aggccgccac agggtgctgg agggaggatc caggagtgag gcgggaacat    6300
atctgggatt gctctctccc tttgctgaga cacagatatg tgtccaccct ctctggccag    6360
cagaaccagc cccctgcgag gagggttagg cccacaggca cccttccttc actccgcact    6420
ctagctcagc ctcagcactc acctcagcgc cacaccctgc ctcagggacc tgccctggag    6480
gcccagaggt cttctttgca ggcctgaaga tcccaacagt ctgggcttcc caaagtccgg    6540
tcaaggccag cctgctgacc tttcccacca aactggcccc cttccttccc ctggctggca    6600
gcctgttcta gttatctatt tctgtggaac aaaaatcccc caaatgcagt ttgggcaggg    6660
ctcagtgggg tcagctcatc cctgctccgc atggaaccca ccagaactaa gcgcccgttg    6720
ccaggacaac tcctgtcctc cacgggcgga aagtgagttc ctttccaccc gggattcttc    6780
acaaggctgc ttggactttc tcacggtatg tcaggtgggg cccaagaatg agtgtttcag    6840
```

```
gagaagggat gtaggagctg ctagtctgga aggtctgggt ccagaaacgg acacagggcc      6900
acttcagcca taagtactgg tcagagcaat cacagaccca aaggcaggag accgaggcct      6960
tccctcctga tcgggagggg tggcagagaa gtcgcccctt agtgtacctc agcgctgtgc      7020
tgcctctgcc ccaggggctg attccccca ccctgggttc ctgccacccc tttccacctc       7080
atctccccat ctacaggcgg caccctgcac ccctccact ttacctcctg taccctgta        7140 gcaaagtcct ctgttggctt tgctcagcaa ctgtgcatgg ctccctactt ctcgccgaac      7200
aatttccaag cccctaggct gaactttcac attcacttgc gaatctagcc ccctcctgtg      7260
ttaccgatga gattttctgc aagcatcagg acacgacact gtggcctcct ctccaaaagc      7320
ccacccactg gcactctgag cttatacgta ttcactcctc tacctggcaa gtttctctgt      7380
gtcctctcct gctggactcc cgttcaacct tctgagcctg agcaaatgc ccctcctcca       7440 caaggccctg ctctcactac tcggtaacgc tagtcctgcc tcactgcaca cggacgtacc      7500
ttctgcctta aatccttgct ggcaatgacg tgtcctcctg aagtgggggcc cgtttctaac    7560 tcatatttct ttcacgaatt taataatagt ttattgaggc ctggagccag ctgccgggaa     7620
tatggcagtg accaagacaa gctgcttcct gtacccagag aacttcattc cggggaatga     7680
gacagatggc gaacagagga accaagggac ataatgatca aagattagga ggactgctgg     7740
aaggcaggag cggcaggagg gatgctgtgg tccagggacc tcgaactctc tcttcaaaac     7800
aaaccggaga cctgggtttt tacatacaca tactctgatt ctaaaggtta caaggtcaag     7860 ttttttcccctt ctgctgcttt cagcttcccg cccatcctgg ccccccagtc tctccgaagt   7920
gtctgctacc ttccctcttc ccattacccc attagcatta gccccaccct cgactcaggc     7980
tgccttacct acagccccca ccctcgggc accccagact cctttctggt cgccctggat      8040
cctgggctta gtgggcactg gctgagaccc tggggcggct accctgaagt tggcctcatg     8100
gagggtaggt cacctggaat ccccagggcc ccagcagtgg gagctccaca ttcccacccc     8160 aagcccccact gcccacacat ctgcattggc ctggaagaag aggagtgaga caagagagta    8220
ggccctcaga gggcttcctc aggcttgtcc ccccggctct gccagggccc tgagggatgg     8280
gtctccagag aatcctgggc caaccctgcc aagggcagt gtatgttctc cggagccaag      8340
agttaggtac aaaccccggc tctgtcactt tctagcctgg tgattttgga cagctccctt     8400
tccgtctctg ggcctcagtt ttcccatctg aacattgggg atcatagcac tactcgcttc    8460
acaggatagg tttgaggata acttgtgcct ggcacacagt gacactcggg aaaggcgat     8520 ttccacagcc tctcccgtga agggccttgc cagcccctct tggaaaatca ctctgttgtg    8580
ttgtccccaa tctctgagcc ctagaggcat cttctgtcta ttataattat ttgggcttg     8640 gcacctgcca gctgagaggg ctcaggcctc tgaaggacct agggtccatg tgtcagctgt    8700
cacatcttag gggacagcca ggccaaccct ccagctccca gagcggtatg gagcaaaggc    8760
tgatccccga agaaatgcct tgtgcctac acccgctgcc cccaagccct aggtgagggg    8820
catgttggct cactgctcct gggattccat gactgtctca gcctcattct caaaacccag    8880
agactcttgg gtggagacag acagttcagg cggagaggag gtgtcaggct ctggaggccg    8940
gtctgccagg gcctagcatg ggatttggac agtcagcact tggccccctt ggggccagaa    9000
cctggcacca gaagggcaag aggctagcca cattctgggg gaggaacctc ctagcccctt    9060
ctcctcccag accctgagg gcagagccc agggaaaagg cccctcagag ggcttgctac       9120 tgcccctaagg tggatttccc tttacccaag ggtcctgagg cttcagccca gcgggcagaa   9180
```

```
gctgcggggg agggcgccct gcggctctca agtgctagct gtgtcctgcc tctggtaacc    9240
agccgtcaga tgagcccaga gcactgggag cccccatcc cgggtttgtt tgcctgccct    9300
aaggggagaa gtgagggcgc agcagaccag gtggcatctc cggctgagaa gggacagaaa    9360
cccagcgtgt ccaccccatg cagtcccact gcctcagcgc cccttctcg ggcaatcctc    9420 tcgtcccacg cccagaggcc gtccagtgag ggtcactggg caaggagcgg ggggggggg    9480 gaaaagggg gaaaaaaaa ggaatccccc ttaaccaaaa cccacccctt aagggggggg    9540
cccacaaatt gagttccaag gcccgggga aggggggaac ttccacccccc cggggggaacc    9600 aaaccccccc cgaacaactt tggggggggg gcttgcccct cttaaccccc ccccaggggg    9660
gcgggttaat ttttttcccc ccccccacc gggccttttg ggggggggaaa gggaaggccg    9720 gccctaattg tttccggctt ttgggccccg ggccggggtt tcnnaaaacc ttgccccccg    9780 aaatacccc ccttttcccc ccnccnccnc cncnnccngg gaagggggttc ggttcctgtt    9840 ccgcctcggg gggcgcggac aaaaaaacgc cccgggggcg gggggggtgca agggggaaacc    9900 ccttaaacgc ccgcccttt ttttcaagaa aaaaaccccc caaaagaagg ggggggcatgg    9960 ggccctttt ctc                                                         9973
```

<210> SEQ ID NO 30
<211> LENGTH: 3069
<212> TYPE: DNA
<213> ORGANISM: Felis catus
<220> FEATURE:
<223> OTHER INFORMATION: GenBank Accession No. AC145332.28 genomic DNA for PKD1 3069 bp contig
<220> FEATURE:
<221> NAME/KEY: modified_base
<222> LOCATION: (1)..(3069)
<223> OTHER INFORMATION: n = g, a, c or t

<400> SEQUENCE: 30

```
tatagggcag ggcctgcgcc tcgtgacccc gccccaggcc ggccggctca tttgcatgcc     60
cccgccccag cgcggccatt gnngccggcg aggggaggcc gggcctgagt ggctccgggc    120 tttgggcgc gggggggcggg gctgcgggga gcctggcgcc cgcgatgccg ccgccgttgc    180
cgccgccgcc gccgccgccg cgggacgggt tcgggtccgt gtcgcgctcg gcgggcgcgg    240
gcagcagagc ggcccggggc gcggcggctg cagcgggagc tccctgagcg cccgcccgtc    300
atgtccagga agaagacccc caagaggaag ggggccagcg ggcccgctgc ctccgcgctg    360
cctgcggccg acgggtcccg gccggcgcgc ccagggactg cacgcccccgg ccccaggcg    420 cggcccaacg gaccccgca gcccggccgg ccctcgcttg gcggcggcga cttctacgat    480
gtcgccttca aggtgagccg gccccgccc caggcgagcg cagcaggtgg cgctccgccc    540
gagccgagcc gggagaggtc ggggagggga tgcagggccc cgcagaccct cggcggggag    600
cccgccggag cggcatccag cagctggcac ggtgcacggc atacacacac agccttcaga    660
cccggatttc agatacccaa cagctggcaa ggtctgcccc ctaacgccac agctggcagg    720
gctggacaaa gggtcccaga cctggcaggt gctccgtccc gggtcccgaa tgacaccgcc    780
cccgcccccg ccccgcgcg gggcccagtc tcaccatttc ccatatgctg ccttccgcac    840
ccccagggtc tgtgggtctt ctctttttgg aggacggggg agattaagaa gaggtttgcc    900
agttgggtag ggagcactag agccttcttc agccctcggc aggagcctgt gaatcgtgga    960
ggggttgtca ggactgtctt tgggtttgga gccttgggca gcaggctggg ggaggggagg   1020
aggggggagg cctgactgcc cctcctgctc cacagacctg acccaggccc ctcatcacac   1080
```

```
caagatctga ccccccatgtg gcaaattcct ccagagtctc actgggatgg gaagaagccc    1140
ctggcacaga gaccccctgca ggcctttcag aaggtctcca gctaccaatc cccagactcg    1200
gctccccacc aagccccaca tgctttcctt ccagatcaag catgatgtcc agggtctggg    1260
ggtgggttgg gtaggaccct ggatggaggc agctgccccc actcctcact ggttgaattg    1320
ggccgctgtt caagagggga cagaaccttc tggaggtggg agcctggagg tctaggttgg    1380
cagccaccat agctgctatg tctcccccaa gtcctgccga acctgtgagc ctgagaccgg    1440
ttcctccact cctggccagg ccagcgcagg aaggccaga caccctctg gtgggccag      1500 caccttggtc ccctctgtcc ctaacacctc tgaccctcct gttcgcccca ggtcatgctg    1560
gtgggggact caggcgtggg aagacctgc ttactcgtgc gcttcaagga cggggctttc     1620
ctggcaggga ccttcatctc cactgtgggc atcgacttcc gggtgagagt ggaagctcac    1680
gtcctaagca ctgagccggc ccagccatgc cctgggcccc tgacaccagc tcactgggct    1740
ctcacaacct ccctgggcag ctggtttctc cgttacccca gtgacaccaa caggctcata    1800
gggtggagct cgagctcctg tctggaccac ccggctctca gggcccaggt ggttgaggtg    1860
ggatgcctta cccaccaaac tacacctcct gacccccctaa gggtcctgaa gacaggtgag   1920
ggctgcatct gactgaagca gggagagcac ccctgtgcct ggagctactt ctgtgcctca    1980
gggtaggtgg gccgtggtgc cttcccaccc ccgggggggt tggctgacag aggacactca    2040
aggcccatgt tcacttggaa ggcgaacatc actgtccttc tgtacagagg tgccaggaag    2100
cctgccaaag gacctaggaa gacggtggt gtggagcacg tacccctct gggagcaggg     2160 gcgggtccct gcccttgggt gaggaggctc acgggaagtg ctgccgcctg gctgctcccc    2220
cctctttgag agcccctcc caggttgccc ccagcgggag gggtgtcctg gggttttctg     2280
gggggaaggg aagtgcccct ggacttcaaa tccctctcat ttccccccac ccggcacctt    2340
tagcagcctg tggagtcagc aggcgacgtt gagggctgcg gccttaggcc tggcgggtgg    2400
cagcattcca gcccccacct cgagtcacca gtctaaattc ttgccttgcc aaggtgctgg    2460
tgtgttctag acaaatccca aatttgcatt ttttctcacc ctttaattag acccagttgg    2520
tgggaggctg ggagggaggc ccattctggg aacaggaaag ggggctcctc ccagtctggg    2580
gagccatggg ttaccctgct tgaaggtcca ggtcccctca agtcttctga gatgaagtaa    2640
gggttcaggt gccgaaaggg ggcagctctg accctggaca gatggtcctt ggcctgtttt    2700
ggacccatct ccccccttct cacctccctc ttggctctgg ggcaggtggc gagggaggtg    2760
aggctgtttg gttcacaccc ctgttcaggg tgccagtgaa ggcagggtgt ccttcccagc    2820 cccccttcc ccccccccc cccccgggg tttaaaaaaa aaaattttt tccttttt         2880 tttttaaaa aaaaaaaac cccttaaaaa aaaattttg gaaaaggggg gggggggtt        2940 tttcaatttg gggggcccc cccccccccc aaaaaaaag ggaacggggg gggggggttt      3000
ttcccctcca attcccctta agggggggg ggggggaaa aaacatttgg ggaaaaaaaa     3060
aaaaaaaat                                                           3069
```

<210> SEQ ID NO 31
<211> LENGTH: 38187
<212> TYPE: DNA
<213> ORGANISM: Felis catus
<220> FEATURE:
<223> OTHER INFORMATION: GenBank Accession No. AC145332.28 genomic DNA
      for PKD1 38187 bp contig
<220> FEATURE:
<221> NAME/KEY: modified_base
<222> LOCATION: (1)..(38187)

<223> OTHER INFORMATION: n = g, a, c or t

<400> SEQUENCE: 31

| | | | | | |
|---|---|---|---|---|---|
| tttcccccc | cccccccc | ccggcctcag | cccagcagat | ggctgtgcca | ttggttcctt | 60 |
| ggagacccag | aagcaccctg | acagcaggag | cttggggaag | aggggggtgg | tggtgttcca | 120 |
| gctgccaggg | gcccccaccc | ccaccacagc | agatggaacc | gtggggttgg | tctttccctg | 180 |
| ccactagccc | tgcaccggga | aggtccggct | aggaaccact | accggccagc | aaacatttaa | 240 |
| tgagcaccca | ctgtgtacca | ggcagtttca | ggctctgtgg | ttactgtgct | gcgacccgcc | 300 |
| ctcgggggc | cgctggctct | taaactagga | agctggctat | ggctaggcac | aggggggaagt | 360 |
| gggcagccag | gctgggctgg | aggggtgctg | gcagagggaa | gggagtgggg | ggaggcggga | 420 |
| gcaacaggac | tcagtgactg | accaggtggg | tggtctgtca | ccttcaaggg | cagggagctg | 480 |
| gtggagcagg | tgctgggcct | ccagggtggg | agtgggctac | caagagaggc | tcaccagggg | 540 |
| gaggtgcagg | aggcgcggtg | aggggggaag | ctggcagctc | cccaccggag | ggcagcagtg | 600 |
| ttctagctgt | tggttgctgg | accgggctgg | ttgttatttc | agaacaaagt | tctggatgtg | 660 |
| gatggcatga | aggtgaagct | gcaggtgagt | ggtgtgggga | gcagcggggg | ggcagagggt | 720 |
| tgagggtagt | gaacacccag | gaggaactgg | cggccctgtg | cctgtcactc | cagatctggg | 780 |
| acacagctgg | ccaggagcgg | ttccggagcg | tcacccacgc | ctactaccgc | gatgctcatg | 840 |
| gtgagcttgt | gggtggggga | cgccagtccc | ggggagtcag | aggctgtgct | ctcgcgggtg | 900 |
| tcaggtttcc | ctggcttctg | cacggaggag | ggtgccctgg | gcaggagcat | ggcaggaagt | 960 |
| gtggaggctg | tgatgcgtgt | gggtgtgggt | gacaagaagc | tgtggtgggc | cctggaggtg | 1020 |
| tcctcactcg | tcctctgccc | ccagcactgc | tgctgctcta | tgatgtcacc | aacaaggcct | 1080 |
| cctttgacaa | tatccaggtc | agtggttttcc | ttcctggtgg | tggtggcagg | aacaggccgt | 1140 |
| gatggcatta | gggtcccagg | gggctaagga | ccctaccgac | ggcagggaga | cggcccctct | 1200 |
| ggtggctcag | gtggagtgtg | agctgaaggg | agtctgagga | ccttccagct | ctgtcagtcc | 1260 |
| aacaccttgg | gtaaggtgct | cgtcgagggt | gcctcaacag | gacccgggga | cctcgatttc | 1320 |
| tgggccttcc | tattagccag | agcccaacgg | gcaccccaag | ccgtgaggcc | tggaggggca | 1380 |
| agggcgagc | agagtgccag | cctccagcct | ggtctcagct | tttcccccac | aggcctggct | 1440 |
| gacagagatc | caggattacg | cccaacatga | cgtggtgctc | atgctgctgg | ggaacaaggt | 1500 |
| gggcacccca | gcccatcctc | tccaccgtgg | ctctgtatgg | gggcagggt | ggtagggtaa | 1560 |
| gccctgggcc | agctctcacc | aagacccacc | ccccatgcc | agtggactc | tgcccaggag | 1620 |
| cgtgtggtga | aaaggagga | tggggagaag | ttggctaagg | tgagccgggg | tggggtgggt | 1680 |
| gtccggggag | cgtccctggg | gttgcaggc | ctggctatc | tccaccaggc | tgccacctgg | 1740 |
| ctggcagcag | ctgtttgcag | gagtacgggc | tgcccttcat | ggagaccagc | gccaagacag | 1800 |
| gcctcaacgt | agacttggcc | ttcacagccg | tagcaaagta | agtgctggta | gtcatcagga | 1860 |
| agatcctcca | gacccagagt | ctgaatcttt | tggtggggga | agctgtccca | tggtcccctc | 1920 |
| tgccccacag | ggagttgaag | cagcgctcca | tgaaggtccc | cagtgagcct | cgcttccggc | 1980 |
| tgcatgacta | cgtcaagagg | gagggccgag | gggcctcctg | ctgcagaccc | tgaacctgac | 2040 |
| tgggcgctgc | cactgcacat | cctccggag | gcccctgcaa | ggctgacag | aggtcacct | 2100 |
| ggcagtcaac | tcgagggcgg | ccgtttctgg | gactcccaga | cagagcctcg | tctttcccta | 2160 |
| gagcctcagt | tccaacaggc | ttcatggagc | cagtgggtct | gcagccctg | actcagggcc | 2220 |
| ttgcccccaa | ggccttgatg | gagaagcaac | ggcctcccgt | acaggagaca | ccccacaatg | 2280 |

-continued

```
taaagcccat gcggggagcc tggtcttgct gccacggcac tctgctgccc tctcctggac    2340
gcgcccagct tcaaggctgg accccggtgc cagcgccacg tgtacagtgc ctaacccctc    2400
aaaagccatg tcttcagcgg cacccgctgc ccaggcaggg aaaggccgga ctcctgtccg    2460 tgcctgggc agagggcttc gctgcacatc caatcatgca tctgtgcccc aaggaccaaa     2520
gctgccagcc cacacactca gagactctgg ttcaaacatc agcagggtct tcctctcgtg    2580
ttgcctggag gacaagtttg cggctttcta atacacgaac ggcatgtggg aaatcagaaa    2640
ccgtcaggga aactagaact gccagcccag ctgaggcctg tgcagagtga ggtcaagcca    2700
ggaggctggc agtgtgctcc agctcatagg tctctaggtt aagagtcttt gttttcagtc    2760
ctggtgaata aagttgtgtt ttctggactg ccggtctctt ctgttacaag aaatcccctt    2820
cttttgcgcc tcggcaaagt aggggttgag gacaacgcta gagcgtagt accctcaact     2880 agggctgctg tctagggagc acggggaacc taggtggttg ggtggttgat gtccacttcc    2940
ctctgcaaga cccaacgaaa cagaaaacag tgctctgtgg ccggtgagga ggaagagttc    3000
ctcacctgct taagacaaag accccggctc cgccccggga tttctgctct tacaggcaaa    3060
aaaaccgaga aggcatccca atagttgaaa ggtcaccgtg tgaacatcca tctttctcta   3120 cccttttcccg agactgccac ggaacgagcc agtcctcccg cggagtcctc tggggagcaa   3180
acgcgtgtga aaataaagac acttgcgctc ccatcaactc accacctctg ctttattgtt    3240
aagcgccgca gatacggacg tggactcccg ccttaccacc aggccccggg ctgacgttca    3300
tttacgtcca cggtctccaa ccacgtcacc gaccgcccta aaagtcagac acacagagcc    3360
gaaatgtaga cagaagcccg ctactccgat ttttggaga tgttttcaca ccagcccctc    3420
ctgtcaaggg ggcgcaccct gaagcctcag acttgcaaaa taatcagact gcacatgcag    3480
ttttcatacg aggtgtcaga aacgaaagca attcatcaca ggctccaaac tgcataggg     3540 aaaccaagcc cggcccaggc ttacctgcgg agagaagtcg gtctgaagtc gcaccttccc    3600
aacagaacgg gaccgatggg ggggggggg gtggaggcgg gcggagcaag gaacgcgtac     3660
aacgctgaag acagaggcgg agcccggcg gatgatggcc ctggaggacc cctcagcccc    3720
attcggggcc cagatcctcc cctaacgtgg actcgtagcg accgcacaga caaacgccca    3780
cggccgccac tggcttccca aaagaaagca cgcggccgag gctgaagctt ttatagaaag    3840
tgccccacct ctgcgattgg gcaatcatgc cggaagtacc cgcccccggt ctcctgaacc    3900
agactcgcga agcttctccc tttagcagag gccttggaac ttaactgtga gcgacagatg    3960
cacagaacca atcagactcc gatctgcaac atagagtgat tctgaagctg ccaatcccgc    4020
cccgcgacgt cggagccgcc ggaattcgta gtttctggag agccgcgcgt gaggcgggga    4080
cccaggcatt gagagacgga gaactacaag tcccggcggg cgtagcgcct cagcgcttcc    4140
ggctcgcgcg tccggtctgt ctcccggcca gcggccgcgg gggcacgatg aagcgggagg    4200
gtatcgctgc cgctcccggg cggccgcggg cgggtgagtg tccgcgcggc gcgcccggcc    4260
cggggctcgc gcctcgggc cgcgcggtag gcgcttcggg gtccgcggag gcgtcgggcc     4320 tgggggcgg ggccgacacg gccgggtc tcggcgtctg tccgtcgctt gcccattgc        4380 cccattctcc ccttctttat tcattccttc ttccttgcgtt cgttgagcgc cgccgggtc    4440 ccagttctcg taggctcttc tgcagctttt ctcagcccgg ccgctgttga cacttctcgc    4500
cgatccttct ctgctgtgct ctgtaggat ttgagtagca tccctggtcc ccacccatta     4560
gatgccagta acctctccca cccccacgtc ttgacaaccc aaaatgcctg caggcaccgc    4620
```

```
caaacgtctc ctgggggaca gaatcctccc ccaaccccac acaccccggc ttgagaaccg   4680
gccatctaga gcggggaggg attgacagta cacacagaat cctaaagagt tgtgataggt   4740
gctatgagag aaacagggcg ctgagaaaga gtacggggcg ctctggagtg gcttggggag   4800
gggggaggtg cctacaagca agcagcttgt tttgggaagt tgctggaaga gcatgccagg   4860
cagagggagc aaggtgtgca aaggcccaga gcaagaaagg gcttggtgcg ccagtgagtg   4920
ctggcagagg ggtgagaggc ctagtccacg gggccacacc agagtgcatg gtggagggat   4980
tgtattgtgc ttgcaaggaa ggctgttgga ggattcgagc acaggagagc cagcatcaga   5040
tccaaggccg gtaaagagcc cctggttgtg tgtagagggg gtgggagacg aggctgtctg   5100
gctgttccgg cctcgttgcc ttgaacaagt ccagggcatt cagctggagc cgaggctgcg   5160
attgtgctgg atcccaccct gctttggcag gacaggggtg gagggtaggg ctggggattc   5220
caccctgctt tgctgcctcc cttgcctaga gctccaagct gcccagactg ttcacccttc   5280
tccccatccc tcacacccct tcctgtgcac acacaggccc cctctcctga gggctgccca   5340
cccctgggcc tttgccaagc atgtgacctc cttcttcctc attccttctc tttgggcctc   5400
tcccttccca caccccttcc ccgcaagcct gtgcggcagg caggcactac ctctctgtca   5460
tacatcccta cttgcattgc tctgggcatt cacgtttctc cggaatccct ggtctctgtg   5520
tgtcaaggtt cctgcatgtt atagctgcac tagccccagg aagccagaag ctccctctga   5580
ggggaagcag ggatcctggc aacctggctg agggaggtaa ccagctggga aggaggggat   5640
gtcttccttc ctgaggggtc cctgtggagc aaccccact gtggctctgt gtcacacaca   5700
atatttctgg aaatgaatgg gaaagatcag agtctgaagc actgactttg ctgggacagg   5760
aacccacaga aaagggtctc tggcagctcg aatggggctt actaatactc ccgaaccggt   5820
ctacctctcc taccaggccc cctagcttct caaggtcaga ctcatgttca gccgtcacca   5880
cgtgccctct caccctcaca gggactggca tgcagtgggt gtgaaccttg gccggccggc   5940
cggccgcgaa atcagagagt ttgggagacg ggagagatgt ggtcgaaggg cctgacccgt   6000
ttggacggct ccaggcggcc tgggctccgc ggtgtggtgc tcctcggcac ggcttggtgt   6060
gcggctggct ttggtgcacc atgggctcct cggtttgctg gcacgacagg gctttggttg   6120
gccgcggtgt gaccctcgt gggctctaag tcctgggggtg gcctcccggc ctctgctctt   6180
gactctcgaa gaggggctgc tgtcagtgga gccctcactg ttgccccgcc tcgcgcagct   6240
cctttcagat gggagtgcat ccactctgtt tgacgagtga gaaatctgag gccctggagg   6300
gcaagcggct cgccccaagt cacgcagctg ttacgtggca gaggtgggat ttgaacccag   6360
gtctgagtcc tgcatttgtg gcctgaccgt cgtgctgtcc gtaaggaacg cttggagggg   6420
tcagtataag cacataagtg aagtgtgcca gcatatgccc agccttggga ggggtcagca   6480
ggacataact tgctccgaac ctgggtcccc agtggcctga ccttgctgtt gagtcggctc   6540
ctaggacttt accgggccat ctggctggct tatgcaggag gtaccctcgt agaggggccc   6600
gaacccctca gctttcagta gatgccccag ggcgtccccg gtgtgctggc ccttccacag   6660
aagaaattcg gttgctccctt ggagggacat ggggtcaggt ggggcagagg agggagaaag   6720
tggtcctgga gtccagtgct gaggtcacat gaagacctgg tactcggcta tcccccgggg   6780
aaggagcagc tcacggaaa ccgggactga aggaatgtgc cagaaagact gtgtagtacc   6840
acagcctggg ctgaaagggc atggaatgga cagtggagcg ggctggtgca tgtctgcatg   6900
tccaggcggg gctccaggct gggactttgt gcacactccc caagcttctg tagggaacca   6960
agaaagagga agtcagggag gcggaaacag ccagggcggc ctggaggtgt agcccgggtc   7020
```

```
cgaggtgtcc ctgggttctt gggcagaggc ccaggacctg tctccacaat tttagactca    7080 ctgattttt ttttcttaagt ttgatttatt taagtaatct ctccacccta tgtgggctc     7140 gaactctcga ccacaagatc aagagtcgcg cgcccttcca actaagccag ccggctgacc    7200
ttagactcac tgatttaaga cagcctggga cttgcttccc ccttgtgcct ctgcagcctg    7260
ggttggccca gacgctgagt tggaggaagg gtgtgggcag gtaaaagtgg ccctatggc     7320 taggtgctca gagaggaggc caaacaccac cttttccag aatactctct ccctgctctg     7380
gatctgggca gccccttcct ctgggaagct ctctaggagc cccccaggct gtgtcagatg    7440
tacacctcct tccagcagag ggacccacgg gtgctggaga ggctgggtgg ggagtgcgag    7500
gacacagcct tggggagagg aggccacaac gggtgtccag tctggcaacc ttgaggccac    7560
cctttaggaa ctgtgggcat agagggaagg atggaaagtg agggcagagt ccagggctgg    7620
gtgctcggag ggaagggggg ccaggcaggc ctcaaacctg ggcctgctga ggtgcttagg    7680
ggggggccct gacatcacac cctgcctatc tgggatggaa aagacgtgct aagggacat     7740 cagggaactg ctgggagagg tgtatatggc tttgctatgg caacccagcc tgtttctata    7800
ggatttgttt ctataggggct tgggccaggg ggccagcagg ggccgaccca ggggctgggt    7860
gggtccatgg gtgataccag gggctgcatc tggagctctg gctgcagtct ggtggccacc    7920
cacagctctg tgccaggcag ggctgaggtg tcctggccac ccatgctcac cctggggcag    7980
tcaccactaa atgtgtggcc tgatggtgct tccagggcca gcctacccc attgctggct     8040 cagcacatgc tgctgagggg accccaccac acccactcct cgaaggacct ccttctggcc    8100
atcccactgt cgtccccccc ccccgcccc gtcccagtcc agcatttaca gcctacacta     8160
cccactctgt tggctgccag ccacagggac cacagtgggg gatctttgtc ccacattccc    8220
aagggtgagc ttagcagacc ccattggcct ccctccaggg ggtgggggtg gggaggggtt    8280
cccaagggag ctggcctgct ctctggtgta ggctgcccag agaacggggc tggtgggggg    8340
cttccctgaa gaggggctgg ggcattatag gtgggtcttc gttcccttgt cgggcaagga    8400
gtgtgcccct ggggcccttt ggacatggac ttgggtggac agagatccct gggccttgac    8460
cctaggctca agcaggggag ctggttttgc actgaccct ggcaccttgg gtaccactct     8520
cccaccagcc tcacctgagg ccccatctcc agcaggacgt gcgtccggtc ttttctcttt    8580
aagagatacg gtccttgtgt ccctcgcctg ggctctgcgg aggcacctgg agcaggcagg    8640
gtggggggac tcggctgggg agggaagggg agctgtgcct ggcaggctca gcccatagct    8700
tttcccagta tgggagtgtc cggtcgtcta gctgacaact ccctgtccgc ctgcatacag    8760
gcctggtgcg gggtggcgag gaggcctacc cctggggggc gggggcatac cccacccgg     8820 acagctgggc ccagcggggt gggggcgta cgcagctgtg ctgttgtttc tggggtttgg     8880
gcccacagag ctgggagaca ccggcgaaga cttattgcaa aatgcagccc ctggggagc     8940 ggggctgaag gctcagggca tcttgctcaa ttccaggatg cttagttagg gtaggatctg    9000
atcgttgtga tctgggggtg cacagctggg ggaggcggtg gctgcagccc agcaaccccc    9060
ccctcccccc gcctcgggtc cctggctggg agtgcaggcc aaaccatgta aatggggaag    9120
cagttacttc cctccttccc tggctccact ctgctctctg gccagtctgt acatctcccc    9180 cccccccca ccccgccccc gggttgtgtg tctgccggcc tggccgctat tggctgtcag     9240
gggactttcc agccgatttg catgttgccc tgcgtgcctt tctgtttact tcacttcaga    9300
gtgagggaga gccagacgcc tgctccctca gactgagcag caggcacaca ggccccacgg    9360
```

-continued

```
gggctggcgt gctggccgcc gtcctggggg gagtccctgc tggggtcccg gctgcctgga    9420
ccacgggagc cgctcgctgg agccagccgc tggccgctgg gcctcgggag cttgcagcag    9480
agggagcaga tgaattgtaa aatccaggtc agtgtgggcc ggccgcctcc ccgtgaccca    9540
cccccagcct cctcctggca cgccccatgg tgccgaggag ggagccgacc tcgggtttcc    9600
caaaaggtga gtcctggagc tcctatgtcg ccccagccgg ggtatccttg ctgcaagcag    9660
ggtggcccca ggatttcctg cttagcgtgg agaccagcag cggcactgga ggtggggctt    9720
ccggacccac cacagccaca cctccaccaa gggcctggta ctgcccactc tcgggagtcc    9780
ctgcctctcc cccatgagga caagccaccg gagagcctgg tctgggactt aaccgccaag    9840
tctcttgagt cacagcaggg ggagtgatgg gcaggagggg gaggctttgg ccaacatctt    9900
gggatccccc catcccctgg tctacctgga cccccaggggc gccgagagca tcggtggcg   9960
tgccttgtgg cagggccaag tgtggggact acagccacc gcaccgaggc ccgagtctag   10020
aagactgggg gcggggggggg cggtggcatt gcaggtggta ttcaaagggg caggtgggag   10080
agaagatggg ggagctgttg gaacacacg gctcgggagc cagcccctcc ccgtagaccc   10140
ctaggttggg ttgcaggacc accgagtggc tgtggcgtgc gtgaggcaga cacggccaga   10200
tggctcagca gcccctccac ccggagcccc ctcctcagtc gtgggggggcc ttcacagcac   10260
agggtggggcc ccagcctgca tgtgcccttg tgccccacga gagcgggacg tgccggcctc   10320
cccgggagtt cccgacactc gttctgctgg cccggcctag cggcaggtga tgagcccgcg   10380
ctgtggcctc ccagggggtct cctggggaga gagctcacgt gtgctcctcc tcgcggggag   10440
cctggcttaa agctggggcc tcgaggctac agctgactcc agaggggaga tagacgctgc   10500
cgtgacgct gaccccagga gggccctgc gaaggcgggc gtcgcccctgg cagtgggggtg   10560
gcttccccag gctatccacg atcgtggctg caggctggtc cccttccttc tctaatgtcc   10620
agaccctcg tctttgggtgg agtgggggtgg ggggagtaat tcttgcaggc ccaggatgat   10680
acccactgtg ccttctcccc accacctcag cctgtgagtc ctgagtcgac agttggaccc   10740
gcacaaggtc tgggatcagg actctcatct cctcccctg tcccaaaggg gctttatctg   10800
tgtgatgagc ctctgagagg ctgggcccca ggtacatcac cgacaggtcg tctggggtgt   10860
ggccagcgtc cttccatcct gcagaccggg actgtcctac ctggtaggaa gcaggcacac   10920
ggcttgatcc cgccccgggt gccacaccac ggcccagtct tggctccagg gacacttgcc   10980
ctcagactca gaggttcggg cagagcacag tgggggcttc cgcctctggg gcggagctgg   11040
tgacgtttcc aaaagcctga gccttgaagg aaggtaaagc tgagtgacag ctgcctgcct   11100
gcccccaggg cctcctccct tccttgggcc tgtgcacacc tgggatggga ggagggaaag   11160
agactttgcc cgcatggacc cacccttgtt ggcactggtg gcgagagggc caaagtgtgc   11220
cgggagtgga ccagccagag caggcctggc cgcatgggtc agcgccggcc aatctgacga   11280
gtccgggcca ccgtccccac caccgctgtg ctccccctc aggagacgct gcccgcggac   11340
cctagatgcc tctctagagc atgagctcgg gcaagagcgc ccgctacaac cgcttctccg   11400
gggggcccgc caaccttccc actgccgacg tcaccgccgg ggtaagcggg aacctcacgg   11460
ggaagggtct ccccctcgtg gccacctcgt gtgccggggt cccgcagag cctccagagc   11520
agtcccctcc ctacgtggag ggcctgtgcc gcgtgtgtcc gcgtgagctc acgcgcgcac   11580
gtgaccatgg tgctatgaag gcgcgtcggt gcccgtccac gtgtgtgtac acatcctcgc   11640
tgggggtcga tgccaagtct catctgttct ctgtccagac cagaatggaa acgaccttcg   11700
ggcctgcctt ttcggccgtc accaccatca caaaaggtga gccagcctgt gagcccaggc   11760
```

```
cagggcgggc tgggcagaat ctgggcgtcc cttactccca ctggggtctg caggcacgtc    11820
ctggtggggc aggaggggc  atcggtgtcg gccctaggct gcctgccgcc ccccccccg    11880
cctctgctgc cgcatccttc tcctccccc  ccaaccccgg gcatcccagc acctccgtcc   11940
cggggcctca cccgttacct ctggggaggg ctgccccacc tttcctgtcc ctcgtcctag   12000
cgtcctctgg ttcatccccg ccctgggctc ctagcagcct ccgggaggtc gggactgggg   12060
gccacgctgg acacgtgtgg gtggtaagaa gtactcgcgg tgtcctttct ccagaccggt   12120
tccagcccgg ggccgtgtgt tcgaggaggt tgtgaggggc taacagcccg gggcactacc   12180
tccttccctg agtcatgagg gtgtgttgcc tctcttgtca gggctggggg ttcagggatg   12240
gactttgttc ctttgccttt ttggtactct gctcctcgta ggtgaagccg atttttaatt   12300
gcttttccgg ggttccctct cgaagcactc agcagtgagg ccacaggacc actgtgcgca   12360
cgtgctcacg ctggcccctc tgccccaggg tggctcagtc agatgctcca aaagtgcccc   12420
ttttccttct tagatgttct gtcctgagaa taaataaacg tctccccaat acaagcaccc   12480
aggtcactgt tcctcaacac ctcatttgct cttagaagct gcaggggccc ccgtcacggc   12540
agtcccgcgc tcctggagca gacagtgatg ggagtctgtc tccctctcgc cctacccagc   12600
agccccatcg gtggcaggga tgggtcagga ctgggtatga acagtcacct cacctgaccc   12660
ctctcacaga tagggaaact gaggcccagt gacagggag  ctgcttaaag cccgactcat   12720
gaaaccatgc ctttgggct  ggttgtgatg tctgggtttg ggtgggcctg aggccggtgg   12780
tggccactcc agggcttccg gcttcccat  ggactcctga ccaacgcctt ccctggagtg   12840
ggctgagaag gcccgagggt ggttccaggt tctggccagg gaacagctg  ggagacaagc   12900
agacccaaac agcgggctgc ctgtcagtcc ccaccacaca ccggcccggg ggcctcaggc   12960
ctctgtccct gtctcctcct ctgggcactg aggacatcag aggacccgcc cactggtagg   13020
gttacctcga gggccaagta agatgacatc ccacctcgtg ccaggcaacc tccagattaa   13080
tcactcagat gttgggctct tgcctcagct gggcacaggg cagccccagg gtcagaccgc   13140
tggcaccttg tagagtcaga gagatgatcc ctccacccca ccttcagcct gccttgggag   13200
tgtgactgtc gggggctccg gagctccagg cacagaggat aggccctgga gaccacctga   13260
gccgggctgg ccccaggctg tgccctccct ccccaccgtc ctggccctgg aggggctga   13320
ggatgcaggg ccagtgcggg gcttgctggg ggctcaggcc cctgacaggg gcagggtggc   13380
tcccagctgc ccacgagccc agccccagcc aagtggccct cagatcaaga aggaggacac   13440
gggagagggt gggggcaag  gagacttccc ggaggggatt agccccctgt ctggcccagc   13500
ccctgccccc accgggcccg tccctccagg gagcccactt cccgcacgg  ggggccagcc   13560
atgcccctcc ggatcacact cgtggcagcc ccaccctctc ttcttggcag ccgatgggac   13620
cagcacgtac aaacagcacc gcaggacacc gtcttcttct agcaccctcg cctactcacc   13680
gcgggacgag gaggatagca tggtaggtct gcgccgtggt cacttctctc cccacggcct   13740
ccggccatgc cgtccttccc cagggccagg tcccaggggt agctgaaggg gaggctccac   13800
ctccaggcac gccctgagct acggtctgca ggctacggtg ggttggtgag acagagggcc   13860
ggtgtgtctg ggcgtcgtga ggcctaagcg cccgtggcag gacttcgtgg aggaggaagg   13920
agcagcgggg ccggagggtg cagagcccgc gagctggggc gaagcgcatt cagctccgtc   13980
ttgaaggcca tggagccac  agaaggttca ggcgtgtggg tcacagatca cgtttccgtt   14040
tttaaagttg tctgctattg agtagaggat tggagggtgg gctggtgggt ggaggcggga   14100
```

-continued

```
cccccgagca ggtggctgga aggaggacgg ccggagctgg gggataataa cgggcctgct   14160
agggctctgc tgacagggag agccagagaa cctcctgccg ctggctctgc ggagtgagga   14220
aggggctggg gtggagtcga ggctggctgt cagtgcccag gctgtgtggc cagggtcaca   14280
gtggctgtcc cctgcctgcc tggccactgg accgtgtcgc tgggctctgg gcctgtcgga   14340
agcgaggagc tgccctggcc gaggggtgg ctcgggccct cctgccgctc acctctgcag    14400
agcctcgctc tctgcttccc cttgtggatt ctcgggattc tcgcccgtgt ggtggcccca   14460
tggactccag ctggttctcc tgtcctccca gcctccagga cccaagtctt ctcatgctgg   14520
gctgctaggc cttcgtttcc tatttaatac taagggaaac agtgtttttt taattactcg   14580
aatgcgctgt gtgccaggcg ctacgctagg ccttctctaa gcacaaagca ggcaccttgc   14640
gccccactcc ctggctccgc ctgcctcggc ctccatgacc tctgactcac ccatggctgc   14700
ccgggagggg attttcccca gagtggccgg gaccaggagg aagcccgtgg gctgggtggg   14760
gagcagtggc tcttacagga tctttactgg ggggttctag gccaaggcgg ggggagggg    14820 acggtttccc cacccaggct cccccagatc ctcatcttcc gtgactcagg cagaggcagg   14880
cacccatggc tcttcctccc tctgagaatc ttggccaggg ttcagtgggg aggtccctgc   14940
cttccctggg agcctcagtg gcccggcccc gtgtcccag ccagggaagc cagacgggca    15000
gccaaaccca aggggacgtg gagccccag cctctgccgg ccttcccttc ctccggcagt    15060
ccgggcgtgg aggccggccc gggactggct gatggaggtg cccgtgtgc agcccacatt    15120 ccctcacgg aagcaggaag caggccaggc gagcgtgtcc ttctggaatt gaatagcagg    15180
aagtctctcc atttacacaa agaaagctgg cagacgtgag cgggtggccc agccacaggg   15240
ccgggaccgc tggccggcg ggggccgg gcgccccatc ggctccctgg gcacaggcgg      15300
cggctctgcg gggtgagggg gccccggcct ccccaccggc tgacgggccc gcctgtccct   15360
gtgcgccgca gccccccatc agcacccac gccgctccga ctcggccatc tccgtccgct    15420
ccctgcactc agagtccagc atgtccctgc gctccacgtt ctcgctgccc gaggaggagg   15480
aggagccggt angtgtgtcc gcccagcagg cggcccctcg aggggcggga aggtctggcc   15540 tacgccccc cccccccact ccccgggcac ctcttcctgt gggctacccg gggtccagct     15600
ttgggaagtg agggcggcgc ccgtgtgggg tcttcgagtc tccatcaccg ctagagaagc   15660
aggtgcgcac ggccaagggc gtggctggag gggtcctccc tgcttcggtc cgtcacgctc   15720
aggcccggcc ccaggcctcc gcggcaggcc cttctcggcc gctacccgcc ccggccccc    15780 accgccgtct gcgccccggc ccccctcac cctgccctgc ccggttctag agcccctgg     15840 tgtttgctga gcagccgtcg gtgaagctgt gctgccagct gtgctgcagc gtgttcaagg   15900
accccgtgat caccacgtgc ggggtgaggc caccctcc ttcctgacac gtgcgccacc     15960
acggggcccg gcgtggccgc ccaggggctg ccctcttcgg tgggcacggg gtgggggcga   16020
ctctgtgtcc atgcccaag cccacccgtt gtctccacag cacactttct gccgaagatg    16080
cgccttgaag tcaggtaggg cccccccctc cccagaccct ggtccggctg acctcattac   16140
cccgcttggg aagggtccct ccggagaggt cccagcctag gcccagcact gatcatgccc   16200
ttggcacatg gtggcttctc cctagccctg ccccagcgt ctctgccacg gggcgctcag    16260
gccgggctct ggaccttgat gggcgaagtg gtgagaccca cgtctcgggg cctcctggcc   16320
tcagcaccag ctgtttccag caagagtgcc ttggccatca gggccccccg cctcacccctc  16380 tcaggcctgg gccctgggc ccggggctag ttcctctcca ggctctgccc cagctccctc    16440
tgccctgtcc cagactcctg agtcagtcca gaggcctccg gtccctcctg ctcacccagt   16500
```

```
ggtcaccctt ggtggcccag ctgtgccccc atcccgattc aggcatggca gcggggcagg   16560
tagatgggtg catcagggcc cagaaagagg ctcggtgcgg ccagcctgag gagcccgttc   16620
cgggcctgcc acaccgggac ttaccaggga agagcccgcc cccagcgcag cctggtcgca   16680
gcactcagag cagagctgcc agggcaggga cagccaggtg gacggtgagg tcagcacgcc   16740
ctcccctcca gagaagtgcc ccgtggacca cgccaagctg acggtggtgg tgaacaacat   16800
cgcggtggcc gagcagatcg gggagctgtt catccactgc aggcacggct gccgggcggc   16860
gggggccggg aagcctgccg tctttgaggt ggatccccga gggtgcccct tcaccatcaa   16920
gctcagcgct cggaagtaag tgctgtcctc ggcccccgcc ccccacccct cccagggggtg  16980
ctgagagccg gtgcctctgg ggactgacgc acgcctccca aagggaccac gagggcagct   17040
gtgactacag gcctgtgcgg tgccccaaca accccagctg cccgcccctc ctcaagatga   17100
acctggaggc ccacctcaag gagtgtgagc acatcaagtg tcccactcc aagtacgggt    17160
gagtgggtgg gggtgggcag gtgggctgcc cccggccggt gggcgggcag ggcgggggcg   17220
gcggggcctc cgggctggca ttcacagtcc ctccttcagc gaaccccttgt tgagatctgc  17280
ttgtgtgctg ggcgctgggg agacagccag ggtcctgggg gacggacct tagcgggagc    17340
ctcaccgtca gctatgtaat tacaaaactga ggtacaggtg ccgtgaagga gaggcctgag  17400
ccccacagga acgcagaggg gtcggagtgg tcggcgagct gggaggtcag ggaagggggg   17460
ggggtccctg agaactgatg catgtgtggg tgtgagccaa agactagcat gagggcttcg   17520
ggcggctgga ccatcatgag tggggtagag agcagggggc ggtgggaggg ggggagaggc   17580
aggagccggg aggccgtcga agggtgcgga agagcccttaa aggagctttg ggagcagaag  17640
gagtagattt cctcccaaag cggcctgatg ggtgctgagt gggagcagga tggacgggtg   17700
ggcagcaggt gggaggtgtg gggaggcgtg gggggggcag gggcagtgcc tcactgggca   17760
ggcaggtggg cagggcagcc atcctgcgtc tccaggtgca cattcatcgg gaaccaggac   17820
acgtatgaga cacacctgga gacctgccgc ttcgagggcc tgaaggagtt cctgcagcag   17880
acggacgacc gcttccacga gatgcacgtg gcgctggccc agaaggacca ggagatcgcc   17940
ttcctgcgct ccatgctggg caagctctcg gagaagatcg accagctgga gaagagcctg   18000
gagctcaagt tcggtgaggg cgcggcccag aaggcaggg tgtggcctct cctcccggtc   18060
cctgacaccc tcttccttgc cactcagacg tcctagacga aaaccagagc aagctcagcg   18120
aggacctcat ggagttccgg agggatgcgt ccatgttgaa cgtgagcggg aggggccac    18180
gtgcggggtg ggggtggggg ggtggggacg caggaccggc cctcggccta ggccccaaca   18240
ggaggcttgc cccgctcccc gccacccgc tgtcggggtt cagtgtctgt gctgggggag    18300
gcggctgctg ccgcgtgggg gcaggggac cgcggaccca cagccagcat gccctgtact    18360
cttggtcttg gcaggatgag ctgtcccaca tcaacgcgcg gctgaacaca ggcatcctcg   18420
gatgtgagta cgggcctgcc gctgcccct ctgctgcccc tgggcgcccc cgggccctca    18480
ccagctcctc ccgtctccgc agcctatgac ccacaacaga tcttcaagtg caaaggaacc   18540
tttgtgggcc accagggccc cgtctggtgt ctgtgtgtct actccatggg ggacctgctc   18600
ttcagtggct cctctgacaa gaccatcaag gtgagtgggg tcttgcccag gggggtggtc   18660
tacagcctgg tggcgggggg gggggggca atgggcactg cctgccaagc tgtgccagct   18720
ctggcctgcc tgtgcccgcc ttccctccac attcccacca tgctgccccc tggcgttggg   18780
ctgaccctcc tgggacccag cctgatcgtg gcctctgcag gtgtgggata cgtgtaccac   18840
```

```
ctacaagtgc cagaagacgc tagaaggcca cgacggcatt gtgctggcgc tctgtatcca   18900
ggggtgagtg cgggcatgca tggtacgcac gtggagccgg ggacgggaga cgccctgctc   18960 cccccacgg gccacacgtg tcctcagctg gctgtgtcta cctctcctgc ggggcaccct    19020
catccttgag cagggctgga tggctgggtg gtggcacgca ggcccccacg ttcacggtgt   19080
gtggccccgg agctgggcg cctcggggag gtaggaactc agccgtcgct cggctggcct    19140
gtagccagag cctcaggcgc agcttgggga caggaccaca gagtagcctg cccagctccc   19200
ccctcgcccg agaagggtag cccctctcga ccttctctcc tgtctcgtgt cgtgagactt   19260
cacgctgtgg gcaggagagg gagagacgtg cattcccgga aagcagcagc ctggccgtcg   19320
gcagcgctaa caggggtagt tacctcagct tgctgtcgga cgcttgccag gcaggcggcg   19380
gggtcaggct tctaccccca aggttccctc gccggaacag gaagacgag ggctgggggc    19440 agcgggagga acccggccga gctgccggtt cctggtggct cccggtggc tgggctccc     19500 ttggcctggc aagccacac cagcgaggac agtggcttct cctgccctga ccctcggct     19560 ccgctccccc aggtgcaagc tctacagcgg ctcagcggac tgcaccatca tcgtgagtgg   19620
ggccgcggca ggtgggtggg gaggggcctg gccgcaccg gctcccgggg gccccaggcc    19680
cgccgtgcca ccacgacccg aggcttcctg tcgtccttcc cgccaggtgt gggacatcca   19740
gaacctgcag aaggtgaaca cgatccgggc ccacgacaac cccgtgtgca cgctggtctc   19800
ctcacacaac atgctcttca gcggctccct gaaggccatc aaggtcaggc cggcctcgcg   19860
tgtgcacatg tgggcagcg ggctgccgga ccctgcgcc ccagcctgca ttcgtggccg     19920
tccccacagg tctgggatat cgtgggcact gaactgaagc tgaagaagga gctcacgggc   19980
ctcaaccact gggtgcgggc gctggtggct gcccagagct acctgtacag cggctcctac   20040
cagacaatca aggtgcgtcc gcacacgctt cgtgtgggaa gaccccctcgc taggctggac  20100 ccctgggctg gcaccgccca ggccggcccc ggggctccg tctgccctgc ccccatgccg    20160
ccgggttggg gagaccctca cacacatcct gggtgacgag cgggctgctt agcgtccaga   20220
ggccctgagg gcaaggtgcc gggcctggga ccgacgggct cgagcttgtc cgtagatctg   20280
ggacatccgg accctcgact gcatccacgt cctgcagaca tctggcggca gcgtctactc   20340
tatcgctgtg acgaatcacc acattgtctg tggcacctat gagaacctca tccacgtaag   20400
gcgggcacct agggcaggg cctgcctccg gggcgctgtc ctccccggag cctgtggctc    20460
tgacctgcct gggccattcc ttcaggtgtg ggacattgag tccaaggagc aggtgcggac   20520
cctgacaggc cacgttggca ctgtgtatgc cctggcggtc atctcaacgc cagaccagac   20580
caaagtcttc agcgcgtcct atgaccggtc tctcagggtg cgtgcggacc tggtgatggt   20640
gggaggttca cggtgggcgg ttgggcccag gtgggcaggc cctcatgtcc cgtgtgcccc   20700
caggtctgga gcatggacaa catgatctgc acgcagaccc tgctgcgtca ccagggcagt   20760
gtgaccgcac tggccgtgtc ccgggccgg ctcttctcgg gagctgtgga cagcactgtg    20820
aaggtcagtg cctcggctca ggccttccaa aggggctgcg tgtgtggagc aggggcggg    20880 gggcgaggag ctagaagcct tgggtcggtg gcaccggagg gcaggtgtgg atggcaggtg   20940 gtggtgggc ggcgtggccg gaggggcagc tgaaacagag cccttcctct gcaggtttgg    21000
acttgctaat ggaatccaga ccagtcttgg cttcctctgg gacctcccct aggcttgtcc   21060
caaccaggct ggccacatga ggggtctcaa ggggcgctca ctgcctgccc tgcgggaca    21120 gaccgacagg ttcaccctgcc caggcagtgc cctcccacc ctgtgcccgg cgagcctccc    21180
tctgcttggt cctgtgatcg tcgccgccaa gacagcgccc agccctcccc gctgggtgcc   21240
```

```
aggtacgatg ctcgcccggc ccaccctcca tccctgcccc agatggactg tgggccttt    21300
tactcacctt ttctactgtt tttagactgt atatagattt gattacttct tgattgaaat    21360
aaaagctgca cagactgtgg ctgtgagtgg ggatagtcct tggggtgaca ggccacccgg    21420
gaatgctgtt gtgctggggc accagcggcc agtgggaggg aggctgggga ggagccacag    21480
aagggctcct gtcagctcca ggatgtggcc ctcttggtga cttctctttc ctgccgggag    21540
caagctagac ccccattctc cccaacacac gtccccaaga agtgagccag gcagctctgt    21600
tttctgctgt ttattgacag ctgacagtag ctccctgccc ggaacccccc tccccactcg    21660
ctggagcccc agcctgggcc gcccgttgaa gagaggccag gcacacccac ctggggaagt    21720
atcagggcat gacagctgga aagggcccac acgctcaaat gccgccttgg ctgaccccTT    21780
ccatccgccc gcctcgcaac cgctggtttt cggcgttttt aaattctttt tttttttttt    21840
tttttttttt aagaaacgtc aaagttgtgc ccaacacacg tggatcagca aacacaatag    21900
aggaggccag tcagtacttt ttggaaaggg gagagagagg agaagagaga gagggcaaga    21960
acgaccacac gacacagcct tggaccatga gcagaagcgt ccatgggaac tcagatgggg    22020
gagggcaggc tgtctgtacg gggccagcga ggagccctga ggagggaggg tcaggcacac    22080
cctgacacac gccacacgca gcctggcatg cacgccctgc acccaccgag gtcacccagc    22140
tgacgtgccc acgctgcacg cacggctccc ccggagcccg ggcgcgcctc acaccggcac    22200
cctgggagag cagggagccc ctccccaccg gctccacggt gtggaggaca cagcccagca    22260
gcgagcaagg cacatccttc gagttcttca gacgcagaga agttaggaga gcgaggggag    22320
gctctagcgg agcacggacc ctcccggacc ccagcctcct gtttgtgcta ctgggccagg    22380
tgtcctagac ggagggaggg aaggatggac agacagacag ccagggcctc taacagcttt    22440
tgtcttgagc tagacttcag tgtccttaca gttggtaaat ggttttctat agaatcgata    22500
atatttttc tttctttaaa tatatatttg ttaaagttat accttttTGT ttctctgggg    22560
aaatctgcct cagctcattc ccaataaatt aatactctcg atagcttata ttctgggggg    22620
tacagtgggg caggggcgt gatcccagcc ccagtccctt gtgctgcgct ggagcggctg    22680
gcagaagtcc ccaatgggca gttctgtgct gggcataggc ctgtgctctg ccacagatcg    22740
gggaggggc caaagcggcc gtccgcctcc cactgcctcc cagggcagac ccggcctggc    22800
ctcagggcag ggggccaggg gctgcccttc ctcgcccgca gcaggcagag cccggcgcgg    22860
gtgggcgggt gtggcccagc agttattgca caggagcag cagacgggga cgggcacccg    22920
ccgggcagca gcatttactt agagccctcg gggtcccctg gccaggcagt cctccaggcc    22980
ggccgtccgg cctgggccca gggggcagga gttgtgcttg tgcaggggat gggcagcacg    23040
ggcccgcccc tgcccgcctg gcccccgtcg gccctccgcc ctgcccgctc gcgctgcgcc    23100
cagaggtgcc caccctgagg taaaggtcag tgtgcgggcc gggggccccg gcggcgcgcg    23160
gcgggcccga cgtgagcagc cgcgtcactc cagcatggcg tccagctggt cggccaggtc    23220
gtcgaacatg ctgccgatgt cgtccagtat gctgccggtg ctcttctcct ccgcggacga    23280
ggggctgggg gcgggcgcgg cgtgagccgg cggcgcgggc gcgcgacacc ctgcccgggc    23340
cccgcccctg tccctcacga cccgccccgc ctccaccgat ccgcaagatt cgaccccgg    23400
ctccgcagcc ccgcacgacc cgcccctgcc tccgctcctc agccctactc gacccgccc    23460
ccgccgcccc gggccccgcc ccgcagcccc gccccgcccc gcccctccct cgactcgagc    23520
tggagcgccg cagcctcgga gcgcgcgcgg accccgcccc gcacctaccg cgcgccctgc    23580
```

```
gcgtcctcct gccggatctt ctcctctacg gcttgcagcg cggccgccag gcacgcgctc    23640
gtctcctcca gcttctgccg ggcgctgtct cccggcgagg cgccgtcggg cgcggcgggg    23700
ggcccggcgg tggcggtggt ggcggcggcn gcngcngcng cggcggcgcg cggtggcttg    23760
gcgggcacgt gcagcgcgga cgcgccgggg acgggggct tggcggggct ggcgcttagc    23820
gagggcggcg tgctggccgg cttagcgagg cggcgggtg gctggcgagc cggcgagggc    23880
gcgggcgacg ggctggcact gcccgactgc agccccgccg cggccttggc cggcttgggc    23940
gccgtggggg gggggggcgg cttgggagac acgggcggcg gcgtgccgtg ggcgcgcttc    24000
acctctgcgg ggaggaggag attcgcacag ggggcggag agccctgccg cagcgctccg    24060
cctcgccctc gagaacagcg ctgcggaccc cgctgcccct cggagccccg gctccctgca    24120
gccgccaggg ggcgcgtttc cctatgcgta tctgctcggg tcaccggctt ccagaccctt    24180
ctctgtccgc acactaccac ctccatcccc cttcaggtgt ggcctgctgc agacactggc    24240
ccttgggttg cttgaatacc acggggcctt cgcatgtctg atccttctgc ttggaagcct    24300
gcccccctctc tctagtgctg gggtgacttt caagcttggt cactctcaag cctcccagag    24360
tcctccgtga cccagcatcg tgcacctgtc ttccctccaa caggtgctgt tatccatggg    24420
tttctgtgcc tcatccactg agcaaggtga cgaacatcca ccctcctccc aatttggggt    24480
cggcagtgtt gtccaatggg tgggtggatg acagggtctg aggtctgagc acagggtct    24540
tcaccttgtg cttcccaccc cattccacct ggccttcctc aagttcaaga ggaaaaccct    24600
tcagaccatg gagtggggag gtgggggggg gggcttccc cagctggctc ccttcaccta    24660
cctgggctgc caggacctgg cagcggcacc ttcttggagg caggtgtggg tgagccctgg    24720
atcttgggaa caggctgagc cagcatgggc ttgggagaga caggcggctt ggctggcttc    24780
cgggaatccg tgtcaggcgg gggcagcggg ggaagatgca tcaggtcaga gggcggggt    24840
tctgcaggtg ggggcggcgg gggcagctcc ggggcccag tctgctcaga ggtcggcctg    24900
cggcgcacgg tgcccgtgcc attctggtac acagacagtg gcggcggcgg ctcaggacct    24960
gcttcccgct ccttggcctt gggcggcgc ttgaccgtgt cagactccgt caggatgaac    25020
ttgacgctct cctgctggct ctgcttggct cggatgcgcc tcttgagcgt ggcactggcc    25080
tccactctgg ccaggggcgg gccctcccca ctcgcctctc ccttggctgg acctcgagac    25140
cgctgccggg cgctcccatc ctccacaaag tggccgtggt ctgcaggccc ccctgactcc    25200
ccaggcgccc tgcgggcggt ggccaggagt cccgtgacag gcccgctgag ggtgcgcgc    25260
ctgttcacca cctcgccgtc aggcccaatg gcttccttgt gcttcaccga ggccagcacc    25320
gtggccaccc ggcctggctc cgggctggc gggcggggcg tgggtggcc ctcgggggc    25380
ctgcgggctg ctcggccccc accccaatg gatgacagct ctagcatggc tgcgatgctc    25440
ttcacgctgc cagcgctgcc tgtgtccacg ctgccagcca ggtcgctggc ccgccggcgc    25500
tgtgcccgga cccccagccg gccatcctcg gtcccagccc cttccgtctc agcatctggt    25560
gccgactcat ctgccaagtt ggcgctggcc atggctgagc tggagcgctt gggcgggggc    25620
ggggcggcc ccttctttcg gggccgcacc gcaaaggact ggctgcggtt gacgttcttg    25680
tcggttccgg cgggcgctcg caccgagtgg ctacggccca cgcgccgctg gacggtggcg    25740
tagggccccg cggcggctgg caccagcagc tcgtcccgct ctggctcgct gtcggatgcc    25800
gcatagcgat tcaggctgtg ggcacgcttc ttgggccgcc ctggctccgt gtcagcctcc    25860
ggaggcaggc acagtgtggg cacgggcggg gggcggccg cgggcacggg cccgggcccg    25920
ggagcggccg gccctgcgtc gctctccacg ggctggggca gcacgtaggc aaagccgcgg    25980
```

```
tgtgtgggtg actgaggcag cgaacggggt gacatgggtc gttctgttgg tggcagcagc    26040
tgcggggtgg gcttcacctt ggctgtggct ggggctggac catgaggccc cccagggct     26100 tgaggggagc ccggctgggc tttcgtgggc gtttggggag gtgtgaagtg gctggcacct    26160
ggcggaagga ctgccgcggc ttgccaggca ccggaggcac gctggcccgc ttgacgctgt    26220
ggccgtggcg gctgggccgg gtctccttgg gtggggtgcc aggggctggc ccttcgtcca    26280
gcaggtactc ctggcttcgt gacatggggc tgccgggccc aggggcccg tcccccagca     26340 gctcctgaga gctgctcatg tgccgcgcct gtccacccag gctgggctcc tgccgcacgg    26400
aggccctcgg cgtcggggc aggtggttgg agggcttctc ggcagtggtg gcggtggtgg     26460
cggcggcggc ggcgccccc tcggccgggc cagtcatcgc agcctgcagc tcaccactga     26520
gctcgctgtc ctggaaggtg gtcatcttgg gagactggca gtcagccggg gcaggctcgg    26580 gcggggagg tgactcaatg gccatcacct cgagcgactg cggggccttc cggcgcaggg     26640 gtccccctc gaacttggcg tactctgcct tctgcagctc cgccagtttc ctcactgcca     26700
gcatcagctt cttctggtgg cctgggtagg gcatgggcag gtcaggccag ggagggcggc    26760
agggaccaga aggcggagga gcccggggcc ggggcctca cccagcttgg tgatgccgat     26820
ctcctgtagg tcttcccagg tgatgtcggt aatgaagtcg atgttctcat agccgttgtc    26880
caccagcact ttgtagtact gggccaggcc gatcatggac agccacacag ccaggttcgc    26940
ctgtggagca ggggacacgg agggcagccc gagctagctg tccacaccct gctcgctact    27000
ccgagctttc ggggtgggg gcaccggggcc agcctggcac agacagacag aaggacggat    27060
agacaggcca gaggtgtcag cttcagagac agcgcgacct cagtaggagc ccaaggccag    27120
cagcacacac gcatgtgcga gcacgcgcac acacacacac acgggtgacc ctatcctcgg    27180
gacaccgttt gggggggagg caagaacgag cttcctcacc tgccaaggca gccgtgggga    27240
cggcaccccg ggggacacgc cttgcacgtc atagacacgg acacacgca ccaccgaccg     27300 gacacgtgta cgcacacggt gcatcccagc catacgcggg caccgacact ctccacgtca    27360
cacgcacgcc ctctcgccac ttccacaccc tcactgggca cacgtcacgc acgcgtggaa    27420
ctacccgtga tgctctttac ccagaagcac gtggtggctc cctgaaccac gtccacctgt    27480
gcacactccc agctggatgt cactcgccca ccaacacgcg gcacacttcg ttaccctgg    27540 gtgcacagag caaagcaggc ccgcgggatg gggacctgtt cgttgggagc accccgagc     27600 cgccgacgga gcacgctgag catgaacccg ccagtcgccg acccacagcc ctaggggctc    27660
cgggtggcca cgggatctct cctcaagccc agcccgaggc tcagagaggc agcgtagatt    27720
ccacaggcct ggggcccgcc ttgcgcaggc ccagaacctg tcacaccacg ggttgacggt    27780
tagccacggc acgaaccgtg gtctgtgtgg gcgtccgcca tccacacagc cagcgcgtgc    27840
ggtgcgatgt gtgggtgtgt gcacgcagtc gtcagcgggc gccttggcta tatttggtgc    27900
acgcgtgctg tctgtacaca cgaagcaggc ggacaccctc cccgcgcacg tgtctgggtg    27960
cacacgcatc cgtcagcacg ggggcctcta gcgtctgggt gggtatgcgg tgggcagtgc    28020
tgcggggtgc caggcgggtg cccgggtggc tgcccgggtg tgagggatc tttgcgggag     28080 cgcgtactgg agaggggcac cctcccggct tcaggctccc cttgccctga cgaacccccag   28140 aggctgtcac ccctgccccc agaaggctgg ctccagcacc cgtgacagat aaacagaggc    28200
catcctcttt tctctctctg gagccccgga gggcgggtga gggctgtagc cagggaggca    28260
gtctgtctgt ctgtctgacc atcctgggca cagccgctgg ggtgcaggga gccttacggg    28320
```

```
tttgtgctca ggcagccagt cgggaatgct caagccgctg atctctgcgg tgatcttctt    28380
ccggtggcct ggcttggtga ccccgatggc cgtgaggtcc taggtagagg agaggccgt     28440 tagcagcagg ctgggggcag ggggtgccat gtcggtcgtg accggcggcc agcctttggg    28500
cagcccacct ccggggtcat gcggctgatg gtgggcaggt cgtagccagc actgatgaaa    28560
ttgggggcat agagttgcag ctggaacgtg gcgagccact ggccgacggc ctcggcgctc    28620
tggaagacac aaggcacccg ctgcaggctc gctcgcctgc ccgcccaccg ggcgtgcgtg    28680
caccccggcc gctgcgctgt ctccttctct gctcagccga aggcctcagc cgctcggtct    28740
gccgtccgcc ggtcccctg tggccgggc tggggcggcc tggcaccggt gccgctcctc     28800
actgtgtgct ccccgacgcc gccgtcgcga gctccgtcag cgtcctggtc tcctcccgtg    28860
gtctccacca gaagagtcca gctgctgtcc gtgtcatggg cttccctgac catcccccg     28920 ttcctgcacc agggacaccc tgtggtgcag cccgtgtaa ggggctcggg accggggcct     28980
cgggtggggc gcctcagcac agccccaca ctccctggcg ggtgggctcc gtccaggggc     29040
gtgggggagg aaacagccag ccgctcacac cttctcagca catggggccc tgctcacccc    29100
cccgccacac acacacacac acacacacac acacacacac acacacctgg               29160
tctcgcctca cacccgcagc cttctacacg cacacacaca agcacacgtg cccggctcac    29220
catcgccacc cacacgcagg cacgtcccct gctcacctca cacccacgtc tcactgccag    29280
gacgcgctag ctgacacaca tgacccacgc gatagataac agctacacac acagactgac    29340
agacggacag aagtacgggc ctggcctgtc aagggccccc cgccacgccg tggccagacc    29400
acgcaggctg cccgggagcc cctccctgct gccagccccg gccctgtacc ttgccctccg    29460
aggctggctc cagcttcctg ggtggctgct ccccatacac ctgccctgcg tgggccgctg    29520
ggagctggga ccgggctgca cctggagaca agagggcgtg gtggggccgg ggcccccgg    29580 ggggccacct cctcgccagg ccggcagtgc cgcgtccttg ctcttacctg tggagccctc    29640
tggaggcttg gcgggccgt ccccagggct ggactcagag accgacttct gcgacaggac     29700
cgtcgccagg agctgcaacc cagacgggat ggctggccag cgccgctctg cacccaggcg    29760
gccccggccc tgcccccaga ccacctacct tgaccccttc ggagcccgca tgcagggtgt    29820
ggcccccact gcttcgtcca ccagccacgc tgcccaggct gccgctgcgg tccccacctg    29880
ccaacacgag ggagcaccct ccgtgggtgc cggcccggct gctgcctggg aagctccgct    29940
gccctgctca ccgggggggcc ccccacgta cctgcaaaag gcttcctcag cacccagatc    30000
tcctcggggg gcgcagaggg ccccggtgag ctgcctgcct gggatgggct tggttcagta    30060
cctgcccgag aacctgtgga ccaggaacag cctcctggaa tctcagacca gccgggtccg    30120
ggggcctgac atggagaggg gggtgtccct ggcctgtctg gccctagctg tctccaagga    30180
gctgagagaa cctcagaaga ccccctcccc accctataca tttgagagca ggagaatggg    30240
gcaagagggc ccaggccagg cagtcctgcc agtgggcctg tggtcctggg tggggagagc    30300
agagggtgta cctcctctct gccagggggag cggggggggg gggaagagg gccccaaaag    30360 cctagatgac actgggcagg ctggccacgc ctcctaactg cccccacac acacacacgc     30420 cgtaccctca ccccacctgt caatgtcctc atcctctcta ggaggtaacc ctctcagtgg    30480
tccccgtctg aaaacaatcc atgccggtg gattcgcccc caaccctct cagtcactcg      30540 gcaccagcca tgctatgctg gcctcctttg ggaaccttat gctctcctct gcctcagtgc    30600
ctttgcatat gtgagccctg ctgtcaggat gctgtgcctg gggccagccc ctcccatttc    30660 tcagggggctt ctctgagcac cctaagaagc aggtctccgt ccacgttccc tatggcatta   30720
```

```
gttgtcacgt ctgttcgtgt atttacgcca ctggcccctg ctcccctccc ttcccagagg   30780
tgagctcctc gagagcaaga atgacgtccg tcattcttgg acgtctgggt caccgtctat   30840
tcctagtggc tggtgcacaa tgtctattaa ataaatgaag gaaaaggtgt gggggtgctg   30900
atgagagcca gcacgacccc actctggatt ccacacctag aagtggccct gccacccaac   30960
acacgtgcac cggcttcctt cgggccccca agcccaggcc tggggggac ttgcctgctc    31020 gcttcacgat ggcctcgccc agggacgacg ggaagtagcc cacccggtcg ttgcccgtcc   31080
ggttgtcatg gatacaaccc ttccaccggc catccggatg ctgctctagg acctgccaga   31140
tgaggcgggg ggtgggggggg gcatgctcag ggggacaccc cacaggccca gtgggcaggt   31200
ggcccccaga ccacccaact gctgcacaag gtgttatggg cgttacgtct ggggtcccgc   31260
ccacccttgc ccgcgcagcc ccgggccacc cttactgtga tgatgtcccc agctttcaca   31320
ttgaggctgg tcaggtcgta attgttgcag taatccttgg tcgcccggac ctgcagggcc   31380
gccgaggcct ctggggacac aggagacaga ccccccccca cagtccttcg agctggcctg   31440
acccagccct gccctcccca ttatccccaa ccccccccca acccgccct ggtcccacct    31500 cgaagcagtt gtttgatctc cttgctggct tgggatgtgg tgaactggtg cacgatgtcc   31560
agggccgtct ggctgtaggt gttcctcacg tgggcattaa tcccattctg tatgtgccag   31620
agggtgaggc ccgtcaggag ccccatgcc cccacctgcc ccagctcccc cggccccctg    31680
actcacatcc agcagcagcc ggaccacttc tgtcttcccg cagagtgcgg cctcatgcag   31740
ggccgtgcca gacttggtct ggcggtttat gtcgatgccg gcttggagga ggagtctaga   31800
aggagggtgg gcgggtggga gcgggcagtg cctcgtggca ggagctccgt cccatccccc   31860
catgggcccc caggtcccag gccctgaggg tgagccagcc ctgccctgcc tcccgggcaa   31920 caggggtct gacagtgacc aagcactggt gcaagtgctg gcctcgtgct aacccgtacg    31980
gcggggtctc ggagaagtca agtgtctcca cgaggtcgcc cagcaagtgt cagggccaca   32040
gcctgggctt ggggctgaag aagccacccc ccaggcccct ccagtgcatc ctttacgtgg   32100
gcggccggag gcatcctttg cacgcggagg cctgatggca tccccgtggc tcctggctg    32160 ctcctgtcac taaaccggga gcaggaagcc cacggccggg tctccctccc cccagccgca   32220
ctcggccata cctgatgatg tcaatgtggc cgttcttggc tgccaggtgc aggggctgg    32280 tgccgttggg gtcggtcgta tcccccggcc ggggctccag caaggccgcg cacatgttgc   32340
tatttagaag cagctggacc accttgagga ggggtcagag aagggggcc cgcacatggg    32400 gcgggaggct gcaggcgtgt ctcccctccc ccaccccagg agggaagaca gagcagatgg   32460
agtcccaccc ggctctttgg ggacacttac cccgacgcgg ccgaactcac aagccaggtc   32520 cagggcgtc ttccccgagt tgtccaccat gcatggattg gactggtgct gtagcagcat    32580
ttcggactgt ggggccgcag ggcgcagtca gactcgaggg cggccgctgg gctggcaccg   32640
cccatgccag ggccctcccc accccaccc tgaggcgtcc cttaccacat catagtgacc    32700
gtgctgggcc gccaggtgca gagggatgtg ccctcgtca gacgggatgt tcaccgccga    32760
gcccgccttc agcaccagct tcatgggctc cttccggccc tgccaggccg catagtgcag   32820
cggccgcatg cctaggagtg ggcagggggc ccgttgggag ctagcccttg acctggacc    32880 caacccaggc ccgcaggata ctgatcccat ggaatcccgc ttcacccag atggagactc    32940 cggactgaca cctcaatcat gggaccattc aggtctctag agacaccacc cctgaccttg   33000
accccctgat ctggctccga ggtccctatc aggccttgcc tttgttgtcc ttgatgtcca   33060
```

-continued

```
cagcagcctg ggcctccagc agcagggtga tcaattctgt gttgccgttc agggccgcgt    33120
ggtgcagggc cgagaagctg cagcgggcga caggcatgaa aaggcaagga cccgggcacc    33180
ccggccttcc gcaggagccc ccctggaacc ccttgccagc cgggcatctc cctggctgag    33240
aactcaccca tctgggtcct ggaagttgac attgatcttc ttggtggagc ccaggagctc    33300
tagggatggg aaagtgacag tgaggggggc tctgcccagc ccctccaggc agcccaagag    33360
caggcagagg gtgctggcta gctctctggc aggctcagag ccaaagctat ctttagtctt    33420
tagccagaaa acatttcatc tctgtcccct gcactcagct ccaggtacca gcttttggac    33480
tgaactaagg tgttggtaag ttcacagagc caaaggctcc aagcctgtcc ccccggggg    33540 aaggaagcca gagctgtgca cccacacagg cacacacatg tgcacatgta ccccctccct    33600
tgggacgctg gctaagcacc tgccgacggc gggagggaga gagccggcac aatctgtttc    33660
tccaaaggac ccagatgggg ccggggtgg cctgggaagg ctggaacacc cggaaatggg    33720
ggtatctctg ggggaagatc tgcattttca gggtgcagcc tcccccatt cccagccctg    33780 ggcctgcccg tgtggttgag tcccacccgg caaggcagga aggggaggca ggctggcggc    33840
ctggtgcccc tgagtgacga cacaagcatg gccaccacat ctacaagggc ccacttgggc    33900
actgggatca gtctgcctga agcccgaggg gcccaagccc tccctttggg tccctagtct    33960
cctcccaaac cgccccccc acccaggtcc tggcctccac cagctgactg tcagaggagg    34020
ggagcccacc gaaaccctcc ctgtgggctc ggttccagcc ggactcaggc caagcccctg    34080
cctgtctggg ccatggttac ataacccatt tgtgggtcag tcgctctgtg agggaggggc    34140
tggcaggaca gaagccccctt tgtccaggcc caggacaggg atggaggcag ggcccccaa    34200 gagcaggaac ccaagggagt tgagtcacag aggggctgct ccaggggctg cttggtgacc    34260
cacagcagcc cccactgccc cagctttggc tctcagccgc gggatgcatg gtgtgaggcc    34320
tcgagggccc acagagccta cgaagtcagt agggctcaaa ttcagagtct cactgggccc    34380
ttactagccc tatagccctg gccttgagct caaagggggc taatgggcc agcctcatag    34440 gcttaagtgt gcgtccaccc ttaaagcatg aagggtctgg cagagagtcg cctccataag    34500
tggcaattac tagttttagc tctgtgggaa tcccacccc aacctctcca gcgagggtt    34560 tctcctgcac agagtagagc agagcagagg ctcctgggaa agaggcgtct ccgctgcccc    34620
actcccgccc tgctcacaca ctttggggca ctgatgtcca tctaaggtgg cagcaaagcc    34680
accctcccct cagtggtcca ggccaaaacc ttggagtcag ccctgagcgc ccaatagtgt    34740
ctccatcagc aagtcctgtt tggctccacc ttcaagacga cctccgaata cactcgggc    34800 cctattattc tccccacggt cactgtcacc accctgacca ggccggcatc tctcaaagga    34860
tcgctgccat cacctctcca ctggcatccc cacttgtacc ctgcccctca gtctttcctc    34920
tgtaccactg aggtcagggg gaccctgtta gaacatgtca catcccatcg ctcctctcct    34980
gaaaccctcc aacagctcct gtgtcactgg gggcgaagac caatgctggc caatggctca    35040
caggacacgg ccctcctgct tcgctttgac tttctcatca gccctcttcc agccacacaa    35100
gcctcagtga tggcgctaca gcacactggc ggccctgcc acagggcctt tgcacacact    35160
gtgtatatgg tggagggggg ctgcttttcc cccatttatc cccatgactc tctcccttat    35220
gtcattcagg actttatcca aatgtcacct gcttggagaa gccccaccgg gctcccatc    35280 tagaacggca accccccttcc tgtccctatc tgttgtgttt ctctctctgg cccctatcaa    35340
taccgcctaa tgattgttgt ctgtctccat cactaaacaa cacgatccag aaggatgggg    35400
tttttattgt gctcaatgcc atatccttgg tggcagaaac agtgcggggc ccatatgaga    35460
```

```
tgctaggtaa attggtgccg aacagatac cctggatccc caacattgct gtcccgtggc    35520
acctgccccc tgggggccat gctcaggatg ttctcttcta gaacactctg cccagctctg    35580
atgtttgctc ccccttctcg ttaattccaa ggtagccagg tctccccacc cctctcacct    35640
ggccacacct gcaggcattg aaattttaga ggggctggag gtcaaggccc cagaagtagc    35700
atagacacca gtggggaagg gcagtcccca tcaggaagac cactccttac acgagggggg    35760
gatcccgctg aggtcccgtc acccctcct cgctgcaggt ctcctcagag gggaaagtag    35820
ctggaattgg tggaggggag cccgagatct tggagcaccc ccaattcctg tggtgggccc    35880
cgggctcaca gggaagtcac acaaccgaag cctgcctggg gttggggagg cgcagttcac    35940
agagacaggc gctctgtgtg acgctggagc aggcacggct ggaggggcct gagaggcagg    36000
ggagaagggg gcaggtgggg acccagaggt ccccttctc tggtccacaa gggcccaagt    36060
cctgcagcct ccacgtggcc gattacataa acttcatccc caacctgccc catgtcttgg    36120
gctctcccag ctcttgtcac ccagtcctct caccactttc ctgggaccgt ccctgccctt    36180
gaggtgggcc ccagactcca aactgcagag gcccaggcag ggggtggggg tgggtctca    36240
gcccctctcg cacgctgccc ttgtggcctc cctccacccc tgcccagatg ctcctccaac    36300
cacagaagcc acttgtctgc cagccccaca gagccacatc tgtccctct agggatgcag    36360
tcctggcctc tgacgccagc acagggcaag gcgctctctc acctcccag gtcaggcagg    36420
gccaggtggt ctcccccctg cccccacccc aggcagagat ctctggccgg ataccgcaag    36480
gaaagtatta gtgggccaag gtgagacgaa acaggcatgt tggtctgtag tgtgcggtga    36540
attcggggaa gggggaggtgg ggccagaaga aagggcacaa ggccagcccc accctggcat    36600
tctccctcca gagcaccatc tccttcccct caaggacagc cgctgagggt cccggtgcct    36660
gagcgtgtga gaggaggctt gcttggaggc agaccctggg gcaacactca gggcttgggg    36720
tggagggaag gtaccagaag tgggtggagg tcacagaaac aactatccag ggaagacctc    36780
tggagtccgg gggtccgaga gagcaccgct ggatgccccc cacccatgg cccaaactcc    36840
agcctgtact ttgctgaatc aaaatacatc ttactccaaa gcaggccagc gttgccatga    36900
caaccgagct aattcatgga gggatttctc tgtctgattt attacgcccg cccctgtgag    36960
tcagagagcc cagatacggg gcccagggca ggtgtctctc ccagaaagca gaccatgcag    37020
ggacaaatgc gaagatccag gtacaagtcc ccaaaccttc cctggacggc ccaatctgat    37080
gcccccgctt cccctgaagc ccgtctgggg ctgcctaagg agacagtcac agcacttccc    37140
gagcacgtat gaagtacctg ttcttcgtgc gtgctcttct gtgaggcagg gaccaaaacc    37200
gcccccatcc tacagatgag gagactgagg actggagagc cggagtcctc ggttcccaag    37260
gtcgcgtgac cactaggtgg aaacctttac cttgtcttcc ctcccttca atccctcctt    37320
tcaatccctc cacctgcttt caaggctcgg ctaaggctgc ctcggcctag aagccctccc    37380
cttctgagcc ctgaggtcgt gaagctgacc ccaactagca gaccgtccct gggcctggag    37440
agcacaagac agagccagcc tgtatatatg tgccctgggt tacctacagt ccctgggggg    37500
gggggggcgg gcgggggag agtgaggcac ccagactgca cgtgccaccc tgcagagtcc    37560
tgcccgtgcc cgcacaggtg ccctgacaca ctgacatggc catacgtgcg cagccgcaca    37620
cccagctggt ccacacaccc atccatccat ctccggtggc ccccggggag gctctgggct    37680
gagctgggat gagtgctggg atcaggactc caagctccca acctttccca ggggccctca    37740
cagcgcaagc tcaggatggc cactgggagc ccctcccc cactgcccag cccctttccc    37800
```

-continued

```
agcagggaag ccagagagga ccagggtctg cggcagggtc tgcacctgcc tggagcacag    37860
gcttgccctg ggctgggcga ccttgggcct ctgctcccgc atgagtaaat ggcccccagc    37920
cggccatgcc tgggcagcca cccccagc atggtcctgc cccccattcc ctgcaaagcg      37980
tgttattaaa catgggcgg ggaggggtc tgacaggac tgtcagtcct gtggtggccc       38040
ctcaccgcca gggccccctc cctccctcca cggtggggaa gcgggcggg gggggggggt    38100 ggcatctgcc tcgcccttg acggcccagc aaagccctcc agctgtcagc ccgtagcccg    38160
ggaagggagg gggacgcctg cggcaca                                        38187
```

<210> SEQ ID NO 32
<211> LENGTH: 6154
<212> TYPE: DNA
<213> ORGANISM: Felis catus
<220> FEATURE:
<223> OTHER INFORMATION: GenBank Accession No. AC145332.28 genomic DNA
      for PKD1 6154 bp contig
<220> FEATURE:
<221> NAME/KEY: modified_base
<222> LOCATION: (1)..(6154)
<223> OTHER INFORMATION: n = g, a, c or t

<400> SEQUENCE: 32

```
atcggtggcg ttggggcggg gtttaagagg ggggggggg ggggcccgg ggcccccggc      60 ccgaatcctt cttgcctccc cccgccgctt tcttcnnccg cccggcgccg gggcccggtc    120
tctcgggctc gggctcgggg ctcgggctcg ggctcgggct cgggctcccg cgccgaggg     180 gcggggagcg cgtcacggc gggggcggc ccagggcggg ggcgcggcac ctggcgccgc      240
ctcccggacg cctgggtccc cctcctgcgg ccgctgacct ccgtccgccc gcgccggccg    300
cgcgcccggc tccttggctc cgcccctaca tcgggcccg tgctcccgag aagcccctc      360 cccaagtgcg ggccgcgccg gccgcgccgg ccttttcgga cagcccgcgg ccccaggcga    420
ccgccagggg ctggggacgg cagccgccgg gggtgggggg gcggtgctgg acactgagcc    480
ccgacacggc ggcggcgcga ggctgagccc gagagaggtt tccagaggtt ttttttaca     540 tggggcgggg ggagggactc ggaggcagtg ggcgggcggg gacccgggcg ccgagagacc    600
cgggcacggg cggcacgggc ggcacgggag ccggcctgcc agaggctgtc agacatttct    660
ggcccgtggt tccgtggga ggtgtcgagg gattgtgaag aggaatctcc caataatgaa    720
ttcggtgtca gggaacccgc accccaccc ccaactgccg tttcttcccc tgcagcctcc    780
tgctctttcc acaaacaatg cagggcaaca gctccctgcc cccagcctc agtctgaacc     840 ccaaccccag ggcagccctc cagcaccaag tgcggtgcag cctcccacac ctgccaccaa   900
tgggggctca acccccatcc ccagcaccga tggggtcaca gtcttgccca gcacccatct    960
gatcccccac caagtgtgtt tactctccag cctcgggcca cagactgtgg caactcccgg   1020
gctggacagt cttgcttaac agacactgac cactccccac ggcctcgtgc tcccagcca    1080 gtgctcacac acagaggtct caccttctg acctcctggg cctccagcgc tcaccttgtc    1140
acagacaggt gggctagggt cgggagtccc ggcccaggct cactgctctc atttgcagag    1200 agggcagat caccacccc cacccctgca ggcaaggct gtcaggagct tttggagggg     1260
cctgcgcata cgatgaccgg ataccccgct tcctacagct agaccatcaa gcaggtccag   1320
gtggagggtg gctggttgg gggcgggaa gcagctggca gtaggatccc ccgatccagg    1380
cagctgatcc ctccccacca tggggtcttc cttggacttt agggagtgag ccctaagtct   1440
ctcagcatat gcctcctggg gtgggggtgg ggggtgtccc taaacacaaa gaccctcccc   1500
```

-continued

```
ccacccttta ttttttttta tttaaaaaaa aatttttttt ttaacattta tttattttg      1560 agacagagag agacagagct tgaacagggg aggggcagag agagagggag acacagaatc      1620
tgaaacaggc tccaggctct gagctgtcag cacagagccc gacgtggggc tcgaactcac      1680
ggaccgtgag atcatgacct gagccgaagt cggccgctta accgactgag ccacccaggc      1740
gccccccctc acccttata gtaaccaatt cctgggcctc tgctagctca gggaccatgc      1800
tggtcacttc acagatttac tgtgtgcgtt ttacaggtga agaaaccgag cctcaagaga      1860
agccaagtga cccgcctaag gtcctagaat ctgaaggtca tgtgtctgag ctttgaaccc      1920
acactggtct ctgcatgtgc cctaggtctg cctctcactg catttgtctt cccggtcttt      1980
gtctttctga gtcgtggttt ccccttgta aaaccgggtt aagaacgatg atagctttcc      2040
ttaagtgttt tgaggattaa tcgtgatgct ctccataaag cattttgcag tagaagttag      2100
taagtgctca ataaatggct tctgtggata ttgtgatatt cttggctctc tctgcctggg      2160
ctctctgggt agcaagtata ctttactcat tccgtatct gcagacccca gcagggtgcc       2220
tagcacacgg gaagcgttac aaaaaataca agaagatag ctgtcctcct caccattatt       2280
tctgtgtttc ggctgaccac ggtaaaccac tctggcccga gcctgacgtt tgcagggcct      2340
ggggcaaggg tacaaacaga ggcccacaca ccaaatgtcc aaatatttaa ctgttataag      2400
ccaggctaat aactcattaa ataaaatagg ctctgtcctc ctaccttgac aaatacgctt      2460
tcatcatggc ccaaaaggcc aagttccaaa ttagaactct ctaattcctc tgagcaatga      2520
actggtcccg cctgcagctg cccgcccgc cccaccccc ctcagctgta tctgtaaccc       2580
acaaataggc accccgtagt cactccccag acctgtaagc gggtaccttg ctgtgtggtc      2640
cactttcacg aactgaagac gagagctgtt acagattctg ctcagttcgc tctgctatgt      2700
gaggctaatg gcctgggagg ggtcaagaag tcctagatgc accactgacc agcccagcaa      2760
ccttggagga gccctgacac tcagccgcca catccgtaaa atgggccagc ggcgctgctg      2820
cctgcagccc agggccgagg ggaaggtcca cgtgaaaaca gggacgtgcg tctgcctggg      2880
gtccccccaa gcctgaggag ggggtcgcag gcaggccggc cgtccgactg ggggtacga      2940 ggatgcagag gcgggacttg ggcagccctc caggaagtcg ggcctccgag gatcccggga      3000 ggagggctg ctgagccagc agaactgctg aagctcagcc tggagtagag ctggaggccg      3060
cctcactgca gcccgggctg gccccccttcc cagctgcacg gcagtctcca ctggggcctg     3120
cgcaagccct gctcctgccc accagctgga ggtgccccctc ccagccccc agagccctgc     3180 tgcctggtcc cttacgtata aagtggggat ggcaagggga ccgtccccac gggctgctgg     3240
gagcacacag catatgtcag ctgccatcgt tcctctcatt ctcgtagacg ccacctctgt      3300
aatgtgctcg gctggtgctt gctacataag acagggtcaa cagccatgcc tcctgtcccc     3360
tctttccgcc cagcagagat gctggagctg ctcggactgg gggggagcc ctgcccggcc      3420 cagcagttac ccctaggcgt gggacatgtg cagtccccag ctgtaccca gagccccac       3480 agaaaaggca aacagttcag ggcctggccc ctgggccaca ggtgggaccc cagagatacc     3540
tggtggaatc ttccagcatt ccctcagctc cagccctccc tcctgcctcc ttctctcagg    3600
ctccttcgtg ggttcagact gttccggatg tctttcaggt gttggggctc acagagctcc    3660
cctgccagcc ttctgacccct acgtattcat ctgccgctcc cagagctgcc tgggcggagc   3720
tcctgtactt acagaggagg atggaggga cacgcaaggt gtcgggctgc cgagaagggg   3780
caaggtcatg ggagagctga gcccagcagg atgggtttta tcatgttcca gctgtgtgcc    3840
cttagacgta tgactctacc tctctgaacc tctgtttccc catctccaaa accagcgtgg   3900
```

```
tttctccttg gcacagccat tgtgaagacc agataccttc tggcggtttc tcaaaaagtt   3960
aaacatagag ttaccatgtg acccaccaat tccactccta gtatacaggg aaatggaaac   4020
acatactcaa aaagatattt gtaccagcac attcacagca gtataattcg taatagccaa   4080
aaagtgtaaa caactcaagt gtcccccagt ggatgagtgg gtaaatcaac gcagtccagc   4140
cacacagtgg aatattattg ggccataaag aggagtgaag tgctacatgc gcccccacca   4200
cctggatgaa ctttgaatca tcatgttcag tgaaagaagc catatatcgt aggattccat   4260
ttatatgcaa tttccggaac aggtgaatcc atagagacag aaagtaggct ggtggttgcc   4320
aggggctggg ggttgagtgg ggagggtaa gggggagaga gggcacagag gtacagggtt   4380
ttcctctggg gtgatgaaaa tgttctggaa ctaaacagag gtagtgattg cacagcaccg   4440
taaatgtatt aagagccatt aaattgttcc ctctaaaaat ggtcagtttc aggagcacct   4500
ggctggttca gtgggaagag aatgtgactc ttgatctcag ggtttgtgag ttcaagctcc   4560
atgttgggtg tagagaccgc taaaaaataa acaaataaaa cttaaaaaaa tgttttttgag   4620 tttatgtatt tattttgaga gagagagaga gcgtgcgcgc gagcagggta ggaacggggg   4680 gggggtggt aaaagaatc ccaagcaggc tctgcactgt cagcacagaa cctgatttgg   4740
gcttgaattc acaaactgtg aaccataac ctcagccaaa atcaagagtt ggacgcttaa   4800
cccactgagc cacccagtct ccccaataaa taaaacttaa aaaaaaaaaa aggttaattt   4860
catagtgtgt gaaaacaatt aaaacaaaaa cacgcccagg ggcggccggg tggctcagtg   4920
ggttaagcgc tgactcttga ttttggctca ggtcgtgatc tcacggtctg gttcgtggga   4980
tcgagccctg tgtcaggcac tgtgctgatg gtgcagagcc tgcttgggat tctctctctc   5040
tccctcagaa cgatgtcaag ttcttctgct gttgtccacc ctggcaggat ggagcacgtg   5100
gcatctggag cggacagagg gagaaagcaa gcccagggga aggaggaagg tggggaaggt   5160
actggaggga aggttcctgg gacccagggc ccagcggcat ggtgggggga tgtggagcca   5220
gaggaaggaa gggaggtgtg ttgctgtttt taagtgtggt gggaagaaac cgtgggattt   5280
ttgtttttcc agttaagagg atgaggccac agtgcacgga gtgtgagcgt gctaaataga   5340
acaagaagca tgagggaccc cagttttgga ggggtcattg ggcagagggg gcagacaaga   5400
gggtcaggcc agggctgaag aggactgaaa gagcccagac taggattgcc atttctagca   5460
aataaaacta caaaacatcc agttaaacat ttgcattccc catggccatc attagctttt   5520
tagtatgagt atatcccgtg gaatatttgg gatatactta caccgaaaaa ataattatc   5580 gttgcttccc tgaaattcaa atgttaactg gcgtcctgt aatttacttg ggcatcctag   5640 acggcgtgg ggagcagggg atagagggaa ggggtgggg cggagccccc cttgggacca   5700
agcctggaaa atgggtagct gtccgaaggg tggggtgccc cagtggggag aaggctgagg   5760
ccaggcctca cggggcctc ccccgcccc aaacgttgg tttcgcccc ccccccccc   5820 ctaattttct tgttttcccc aaaggccctt ttttaatttt cccttgggcc gggccttt   5880 taaatttgtt ccgccccct tccccttctt gggccgggg gaacccaaaa cccctttta   5940 aggtccgggg ccccgggc aaggcccaa aaccgtttcc tggttgccca aaaaaaccc   6000 cctggttaaa ggtgccccac cggaaaaaac ccggaatttt cggaaaaccc ccggaaaacc   6060
caagggtcgg gccaaaaacc cccccccc attaggccta cccccgggct ttttcccag   6120 gcccaggcgg gggtcgttat aattatataa aaag   6154
```

<210> SEQ ID NO 33

-continued

<211> LENGTH: 26180
<212> TYPE: DNA
<213> ORGANISM: Felis catus
<220> FEATURE:
<223> OTHER INFORMATION: GenBank Accession No. AC145332.28 genomic DNA
      for PKD1 26180 bp contig

<400> SEQUENCE: 33

```
ttaatttgtg tcactctttc ttttttgggg gcaggggaa aaggggaagg gggcggccg    60
ggcccccccc ccccacaaaa cttggtaatt gggaaatccc cccaaggggg gggggccccc  120
ggggggggaa ggttagggcc gggccccccgg gggccccccc ccccccccag aaggtgggtt  180
tccccccccc ccccgccta agtctcgtgg tgtcgcccaa ggcccatcga taactctacg  240
ctcggccgcg gcctctatcg acttgctccg gctccgctcg ccgtcctggg ccgcggcgga  300
gcgcagagcc gcgtgtaagg tacggggggcc gcggggcgag ggccgcaaag cggctcctgg  360
gtggccagga gagagcgcct gggtgaaggt ggcccagcgg gacagagcca ggactctcgg  420
cgaagcaccg ggaaacccga gggtcgggcc agagagcgcc ccctcccatc aggcctagcc  480
gcgggcctgc tacgcatgcg cagccgcagg gctcggcttt cctctccggc ccgtccgctt  540
ccttgcgcat gcgcggcccg cccctgcggc agagcggcgc cccgggcgtg accgcccccct  600
gccggcgacg ggtggggtgg cgtcctgtcc cggtccgtgg ggcgcggaac ggagcacgtg  660
ccttggagct gggagctgtc cgtaggttgt cacgcgttct ctgaacctct aagcctgttt  720
tctcatctct aaaatgagag tgataatgcc tgtctctcca cacccagtgg acccagaggg  780
tgttccctaa atactgcacc tccctctctt gtgcagatgt tctgacctt gaccctact  840
tttcagaagt cgggtccagt gcagacccaa gccttcttcc acaccatgaa cacgtcccccg  900
ggcacggtgg gcagtgaccc ggtcatcttg gccaccgcgg gctatgacca cacggtgcgc  960
ttctggcagg cccacagtgg gatctgtacc cgcacggtgc agcatcagga ctctgtatcc 1020
tccactcggg gaaggacgcc gggtgggggt gccagcttag gcaaaggacg ggtgcctggg 1080
gtgggaagga tgcagcagcc gagccagacg gtggaggcct cgagggttct ggctccaggg 1140
ctccgttcgt cacgctcctt aacagaccct agcaggtgaa ccccctggag atcacgcctg 1200
accgcagcat gatcgcggct gcaggtacct gtaccctcga ccccgaccct ccatctctgc 1260
tgagcctctc caggcacagc cactcttcag tttaccctgt gcccctaggt taccagcaca 1320
ttcgcatgta cgatctcagc tccaacaacc ccaaccccat catcagctac gacggggtca 1380
acaagaacat cgcgtccgtg ggcttccatg aggacggtcg tggatgtac agggtgggg 1440
aggactgcac tgctcggatc tgggacctca ggtgtggggc cgtgggtagg aggggcctgc 1500
tgctggttgt gtgggggctgg gggccagcca ggagaccgtc tcgggggcgg gccctccaag 1560
cagaggctga gatgggctt cccgagcggg tgatttattg agggcagtga caaaagcagg 1620
gtagcgcagg ggtgaagcca caaaaagaag agcccggcct cagcctgaca ccgtagagag 1680
ttttggagca cgaactgcaa tcaagtgcca ccttgaggcc aggggccgcc cccgggggtg 1740
ccgaatgcag agagcacgtt gtgggggggct gattgcaccc aatacagcgt gtgcccccgcc 1800
ccaaaggtcc cgcaacctac agtgtcagcg gatttttccag gtgaacgcac ccattaactg 1860
cgtgtgcctg cacccccaacc aggtgagggg tgcgcacggg gccgggccac gaggtgtgca 1920
ggaggggcggg aactcccccc ctcccctcacc tcccctgcac cccagcggga gctcatcgtg 1980
ggtgaccaga gcggcgccat ccacatctgg gacttgaaga ccgaccacaa cgagcagctg 2040
ataccccgagc ctgaggtctc catcacgtct gcccacattg accccgatgc cagctacatg 2100
gcagccgtca acagcaccgt gagtcctggg tgtgagcgcg cggggggaggc cagtccacc 2160
cggccccctta tcctccttac tcctccgcgt ggcttattcc ccagatgttc cctcacactc 2220
ccccaccccc cgcaggcctg ctccccccac cctgggctcc aacccagcca caaagccag 2280
aaacccgggt gtcgatcctg acgcccccctc tcgctcctac catggctcat ccagcggctg 2340
tcacctccac ctccagagcc tctcgattct acttccctct cctccccgtc tcctcctggt 2400
cccagtttgg cttgtgtccc cgcacatcgg ctgcggccgc tctgtgtcct ccctccgccc 2460
tcactgatac cctccagccc tgtgccactc tctctcagct gcccgagggc tccattccct 2520
gcacagaccc ctaggtgacc tggctcttca ccctggcctt gggacgccgg ggtttagccc 2580
cgatgccccg tctggcctca tcttctccct gtaacgtcct tacatctcaa cagatcagct 2640
gtcccatggt gtcccccaga ccgcccctcct tctgtccaca ctgtctgagg ggcccgactc 2700
ccttctcatt cttcacactc ccattggcca gcagcactca cgaaggccac gcgcggcctc 2760
tcgctctcag cttgccgggc agtccgtgcg gcaggacca gaggtgccgg ccacacgtcc 2820
cgggccccca gatctctgcg tgtcgagtgg cagcccctgg gtctgggtcc agctgccagg 2880
gcagccttcc ctgtgcgtca gatggaaggc tccaggcttc ccatgactcc ccctccgccc 2940
gcagggggaac tgctacgtct ggaatctgac tgggggcatt ggcgacgagg tgacacagct 3000
catccccaag accaagatcc ctgcacacac ccgctacgcc ctgcagtgcc gcttcagccc 3060
tgactccacg tgtgtgcggg ctcaggggggc ctgatgggtc ggggcctgcc tcgtggatgg 3120
cggaggggtg caggggtggga gtgactgctg atgacacccc cgccgcactc acgccccctcc 3180
ctaggctcct tgccacctgc tcggctgacc agacgtgcaa gatctggagg acgtccaact 3240
tctccctgat gacagagctc agcatcagga gcagcaaccc gggagagtca tcccgaggct 3300
ggatgtgggg ctgcgccttc tcgggggact ctcagtacat cgtcaccggt gagcccggtg 3360
taccggccct gtctgtcccc atccccgcca gccccagtg ctcctgccct ggggctgcgt 3420
gctgagccac tgcttacacc ctccccgcag cctcctctga caacctgccc cccctctggt 3480
gcgtggagac aggagagatc aagagagagt acggggggcca tcagaaaagct gtggtctgct 3540
tggccttcaa cgacagcgtg ctgggctaac ctgggccccc tcggagccgc aggcagcgt 3600
ccaggcagcg cctgctgaat acgtctgttc agatgcccgg ctcagaggga acctccaccg 3660
gcccaggcca gctgccccctg cctggctacc ctggtcctcc ctccagggcca 3720
ggccggtatg gcctgggatc ctctcagctt ccagttgctt atgtggatgt gacaggcagc 3780
cgacctgagc cagcctaccc tcgtttcaga aattccagag ccacatgact agggggatcc 3840
gaggctggtg tcccgtccca agccagtgtt ccctccaccg cctgcccgtt ctgtgttctg 3900
aagccacaaa gaacaccgtt gcaggcaggt gcaggggttta ttagcccggg cggcagccac 3960
cctccttgcg actgatgcg gggacggcca gctggctggg ctgtggggccg ggtcgggctc 4020
tgaactcagt ctgggaggta ataaaagcag accgacacgc agatgttgct gggggaagcag 4080
atgtcgatgc acaggtagac cagccgctgc ctcccgggtc ctgggggaag gggcctgctt 4140
gagcccccagg ggctcctca cccttctctc cagactgtcg tgcaggagcc cgggcctctc 4200
```

```
agcacagccc caacttaccc tctgctcgac gggcccagta aatgggcgtt ttcgtgcaaa 4260
ggtgccgcac cgactccccc acctgggcgg ggtccacctc acggtcccca agcaccgcca 4320
gcagctcctg gacgtagcgg gtgtcctggc tggggccgtg agaccctcgg gcctgcggag 4380
aagactcctgg tgggccatgg cactgggcca cctgcacctg ccctgctcgg ggcagggcct 4440
gtcccctgga cacgctggcc cagtgccggc accaccctca gctcttgtca gcagcctcag 4500
ccaagggaag acagggcttc tgttccctga aaccagagct ccggcccgtt gcagggccgg 4560
gctgtacaca ggacccttg tcccctggcc ccggagcct ggccgcatgg gccgcacggg 4620
ccgcacgggc ctcttacct gtgagctgtt caccagcagc tctagggtct cgcgatctcg 4680
gggttccatc gggcggagga agcaggcccg gtgttctgag gggcggtaac agacgcagcc 4740
ctggggaggc aggcgggtga ggcagggcca cctgtacatc cgtgggtgct gaccacaccc 4800
ccagcccact cacgctctgc ccatcgaaca gcaccgccca gctgtggttg ctctgagctg 4860
gggtcacccg gatggtcgcc acgttccggg ccgtgtccac ctgggtggtt tggttggacc 4920
ggggtgccct ggggccggg agggtcagac ggagcatctg cagcagaggc tgacatcagg 4980
aagccagagc tcagctgggt aggccggggc ggccccgac acgcccccag ttctccctgt 5040
gaggtttctg acccctccac ccgcctgggc ctcctgcctc tgctcagggc cctggctcca 5100
ctggaaggct gggatgtgct gtcctccccc cacctcccag tgtctgtgtc cctggccggg 5160
tcctgaggag gagctcacct tgggagggc gtgagtgaag ccaagaagcc ctccagccac 5220
gacccccgca gcgccagtg ccagcagcag caggagcagg ccgggggtct tccagggctt 5280
ggccttcacc tggggcaca tcgcagtccg tggggcctag agcagagacc ggggagcagg 5340
ctggttcggg aaggcgaggg gtgggaggtg ggcacttgcg ctcctgtccc ctgcccaggt 5400
caagccctgg gtctctgtcc ctggagaggg caccaggtgt ttggaggcac tcacctggcc 5460
gggcccgggg ctctcctcgc agcagcccgt ctgctccatg ccgcggcct ggtgacaatg 5520
cgctgattgt ctgctgcccc ttgcagtcag ctggggaaac ctcggtacag tgatgagcca 5580
acaaccatcc cggcccctc ctctcctgcc cccttgctt cccgcagcc cagctacctg 5640
atatcagggt cagagccggg acagcccca tccttgcggt gggggtgggt gcttgtcact 5700
gtgcctggct ctcggacacc tggcctgtgc tgactgagca ctggaagtgc atggctgtcc 5760
gggaaaccag gtcccactga ttggcaccga gggcggccca ggcagaacga ctttacagag 5820
tctgcttggg gacgggctta agttttctca agaggctgtt ccagtctctt tactgttact 5880
tctggattcc tggggcttgg ctcgtggcaa accatcaata aatgcgtttc atgaatgacc 5940
ggtaagggag tccgcgctgc ctgtgtcctt cgatcccatg tccccccagc cgcttcccaa 6000
ttcctcagac gtagccgcag gtgtgagacc aggacgggtc caggcagcct actggagccc 6060
ccgcacacct gggggctgccg gcccggccct gccaggggtg gtttcctttg gggccctgct 6120
cccagcctgc gtctccagct tcttcaggac gcgggtcgtg acagggctcc gccaggaccg 6180
ggcagctcac aggatgtgtg ctcccaacaa gcttcacacc ctgtggtcct tgcctgtggc 6240
tttcctctgt gccttttcc taattccccg gaacccactc acccgcccct ctgtaacggg 6300
cctgggatgc ggtgtcgtcg tggtggtcgg caccccggct ctggaaccgc gatcccagaa 6360
cacgtcctcc ttggagaccc ccacacccac actgggcgag gctgctgcag cctctgcacg 6420
agggctgctg tcaaaacacg ggcaaagaac gccagagtca gcgcaggttt gagagtttaa 6480
tacagatttg ggttcacaca gtgcaacagg gagagagatg cggcgcactt gggctcccgg 6540
gccgctgccc ggcggaagtg ttgccggctg ccgcacctgc cgcgtgctcc tggtgtgggt 6600
gacaacgccc tgacaggcct gctcaatatc cagacccacc ttgagccgac ctcgcagagc 6660
caacgtcagc accaccaacc tcacaggtgc cggccgccct cgcgctgccc cgccgcagag 6720
ttcaaacccc agacaccccca ccccggccct gggaagagct gcaggcttgg gacacccttt 6780
attgctatga gaacttaaga gattcagtga aggagcggct ctgggctag gagagaaact 6840
gggggcaaat gtcagtggaa tacagggaga ggcgccagga aggagtcggc caaaaggaac 6900
agcttccag gccccgccct acaagtacgg ccggacagtc tgcttctcag gtcagcaact 6960
taggggaagag gcagaaaagg ccagggccca ctgccaagga cccgtggcta gcaggtggac 7020
ccagccagtc cttccgctgg cctcccacaa ggggctccag agccgacacg agcggcctcg 7080
cggaccactg gcatctcacc cccacccgga cagggcgcgg gaggacggga agacgtcgga 7140
tgccttgtaa aagggcttcc tgttcttggg gacacctctt tcctcccccac ctccccctcc 7200
ccacaggggcg cccggggcga caggcattcc ttggccagca catgccttta gccgtgctgc 7260
tggctgcggg gcacggagac ttctccaggg gattttccc tacaagacag agcacagcta 7320
ttaattaaca cacttaagat tcaattccac cgtttgacaa aagttgttca aaactgtaaa 7380
aaaataattt ttggtaccaa cactactctg agctctctgc cagctgccc agagttcagc 7440
aaaggcatcc acaccctctc ggctgctcag ccaacgcttt gctcagttca agtcagctgg 7500
atttaaacgc acacttgaaa aaactgaggc ttagcaggac gcagttgcca gaactccgtg 7560
accacatatg aggtgtggca gccctgggta tccgaagcgg aacagaccct tgattgtgac 7620
atcagagtgg tttttaagga agcgtggggc agtggtggtg aggtcagcac cctgcgggcc 7680
agggacaggg tcatccctg tcctccactc ccacccctga ggtgaggagc cgggatcccg 7740
gagcaggatc atccgagacg accacacaga caggccctgg ggctctttgt acaagttcct 7800
cacaacagtc aaaataaccg gaccgtcctc cccttaccc tgtataggag gcccaatccc 7860
tgaataaaat tttcaataaa acatgaaaca tcctagaacct gcttcagtcc catgagcagg 7920
ttgggtaacc accctgaggt gacccgaatc ctggacagat taagcctgcc cttgtcaatg 7980
gcaccggatg cccaggaccc ccacaacgcc ctccaggttt aaaagtgcat cttcaaatat 8040
aagcatctgt aaacaacatc gcccccccaaa cgttttactta caaggttaac aactagtgcc 8100
tttacttaac tccaagtata ctctctgaag ccacctagct gagcggatgc ttaagcccaa 8160
cctattaatt tgggtaagtg gttttcaatt tgtttttattc tggagattaa agacactaag 8220
tctttaacct tgaagggcgg gcaaaaggtc agctatgctg tcaacatag agtcaggaac 8280
cattttcttc ttagacatgc agtcactttc ctgattactc ttcacgtccc ctagagtgga 8340
aacgccggtg agggtcagga tggtcttcag accacaggtg acgcccagga ggatgtctgt 8400
gtccaggcga tctcccacca tgacggtgcg cctgtggtg atgccgtact cctgggacag 8460
gcagtcgaag atgaagcggc tgggtttccc tatgatgtcg gcctggcgct gggcggccat 8520
ctccacggct cggaccagac agccggtacc tgcggggcgg agaggagggg gagagagca 8580
ccgggggtca gaggacaggg gcggccgcg cccgccctg agcctcccgc cgcccccgcc 8640
ccgcacggac ccgcgatgaa gcggccgttc tcgagcgggc gccgttgtc catgttggtg 8700
cctacgagca ggcagccggg ctgctgcagg tagcgcaccg ccttggtgag cttcatgtag 8760
ctgaagtgcg ggtcgaagcc caccacgacc gcgcgcacat ccggatcgag aggcgcgtcc 8820
agccaggcgc cggggctgtc gcccagcagc ggctcgggcc ccacgccac gcaggagacg 8880
cccacggcct tcagctcggc ggccagggcc tcgctgccca gcacgtaggc cttaggggcc 8940
```

-continued

```
ggtgcgcccg ccaggcgctg gcgcaggtag agcgcggtgc agtaggccgt gccgaaaacc 9000
tcgaggccgg cgccgggccc cgccgggccg ccgaagccca ggcgccgcat cttctcggcg 9060
taggcctcgc gggtcttgct gcttttgttg gtaatgaagc cgaggcgctt gccgctggcc 9120
cgcagcgcca acagggcctc gggcgcgccg ggcacggacg tctcgccgcg ccacaggacg 9180
ccttcgcagt cgaacagcag cgtgtccacg tcggccagca gcgcctgggc ccgctcggcg 9240
ctcagccgca cgcagcgggc gtcgtcaccg ccggcctccg ccaccgccgc catggccgcc 9300
cgccgccgcc accggccgcc cgccgccgct gccaccggcc gctccttgca gccgcccgcc 9360
gcagctcccg ccccgccccc ggcgcgctca ttggccccgc tcctcgccgcg cgccgcccat 9420
tggacgccac ctgcgccaat ccgccccgc ctcccgcggg atgcgggaac ttagcgccaa 9480
ccgtcgcggc ccggcactgg gagcggggcg gccattggct attgagtccg aggctccccg 9540
gtgattggct ggaagggagc caaccggcat tcggagagga gcgttcactg cggaaacgct 9600
gcggaggagc ccagagccgg cgctggacgt aaggccgcag ctcattggcg gccgcagggc 9660
agctcgccca ttggcgccgc gtggtcagcc taggtgacgg aggcccctaa tcgagtgacc 9720
ccgggccggg ccggctgccg attggctggc ttctccgcgg caggagcgcg gcggggcgtt 9780
gtggcgggcg gagaggtccg ccttgggggtc ggcgtcacgc ctgcacctt cctgggcggc 9840
gccggccgt gccctccgcc ctgggcacgc tgcggaccga cacggtgtta gcgcgtgagc 9900
cgatgacggc tgagtgccga gtgcagcccg gggctccgtc ccggcaggcc tcgcgttccc 9960
atatctggcc ctttgcaaaa acgctctccc taagggggcgc cggggtggct cagtcggtta 10020
agcgtccgac tttggctcgg gttatgattt cggggttggt gagttcgagc cccgcgtggg 10080
gctctgtgct gacacctgag agcctggagc ttgcctcgga ttccgtgtct ccctctctct 10140
tgccccctc cccgcttgtg ctctgtctct caaaaatgaa taagtgtaaa ataaaaaaat 10200
gtttttttt ttttaaacgc tctccctgtg ccttagtggt actgtgaacg ggttattat 10260
tataaggcgg cgggattgcc ttagtgatca tgcgaacgag ttattacaag gcggcaggtt 10320
taggggttaa gaagacactg cgtagaacac agcacttacc atcatcttat ttggtatcat 10380
tgttaacttt tattgagacc tcatacacag taaaagtgca tcgaccttaa gtgtgcagct 10440
tgatggattt ttccatacct atacgcctgt gtgaacacaa cccacatcaa gccagaggat 10500
atttccctcg ttccagaaag ttccctcaca gtccctcagc cagtcaatag cggataccc 10560
tcccccaacc acttttccga cttctgtcac catgggatga gtcatagcct cctctgcctg 10620
ttccagatgg tctcacagac ttgccatgag tctcgctgct atggatcgac acaatgtctg 10680
ggaaatccac ccttttctgt tgttttaatt gccatgtgag cccttgtaag aatacatccg 10740
tcggtctgtt ctccagtagg tggacattgg gtcgtttgca gtttaggagc attgtaaata 10800
atacttctgt gaacattctg gttcctacac actcatttgt ggacccaggc actcatttct 10860
cttggtgtgaa ataaattgc gattggaact gcaagttcac agtaggtgt atgtttatcg 10920
ttattacttc cagtagggggcc agggagcaga attacaaagg gccgggtttc ttgaaagcct 10980
accctgtgac aggtgcccca gacccccagc tcccagagtg tcaaactcct gctcttctct 11040
tgggcccccag gtctccataa agtctgctct ggacccactc ccaccccaa acccatgagg 11100
taaaaccagt gacctcagtt cccttagggc cctgtttatt tatacgtgtc tcgttttctgc 11160
tggtctctgt tggcctggga acccctggag gagattggag gggccgtggc ccacaaaggc 11220
agggcatgca aagtgttcct gcctggtgca cccactgccc acaagggggag caccttcctc 11280
cctgtgtctt cccgcttagt tttggtggtg gagctgacgc ggggaagagc tggattagac 11340
agaggatcag aaatactgct ttcacccaga agcatccaga gtatatggta cactggccag 11400
tgctgttgct gtgcagccat gggcagcgt gtgcaatacc tgcccgggtg ccttggtctc 11460
ctgggcactg gtaagcatct aggcactgag ccctgctcct cacctgcatc acagccctaa 11520
gaggcagagg ctagtagtgt ccccattcgt ggatgaggaa actgagccag agagagtcac 11580
cggctggacg aggtagggtt gggatcaaac tcagttgact ccaaagtgga gctctgccat 11640
acctgattgg tttgacacgt cctgtgggtt gtagggactg ggaaaggtgg ggcggccagt 11700
gtcgagaggg gaggtggttg tggtcatggt cctgcaggag gccggaaggg acagtgcact 11760
ttatggcagg ggggctgacc ttgagtgagg tgccctgtat agatggggga ggaggagtgc 11820
atcatggtca tgatgtgttc ccgacacacg gtagacgttc agtgtatatc tgcgaatgga 11880
tgccgccagg gttccccaaa gtgaggaagc cccctcccc ccgcgggct atatggggaa 11940
cggatttaga tggtacaagg acaaacacca gacgctattt aattttaaca gccttgcatg 12000
gatttaaatt gtattaggaa ctaatggggg tgccgggggg gctcagcagg ccgggtctga 12060
ctcttgatgt cggctcaggt catggtccca tggttcgtgg gatcgagccc cacgtgggggt 12120
tctgcgctga cagtgaggag cctgctcggg atttcttctc tccccctctc tctctgcccc 12180
tcccctgctt gcatgctcac tctctctctc tctctctctc tctctctcaa aataaataag 12240
caaacatgaa aaaagttgta ttagaaaatg cgagtagcca ttgaatcgtgt cttcgcagat 12300
ggtattgctt ccaatgagcg aagtaaaaaa gggagtcatt tcaaaaggac tcaagtggca 12360
cacaaaacaa ttcggaagca agctaaaatat tcttcagcat gggactggtt caatacgtcc 12420
atcaaagaac agaggttgag cagtcctcat aaagggtgat ggagtctccg tggctctggc 12480
cacggcaggg cagcacagca ccgactctaa aaacacacag ggtgccgctg gagcccgtgc 12540
cgcggagggc tgggtcgggg aggaggctgt ttgggggcgt ggggactccg gttttcctgt 12600
cttttctctgg ccactctgcc tttcagtgac cttgggcctg tctgccctg tacccgctgg 12660
cctgcctggg ctctcgctaa cgcaggacct gggactcact ggtgcaggat gcccttcct 12720
gactcccagg gagccgccag gcaggagctt ggtccgctc cggacacggt tctgagcac 12780
gcggcagtca ggctctctgt ctcccctggg ccggctcctc ctcgtgtcca cccacactca 12840
ggggggtcctc tgcctttgag accctgcct atccccattcc tctggggctt cctctctctc 12900
tctgatggct tcaccattac tcttcagcac atccttaagt gaggtgtctt cctggtcctc 12960
ccttcccaga agcccctcc acaagctccc cgcagccccc ggtcttcctc cggtttgtcc 13020
ctctcagaga ccatccatct gggatcttct tgcctctatg ggccctgagg tccttttatc 13080
cgcacagcag tcagagggat cctttgaaa tgcgttcaca ccgtctgcct atccccctgc 13140
attggcgcga aagcctcatg cagaaagcaa cctcatcgtt atcccagtct gacctctgac 13200
cgtctgacct gtgcttcaca caggccagct tctgccaggc caagggtccc cgggggccca 13260
gctgggcagc cccagcatgg agacagtctc tgcttggtgt ccttgccggg gcagaacagt 13320
ctactctctg ccccgtccct tgagtctctg cttggtctttt tctagagatt agccttcctg 13380
gaggagacca gttctgattc atctgagtct ctgggattca gacagggct ggacacacaga 13440
agataactga tgtgggagag agcacatcct gtgggtttcc agcccatggc tctgtgcaga 13500
cttccgtctc cagtccgccc ttgggcaagc gtcctatcag tactgtgcct cagtttcttc 13560
atcttcaaaa tgggggcgat tggtacttaa atgagaaaat cctgtaaagt gtttagcttc 13620
atagagctaa ttaaatatca cctgaaaaga ataaaaggaa tttgtacatg tgtgttcatg 13680
```

-continued

```
gcagcactgt tcataatagt ggaaaaggtg ggaacgaccc aaccgaatgc gaagactaaa  13740
taaattgtgg tctttcctgg cgatgtaata ttattcagcc tataaaaaga aatgtagtga  13800
cgtgcttcca gtacagatga atctgggaaa cattatgcta agcaaaacaa gccagatgta  13860
caagaccaca tgtgtaattc cacttatttg agaatatcca gaaaaggcaa atccttacag  13920
actgaaagta gttgccaggg gctgggagta ggggagaatg gggagtgagt gctaaggggt  13980
taggtttcct cttggaatga cgacaatgtt ctggaacttg gcggtggtga tgcacattgt  14040
gtgcacgttg tgaatgcact aaatgccatt aaaggcaagt cttatgtata tttattacaa  14100
tttaaaaaat acgcgtaagt ataaaaggct tagcgaagct acgccaaacc caaatcgggt  14160
gcctcccggc gaccgtgcca acaagggagg ctctgacccg aggggtgggg gctggggcga  14220
cgagcgccgc actacccgcg caccacacta ctcgccggag ctgggtggg gcagtgtctc  14280
gccggcggag cgcccgcggc tgcaccaccg gctcagaacg tctgcttcaa cctttcctga  14340
agcttccggg gccgctcggg ggaaccaagc ccttcgcccc tccggcatgg ccacgccccc  14400
gcctcacccc gccccgtccc tcgggcccgc cttttcccc gccccctccgc ccgccagtaa  14460
gtccgttcca gcgtacccac gcccccaagc agccctcc cctgccttct ctcgggagt  14520
gtggccccgc ctctgagatt ctaggcctct cttcctaggc tccgcccgc tgcctgtctg  14580
tcaaacccac ctggctccgc cccgtcggcc tcgtctcgtc gttttctctc gctcgcctca  14640
gcgcggcccg ttgttatgac gacacggtcg taaatccgcc atcttcctgc ggcgcgttgc  14700
gacatggagg gcgcgatggc agtgcgggtg acggccgcgc atacggcaga agcccggggcc  14760
gaagccgggc gggaggcggg cgagggcggg gtcgcggcgg cggcggcggc cttggctcct  14820
ggcgggttcc tcggcctccc ggcgccctt aacgaagaag gtaacagggc ccgacggggc  14880
ctgacagggt cgggcgcggc cggggtgggg acggctcagt cctggttgga ggcgggttcg  14940
agggccttaa gctgtggacg cgaccgaccg tcccagaccc cggttccttg cggacctcac  15000
gggtccccaa ggggtcctgc atgggcctcc acgcgctccc cggcttcctc agaccctcgg  15060
gcctctcctg tgggacgccc atcacccgt gggcctcggt gccactcgc gggtactcac  15120
aggtgcccaa ggctgtgggg ctgctcgtgt gtagacctct ggccgtcgcct ccactgccgg  15180
ccttggccct caggccggcg gtcaggcgcc tcttcgcctc cctgtctggg caaggccccg  15240
tcctcctctg gccccctcc caatgcacct gacgggtttc tagagccccg gctggggtgg  15300
ggctggaggc taggggtgcg gtggggcggg gcctcgcccc caggccccg gctgcccctc  15360
gggaggcag cagagcccag tggtggagag ccggtgccct gcagccggcc tgcgggctcc  15420
atcccacacc tgccactttc gccacgttct ggctgtttgg tcctgggcag gggatgctgc  15480
tgccgccgcc gccgctgctg ctgctaaaaa cgtgttaagc atttacccgg catcagcgtt  15540
tttgtcctca aaccaaccct ggacgctctt gttgttgttg ttgttgttgt tgttgttgtg  15600
attcattccc attttgtgga tgcgggaaat tggggttcaa aggtgtgaag gtgaccaggt  15660
cacccagcta gtaagtagca aggactggac tggatgccgg ggctgtgtga ctcctcaacc  15720
gactccccta acttctcggc tgcgctgcct ccccggaccc cggtgagaag gaagacggag  15780
cccgtgcaa ctgctgagg gcagagccga cgaccgggcg ccctgacagc ttgtgcagac  15840
agaagttggg tctctctcct ccgagctttgt ctcgtgaggc tatagactgg gccagacagg  15900
aggggggctg gctggcgata ttgggggtagt ggccccgtc tccgcagaac tcctattctc  15960
agcgcatggt ttttccttgc tccttcttat tccagctggg ggaggggcag taccactagg  16020
ggcagtgcca gcctggagag ggatctcttc ggaggttgct gggccctgct gtgcttgccc  16080
ccagccttgt cactgttaca cggggcggag tgtgtccct tctgtggtag gtgttccttc  16140
gctggcaaca gcgagtcaga cttggagagc aagggggaa ggttaaaagg gtggtgggca  16200
cgtcagtgct tcgcttgtga ctgcgaacca tctggagggg atcgccctct gacaggtggt  16260
cttgtgtggg cccgtcatgg gtgtggtgtg ggcctctgtt tgctcactga gtcaaaagac  16320
atggactggg ctccttccgt gtgccaggcc tgggtttgac cttgatgtgg gaccggatgt  16380
gaggtggtgg gaactggcag acttttacag aagcacaagc aacatcctcc catcccttg  16440
tgcaaatagc ggggcatctg gagtagaccc tcaggttcag actctggccc gaacactcac  16500
cagctgggtg gtcttgaatc tcaggtcctc ttcctggaat gagtatatgt gctgccgaag  16560
cgagcactat tttcctggaa tgagaatagt catccttatt tccccagggc gctggctggg  16620
tttggggact tccccagtga ggtgcctggc acccaggagg gctcagtga gtgggaagtg  16680
cctgctgtag gacctggggc aggcatggtc agcctacatg gtgagggact tgagcctggg  16740
gtgtggagcc tctctgggaa gttccaccct gagtgtcttc tccagaagag ggagctcctg  16800
cccgttcgga gccgatgaag caatcttaaa ctctggtcct ccactgtccc cagaccggct  16860
tcggtgaatc cctccacctc ttagctgtcc cctggggctc tgtccctca tctctgaagt  16920
ggggctttg ggcacggcag cctcactgga tctctgcagt ctaactctca ggttggggcc  16980
cccacctgct ggatgctgtt ctccctgggg tgggcacctc ttccgcaggt caccaggggc  17040
tggaaggtgc ctgtggtccg atggcacctt tcggtggtt tggcctgggg ctggaggccc  17100
tcccaggccc cactgagcac aggcttgttg cagatgagga cgatgtgcac agatgtggcc  17160
gctgccaggc cgagttcact gccttgaaag actttgttca gcacaaactc cagaaagtct  17220
gccagcgggc ccctcaggag gccctgcctg ccgcccctgc tgctgctgcg ctgctgggcc  17280
aggaggtaag ccctctccac ctgccaccac acgtccacgc acatgtgcgc cctcctcctt  17340
gggctcacct ggtggctggg aagggtgtg ccgtgcccgt acagacctgt gcagccggtt  17400
ccctgtggca cggggtggga cagaggacag gcatctggtc atgggtgagg gagcctgggc  17460
cctgtcccta agagcttggc agtgttcctg gtttcctgga tggcctggga tggccctgcc  17520
ttcccagcag cctctggctg aagcctgcac aattgacatc cctcctttct tggagggagc  17580
ctcagggtct gtcctggctc agtggctcag ggctgtcatg gtggcttttg ttcttttggc  17640
ttctcctcctg ccctgtacgc acggtttctt ttttcttttcc ttttttaaat ttatttattt  17700
attttgagag agagacagag gctggggag aagagagag agagagaa tatcccaagc  17760
aggctccgca ctgtcagcgc agagcctgac gtggggcttg aactcaccaa ctgtgagatc  17820
atgacttgag ccgaaacaag agtcagatgc tcaaccacct gagcgcccag gcaccctga  17880
cacatggttt ctcgggatcc tgcaaagggt ggctctggga gtcctgccac tttgtcataa  17940
acatggccaa ggttgtcatg ctgcacgtgc ttgggcgta cgcatccagg cctctgaagt  18000
tccccagcac ctttgcacgg tggtgttctc gggcccctcg tcggatggca ttgggaaagg  18060
aggctctggg agatgtcagc cgcctcagct cgtcacaggg aatggcccag aggacggtgg  18120
gactacagcc atctccctca gacccctgtg tcttcctggg ccctccccgg tggtgccctt  18180
tcccctagga aggcccctgg acccacatcg cttgatagct tggctgggg tggtgggtga  18240
gggtgctgac cttcatggcct gcacagccag ctgggcttcg ggctgaaact gccggtcact  18300
tctccgggga gccctctgca agggtgctcg ctgctctgca tctggcccat ggtgaccagg  18360
ggcattgag tgacggggct gacccccttag gcctggggtt gagggactag ggtgggagag  18420
```

-continued

```
atgtcggggg agatgacagg tcccaccgca gccttccccat gtggagataa acccaagcct 18480
tccctctcca agccaaggga actctggagc cctgtaggag aatcctttct gtcccctgtc 18540
cccccatggc aggtggtgcc agcggtggcc ggcccgagg agcccatcac ggtggcccac 18600
atcgtggtgg agacggccgc attaacgaca gacatcgcac acgcacccga catcgtgggt 18660
aagccggcgc ggtctcccag tgtctgtcca tgtgtggctc tcagcacagc tgtttgtggt 18720
tagggctgga ggcgagggac ccttgctgct gtgaccctct gctctcctga gagcaaagcc 18780
tggctgagga gggccgaggc cctccagagt gagcactggg caccaagccc tgcccgccag 18840
gagagggag gcgtgtggcc tgcgctcagg gagtcctccc tttgtgcaca gtcacgagct 18900
ggctgcttgc tcctgctgct tccctggtcc ttccctggtc cttctggaat cttccccatt 18960
tttctgccaa ccctggttcc tgctcccccac cccacagtcc actctgatgg gtcaggttgg 19020
ggtatgcaca ggatgcactg gtggctccag ccctgtctgg acctgctgtc tgaccttggc 19080
tgtccctcc cctgtgggg tggcaactcc tgccctgatt ctcacctggc ttttatgagc 19140
gtatagtgcc cagtcagcct ccttgatggc tcttttttaag ttcgagtgcc ttgctggtgt 19200
gcagcgggag acggggggagt tgataggtct ggaatgggaa gggggagcct tcaaagggca 19260
gccggacagg agggtgcagc ctgctgccca gcttggaagg aagggttgtt atctaggggt 19320
ctgctgggca ggagtcttgg caggtgcctg agtgggaggc tgcacaggat gtggggtttgg 19380
gtgacaggta caccttggcc ttgggaagcc cttgggacca gatggggcag gaagagggggt 19440
ggagacctcg ggagggggagc cgcagagtag gcctttctgc cacggaccca cctcaggag 19500
gcagccggac atccgtcctt gtctccatgc tgtcccttcc cctgcctgac attcctgtgg 19560
acagggacat tcacctgttg ccattctgga taggaatgtt gtcatgtggg ggtggggcc 19620
gtgctctggc cctggatggt gtcatatggg aaaacaaatc ccctgggggtt gggtggcacc 19680
tctagccagg cccccttccccg cccccttgac ctccagctgg cccacacctg ctgctcggtg 19740
gctcgtccct gtgctctgag ggctcccctc tgggtaccttc ctgcctctct gtcccccttgg 19800
gagtttccc ctttgcaggc atcttgggtg caccacatgc ctgctaggag tctgctactc 19860
cttgctcggg ggttggctag agtcctaaac tgccagttgc tggcttccca ggattggggg 19920
gccaggggcc acagtcggca ggggctgtgt gggggggccag atacctcttc ccggcccctcc 19980
tgcctcttgg ctggaaacaa acttgctttt catctctgga ctcagggcag ccctgttctc 20040
ccttccttga gccgtccgcc tgcggtgtct tgtgccacgc tctatcccaa gtcctcgcct 20100
ggcagaggtc cctggccttc tggaggtttg cttctgggag ggagcaaaga tagagcatcc 20160
agcgcataag ccaggggcatg ggcgagagat ggccttaatt gtctgagtca cggtgcttgc 20220
gttctgtgtg agaatggctt gtcaacacac tatgtctgac tgactgagat ggttccaaag 20280
aagtggcttt acagccgctt cccacgtgtc gttttttacga gcagaaatta tgaagcgtgt 20340
ttacagctta gcttttgcgcg tcgtcagatc ttttcatcac ccgtgagagg cgccaaggcc 20400
aggcctcctt cctcaggcag ctccaggttt tcgggagca ctcactctcc cgggagggtc 20460
cccagcctgc cggccgcaag acacagtggg tgacctcccc cccccgccccc cgaggcatct 20520
ttcttacctg acagtgggag ccggtgcagt gagcgggggcc ggcccatcca ccgtctctgt 20580
gctgcactc agttgtcctc agagggggca ggaccccctgc gcacatccgg tcctcgctc 20640
cttggcttag gaggggggcac cggtgctcat ggtgggctctc ccccctgggc accttctggg 20700
gtcccggagc tcctctgggc ggcctccagc tcagggagca gatactaggc cctggagctg 20760
gagggcggtc aggacagctc caccgtgtcc tagcaacgtc cccgggcagg gatcaaagga 20820
ggtgcaggg cccgcagagt ctcgaggctc aggctgaccc tcttctcctc aggcggcgga 20880
cacatcaaag aggtcattgt ggccgccgag gcagagccgg gggacagcga gatggcggaa 20940
gccccgggca gccccagccg tcagggcccg ggccttaccg gggagggcga gcaggcccag 21000
gtcaagctgc tggtgaacaa ggacggccga tacgtgtgcg cgctgtgcca caagaccttc 21060
aagacggtga ggccgagctg cgtgctcggg gccctgccgg caggaggggc cgggcctccc 21120
tcccgcttcc gccgggggagg tgcctgagcc ctgcttcctcc ccctctcccccc agggcagcat 21180
cctcaaggcc cacatggtca cccacagcag ccgcaaggac cacgagtgca agctgtgcgg 21240
ggcgtccttc cggaccaagg gttcgctcat ccggcaccac cggcggcaca cgggtgagcc 21300
aggaggcggc cgtgagccgg ccttgtggca cctgcctctg gggggaacgt gaggctgtgg 21360
ctggggggcct ggctgcccct tggccccggg gctgaccctg ccctctttgt agatgagcgc 21420
ccctataagt gcgccaagtg cgggaagagc ttccggagt cgggtgcgct gacccggcac 21480
ctcaagtctc tgacccccgtg caccgaaaag attcgcttca gcgcgagcaa ggacgtgctt 21540
gtgggcaaag aggacacgcc tgcaggtccg cgaggtaggg gctccccgcc ctggcccggg 21600
cctgggtgct gccctggtca gcggtctctt cagggactct cctggttctg ccttaaagga 21660
tctggcgcct ccaccgtggg gaccgttaca tcatcatcgg tgacgggcga acctatggag 21720
acatcgcctg tgattcacct ggtgacagac gccaagggca ctgtcatcca cgaagtccac 21780
gtccagatgc aagaacttcc cttgggcatg aaagccctgg ccccagaggt gcgggcaggt 21840
caggggcgtgg cctctgtccg ctcagtgccg ggctctgtgc cggtcactgg ctccagcggg 21900
aacgggacca agctgccctg ccttcctggt gctcagtgtg gttgcaggggg agacaggaga 21960
ccaatggcat gccagagggc agggaggggt gagggacagg gagctggagg tgaggtggaa 22020
tgggctgtgg ggctccccaa gacgtatgca cggtgcccct ggggcccctt ggctctgctc 22080
cgtgtagtgc gtgcaagtgg gtaccgagtg tctctgcctg cccagctgcc ctccgtctgg 22140
ctgcccacag ccccccggct ccgaggagct tccctgttcc ggtgagggtg gccgtgagaa 22200
cctgctgcac caggccatgc agaactccgg cattgtcctt gagcgtgtca ctggagaaga 22260
gggggccctg gagcaagccc ctcccgcggc gccagtccc cagcccctgg gagacggtcc 22320
cccggagctg ccgctgctgg aggtggagcc agtggagaca gtaggtgcgt gcgcccgctgg 22380
cgagtccctt tggggtcag gccttggta cagggtcacg accctggccc tggagccgtc 22440
cttgctgtgt tccctgggggt ggaaacattg agccactttc tgcagtgatt ttcccccatt 22500
tactgccttc cctgggctca tggtggagct tgccggtgtg ggggtgccca cggctctgtt 22560
cctggtgctg ctggggtcca gcccgcagtg ggtgctggag gcatgctggg acacctcccc 22620
ccgccccgca gcaggtggcc agcgggccct cagccgtgcc taggacccac ccgtgcctcc 22680
agtgcagtga gaccttcccg acggcggcca cctggaggcc ccacaaaagg ggccacgcag 22740
gtgggtggca ggagtggggg gcacctggca gccagccagg atgtgtgttt ggggcccttg 22800
ggtggcaacc cggcctgaca tcccgtgcgg ccccagggcc gaggccgttc acatgcgtgc 22860
agtgtggcaa ggccttcccc aaggcctacc tgctcaagaa gcaacaggag gttcacgtgc 22920
acgagcgacg tttccgctgc ggagactgcg ggaagctcta caagaccatc gcacatgtcc 22980
gcggccaccg gcgcgtccac tcagatgagc ggccctatcc gtgtcctgag tgtggcaagt 23040
gctacaagac caaggtgggt gctcgggccc cgaccccctga cccaagggct cccctctcct 23100
gggccagatc cctgtcccgt ccctgcctct tgaccacaca gcccctcccc cagccctcc 23160
```

```
ggcctggccc agaggccgag gccaggccgg cactgacggt gcgggtccac agaacgccca 23220
gcaggtgcac ttccggacgc acctggagga gaagccgcac gtgtgcccgt tctgtagccg 23280
tggcttccgg gagaagggct ccctggtgcg gcacgtgcgg caccacacgg gcgagaagcc 23340
cttcaagtgc taccgctgtg gccgggcttt cgccgagcac ggcaccctca accggcacct 23400
gcgcaccaaa ggtcagggcc cggcgcggtg gggggcgagg gcggggaggg gtgcccggcg 23460
tgctgaccaa gcccccccg ccccaggcgg ctgcctgctg gaggtggagg agctgctggt 23520
ggccgaggag agcccgcgg ccgccgcgc agtcctcact gaggacccgc acgccgtgct 23580
ggttgagttc tcttccgtcg tggccgacac ccaggagtac atcattgagg tgggtgcggc 23640
aggggcgggg tgggacggtg gcgtggggga gcctcccctg gggtcggctg acctctgacc 23700
cgtgtccagg ctgctgcgga cgacgcggag gctagcgaag ccgcgagat cattgagggg 23760
gcccagacag aggtgagggg ctgggggaag gccgaggagg gtggtgtggg cccccgtccc 23820
cgccctccg cagcgcgagc tgacggtga gcccccaca ggtggacagc cacatcatga 23880
aggtggtaca gcagatcgtg caccaggcca gcgccgggca ccagatcatc gtgcagaatg 23940
tgactatgga ccaggaggcg gggctggggcc cagaggcggc tgccgccgac accatcacca 24000
tcgccacccc tgagagcctg acggaacagg tggccatgac gctggcctcg gccatcagcg 24060
agggcaccgt gctcacggcc cgtgcgggtg caaatggcgc cgagcaggcc accgtgacta 24120
tggtttcatc ggaggacatt gaaatcctag agcatgcggg cgagctggtc atcgcctcac 24180
cggagggcca gctcgaggtg cagacggtca ttgtctagcg tggccgcctg cagggtcctg 24240
ggggctgggc tgggtagggg cgagggccca gagaagaaag aacacagaat tcagatgttc 24300
agaggggatg tgggagtgta aatagttttt tgttgcttta caataaaacg tgaaaatctg 24360
ccacttgtga tgttgccgtg gcagcggcag cctcgggtc tggggccact gtcctggcag 24420
gtttccctgt ggcagcatgc ctgcccgggc caccctctgg actctcatgc caggccgccc 24480
cgcccagggc tccggagggg ctgcggcac cttggcggtg tgtgggtgtc actggcatgt 24540
ggacaggcag cctcctcctg ctgccctgcc cagtgggagt cgtgactcca gcttcctgag 24600
ccccccgc caggtgggtg gaaggggatg ccgtttcccc gcctccggcc cctctcggcc ctggtgctgt 24660
ctgttgggac tggggaccaa ggcttttttcc cttgaggtga cagcgtgtgg ggggacaggc 24720
ctgcactgcg ttgttttccc agaaggtgcc actgaaggcg ggagattttg gatgacctag 24780
ttttgggggg tgggggagg acaggaacaa ggactgacc ttggatggct gaccctctta 24840
tccagtcctg acatggtgct gggaggcggt cagagtctgc ggagtcccgc ttctgatggg 24900
cttaggggca ccagagcagg cccagggtgg atgcccctgc cacctggccg tcagggctct 24960
ccctgggacc ggccaccagg agttccagcg tccaacttca ttgagggggc ggacccagag 25020
cagtccagcc cctccctgga ccagggcctc aaataccccgc ctgagccctg gcaccagaac 25080
tgctgccccca ccaagcaagg agtctgtgtt gtgccacaga cacaccccca gcctggatct 25140
ctgacctaga tcctgagcct cggctgctgc cccatccgca tcccaggtga gtgatgagt 25200
cggcctgtgt gggggtgccg tggctgggga ggactgggct gaccagggg ctggatggga 25260
atgggggtgct tgtatttggg gctcagtttc cctacgatgg agaagggcca cggtaagcct 25320
agtgcaccac tgggagaca tggagacgca gggaacctct gtgtcaagcg ttctcaccgg 25380
ccccccgtggc cccggggctg gggcggagag gggcggcttg gtgtgtctga ctccagattc 25440
gagctcagga gcgtctctgt cactcccagc cgccccgctcc gcgccatggg tgggttccgc 25500
gccctaatgg ccgcgctctg ggcgctgggg ccgccggggg ccgcggcgct gcgcatcgga 25560
gccttcaaca tccagagctt tggcgacac aaagtgtcag acccagcctg cggcggtgtc 25620
attgcgcaag tgaggccagg ggccggggagg cggggccaca gctgggcttc tccggtgatt 25680
ccgccggcgc gtgaccccgc acctgccggt ccctcccca gatcgtggct ggctatgaca 25740
tcacgctggt gcaggaggtg cgagacccgg acctgagcgc cgtgtccgcg ctcatggagc 25800
agatcaacag gtgcggggga cagggtccag cgttcggagc ccaggccggg ctgcagggc 25860
ccggccggga acttgaccgc gggcctggcc ctttgtctccg cagcctgtcc aggcacgagt 25920
acagcttcgt gagcagcgag cccctgggtc gggaccagta caaagaaatg tacctttcgg 25980
tctacaggtg aggggcgggg cggcgggcc tgggcgcgca gggcaggagg gggccggctc 26040
agcgccacca ccagtctcct tcccccagga aggacgcggt gtcggtggtg gacacgtacc 26100
agtacccgga cccggaggac gccttcagcc gggaacctt cgtggtcaag ttctccgccc 26160
ccggctcggg taaggcccccg                                          26180
```

<210> SEQ ID NO 34
<211> LENGTH: 27419
<212> TYPE: DNA
<213> ORGANISM: Felis catus
<220> FEATURE:
<223> OTHER INFORMATION: GenBank Accession No. AC145332.28 genomic DNA for
    PKD1 27419 bp contig
<220> FEATURE:
<221> NAME/KEY: modified_base
<222> LOCATION: (1)..(27419)
<223> OTHER INFORMATION: n = g, a, c or t

<400> SEQUENCE: 34

```
    cgccccgccc cacccccgct tctgacacgc gccttccgca gctgccgggg agctcgtgct  60
    gatcccgctg cacgcggcgc cgcaccaggc cgtggcggag atcgacgctc tctacgacgt 120
    gtacctggac gtgatcgaca aatgggcac cgacgtaagt cccgctcccg ccccagcgg 180
    gcgcgtccgg ggtgggggtg gggggcgcgt ccctctccgg ggctcagccc cggcttcgcg 240
    gccccgcagg acttgctgtt cttgggcgac ttcaatgcgg actgcagcta cgtgagggcg 300
    caggactggc cggcaatccg cctgcgcagc agcgaggtct tcaagtggct catcccggac 360
    agcgcgggaca ccacggtggg caactcggac tgcgcctacg accgcatcgt ggtgtgcggc 420
    gcccgcctgc gcaggagcct gaagcccccaa tcggccgctg tgccgactt 480
    ttcggcctgg accagactca ggtgggcgtg gggggggggg aactgacggg tgtggggtg 540
    gccagtgtct tgctgcccag ggcgggggc gccctcccc ggactagtgt tccggaagca 600
    cccttagggg ctcagttcta gccgaaagga acaattgtgg gatgcggga ggagatgccc 660
    ttgcctcttt ctggagtggg gtccccagtc cgtgccccat gccacctgca ggcagcacag 720
```

-continued

```
tgatctgtag atgcccgcgg cccccgccc tggggcgggg tgtggggtg tggaggggtg 780
ggaggtggag ggggtggagc ctgcaaggga ggagaggctg cccagcaggc cccacttcct 840
ctccctccag gcccttgcca tcagtgacca tttcctgtg gaggtgaccc tgaagtccca 900
ctgaaaacct tcaaggcctg gtcagggccc gctgcctcca gactcgacct gaggaggact 960
ctggccccca cagatctcct tccggatggc tggccaagcc ccagcaagcc gtggggcagg 1020
gctggctgga caagaggctg tggacacatc acaggcccac tcagcctgtc tccccatctg 1080
taaaatgggc tacgacatct ctcctccttg tgaggagcac ctacagggtg ccgggcgcgt 1140
ggctgtgctc aataaacggg agtgagcgct tagccaggac cacacgctgg tcggcttcaa 1200
ggcctccgtg tcctttctta ggactccacc cctgtgaggc ccagactttg tgtgctgcagc 1260
ccagtgggtc ccaggtccca gccctctagg ggaacaggga tggcccggcc caccccgtgtc 1320
acaccctgct gggaactgac gcctccaga ccaggctcta gaatgcagct cccgagtgtg 1380
cttgctttcc ctccgtgcca accgtaaatg cgtccgagga ctcgtgctga gcgcagctgg 1440
ggggacacac acacacacac acacacacac acacatgc gggcagtgct gacagggcca 1500
acctcacagt ccctgccgcc ctctctctcc ctcaggggcg agcaggcagg acgcctcgcc 1560
caggcgggc gggttccttc tcaggagccc tgggctggac aaagacttgg ggagaactgt 1620
ggcctgtgga tcaggatcgg gaacgagcat gaatggggga cagggtgtga ctgacaggcc 1680
cagggaggtt gctggttgga gaaacatctc acgtttggca acttttgggaa ctggcctgaa 1740
ctgtgtggag gacatacgtt tgcttcaaga gcctgcgtga ctttttctca ggtcaccttc 1800
ctaaagtaag gccggggcgc ttgtggcaca gacgggctca cccctccctg cttcccaagc 1860
acccggtctc tgaaccttttg tgccccctcc acgtaaacag gcagatgggg tggccagagt 1920
gctttcctct gggggtcccg tgcggctcac cggcccacac ccgctggtc acgtgcccct 1980
agcagtcagg cggccgggca gccagttacg ggacaacgtg aggactttat tcacacttct 2040
gctcggggaa agggagacatt cagcagcgat gtcgctgaat cctgcactgc ccctcctgcc 2100
agttcacggt tccccaacag agatgccgcc cccgatccg ccgtgcccac ttgccaggcg 2160
gaaaaggcgc tcttgggggg cagtggcctt gggatactag ctaccaggaa cagaccagcg 2220
agaccaagag ctgaaagtac cttgaaatcg gaaaatacct tgcttaaaac ccattggaag 2280
aagagggccc ccagaaggcc acatgtggtg caaaccccgc gtgcgcggcc cggaccctag 2340
cctttcttct gtctgagctt gtctaagtac acgcgcaggg actttttggat ggagtccctg 2400
gagatgtact ggaggaagta ctggatgtcc gcgtcgcgct gtttgaccag gcggtcggct 2460
gtgggcttgc gcatcagatt cttggtcagc tgtcgagcgt ggtctacaga aaggggtccg 2520
tgtgtgagaa cccaccccaa gacggtcgta tcgtgcccaa cctttccgag agacttccaa 2580
cagaagctct gccaggacac tgagaaaata caactaagca aagaaaaaaa tgaaaatcac 2640
ctgttcccca ctgcctaccc atttccttga aaaacatcca gggtgccttg cctttttatcc 2700
tgttattctc actcaagtat actatggggg atagtttccc tccactacag gttctcttac 2760
gacgtaaata acagcggcac agcatgtagc cgtgtgtctg tgtcaggggt cagcaaacct 2820
ggccccgtg gcccgtgagc taagaatcgt ttctcctttt ttttttttttt ttttaaagta 2880
ggcttcacac ccacggcaga gcccaacgtg gggcttgaac gcacgaccccc gagctcgaga 2940
ccctgagctg agatcaagag tcggacgctt aacctactga gccaccaagg tgccccggtt 3000
tttacatttt tatataattg gaaaaaaaga actgaaaaaa agacatttt gggacacgtg 3060
aagattatat gaaatttagg tatcaggggc gcccgttcta ctgaacacag acgggctctg 3120
gcggcctccg tgctccgaca ccacgtgtg gcggacactg accaccagg ctgaagatcc 3180
acccggcct ttagacacgg tccgctgacc tccggggctcc gtcacagctg acgtcaccag 3240
ccctatttct ataaacggac acgcaggctg tttctacttg tgcagtgggt tgaacagtgg 3300
accccccaaa agatccatcc aagtccacag cgcagctcta gaatctgtgc ctgtggcctt 3360
atttggaaag gggtttctgt ggaggtagat ggaatgaggt catcgtgggt tttagggtgg 3420
gccctaaatg ccacaaacgt cctaagagga gaaaggggg ggggtgtgca actggaggcc 3480
acgtgaaggg gaaagggaa agcggagctg ggcgcgacgc atctacaagc caaggaatat 3540
ctggagcccc cagtggcagg aaggagcctc cctagggcc tctgagaga gcaccgccct 3600
gccccaacac tgattttggt ctcctggtct gctgactttg agaacacatt ttgttgtttt 3660
aagcacctcc tcccacctcg gggtcatctg ttacagtgac ctcaggacac taagtctgct 3720
cttataaatg gcacgtccac gacttgcacg gagcaccttg gcgtgaaggc tctggtctca 3780
ccagagcatc cggccgtgc ggggggaggc tcgcccgtcg gtgcgcacac ctgcagcccc 3840
tccctgtgcc cctcacctgg aatggccagc cactgggcca tcaccgacag tgccgtgctg 3900
tgcacttggt cctcgggcac cacctggtct acgatgccca cccgcaggc ctccgcgggg 3960
gggaagagca gcccagctg caggcgcgc tctgccatgc ggtggccgac ggtgttcacc 4020
agggtgtctt taaacctgga acacaattcg cttgctggag gctcccaggc agacgggctc 4080
gcccagggca gagcggagtg cgggcccagc cccgcctt accagaaggg ggcgacgatg 4140
cccagcagag tctcgttcag cccgatgttg tacttgggt tgtccgcacg gacgcggtag 4200
tcacaggtga ggttgatcaa gcagcctccc gcaggctga ctccctgcgg ggggaagatg 4260
cgccggtctg gctctggtgc cgcggggcg cgtcccgacc gcgctccgga gagccaggtc 4320
ccacgtgggg tgtgcgcccc cggggtgctg cacccacacc ggctgggctg gccgtgcacc 4380
acacggactc gggcttgccc gtcagccccg tcacctcgta ggccaccag ctctcggggg 4440
ccagaaaatc tccctcctgt ctgggtggca agccgtcttt cttttcacgg cttcggtccg 4500
gatgctaaaa cgccaaacta gcatccggcc ggagtggtca caacctgtca cggcccacgg 4560
gacccatcgc catcccagc gggatgtcct gggaacccca aactcacacc gccctcatct 4620
cacgcaccgc actgccttga acagagacgg caagctgccg tcggctgtca cgcgcctcgt 4680
gggtcgtcct gactctcgcg accctccgt ctcctggctc agacccttct ggcacctcac 4740
ctggggtgtc ccctgtgttc aggcacactg gttcctgagc gtgaacagcc cctaccttct 4800
cgagggcaga caggaacgat gttcccagat gtgaatctga tccctcctc aagcccctct 4860
ccctatacaa gccctcctgc tgggccgcgt cgaccacgtg ccctggtccc tgccccgcc 4920
ccgcgaagta ccccgtcacc aggtcacgcc tgtctgcagc ctccgctgtg cacat 4980
ccgagggtct cccccaactg ttcccttccc agccttccca aggacaggag ctcttcatgc 5040
cccccccgtg cgctgggctg gtctctggtga ccagcgagg ccactcagga gcggggacac 5100
tcacgttgat ggcagcaatc agcaccaggt tggacaggta gagccgcagc cacagctcct 5160
gcacggccct ccagtactcg gcatagtgcg cttggctctt cccgcacatc tccgtcaggt 5220
ccaggccagc cgagaagatc ccggggcagt cctaacgag tggaggagcc aggggcccg 5280
tcacgtccca tctcctggca gcaacccgtt cccggggccc gggagcccac aggcgctcaa 5340
gacacagtgg gggcgaggtc acgttcaagg tggcaggatc aggcccccgg gagccgaggc 5400
tgggacctcc ctcggactta gctcctccta ctttccagtt tcaaatggga aaaggcaaaa 5460
```

```
caggcaggca gggtcggtg ctcccccagg aacataaaca gcgggctctg ggcacggctg 5520
cgtgtgctgt cccgggcagg ggaactcaga ggcccggagg gggcacacgt tctgatttac 5580
cctcgaggtc aagaacgccg cggacgccag cgcaggccgg gaggtgctgc cgtcagaagc 5640
aagccaggac gggaagggac agcaatgagt tgaggagcca gaactctgcc ctgggtggtc 5700
acgcacgaga cagaagtctg gcctagaagg ccgtgggtcc cgtgtggacg ccccaggtcc 5760
cgccacagcc gccacagagc gggggaagca gacacagggg accgccagca cggcgcggct 5820
ttccagcaaa cactgccggc ccagaggcgg ggcggggctg ctccgtggcc accacgcggg 5880
gccgtcgcgt ggtcacaacg tttctaagtg aatgagatgt tcccatggtt ggagcgtgtc 5940
cggggctgaa gtgacctgtt accgacacgt gaagtacggg acggtcacag gcgacgtctc 6000
cgcgtcctca cgttaagcaa caggaccaag ctcgtgtgca gggtgcaatt ccacgtggac 6060
ctgtgcacgc agacgcttgg aggccgacct gtcgtctccc taggccgcgt gccagcgtga 6120
cctggctgtc acaggcgccc tgggacagg gtgcggtgg ggcagggct gccctgctc 6180
tgagcgcgtg cctccttccc taaccaatgc cgaacgcggg caccctctcc cgccctccaa 6240
ataccccacg cagatcatct gcacgtggcg gggaagaggg cgcccacggt ccggacgctc 6300
gaggaaagct ggtggctgcg ggagagacac cgaggtcatg ctgacggggg ctcgcccgc 6360
cagacggacc ggacgggctg tgatctggga ctcggcagca cgtctgcagc gggccgaacc 6420
gtgtctgcct ttacccccag tgcccacgag cgtgactgtc ttcaaaacag ggtcttcgca 6480
gatgtgacca acgtgagacc acgtgagagc aggggtcctt ctaagggag ggaaacgtgg 6540
acacagagac ccggggtgga ggaggcggga tacaggggtg ccaggacccg cagcagctg 6600
caagaagtgg agagggacg tccaggagag cggagaaaaa cgcgctgctg ttgtcgcgag 6660
ccctcgtgtg cggcctctat cgtgtgtccc cacaagagca cgtcaggtc gcaccgtcat 6720
ctgctgaggg cccactgggc aggccttgtg ctgcagacac agtaggcacc cagccgaaga 6780
cacacggaga cacatttgta agatgacaca gtcccgggga caatgtgggc tttggaggga 6840
cacacgccgg ctccccatcc ccgggggcc gtgccgcttt gagaccgggg cggggggggg 6900
gggggccgca cggagccccg ctttgttgtc gagggacaga ggtcatgggt cttcccagct 6960
ctcgtttcct ggcatgatca atcacgctgt gaaacttccc gaagggaata ttttcagaaa 7020
tttccccgag caaaacactc ccagggaact gcaacacgtc cagacaggtc agcctcaact 7080
gtcacagtga cccgtgccca cgagcgccag ccctgcccct ggagcgccac cctcttcccc 7140
ggggggccac tccacggac tcccctggtg tgtgcatcag accccacccccg agagctcaga 7200
gctggaccaa caccaggtca cacccaggac cggctgaggg ttcaaggaaa gcaggtgcgt 7260
gcccagtgga cgtgccaagc cttgcccgga agagaccgcg accctctgcc tttaacaatg 7320
gtgcgacaag acgtcctcac tggtctctgt agaacggtgg cccttctact gggagacact 7380
catgcggagg ctccccgcaa ctcaaaaggc gacttcagga tcttcctga cacgacgaag 7440
ggcttgttac atcaggccgc gctcccatct acttcctctc ctggcaaagt aggtggggct 7500
gccggagccg gcgtggcccc cgatcctgtc ggtctatggg gtctacccgg cccaagccga 7560
ggaccgcccc ctccccgccc tcaccggtga cacccctccc acagatgtca ttaaacagca 7620
gcatctgtcg gctcttggag gcaacaccaa ggttccctag agaattcaga agggaaaatc 7680
tgccctctga gaacttgact ctaaggccca ggcgaagggg aacgagggag cgtggccacc 7740
agggaacacg cctagtggct ccaccgccaa caggatatcc tggtggacta cccgtcacca 7800
atcagcgcgg gctccaggcc acccctgcag acaattcact gcctcccct gagttctggc 7860
ccgactgcag ggcactgagg ctctccccac agtccggcct ggggccggac tgggcagag 7920
gtcgcggtgc tctgggggga gccatctgcc cacagcatgc caggaccatt gggggccccc 7980
ctggaccagg cccaggacta gggtccctgg tggcaccggc atccgggtct acctggtcat 8040
tctacagcac gtgacgtgtg gacgtgacct cgcagcaggt tcctgccgtg atcggaactc 8100
ggggaaccaa cgagcaccca ccgaagtcac gatgacgcct cggaaggtct tgtcgttttc 8160
cagtttctcc aggctgatgg caaactccgt cagcacctcc aggctgaggc tgttcaccgg 8220
ggggttcttc aactttatca cggcgacccc tagtttgaaa atgaagagga gaaagctcac 8280
acccaggact ggaaaagcac acccaaccat cccgcaccct caacctggcc atgggaagcg 8340
acagttttca ttttttaactt ttggttatta aaattggtta agtttattta tttgagagag 8400
cgagccagct tgtatgtgcg tgtggggaa gggcagaagg ggaaagaga aatcctaagc 8460
aggctctgca ccgtcggcac gaagccccat gcggggcttg gactcccatc tcgagatcat 8520
gacctgagcc gaagtcagga cgctcaagcg acggagccac ccaggcaccc cggttttggt 8580
ttttcaaatg caagtgagat tcacctaacg taaattaact atttaaaagt ggacagtcca 8640
cggggcgcct gggtggctcc atcggttgag cgtccgactt cggctcaggt catgacctca 8700
cggttcgtga gttcgagccc cgccttgggc tgtgtgctga cagctcagag cctggagcct 8760
gcttccgatt ctgtgtctcc ctctcactct gccctcccc tgcttctgct ctgtctctct 8820
ctcaaaaata aacattaaaa aataaataaa taaatgaaag cgggcagtcc aggtctatag 8880
ggacatgtac agtgtcccaa tgctaccacg atctaattgc ggcgcatttc tatcccacac 8940
aggaccctgc gcccacgagc agttccgct cctccccggc ccctggccac tgagtgtcta 9000
ctttctgcct ctacggaccc atctactctg gacgtttcgt gtgcatggaa gcacacaacc 9060
ttttatgtgt ggctcctttc actgagcacc cgttcccca ggccggcctg tgccgctggg 9120
tcaatgtccc cccgctttct gaggcccagt gtctccctgc acacgtgtgg accgcactgt 9180
atctgttcgt gtgctggtgg acactgggtc ccttccacct tgagagtctt gtgactactg 9240
cggccgtgaa cgttcatgag caaatatctg tctgtttatc ttgttcctcc agatgccagt 9300
cctctgtccc caggggagta gaagatggcc ttactttcct gaggagtgag cgagcagact 9360
ctaagaccgc atatgaagga ggaactgcac tgggggttctt ggtcttgct aaacatgttg 9420
gcgggctgac gttcttaaat tctccacgat ccgcttgtgc gtcctgccag cagcggggca 9480
ggccgggggg ggggggcag accagcactt gggacagggc agccaccagc ctgggccagc 9540
tgaggccatc tgttctggct acctggccca aggacagacc caagggctt tcgaagggcc 9600
accgttattt taggctacat tcccctggtc aggaccttag aaatcttcag acggtcaacg 9660
taaacagtcc tctaggagtg agaaccaagt cctgaagaca aacaggctgt tttgagacct 9720
ccggcttctg agggagaggt tacttactaa ccagctacag gaacgtacaa gcgatccaaa 9780
ttcccagaag caagctccct gaacttggtt cagagggaag tttttgaggc tgactggatt 9840
tttatagagc ccggtccagc agaatcaagg acactcaggg gagagggtaa aggtgtccat 9900
gagttgacac agaggacctg gggcgaatcc aggttgcggg gaggtgggc tgaggccgca 9960
gcccccaac cacaggcagcc ccccagctcc tctcgtaggc ctgagcacag cgtgtcccca 10020
aaacctgcaa gtaggcccag ccctggctgc aagccttctc aggacccagg tcgggaacat 10080
tctcaggtag agaaaactca agggtgcttc ttctaccttt tctgtccctt tggagagttt 10140
ttcccagagg ctctgatggg ggtgggaggt ggctcctggc tttaattagt aaaccatctg 10200
```

-continued

```
ctaggtcctg tgccatgcca gaataaaaaa aaaaaaaaaa aaaattactt tactctaaaa 10260
gacttccatt attttcaatt tccacctgaa gagtttagat ggaggagcat accccctcaaa 10320
ctttacaaac caaaacactt tcatcttcat aatgaactgg ggaaaagcac gtgggctgat 10380
gacctttaag ctttgaacgc aacagaaacg gtcttcgtac agggcttgat ctccaatgcc 10440
cttcaggggt ccccaggagc cgcggtcagg aagacaagcg gcgggcgagg agggagcggg 10500
cgtgggacgg cgtggcaccc ctgcttcgag tcctccaggc cccggggcgg gccgagccag 10560
ggaaagccca gccggcgggg cccggcgtag gcgccctcgc ccgaacgtgc ggacgcagga 10620
gcgcttacct ttcgcgggt ccgtctccac cagcacccga gggcttccga aacaccgcac 10680
accgtcccca ccgccggcgg ccggacccgt ccgcccggga accgcgtgcg gcagccggga 10740
ccctacgaac gacagcgcga ggcccgttag ccccgggaccc cagtcagctc cccggctgcc 10800
tccagctccc tgaggtcccc ggcacctccc tgtccccaat cccgccccccc ccagctccct 10860
cgggtccggg gcccctgtct cctccggccc ccctcccggc tccccggacc cctgctgccc 10920
cgcacccccc aactccagcc ccccggagtc acgcacacgg gcggagcagg ttgcgagcca 10980
ggacgcgcgc tccgaccatc agcgccatct tgaccaggcc acgttggagt ctggccgccc 11040
tggcccacgc cccgcctcca gcagccccgc cccacttggc gcgtcaggtg tcgagggcgg 11100
ggcactgccg ggagacagtg gttagcagga gagttgggg agcgccgcag tgacgctagg 11160
tggcggcggc aggatggctg gcgtgggcc gtctgggacg aactctcctc acaaacccgg 11220
aggccaccgc gctcgcctcc acccacgtct gaacccctgg gaggctggca cgcttcccac 11280
gctgcccacc aaccaaagct acggtcaagg cagcgacagc tgcggatggg ggtgggggtg 11340
actgcacgac tcagggagcg tgtgagtccc ggagttggtc gtgagcttga ggccataagg 11400
gccttttgcgg gtagcagccc cagccatccc agcaggcgca acaaaggcaa gcggattacg 11460
ccagggtcat ttctcaaaac cgccccccctg cagagcccga ggactaaaaa gggtgccacg 11520
gggcggggt gaggtggagg cggtgctggt gggcagaaac aggtgccctc acactgttga 11580
caggaccgcg gtgccaccgc ctccttgaca gcaaagggag cacctgattt tatttgctct 11640
gtcctgcatt cagaaacacc gaaagggtcc ccgctcaaca ctggtgtccc ctgccgggta 11700
ggaagccact gtgctgcctg gcaggaggtg gtctcacaga catcccattt gcatatggac 11760
acaggaaggg ccaagctcag ggctgggtga ctgaaacctc aattgttttt tacagtttct 11820
aagtctttgt tgtgacacaa ccgacttttg aggtggaaaa ccatttttc attatttcgt 11880
ggctaacata gcagcagcca aggagatcgg tttctggtca ggcaaaatgc caagctcctg 11940
ggaatataag gtgataagag catctctctc tcggtgcagg tcaacccaca gaatctgccc 12000
aactccctgg cgtgctcacc ggctgttctg ctcagactct ggaagtgtgc ctgcggaaat 12060
gaaccaagat gcggtcgtgt gttttttagtg cctgagtttt tagcttcaga agtgaagctg 12120
tttctgggggt cacagacagg aaggggcag cgaaggcagt actcagtctg cagtctaatc 12180
ccgtttattc aacacaatcc cttcactcta cacaacaaag tacaaacaca acagcgccta 12240
aaatgctaca agttacaaaa ctcaaaacaa caaatttata gtactgactg tacaataaaa 12300
gccaaaaaag caatgtacac gttgccacgg taacctgcga gaccacagtg aatgacaggt 12360
acaagggggg gggggggggt ccttgatggc cctgtgagtc tggctcccaa cttgttcacc 12420
aagtgcagag agaaaggggag ccgcgggatg tggtgtgtgt gcatgagtac gtgtaaaacc 12480
aaccatttcc ggtgatgaac acaggggtgtc tgactgtaga tattggagga ggaccggagc 12540
agggggagca gggccaggcc agcaggatca gcagccgcac ggaaagcagg ccccttcctg 12600
agggacccccg cagaccggca agcttgggca cgaccaggcc actgcccag ctcccaccc 12660
cgggctgggg ccgcactgcc acccgggagcc ctgcgttgtc cctgctggct ttgccactga 12720
atggactctg aggaactgcg aacgtgggag cttttctagcc agagacctcg cgggcgtctt 12780
tagaggcaca accccaagcc actaacgctc ctgcagctag aactctgcct tcagaggaaa 12840
cgcctcaatc gccgcttcg aagcctgccc tgagtgagga atttctctcc taccaatcct 12900
cctgccgcta cacaagtgac cgaactgaag tggacggac aaagttccag ggtgcagagc 12960
cccggtggcc tgcttatcgg gaggagttgg agctggagcg gctcctgtgg cggcggcggc 13020
cgggcgagcg ggaccgccgg cgcaccgggg acctgcgtct cggggagcgc gacctgcagg 13080
gagaggaaag accaagtcag acaccgaagc tggcaccaca gacacagctc cgcatctccg 13140
gccacagggc gaagctggct tctggaagga acgttctgtg gagttgcaca cgtcaatgct 13200
ctaagccagg acggctctct gacggcaccg cctgggagcc cttccttcct gagggccgtg 13260
cacggggcgg ctcaacacca ccagcagagg agggccgtgc tctggcctct gcccagggac 13320
agccccctccc tcacctgact caaattcctc tcctgagcct tcctgtcctg ttagctagga 13380
aggggacagg accccagactc caggaatagt ggtgccaccc ggtgcccag ccccataggg 13440
ccgtcccatg ccagcccaca ggctgagcag ggctccgagg tcagcactat catgctgtgt 13500
gtgtaaatga aacaaaccca cacaggcctc aagcagtcct ctgggagact ccaaacacac 13560
ctaccttctt ctcatccgtg ggggcgaccg acgccacatg ggaggtggag gcagcattct 13620
cctgggaggg ctgaatctcc tgggcggtgg cctcggccat gggccagca cagcggtggc 13680
ggtgatctcc tggccatcaa tttgtcctgt tgaaaaaaag atcaagtcac aaaatatcac 13740
acccagtcac tactgtgggc ggttttggcca ggaaacgtgc ctatatagcg tggaagcgaa 13800
gagggaactc agtctcgagg caccaagacc cctcatgcac agcagccacc aaggggaagtg 13860
caccaagtg gacacctgag cccgttcact gatggggaag ggctggctcc tgacctgagc 13920
cggaaggtgg gcctagcact gagctgcctc ctctagaagg ttgggaggga caggcaagag 13980
gagggcagc actgtggggg ctgtgggggt gaaggagggg cagcactgtg agggaagcag 14040
atgggtgaa atgtaagaga tccagaagga ctgccctcaa agacgtgtgg cctctgagcc 14100
aggaggcctg gcctcctctc ccgatacccg ccgtgggagat actttcctca gagagctcct 14160
cccaggggac cagaaggtgg cctctggggtg ctgggtcccg acgagggcag tgtccactgt 14220
aaatggggcg ccgggtcact acaacgtggc ggtggatggg gtgggaggga tgatcggcac 14280
ccctgtttct agatgagcta tgactgcatc gtggctcggg aagaagaag tactactggg 14340
gcaggggagc aaaaccaaac caaggttcag ctgtcaagtc tgtcttcagt gtgtggaaaa 14400
agtgacttgg ggagggggact ctgagtgcag ccacgtacgt gaatgtagcc gatgagaaca 14460
gtgaagggag gcggctcagg atgaggcca aggagccttc agggcctcag aaaaagcaag 14520
caaaggagac caaggcgcag acccaggaac ctcaggggag cacgcaccct ggcccagtcc 14580
agggaccgct cgggaccgag cacagccctc gtgtgccctc tcttatcttc tcagctccta 14640
ccctcaaggc gacagcagga atggcaagga ggtggctcag tgcatgtaagc ctgtgttcag 14700
aaccccactca cgagacttaa gtaaacgcag cctaaggcac ccctgcctc cacatggccc 14760
attgccaaga ccagcccaaa tcaggaacgt caaggacacc gatcatacag caatgaagac 14820
aactctatct tctgggcagc tgccaggaaa ggccaagccc ttccacattc cttctggagc 14880
cagcacggag ttgctccact cgatggggcg cagtacagta tgtggacaca cacacagatc 14940
```

```
ctaccagaat cttaaaaaac gtgggctacg accatgcaca ccctggacgt ggccgagtgt 15000
cctgaattct tagcaagtgc tccagctctc aaagacgcat gtttgacagt ctctaaaatg 15060
aaggtgtggt taagatcaag aggtggtggg cacagttcat gacaaactcc taaaaaactt 15120
caaagggagc gactggttat gttttaggat ttatttttgag agacagaggg gggcagagcg 15180
agcacgaaag agagagaaag agagagagac agagagaaag aaacccaagc aggctcttca 15240
ctgtccgcac agagcccgac acagggctcg gtcccacgaa ctgtgaggtc acgacctgag 15300
ccaaaatgaa gaactggacg ctcaaccgaa tgagtcactc acgcgcccct caaagggatt 15360
tcagtagact gaagacagct agcttagcgt taagggaaag ttcctagtgt ccaagctcca 15420
tcagggctcc aggaaaacta gccatcacac cattacacta tttttccagt gggtaacagg 15480
cttctgagga ctccaaggtt ctggggtgtt cagattcttc cctgcgtggc cagatgcccc 15540
atgcacagtg ctgtggacgg agccagctct cggccccagc tgcgtagatt ataagagcga 15600
gctggggcgg agaccgatcc cacgctcttc aaagacacag acgtgaagac aagatggaaa 15660
ccggccatcc aaaactattc acaagtgctc agccgccgtc aaaaccattc tgctcaatac 15720
aaaacagcta taaatgtcac aaatagttcc gatacaagct tgagggagat gggtaagatg 15780
tatgaattca gcaaagtaaa cctaaaaatg ctgaaatgtc agcataacag aagatgactc 15840
tcagagagga ctggagaaaa cactgccata caaaagccaa atgctgcatt attcacattc 15900
ataatattgt ataaaataaa cccccttcgtt ccttaagttc tcacagattg gaaaactcgg 15960
aagatgttaa tgtattcatt tttgctgaaa ttttcccaag aatgatacct catcaacttg 16020
tttttggtga acacacccc actggtcaaa gatggagtcg ggcaagagct gcagggagct 16080
ggggggaaact ggtctgaaag gtccccccgc tgggccgagg ccagcctcgc gcagggagca 16140
gagaggggggc gcagcagggt caccccacctc catccatgtg cttcagagcc ttctcggcct 16200
cgtccggatt ctcaaactcc acgtacgcgt agcctttaga caggtggggg tgcatcctttt 16260
ccacaggcat gtcaatcatt ttaattttcc cgtaggtgga gaatatctcc atgatgtggt 16320
cctagaggaa agaagggtca ctctgatgtg cacccaccaa ctaccgtgt gggagctgag 16380
aagtcacccc atgacgggga caagctgggg cgtctctctc acacggaaca actcggataa 16440
aggactcccg ccagtgtcct cagagcctat gttctcggtt acctccagca aaggccagct 16500
tctctggttt tccatttaaa acatttgcag aagagacgtg cccctctgc ccactggaca 16560
gatctgtgat ccctcacctt ggtcacattc ctagtgagcc tcccgatgtg cactttggtg 16620
ggtttaggggg aaggactccg ccttttcctt tccttttcat ctcttttggg tggttttgaat 16680
ctgattgaaa aaacacaaca acagaaacaa tttctgtcaa gtcaaaaaaa ttttttaagt 16740
ggggctgcta agtgctactg ttgagttttt tataaggcag cttcccctac cagttcgtgt 16800
atattcctgt tatctctgcc tcagaaatcc gactaagtaa gacacagact cctctacagg 16860
ctactttct aacagctact gtcacctttat agtccccagt ttgcaaacta agttcccaga 16920
tgactgacaa gttttggggc aaccccttca aaccaagacc cccccaccc ccccgccgtg 16980
ggaagcggcg ccggaaggga gctcacttgg agcgggagcg cctcctgttg tcgtgcctgc 17040
gtcgagaagg actcggcgag ccagacgagc tgctggagct ggagctgcgg gaggtgctgg 17100
agcttcccga gcggctggat gcggaagaag agctcgagcc gctgctcgag ccagtgctgg 17160
tgctggagcc cgagctggag gtagagctgg accgggacct gaccagggac acagaagtgt 17220
cacaagcagc ggcggagggg agcctctctt cccagcagac gcagacgagc ctgtacgtgc 17280
tcatgctccc aagaggccac cgctgtcctc attatttccc aacctccatg tcgtcccccc 17340
acccccgggggg ggggtgggtg ggtggggatg atatctaccc cagccttctc tagccaaagc 17400
ccctggcagg gacagaaaac cgcattcaaa ctgcgcaggg gcaggaaagg aaggagccgc 17460
ttcctagcca cacagaagcc ttgactgctg ggaggtacag aaagagcctg caggtcagaa 17520
caccaatcca tcctggaagg tggctaccga ggggctcggg ctggcgctca agtgaagaaa 17580
tgcaagcttt aggctcgggc aatccaatca caactaaaga aaaaagcact tgagagaaaa 17640
atctatcccc agatgtctca ttcgtcaaca ccatcctcca tagggaaccg gagcaaaccc 17700
caaagcattg tgctgcagtt aaggccttta ttaacaatct cacaatcttc tgtgtgaata 17760
attcggacta cacagcagtg ggcaggctca gcggacagaa aggggcgtgg ctctcagggc 17820
cccgccccgc ggccccacct ggtgctgctg ctgccgctgg aagcgctgcg cctcttccgc 17880
gtttttctccc tgccccggtc cttctcacta gactccttgg tggcccttt atctttagaa 17940
cgatccttgg acttctcatc agagcggtct ttgcgtttgg taggagaggg agccctggat 18000
ggtgaggaag agtgtgagat cacgagcccc tctgaccaaa ccctgaaaca cactaccca 18060
ggagggatc caaagggcta cagagaccc aggtgatcac agaacaaaac gatctgtggc 18120
ttaggacact tcactgtaga atgtgagaca tttccaatct tccccttttct gagggtcct 18180
agtaacgagc accccccaaag tagcactaga aaaatctgac agaaggatta cctagtgctg 18240
gactttttat tatttttcttt gactccagc aagctcttct ttttcactcc tgataaatcc 18300
attctcccct tctgaggtgt tcaaagcagc aatggcggcc tcacttatct gaactctcac 18360
ttctaactcg agtctgagaa acgatcccta atcgattgca atttacgcca aagtgcagcc 18420
taataacaag ataaaggat ttacagagtg aacgtattgg caaggcaaca aattcgcttt 18480
gcagtcaaaa ggcgagcaca cgagaagatg gcaaggaaca cagtgagcag cgagcgtcca 18540
caaagccagg aacacacagg gacctcttcc atttccttgg ggagggtccc accccacag 18600
gcagaccctc acctcagttt gtggtctctt ccttaaggaa acggtggtgg cgcccgtcag 18660
ttattttaca ggaggtacaa tacccatttt gcactcatag gtttgatgag ccctctaccg 18720
ccccccccccc ccaccatacc acagcaccac atttgcatgc agaacagaaa aaaaccccca 18780
agagtggctc tcctgaaagg gttactggtg tggtcagatc tcttgtttaa ctgctgtaat 18840
ttcctcgtag gatactttgt gtctaggcta cgactggaag caaaaaccat ttcaaaagcg 18900
acaggtagca tcaaaacatt taataccaa atgcaaacaa ataaaatgtt cccctatgaa 18960
catttaaaaa gcagtcattg catggtgcgc ctggggggcgg agggttcagt cagttaagcc 19020
tccaactctt gacttcgggct caggtcatga tctgtttgtg agattgagcc tgcatcagac 19080
tcctcgctga cagtggaggg cctgctcggg attctctttc tctctctacc cctccctgc 19140
tctctctcaa aataaataaa cttaagaaaa aaacccaaa aagagtcatt gcaaatgcaa 19200
ctttagttaa tgataggcag atagaagtgt tacaccagag gctacaatgt acttcaaaat 19260
ataataaaaa tattgacgcg taaaagcaa atgtggtaga atgggacttt gtatgatcta 19320
ggtggtggtt atgagggtag tcactgcaat tctttttaact ttatacttac attttttccc 19380
caaaatcaca tgcgtgtggg gagggcact agaactggat ggcactgctc ataaaggttt 19440
aacaaagtgt ccggattgca gcatgtgctc aataaatggt cattagtacc attacgcgagt 19500
gttacttaga acaaacttca atatttgcag tgaggttttc tacaatttgc tcgagttgca 19560
agcaaaggtc tcaggtactg gtctccacta ctcctagttc ctcttcctca acagcctgta 19620
agtaacctgg acacagcagc caactgggat cctgtttcac gttgtgtagg ggtgcccaag 19680
```

-continued

```
atcctgaata aattctgtga ctccagagtg aaggccagct tcggatgatc agattagagc 19740
agaagcaagc agaatgccac ctttgctgct cttttccaag ctgataacgt cgtttaagat 19800
gttctgcctt aaaacagtaa ggtgctatgg gcactgagca agcaacactg gagaagctca 19860
gcgtcctcca acaagcggga agtgtaattc actggttaag cgtccggagt cagtgtatct 19920
gtttaattca gagctttgct gtgtgacctt gggtaagtca cttaaccgtt ctgagcctcg 19980
atttctcaaa agcattatag tgacaattac agttcctaca cctccatagt caccaagatc 20040
attaaccaaa tttattactc atgaaagaaa cttggcacct agttaaggct caatcaatgt 20100
tagctttcct tagaagaaag ggacgttttt ccatgttttgg aagctttttc cccacgtgaa 20160
ctctggtctc ccaaagtcac acataatctc ttgaatgctc accagggtc cctgaaccac 20220
ccggtcagga tcaccaagtg cagtactgtc caatagaaat agagtgtgag ctaaaatcct 20280
aaatcttcta gcagcctcat taggtaagtt aaagatgaaa ttgactttca gtaatacagt 20340
ggacacgcta taccccaaat gttatctttt caacatacaa tcagtataaa aactcattag 20400
tgaaatatct gcaccccac ccccactaa gcctttaaac ccttcagttt ggcctaggtg 20460
tatttcaagt gctccgtagg cacacgtgac cgcagactcc cgcgccctcc ccccccccc 20520
cgtgtgctcg gtgacaacaa gcaccaccgg aattcttaaa ctctacgaat taagaaccac 20580
aggctgagcg aacactttgc tgggcgtggc cgagtgctag aaagcaaaga ttgaggcctct 20640
ctgttcacac aagttcaggt aacagcacag gaccttggtt acctccccca tcctccggaa 20700
aggtgcgcgt ccaacagcca gagagagaga gaacaattag ttaaacctcg agcagatggc 20760
gtttcggctc aactcttcag agcaccttcc ccatttaaaa gcacatttta ggcacaattc 20820
atgcgaaata aaagaaaaag ccacgacttc ccttcgtgga ctcgaaccttt cccgtaacct 20880
cccttgtggg gggtaaccccg tccaacggag ctgcatgaca tcagaggccg tatctccaag 20940
gactcgcgcg gaaaacggca cccgggagcc tggtaaacgg ccgtggagtc atgtctgaat 21000
taatgcctc gaagggaggc tcagccggtc tcccaggga ccccaccaaa gccactccgc 21060
acccactggc acgggcccca cgcgcgacct cgccgccccc gtccgcgttc actcacaact 21120
ccccagtcca ggcgccgggc cgcgagcgct tccagggcag ggctgggcg ttgcggggcct 21180
gggtctccaa cccgcgaga gagccccgaa ggcggaagcc gcgctcccgg ctgctccgag 21240
tccggcgggc ctagcagggc ccgccgcaga gggggacgat ctgaggcgcc cttccgcccg 21300
ccgcggcccc gaccacttcc gggccgcgcg ctcggcgcct cccactccac ccgccccggg 21360
ccacactctt tcttcttaga cccggtgccg cgccgccagg ctgccgtccc taccgagagg 21420
ccgaggagcg ggccggctcc accacgcgcc ccgccgagct ttgcgggcgg tccccggagc 21480
tcggatgggg tcggattccc ccaacttaca tcttcccgcc gccgcaacct cctcccgctc 21540
tcctcagccg ctaaggccgg cgccgctctg cgtcagggt tagggagcgg gaaggcgccg 21600
ctgtcgggcg cgcagcgatg acgtagagcg ccctagccaa tgggcgcgag cgaggggaat 21660
gttaaagggc cacgcgccgtt tttggcgagc tgcgtcgcg actcttgctc tagctcccctt 21720
tctgaggagg tgtctgggac tgccaggggc tggctgcacg cctcaggggg ccggccgatt 21780
gtgggaccgc ggtcggcagg gccgcgccgc tgggcagcc cccgggggcgg cgcggaggga 21840
gttaacgcag tggcggcctt gccccagccc tcgcgcgtgc gcactgggca ggcggccggt 21900
ctggcggtag ccccggcgcg ccacccttga cccctgtgct tcgcaggctg tgcggccggc 21960
tgctggaccg agggcggtgc gggcgctccg gcttctggct gcgggccgtg gggggtccc 22020
gcggggctca ggcggctcag gagcctgagt gggtgcgggg ctgggttcct gcggttaaaa 22080
accacgtaag gtgggcggag tgaccgtgcg gacgccgctg ctgcgcggac ggagctcggc 22140
cgggttccga gactagacgg gggacagtgc gaccgtcacg aactgggagc gaacatcagg 22200
gtagaagaca ggatgcggag ggggaagcgc ttccgaggag gtgacactgc ggctgagacc 22260
cgaggggag ggggcgcccg gcagagggaa tagccgcgct acggcgttgc aagaagggag 22320
gggaggccag tgtggcggct cgcaggccag gctacgaagg tggagttcag cggtggtggg 22380
gcgacgtgga ggatgtgcaa catccggcgc cgaggcttct tcactctggc cggtgaacag 22440
cgcaggcagg gaggcagtca gccttctggc aaagcagtgg cccgggccca ggcaggaggc 22500
tgggagaata aaacccgcg ccaaagaggc tagcgctttc gggttttgtt ccccacgggg 22560
ccgccagcgt tccccacccg atgtccggca agcggttgtt actgcatgac ccttggtggg 22620
agcaaggaag gtgcacccg cccagacgt tgtccgaaca ggtaggtca tcaaggaaga 22680
gaagggaaca gatcgaaatc ggatctttct ggagaaagga atcactgtga tttggagacg 22740
gataaccgct aggacaagga caggggagtc caggttgcag cttggtgacc agacggttgg 22800
tgctgcagac gctgtctgca cgtcattgtt ctctgtgctc tgtggttttc ccagcctgtg 22860
gatggtgggta ccttttccctg tccagccaat ctggcccccat cggcaggttg tcagctgtgc 22920
cccaacacct ttaccccggg ctgggggtg tctcagagtc acggacaaaa gggagcccgg 22980
aaggagcagc ccctcctgt gtccccttctg ctaaggcacc aacacatttc taggggggga 23040
tgtgttggca ggcaggcagt cagtccggtg caggggcctc cctctggatt tagatttgcc 23100
ctggtgtggt ggggggtcat ttagagcatt gaatcctcta ctgtcattgt cacgtctgcc 23160
atggccacgc acggaggagt gagttgaaca gagggcagcc ctggctctgc cccgcagccg 23220
tcaaggggcc cagaggggtca gcactgggga cagggtggcc gtggcagcat gtcggagccc 23280
cacacatcct gggcccacca tcagtgcatg cccagggccg caccggcacc ctaggtgggg 23340
agggagtggg cgagcaaccc caccttggca agggtgggaa caattcagcc gggcagccaa 23400
ccccgctac tttttaaaaa atgagcggaa tgctgtagtt tggcatgcat ataaattta 23460
acacgttta tgttaaatct aaaagcatga tttattcata cacatgaatt taatcaagtt 23520
tgtttctaaa tattgctgat ttttgttacc aagtgtgtta tcagctgttg agctttaaaa 23580
tttgagcatc ttttgccgtt ttgaagatga acagaatgtg ttcagaagaa acataaggaa 23640
ataaatctgg aggccgcctg cccctgggcc ttccaggagt tctggcttca cccttcttac 23700
acccctgtgc caacttactg aggccctggg ggctgagggc tggacgctac gtccttttggg 23760
gacctcggga ggcctttggc ccaggcttgg tggagggggg tggggcaggg ctcccggaga 23820
ctgcattggg cagccagccc caggcctgga gcactatacc acaggcatct ttcaggcttt 23880
gccagtgtcc tgagccccctc ccttccctc caggggcgg ggccacctgc tggcatgtgg 23940
cgctgctctc catttggaaa ggtaccttg tcaagacaga atattccctc tgccttcatc 24000
ctctgtgggc ctctgcagtg cttgcccttg gaggctggtg accggggaca cggagagggt 24060
ttagtggtag tctggatggt gctgagggtc atagtgcgcc ttcgggagc ctcaagtagg 24120
cattgcctcc ccaagaaagg actcctacct accgctgcac caaggacagg 24180
ggtggcccgg ccaggtagaa cagaagagtt tgggtggagt cagggaggcg gtgatggctc 24240
ggtggccttg agggaggcat tcgaagagga ggcctgggtc tctgtgtgga ggtgagagcc 24300
tgcagcccct gcaggagccc aggaagaggc actggctggt ccttctcggt ggccaggtgg 24360
gcgttaaagg gtcagacagc cagcgagggt ctggagttgt ggggagcctc tctggctgca 24420
```

```
ggcttgtgcc tctaaggtgt gggttgtcgg gtcctgagac ctctcccatc tccctgccag 24480
caggtgactc tggactctcc tgggggtggc tgagcagtga gctgggggct tgtgctggtt 24540
ttcatgccca aagccccatg ttcatttctg ccccagggaa gtcaaggata gtgtgcctga 24600
gccggggcgg tcacagctgg gcgcggagca gttggagctg tacgctgcat cgttggcgga 24660
cctgtgggcc gtgtcgcagt gtcgactggg gccaagatgg cttggccctg ctcccaggac 24720
ctacgttgtg ccatccacag ccagccgact tgggacttct ccagccctgc aggcgtctga 24780
tgccagcatc tgtgtggtgt aggccgggcc ccaggagcgg ggcctgggca gccctgtgtg 24840
ttgaggaagg aaggcagggc ccccgctccc cgggcccgac cccgtagctt cagctcctcg 24900
tgcctgtttg aggacaacac cacgtgggcc tgtcaggtgg ggatgggact ccagggccca 24960
gcgcccgctt cctggtgctc tcctgggtgg gctgccgggg tcgagacctc tgccttgtca 25020
cgccttctca ggcagcccct caacctacct tccctgagcc ccctcgtgca gggaccccag 25080
gggctttgct gtcctttggg aaagggagat aggcttcagg gactcgaacc tcccaggggtt 25140
tggaggtgga cctgagccgg ggttcaagga aggcacctcg tgtctgcaga gtgggatatc 25200
acacatggct cgcttgcctc agctgagggg tggagtgagc agcctaatcc tgactttggt 25260
tttgggggga tgtcttagag cctctgtggc cacctctttg ctgcaggagc ccctctgggt 25320
ccagatagag cccaagctgt ctacccagga acgtccctg gtgtgcagga aagggccaca 25380
gggtctgggt gagcacaggt ggccctccct tctcactgac cagtctgtgt gggaatgggg 25440
gggggggggtg gtctcagagg acctggctgg cctacgccat cggtgtcgtg ctggttccca 25500
gaagcgagcc gaacagcagc tggcatgggg tgtcctgcag atgccatcgc caaatctgtt 25560
gccctggctg gtggtctagc cccgggctgg cctctcggaa acctcccccc tcacctccag 25620
gttctggcac tgtgggtgtc cgggctgact gctctgggtg actgggacgt tgctgtctct 25680
gtggtcaagg gactgactga cttcagccca cgctcacgtg gtccaggct ggaccggacg 25740
ggctggctcc tctcccacct gcgatgtgtg gtcatcccca ggcagcttgc ggccacccttt 25800
ggaccagcct tccggccttc cttccagctg ctggccttgg ctcactcctt cttctgccct 25860
ggtcctgtca gctgctttgt gagacagggc tgaaggtccc tgagactgag gtgaccttcg 25920
ctcctcctgg agtcctggat tgaagatctg gattggcgtt tgcccagcaa aaaaaactgt 25980
ccagtttgtt tttctgtgtc cctgcgacca tagggtcagg gacaccatgg ggggcagggg 26040
ctgggcccta gggtagggtc acttctgcta gcctgtgggt cttcctaagt gaggtggggt 26100
ctcgccagct caagtggacc acgaaggcac acttgtggac cccttgatgc gaacctgcac 26160
actgcagtcg tggtggagac tgggatcgtg tcctgggacc tggctcttat ctggggtacc 26220
cagctaaata aaggaccctg tgtcccggct ccctcccct ggagcagcca tgtgcctgcg 26280
ttctgtgcaa taacgtggac gcagaagcac atgacatccg ggagctgtgt cctcctcccg 26340
tcccctgct gcttctgtct ggagcctcag ggtgacctg aacccaagag cagagcttga 26400
gggaggcctg cacctggaca gagcaggcag atggaggctg gcttcctgag gccttgtcgg 26460
tgacaacacc cagaccactg tctctggact ttgtacttga ccgagaaata aacgcctgtc 26520
tggtttcaaa gctgctggga ctgggccttc tgatgtgcac agcaagccgg ctgcagtctc 26580
cattccacag gagtggtttc tggggcctgg gggtggggtc ccctcgccct gtgacctgct 26640
gcctggcatt cttttcccac agggaaagca gtggatgggg ctcggcctaa gccctgaccc 26700
cagcagggtc tgcccaaccc tccctgtgga gcagcccct ctgagtgcag gtgtcctgcc 26760
aaggggcagt tcacggtctg tgtttcggtc gagccacacc atcggacggg gcaggatctt 26820
acacaggttt gctctcggcc ctcacgtcgg tgtccgcccc ttgggagccc ccgaccaggc 26880
ccacgggta ggcaaggtgc gaccttgtct tctggtctg ctgatgagct ggggagggg 26940
agggtccag cagatgcagc agctgtttgg gaccagcatg tccagggacc ctctgggccc 27000
cagcgtctgg gggagagcgg gatgggctgg cggggatgaa gcaggccagc tctcctgtag 27060
gggtgtccgt ggtccttccc cctctcccct gggcccggag ctgcatcagt tcaaaccaca 27120
tcaggtgggc tccagcccg gctccttgag ctctactgct aggtttccag tagccttgca 27180
gatgacttgg gggtgccacg gggaccccaa aagtggtgcc ccttcctgct gctcctgggg 27240
tcccttctcc ctaactgcag ttgccaagct ctatgctcct cccactgccc cccccccag 27300
gcctggtgtc gggccacagg cccacctccc agaacacgcc ttctgtgggg ctcatcttag 27360
accacgccga cccccgaatt tattttttat aatgtggaac taaatgctga tggtgtaaa 27419
```

<210> SEQ ID NO 35
<211> LENGTH: 209
<212> TYPE: DNA
<213> ORGANISM: Artificial Sequence
<220> FEATURE:
<223> OTHER INFORMATION: Description of Artificial Sequence:consensus PKD1
      exon 29

<400> SEQUENCE: 35

```
gacgcggctc tgcggcggtt ccggcgcctc ctggtggccg agctgcagcg tggcttcttt   60
gacaagcaca tctggctctc catatgggac cggccgcctc ggagccgctt cactcgcgtc  120
cagcgggcca cctgctgcgt cctcctcgtc tgcctcttcc tgggcgccaa tgctgtgtgg  180
tacggggtcg tgggagacgc cgcctacag                                    209
```

<210> SEQ ID NO 36
<211> LENGTH: 209
<212> TYPE: DNA
<213> ORGANISM: Mus musculus
<220> FEATURE:
<223> OTHER INFORMATION: mouse (Mmus) PKD1 exon 29

<400> SEQUENCE: 36

```
gaagctgcgc tgtggcagtt ccagcggctc ctcgtggctg agttgcagag aggcttcttt   60
gacaagcaca tctggctctc catatgggac cggccgcctc gtagccgctt tactagagtc  120
```

```
      cagagggtta cctgctgtgt tctcctcctc tgcctcttcc tggctgccaa tgctgtgtgg    180
      tacggagttg tgagagacac cacctacag                                      209

<210> SEQ ID NO 37
<211> LENGTH: 209
<212> TYPE: DNA
<213> ORGANISM: Homo sapiens
<220> FEATURE:
<223> OTHER INFORMATION: human (Hsap) PKD1 exon 29

<400> SEQUENCE: 37
gacgcagccc ttttgcgctt ccggcgcctg ctggtggctg agctgcagcg tggcttcttt    60
      gacaagcaca tctggctctc catatgggac cggccgcctc gtagccgttt cactcgcatc    120
      cagagggcca cctgctgcgt tctcctcatc tgcctcttcc tgggcgccaa cgccgtgtgg    180
      tacggggctg ttggcgactc tgcctacag                                      209

<210> SEQ ID NO 38
<211> LENGTH: 209
<212> TYPE: DNA
<213> ORGANISM: Canis familiaris
<220> FEATURE:
<223> OTHER INFORMATION: dog (Cfam) PKD1 exon 29

<400> SEQUENCE: 38
gaggcggccc tgcggcggtc ccggcgcctc ctcgtggccg agctgcagcg cggcttcttt    60
      gacaagcaca tctggctctc catatgggac cggccgcctc ggagccgctt cactcgtgtc    120
      cagcgggcca catgctgcat cctcctcgtc tgcctcttcc tgggcgccaa tgctgtgtgg    180
      tacggggtcg tgggagacac cgcctccag                                      209

<210> SEQ ID NO 39
<211> LENGTH: 209
<212> TYPE: DNA
<213> ORGANISM: Felis catus
<220> FEATURE:
<223> OTHER INFORMATION: domestic cat (Fcat) wildtype (wt) PKD1 exon 29

<400> SEQUENCE: 39
gacgcggctg tgcggcggtt ccggcgcctc ctggtggccg agctgcagcg tggcttttttt   60
      gacaagcatc tctggctctc cctctgggac cggcctcctc ggagccgctt caccgcgtc     120
      cagcgggcca cctgttgcgt cctcctcgtc tgcctcttcc tgggcgccaa tgctgtgtgg    180
      tacggggtcg tgggagacgc cgcctacag                                      209

<210> SEQ ID NO 40
<211> LENGTH: 209
<212> TYPE: DNA
<213> ORGANISM: Felis catus
<220> FEATURE:
<223> OTHER INFORMATION: domestic cat (Fcat) mutant (mut) PKD1 exon 29

<400> SEQUENCE: 40
gacgcggctg tgcggcggtt ccggcgcctc ctggtggccg agctgcagcg tggcttttttt   60
      gacaagcatc tctggctctc cctctgggac cggcctcctc ggagccgctt caccgcgtc     120
      cagcgggcca cctgttgagt cctcctcgtc tgcctcttcc tgggcgccaa tgctgtgtgg    180
      tacggggtcg tgggagacgc cgcctacag                                      209

<210> SEQ ID NO 41
<211> LENGTH: 69
<212> TYPE: PRT
<213> ORGANISM: Artificial Sequence
<220> FEATURE:
<223> OTHER INFORMATION: Description of Artificial Sequence:consensus PKD1
      exon 29 translation

<400> SEQUENCE: 41

Asp Ala Ala Leu Arg Arg Phe Arg Arg Leu Leu Val Ala Glu Leu Gln
       1               5                  10                  15
      Arg Gly Phe Phe Asp Lys His Ile Trp Leu Ser Ile Trp Asp Arg Pro
                      20                  25                  30
      Pro Arg Ser Arg Phe Thr Arg Val Gln Arg Ala Thr Cys Cys Val Leu
```

```
                       35                  40                  45
        Leu Val Cys Leu Phe Leu Gly Ala Asn Ala Val Trp Tyr Gly Val Val
                 50                  55                  60
        Gly Asp Ala Ala Tyr
         65

<210> SEQ ID NO 42
<211> LENGTH: 69
<212> TYPE: PRT
<213> ORGANISM: Mus musculus
<220> FEATURE:
<223> OTHER INFORMATION: mouse (Mmus) PKD1 exon 29 translation

<400> SEQUENCE: 42

Glu Ala Ala Leu Trp Gln Phe Gln Arg Leu Leu Val Ala Glu Leu Gln
         1               5                  10                  15
        Arg Gly Phe Phe Asp Lys His Ile Trp Leu Ser Ile Trp Asp Arg Pro
                        20                  25                  30
        Pro Arg Ser Arg Phe Thr Arg Val Gln Arg Val Thr Cys Cys Val Leu
                       35                  40                  45
        Leu Leu Cys Leu Phe Leu Ala Ala Asn Ala Val Trp Tyr Gly Val Val
                 50                  55                  60
        Arg Asp Thr Thr Tyr
         65

<210> SEQ ID NO 43
<211> LENGTH: 69
<212> TYPE: PRT
<213> ORGANISM: Homo sapiens
<220> FEATURE:
<223> OTHER INFORMATION: human (Hsap) PKD1 exon 29 translation

<400> SEQUENCE: 43

Asp Ala Ala Leu Leu Arg Phe Arg Arg Leu Leu Val Ala Glu Leu Gln
         1               5                  10                  15
        Arg Gly Phe Phe Asp Lys His Ile Trp Leu Ser Ile Trp Asp Arg Pro
                        20                  25                  30
        Pro Arg Ser Arg Phe Thr Arg Ile Gln Arg Ala Thr Cys Cys Val Leu
                       35                  40                  45
        Leu Ile Cys Leu Phe Leu Gly Ala Asn Ala Val Trp Tyr Gly Ala Val
                 50                  55                  60
        Gly Asp Ser Ala Tyr
         65

<210> SEQ ID NO 44
<211> LENGTH: 69
<212> TYPE: PRT
<213> ORGANISM: Canis familiaris
<220> FEATURE:
<223> OTHER INFORMATION: dog (Cfam) PKD1 exon 29 translation

<400> SEQUENCE: 44

Glu Ala Ala Leu Arg Arg Ser Arg Arg Leu Leu Val Ala Glu Leu Gln
         1               5                  10                  15
        Arg Gly Phe Phe Asp Lys His Ile Trp Leu Ser Ile Trp Asp Arg Pro
                        20                  25                  30
        Pro Arg Ser Arg Phe Thr Arg Val Gln Arg Ala Thr Cys Cys Ile Leu
                       35                  40                  45
        Leu Val Cys Leu Phe Leu Gly Ala Asn Ala Val Trp Tyr Gly Val Val
                 50                  55                  60
        Gly Asp Thr Ala Ser
         65

<210> SEQ ID NO 45
<211> LENGTH: 69
<212> TYPE: PRT
<213> ORGANISM: Felis catus
<220> FEATURE:
<223> OTHER INFORMATION: domestic cat (Fcat) wildtype (wt) PKD1 exon 29
      translation

<400> SEQUENCE: 45
```

```
        Asp Ala Ala Val Arg Arg Phe Arg Arg Leu Leu Val Ala Glu Leu Gln
        1               5                   10                  15
        Arg Gly Phe Phe Asp Lys His Leu Trp Leu Ser Leu Trp Asp Arg Pro
                        20                  25                  30
        Pro Arg Ser Arg Phe Thr Arg Val Gln Arg Ala Thr Cys Cys Val Leu
                    35                  40                  45
        Leu Val Cys Leu Phe Leu Gly Ala Asn Ala Val Trp Tyr Gly Val Val
                50                  55                  60
        Gly Asp Ala Ala Tyr
        65

<210> SEQ ID NO 46
<211> LENGTH: 23
<212> TYPE: PRT
<213> ORGANISM: Felis catus
<220> FEATURE:
<223> OTHER INFORMATION: domestic cat (Fcat) mutant (mut) PKD1 exon 29
      translation after mutant stop codon

<400> SEQUENCE: 46

Val Leu Leu Val Cys Leu Phe Leu Gly Ala Asn Ala Val Trp Tyr Gly
        1               5                   10                  15
        Val Val Gly Asp Ala Ala Tyr
                    20

<210> SEQ ID NO 47
<211> LENGTH: 24
<212> TYPE: PRT
<213> ORGANISM: Felis catus
<220> FEATURE:
<223> OTHER INFORMATION: domestic cat (Fcat) mutant (mut) PKD1 exon 29
      translation after mutant stop codon

<400> SEQUENCE: 47

Val Leu Leu Val Cys Leu Phe Leu Gly Ala Asn Ala Val Trp Tyr Gly
        1               5                   10                  15
        Val Val Gly Asp Ala Ala Tyr Arg
                    20
```

CARRIER TESTS FOR POLYCYSTIC KIDNEY DISEASE IN THE CAT

CROSS-REFERENCES TO RELATED APPLICATIONS

Not applicable.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Autosomal dominant polycystic kidney disease (ADPKD) is a commonly inherited disorder in humans, with a frequency in the general population of 1 in 1000 (Dalgaard, Dan, *Med Bull* 4:128–133 (1957)). Approximately 85% of ADPKD cases are caused by mutations in the PKD1 gene (Consortium TEPKD: The Polycystic Kidney Disease 1 Gene encodes a 14 kb transcript and lies within a duplicated region on chromosome 16, *Cell* 77:881–894 (1994); Consortium TIPKD: Polycystic kidney disease: the complete structure of the PKD1 gene and its protein, *Cell* 81:289–298 (1995)), located on human chromosome 16p13.3; the remaining 15% are caused by mutations in the PKD2 gene, located on human chromosome 4q21–23 (Kimberling et al., *Genomics* 18:467–472 (1993); Peters et al., *Nat Genet* 5:359–362 (1993)). ADPKD is characterized by the formation of fluid-filled cysts in the kidneys and the average age of onset is 40 years, with end-stage renal disease (ESRD) occurring by age 60 in 50% of cases (Gabow, N, *Engl J Med* 329:332–342 (1993)). PKD significantly affects quality of life for an extended period of time (Dalgaard, Dan, *Med Bull* 4:128–133 (1957)); it is estimated that approximately 1 in 2,000 Americans is on kidney dialysis for approximately 10–15 years of their life. Hence, a majority of PKD cases lead to costly, invasive and chronic health care. Efforts to study PKD have been hampered by the lack of a reliable model system for the disease.

Companion animal species, such as the domestic cat, are effective models for several inherited diseases and should be used to develop better drug and gene therapies for PKD. Feline PKD is an inherited disease in Persian and Persian-related cats. As with humans, PKD in cats is characterized by renal as well as hepatic and pancreatic cysts (Eaton et al., *Vet Pathol* 34:117–126 (1997)) and has an autosomal dominant mode of inheritance (Biller et al., *J Amer Vet Med Assoc* 196:1288–1290 (1990)). Approximately 37% of Persian cats in the United States (Cooper, *Feline Prac* 28:20–21 (2000)), and 38% worldwide (DiBartola, *Proceedings of the 18th Annual Veterinary Medical Forum of the American College of Veterinary Internal Medicine Seattle*, 438–440 (2000)) are PKD affected. Only 20% of the cat population in the United States is represented by purebred cats, but of purebreds, Persians and Persian-derived breeds constitute approximately 80% of the cat fancy. This implies that approximately 6% of the cat population in the United States has PKD, making it the most prominent inherited feline disease, hence PKD is the most prominent inherited feline disease. Thus, the cat is an exceptional animal model for studies of PKD. However, methods for identifying cats who are carriers for PKD prior to development of disease have been limited.

Further investigation into the cause of PKD will be valuable for feline health as well as provide insights into human ADPKD. As with humans, cats have a wide range of disease progression and severity, thus other genetic and environmental factors could influence disease progression (Bogdanova et al., *Hum. Genet.* 95:645–650 (1995); Parfrey et al., *Kidney Int.* 61:1925–1934 (2002); Tahvanainen et al., *J. Hepatol.* 38:39–43 (2003); Magistroni et al., *J. Nephrol.* 16:110–115 (2003)). Currently, the disease is highly prevalent in the cat population, making the identification of severe, early-onset cases and mild, late-onset cases feasible. This could lead to the identification of genetic modifiers of the disease. As cats have similar clinical presentations, therapies that are under development for EGFR receptors could be tested for efficacy in the cat, prior to use in humans (Magistroni et al., *J. Nephrol.* 16:110–115 (2003); Torres et al., *Kidney Int.* 64:1573–1579 (2003); Sweeney et al., *Kidney Int.* 64:1310–1319 (2003); Dell et al., *Kidney Int.* 60:1240–1248 (2001); Davis et al., *Semin. Nephrol.* 21:430–440 (2001); Avner et al., *Int. J. Dev. Biol.* 43:457–461 (1999); Sweeney et al., *Kidney Int.* 56:406–413 (1999); Sommardahl et al., *Pediatr. Nephrol.* 11:728–733 (1997); Murcia et al., *Pediatr. Nephrol.* 12:721–726 (1998); Bagowski et al., *EMBO J.* 18:5567–5576 (1999)).

It is currently recommended that Persian and Persian-related cats be screened for PKD by ultrasound before they are bred (Cannon and Barr, *Vet. Rec.* 147:639–640, (2000)). Knowledge of the mode of inheritance, coupled with the accuracy and availability of ultrasonography, a non-invasive technique for diagnosis, has made the elimination of feline PKD possible (Barrs et al., *Austral. Vet. J.* 79:257–259 (2001)). Although breeders are advised not to breed positive cats, they are often bred for several unrelated reasons; 1) clinical signs have not yet appeared, which is generally when approximately 66% of the normal kidney function has been lost, 2) many breeders are still unaware of the disease and its prevalence in their cattery, 3) ultrasound is either unavailable or cost prohibitive for generalized screening, 4) breeding decisions are made prior to adequate accuracy of diagnosis as determined by ultrasound, and 5) the disease is highly prevalent, thus many catteries could lose approximately 50% of their breeding population, causing a large loss to the gene pool. With the identification of a causative mutation, a genetic test for feline PKD will provide breeders with an efficient and accurate means by which to selectively breed their cats and remove PKD from the population. The point mutation alters a restriction enzyme site, thus typing for PKD could be efficiently performed by RFLP analysis. Additionally, various other techniques for point mutation typing such as, denaturing high performance liquid chromatography (dHPLC), single-strand conformation change polymorphisms (SSCP) and various sequencing techniques could effective identify the PKD mutation. Since PKD has been found in random bred, Siamese and other cat breeds that have relationships with Persians, it will be important to monitor the progression of the disease in these breeds as well as in Persians worldwide.

Thus, there is a need in the art for compositions and methods for detecting genes associated with PKD and for identifying carriers of polycystic kidney disease. The present invention satisfies these and other needs.

BRIEF SUMMARY OF THE INVENTION

One embodiment of the present invention provides isolated polynucleotides comprising the sequence provided in SEQ ID NO:1 or a complement thereof. In some embodiments, the invention provides expression vectors comprising a polynucleotide comprising the sequence provided in SEQ ID NO:1 or a complement thereof, operably linked to an expression control sequence and host cells comprising the expression vector. The host cell may be a mammalian cell, a yeast cell, or a bacterial cell (e.g., *E. coli*). In some embodiments, the invention provides polypeptides comprising an amino acid sequence encoded by SEQ ID NO:1 or a complement thereof.

Another embodiment of the invention provides methods for detecting a mutation associated with polycystic kidney disease in a cat by detecting a subsequence of a gene encoding PKD1, the subsequence comprising a C to A substitution at position 138 of exon 29 of PKD1 in a biological sample from the cat. The subsequence may comprise SEQ ID NO:1 or a complement thereof. The cat may be a domesticated cat or a feral cat. In some embodiments, the mutation is detected by specifically amplifying the subsequence comprising a C to A substitution at position 138 of exon 29 of PKD1 in the biological sample from the cat, thereby amplifying nucleic acids comprising the mutation; and detecting the amplified nucleic acids, thereby detecting the mutation. The subsequence may comprise SEQ ID NO:1 or a complement thereof. The nucleic acids may be specifically amplified using primers comprising the sequences set forth in SEQ ID NOS: 19 and 20. The mutation may be detected by contacting the amplified nucleic acids with a restriction enzyme (e.g., Mly I). In some embodiments, the amplified nucleic acids are detected by sequencing. In some embodiments the mutation is detected by contacting an antibody that specifically binds to a polypeptide encoded subsequence of a gene encoding PKD1, wherein the subsequence comprises position 138 of exon 29 of PKD1 with the biological sample from the cat, thereby forming a complex between the antibody and a polypeptide in the sample; and detecting the presence of the complex, thereby detecting the mutation. The subsequence may comprise SEQ ID NO:1 or a complement thereof. In some embodiments, the complex may be further contacted with an Ig-specific antibody. The Ig-specific antibody may be labeled with a detectable label (e.g., an isotope or a fluorescent label).

A further embodiment of the invention provides kits for detecting a mutation associated with polycystic kidney disease. In some cases the kits comprise an isolated polynucleotide comprising a subsequence of of a gene encoding PKD1, the subseqeunce comprising a C to A substitution at position 138 of exon 29; and primers that specifically amplify the subsequence. The subsequence may comprise SEQ ID NO:1 or a complement thereof. The primers may comprise the sequences set forth in SEQ ID NOS: 19 and 20. The kits may further comprise a restriction enzyme (e.g., Mly I). In some cases the kits comprise an antibody that specifically binds to a polypeptide encoded by a subsequence of a gene encoding PKD1 wherein the subsequence comprises a C to A substitution at position 138 of an exon 29. The subsequence may comprise SEQ ID NO:1 or a complement thereof. The kits may further comprise a Ig-specific antibody. The Ig-specific antibody may be labeled with a detectable label (e.g., an isotope or a fluorescent label).

Even another embodiment of the invention provides isolated polynucleotides capable of distinguishing between the sequence provided in SEQ ID NO:1 or a complement thereof and a nucleic acid encoding a wild type polycystic kidney disease type 1 protein.

BRIEF DESCRIPTION OF THE DRAWINGS AND SEQUENCES

FIG. 1 illustrates a schematic diagram of the feline PKD1 gene. Intron/exon boundaries are predicted by comparison to human, mouse and dog sequence. Symbols: ☐=Simple repeat, ▫=UTR, →=Exon, ■=Gene.

FIG. 2 shows nucleotide (SEQ ID NOS:35–40) and amino acid (SEQ ID NOS:41–45, 5 and 46) alignment of PKD1 exon 29 from mouse, human, dog, and cat. FIG. 2A shows the DNA alignment of PKD1 exon 29 from mouse, human, dog and cat. Both wild-type and mutant sequences are included from the cat. Bold-type in cat sequence indicates the transversion observed in PKD affected cats causing a change in the amino acid translation resulting in an OPA stop codon. FIG. 2B shows the protein alignment of PKD1 exon 29 from mouse, human, dog and cat. Both wild-type and mutant translations are included from the cat. Bold-type X in cat sequence indicates the OPA stop codon observed in PKD affected cats.

FIG. 3 is Table 1 which summarizes the results of PCR analysis of PKD1 (i.e., of exons 6, 14, 15, 23, 24, 29, 30, 37, and 38) in the domestic cat and primer sequences (SEQ ID NOS:9–26) used for the analysis.

FIG. 4 is Table 2 which shows a sequence analysis of feline PKD1 compared to human, dog, and mouse PKD1.

Figure 1:
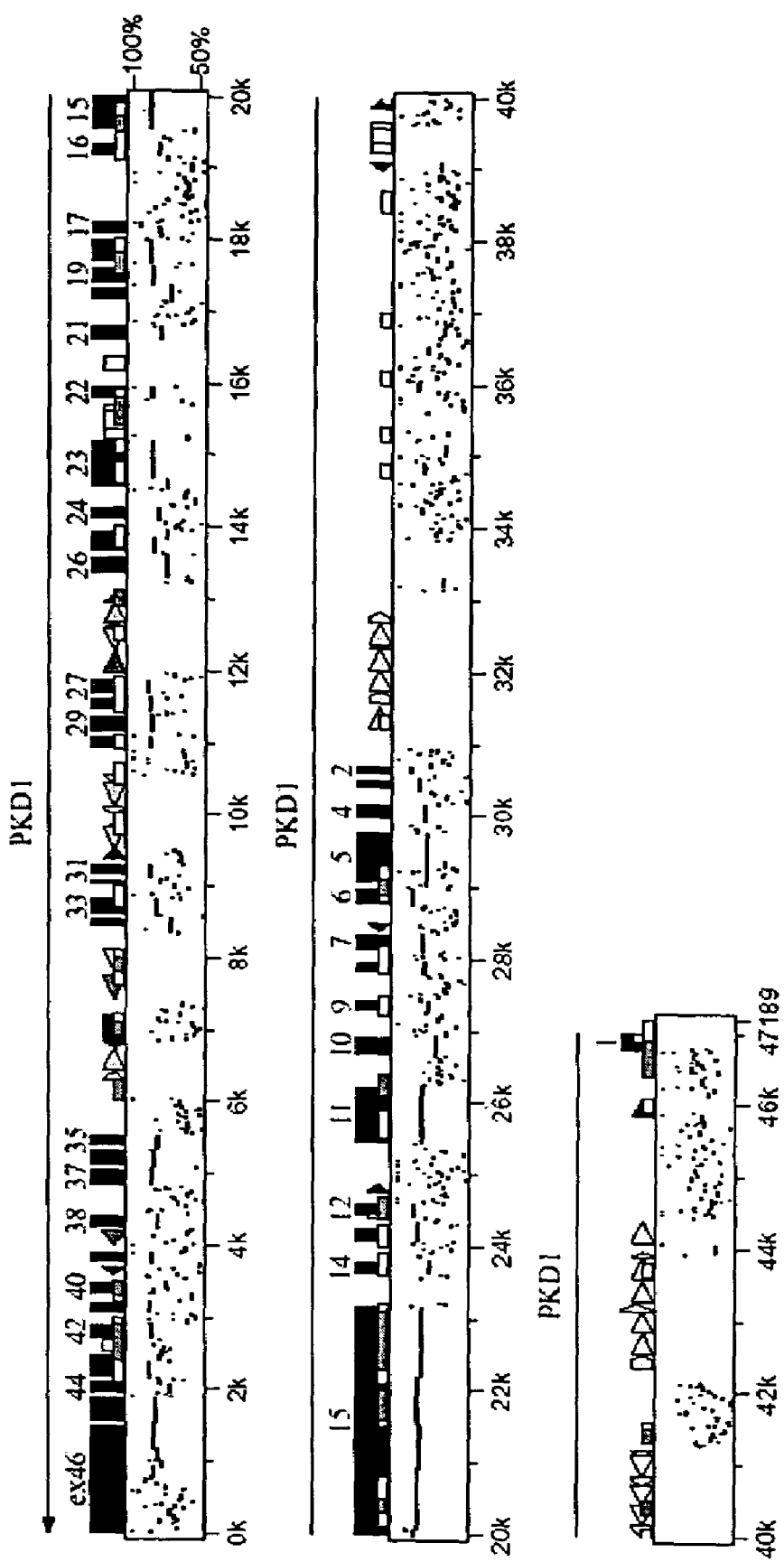

FIG. 5 shows SEQ ID NOS: 1 and 5. SEQ ID NO:1 is the sequence for Genbank Accession No. AY612847 which comprises a subsequence of the PKD1 exon 29 variant described herein and amplified by primers comprising the sequences set forth in SEQ ID NOS: 19 and 20. SEQ ID NO:1 comprises a C to A substitution at position 307; T to G substitution at position 102; a 1 bp del after position 105; a G to A substitution at position 132; and a 11 bp insertion at position 390, compared to the corresponding wild-type subsequence of exon 29. The C to A substitution at position 307 of SEQ ID NO:1 corresponds to position 138 of exon 29. The position of the C to A substitution is indicated in bold and the position of the Mly I restriction site is underlined. SEQ ID NO:5 the translation of AY612847 starting at bp 3 of exon 29. ● indicates the stop position.

FIG. 6 shows SEQ ID NOS:2 and 6. SEQ ID NO:2 is the nucleotide sequence for Genbank Accession No. AY612846 which comprises a subsequence of exon 24 amplified by primers comprising the sequences set forth in SEQ ID NOS:17 and 18. The position of a G to A substitution is indicated in bold and the position of a 5 base deletion is indicated as ●●●●●. SEQ ID NO:6 is the translation of AY612846.

FIG. 7 shows SEQ ID NOS: 3 and 7. SEQ ID NO:3 is the nucleotide sequence for Genbank Accession No. AY612848 which comprises a subsequence of exon 37 amplified by primers comprising the sequences set forth in SEQ ID NOS:23 and 24. The position of a C to T substitution is indicated in bold. SEQ ID NO: 7 is the translation of AY612848.

FIG. 8 shows SEQ ID NOS:4 and 8. SEQ ID NO:4 is the nucleotide sequence for Genbank Accession No. AY612849 which comprises a subsequence of exon 38 amplified by primers comprising the sequences set forth in SEQ ID NOS:25 and 26. The position of the C to T substitution is indicated in bold. SEQ ID NO:8 is the translation of AY612849.

SEQ ID NO:5 is a is the amino acid sequence for the translation of AY612847.

SEQ ID NO:6 is a is the amino acid sequence for the translation of AY612846.

SEQ ID NO:7 is the amino acid sequence for the translation of AY612848.

SEQ ID NO:8 is the amino acid sequence for the translation of AY612849.

SEQ ID NO:9 is a 5' primer sequence for exon 6.
SEQ ID NO:10 is a 3' primer sequence for exon 6.
SEQ ID NO:11 is a 5' primer sequence for exon 14.
SEQ ID NO:12 is a 3' primer sequence for exon 14.
SEQ ID NO:13 is a 5' primer sequence for exon 15.
SEQ ID NO:14 is a 3' primer sequence for exon 15.
SEQ ID NO:15 is a 5' primer sequence for exon 23.
SEQ ID NO:16 is a 3' primer sequence for exon 23.
SEQ ID NO:17 is a 5' primer sequence for exon 24.
SEQ ID NO:18 is a 3' primer sequence for exon 24.
SEQ ID NO:19 is a 5' primer sequence for exon 29.
SEQ ID NO:20 is a 3' primer sequence for exon 29.
SEQ ID NO:21 is a 5' primer sequence for exon 30.
SEQ ID NO:22 is a 3' primer sequence for exon 30.
SEQ ID NO:23 is a 5' primer sequence for exon 37.
SEQ ID NO:24 is a 3' primer sequence for exon 37.
SEQ ID NO:25 is a 5' primer sequence for exon 38.
SEQ ID NO:26 is a 3' primer sequence for exon 38.

SEQ ID NOS:27–34 are the sequences of AC145332.28, genomic DNA from *Felis catus* for PKD1. Bases 1–39536 represent a 39536 bp contig (SEQ ID NO:27); bases 39537–39636 represent a gap of unknown length; bases 39637–55645 represent a 16009 bp contig (SEQ ID NO:28); bases 55646–55745 represent a gap of unknown length; bases 55746–65718 represent a 9973 bp contig (SEQ ID NO:29); bases 65719–65818 represent a gap of unknown length; bases 65819–68887 represent a 3069bp contig (SEQ ID NO:30); bases 68888–68987 represent a gap of unknown length; bases 68988–107174 represent a 38187 bp contig (SEQ ID NO:31); bases 107175–107274 represent a gap of unknown length; bases 107275–113428 represent a 6154 bp contig (SEQ ID NO:32); bases 113429–113528 represent a gap of unknown length; bases 113529–139708 represent a 26180 bp contig (SEQ ID NO:33); bases 139709–139808 represent a gap of unknown length; and bases 139809–167227 represent a 27419 bp contig (SEQ ID NO:34).

DETAILED DESCRIPTION OF THE INVENTION

I. Introduction

The present invention is based on the identification of a mutation in the feline PKD1 gene that is associated with polycystic kidney disease. A linkage analysis for feline PKD was performed and feline PKD1 was scanned for causative mutations. A C>A transversion was identified at c. 10063 (human ref NM_000296) in exon 29, a mutation that has not been identified in humans. The transversion was identified in the heterozygous state in all affected cats examined. No unaffected cats were identified with the mutation, suggesting that the mutation causes feline PKD, making a carrier test for PKD now possible and demonstrating that the domestic cat is an ideal model for human PKD.

Thus, the invention provides compositions, methods, and kits for identifying carriers of PKD. Cats identified as carriers of PKD can be used as models for study of the disease and development of therapy for PKD. Cats identified as carriers of PKD can also be removed from breeding populations to enhance the overall health of cat breeds, both domesticated and wild.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "Polycystic Kidney Disease 1," "PKD1," and "PKD1 " refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a PKD1 nucleic acid (for a cat PKD1 nucleic acid sequence, see, e.g., Accession number AC145332.28) or amino acid sequence of a PKD1 protein; (2) bind to antibodies, e.g., polyclonal antibodies, raised against an immunogen comprising an amino acid sequence of a PKD1 protein, and conservatively modified variants thereof; (3) specifically hybridize under stringent hybridization conditions to an anti-sense strand corresponding to a nucleic acid sequence encoding a PKD1 protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a PKD1 nucleic acid. A polynucleotide or polypeptide sequence is typically from a mammal including, but not limited to, domestic cats and wild cats (e.g., of the family *Felidae*; the subfamilies, *Felinae, Pantherinae*, and *Acinonychinae*; the genera *Caracal, Catopuma, Felis, Herpailurus, Leopardus, Leptailurus, Lynx, Oncifelis, Oreailurus, Otocolobus, Prionailurus, Profelis, Puma, Neofelis, Panthera, Pardofelis*, and *Uncia*; and species *felis, lybica, jubatus, caracal, badia, bieti, chaus, margarita, nigripes, silvestris, gordonii, yaguarondi, pardalis, tigrinus, wiedi, serval, canadensis, lynx, pardinus, rufus, colocolo, geoffroyi, guigna, jacobita, manul, bengalensis, planiceps, rubiginosus, viverrinus, aurata, concolor, nebulosa, leo, onca, pardus, tigris, marmorata*, and *uncia*. The nucleic acids and proteins of the invention include both naturally occurring or recombinant molecules. The human and cat PKD1 gene has 46 exons, stretches over 53 kilobases (kb) of genomic DNA and encodes a 14.1-kb mRNA transcript, which is translated into a 4,303 amino acid protein with a calculated size of approximately 460 kd. Mutant PKD1 sequences include, e.g., sequences that comprise a causative mutation for polycystic kidney disease including, e.g., nucleotide sequences comprising SEQ ID NO:1 and amino acid sequences encoded by the sequence comprising SEQ ID NO:1.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated mutant PKD1 nucleic acid is separated from open reading frames that flank the mutant PKD1 gene and encode proteins other than mutant PKD1. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); Rossolini et al., Mol. Cell. Probes 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I) fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide comprising a sequence encoded by SEQ ID NO:1 can be made detectable, e.g., by incorporating a radiolabel into the peptide, and used to detect antibodies specifically reactive with the peptide).

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683, 195 and 4,683,202; *PCR Protocols: A Guide to Methods and Applications* (Innis et al., eds, 1990)), strand displacement amplification (SDA) (Walker, et al. *Nucleic Acids Res.* 20(7):1691 (1992); Walker *PCR Methods Appl* 3(1):1 (1993)), transcription-mediated amplification (Phyffer, et al., *J. Clin. Microbiol.* 34:834 (1996); Vuorinen, et al., *J. Clin. Microbiol.* 33:1856 (1995)), nucleic acid sequence-based amplification (NASBA) (Compton, *Nature* 350(6313):91 (1991), rolling circle amplification (RCA) (Lisby, *Mol. Biotechnol.* 12(1):75 (1999)); Hatch et al., *Genet. Anal.* 15(2):35 (1999)) and branched DNA signal amplification (bDNA) (see, e.g., Iqbal et al., *Mol. Cell Probes* 13(4):315 (1999)).

"Amplifying" refers to submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification reaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 25 nucleotides. The "integrity" of a primer refers to the ability of the primer to prime an amplification reaction. For example, the integrity of a primer is typically no longer intact after degradation of the primer sequences such as by endonuclease cleavage.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as exon 29 of the PKD1 gene or another region of SEQ ID NO:1), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to PKD1 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec-2 min., an annealing phase lasting 30 sec.-2 min., and an extension phase of about 72° C. for 1–2 min.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552–554 (1990)).

For preparation of monoclonal or polyclonal antibodies, any technique known in the art can be used (see, e.g., Kohler & Milstein, Nature 256:495–497 (1975); Kozbor et al., Immunology Today 4: 72 (1983); Cole et al., pp. 77–96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552–554 (1990); Marks et al., Biotechnology 10:779–783 (1992)).

An "immunogenic fragment" is one that elicits or modulates an immune response, preferably the composition induces or enhances an immune response in response to a particular mutant PKD1 or a portion thereof. Immune responses include humoral immune responses and cell-mediated immune responses, such as antibody production.

An "anti-PKD1" antibody is an antibody or antibody fragment that specifically binds a polypeptide encoded by a PKD1 gene, cDNA, or a subsequence thereof including polypeptides encoded by a mutant PKD1 gene, cDNA, or a subsequence thereof, e.g., the sequences set forth in FIG. 2 or subsequences thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, detect, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to mutant PKD1 can be selected to obtain only those polyclonal antibodies that are specifically immunoreactive with mutants of PKD1 (e.g., a mutant PKD1 comprising the sequence set forth in SEQ ID NO:1) and not with other proteins (e.g., wild type PKD1). This selection may be achieved by subtracting out antibodies that cross-react with molecules such as PKD1 from other species. In addition, polyclonal antibodies raised to mutant PKD1 polymorphic variants, alleles, orthologs, and conservatively modified variants can be selected to obtain only those antibodies that recognize specific fragments of mutant PKD1. For example polyclonal antibodies raised to can be selected to obtain only those antibodies that recognize polypeptides encoded by exon 29 of PKD1 or antibodies that recognize polypeptides encoded by a nucleic acid comprising the sequence set forth in SEQ ID NO:1, but not other PKD1 fragments. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that is suspected of containing a nucleic acid encoding a mutant PKD1 polypeptide or a mutant PKD1 polypeptide. These samples can be tested by the methods described herein and include body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples may also include sections of tissues such as biopsy and autopsy samples or frozen sections taken for histologic purposes. These samples are well known in the art. A biological sample is obtained from any mammal including, e.g., a cat. A biological sample may be suspended or dissolved in liquid materials such as buffers, extractants, solvents and the like.

III. Nucleic Acids Encoding Mutant PKD1

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859–1862 (1981), using an automated synthesizer, as described in Van Devanter et. al., Nucleic Acids Res. 12:6159–6168 (1984). Purification of oligonucleotides is by either native acrylamide gel electrophoresis or by anion-exchange HPLC as described in Pearson & Reanier, J. Chrom. 255:137–149 (1983).

The sequence of the cloned genes and synthetic oligonucleotides can be verified after cloning using, e.g., the chain termination method for sequencing double-stranded templates of Wallace et al., Gene 16:21–26 (1981).

B. Cloning Methods for the Isolation of Nucleotide Sequences Encoding Mutants of PKD1

In general, the nucleic acid sequences encoding mutant PKD1 and related nucleic acid sequence homologues are cloned from cDNA and genomic DNA libraries or isolated using amplification techniques with oligonucleotide primers. For example, mutant PKD1 sequences are typically isolated from nucleic acid (genomic or cDNA) libraries by hybridizing with a nucleic acid probe, the sequence of which can be derived from SEQ ID NO:1, or a subsequence thereof. Mutant PKD1 RNA and cDNA can be isolated from any cat.

Nucleic acids encoding mutant PKD1 can also be isolated from expression libraries using antibodies as probes. Such polyclonal or monoclonal antibodies can be raised using, for example, the polypeptides encoded by the sequence of SEQ ID NO:1.

PKD1 polymorphic variants, alleles, and interspecies homologues that are substantially identical to PKD1 can be isolated using PKD1 nucleic acid probes and oligonucleotides under stringent hybridization conditions, by screening libraries. Alternatively, expression libraries can be used to clone PKD1 polymorphic variants, alleles, and interspecies homologues, by detecting expressed homologues immunologically with antisera or purified antibodies made against the core domain of PKD1 which also recognize and selectively bind to the PKD1 homologue.

To make a cDNA library, PKD1 mRNA may be purified from any cat. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263–269 (1983); Sambrook et al., supra; Ausubel et al., supra).

For a genomic library, the DNA is extracted from the tissue and either mechanically sheared or enzymatically digested to yield fragments of about 1–8 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180–182 (1977). Colony hybridization is carried out as generally described in Grunstein et al., Proc. Natl. Acad. Sci. USA., 72:3961–3965 (1975).

An alternative method of isolating PKD1 nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of PKD1 directly from mRNA, from cDNA, from genomic libraries or cDNA libraries. Degenerate oligonucleotides can be designed to amplify PKD1 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of PKD1 encoding mRNA in physiological samples, for nucleic acid sequencing, or for other purposes. Genes amplified by the PCR reaction can be purified from agarose gels and cloned into an appropriate vector.

Amplification techniques using primers can also be used to amplify and isolate PKD1 DNA or RNA. For example, nucleic acids encoding PKD1 or fragments thereof may be obtained by amplification of a cat cDNA library or reverse transcribed from cat RNA using isolated nucleic acid primer pairs having the following sequences: For example, nucleic acids encoding mutant PKD1 or fragments thereof may be amplified using isolated nucleic acid primer pairs having the following sequences:5' primer: caggtagacgggatagacga (SEQ ID NO:19) and 3' primer: ttcttcctggtcaacgactg (SEQ ID NO:20) (exon 29); 5' primer: acctactcccacaggaaacc (SEQ ID NO:17) and 3' primer: ggaacgaggcaacagtga (SEQ ID NO:18) (exon 24); 5' primer: cagacacgggacaggaga (SEQ ID NO:23) and 3' primer: ctcaaggtgagtgggatgtt (SEQ ID NO:24) (exon 37); 5' primer: gacaagategagatgggatg (SEQ ID NO:25) and 3' primer: cacactgggattggctga (SEQ ID NO:26) (exon 38).

These primers can be used, e.g., to amplify either the full length sequence or a probe of one to several hundred nucleotides, which is then used to screen a cDNA library for full-length PKD1.

Gene expression of PKD1 can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant PKD1 genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the PKD1 gene. The specific subsequence is then ligated into an expression vector. PKD1 chimeras can be made, which combine, e.g., a portion of PKD1 with a portion of a heterologous PKD1 to create a chimeric, functional PKD1.

The gene for PKD1 is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding PKD1 proteins comprise a nucleic acid sequence encoding a PKD1 protein and subsequences, interspecies homologues, alleles and polymorphic variants thereof. In preferred embodiments, the isolated nucleic acid encoding a PKD1 protein comprises SEQ ID NO:1 or a complement thereof.

C. Expression of PKD1 in Prokaryotes and Eukaryotes

To obtain high level expression of a cloned gene, such as those cDNAs encoding mutant PKD1, one typically subclones mutant PKD1 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the PKD1 protein are available in, e.g., E. coli, Bacillus sp., and Salmonella (Palva et al., Gene 22:229–235 (1983); Mosbach et al., Nature 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the mutant PKD1 encoding nucleic acid in host cells.

A typical expression cassette thus contains a promoter operably linked to the nucleic acid sequence encoding mutant PKD1 and signals required for efficient polyadenylation of the transcript, ribosome binding sites, and translation termination. The nucleic acid sequence encoding mutant PKD1 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a PKD1 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of PKD1 protein, which are then purified using standard techniques (see, e.g., Colley et al., J. Biol. Chem. 264:17619–17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349–351 (1977); Clark-Curtiss & Curtiss, Methods in Enzymology 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing PKD1.

After the expression vector is introduced into the cells, the transfected cells are cultured under conditions favoring expression of PKD1, which is recovered from the culture using standard techniques identified below.

D. Purification of Mutant PKD1 Protein

Either naturally occurring or recombinant mutant PKD1 can be purified for use in functional assays. Naturally occurring mutant PKD1 is purified, e.g., from cat and any other source of a PKD1 homologue. Recombinant mutant PKD1 is purified from any suitable expression system.

Mutant PKD1 may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant mutant PKD1 is being purified. For example, proteins having established molecular adhesion properties can be reversible fused to PKD1. With the appropriate ligand, mutant PKD1 can be selectively adsorbed to a purification column and then freed from the column in a relatively pure form. The fused protein is then removed by enzymatic activity. Finally mutant PKD1 could be purified using immunoaffinity columns.

1. Purification of Mutant PKD1 from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of mutant PKD1 from inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Mutant PKD1 is separated from other bacterial proteins by standard separation techniques, e.g., with Ni-NTA agarose resin.

Alternatively, it is possible to purify mutant PKD1 from bacteria periplasm. After lysis of the bacteria, when mutant PKD1 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

E. Standard Protein Separation Techniques for Purifying Mutant PKD1

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of PKD1 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

PKD1 can also be separated from other proteins on the basis of their size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Alternatively, PKD1 protein can be expressed transiently in a cell by introducing into a cell an RNA encoding the PKD1 protein. The RNA is transcribed in vitro according to standard procedures and then introduced into a cell (e.g. such as *Xenopus* oocytes, CHO, and HeLa cells) by means such as injection or electroporation. The RNA then expresses the PKD1 protein.

IV. Detection of Mutant PDK1 Nucleic Acid Sequences

Determination of the presence of absence of a particular mutant PKD1 gene is generally performed by analyzing a nucleic acid sample that is obtained from a cat (e.g., of the genus *felis, panthera, neofelis,* or *acinonyx*) to be analyzed. Often, the nucleic acid sample comprises genomic DNA. It is also possible to analyze RNA samples for the presence of PKD1 mutations.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994–1999, including supplemental updates through April 2004; Sambrook & Russell, *Molecular Cloning, A Laboratory Manual* (3rd Ed, 2001).

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the PKD1 mutations described herein.

Although the methods typically employ PCR steps, other amplification protocols may also be used. Suitable amplification methods include ligase chain reaction (see, e.g., Wu & Wallace, *Genomics* 4:560–569, 1988); strand displacement assay (see, e.g., Walker et al., *Proc. Natl. Acad. Sci. USA* 89:392–396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173–1177, 1989); and self-sustained sequence replication (3SR) (Guatelli et al., *Proc. Natl. Acad. Sci. USA* 87:1874–1878, 1990; WO 92/08800). Alternatively, methods that amplify the probe to detectable levels can be used, such as Qβ-replicase amplification (Kramer & Lizardi, *Nature* 339:401–402, 1989; Lomeli et al., *Clin. Chem.* 35:1826–1831, 1989). A review of known amplification methods is provided, for example, by Abramson and Myers in *Current Opinion in Biotechnology* 4:41–47, 1993.

In some embodiments, the mutant PKD1 is detected using oligonucleotide primers and/or probes. Oligonucleotides can be prepared by any suitable method, including chemical synthesis. Oligonucleotides can be synthesized using commercially available reagents and instruments. Alternatively, they can be purchased through commercial sources. Methods of synthesizing oligonucleotides are well known in the art (see, e.g, Narang et al., *Meth. Enzymol.* 68:90–99, 1979; Brown et al., *Meth. Enzymol.* 68:109–151, 1979; Beaucage et al., *Tetrahedron Lett.* 22:1859–1862, 1981; and the solid support method of U.S. Pat. No. 4,458,066).

A. PCR Identification of Carriers of PKD

PCR can be used to detect carriers of PKD by amplification of nucleic acids encoding mutant PKD1. A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202.

PCR permits the copying, and resultant amplification of a target nucleic acid, e.g., a nucleic acid encoding PKD1. Briefly, a target nucleic acid, e.g. DNA from a biological sample from a subject (e.g., a cat suspected of being a PKD carrier), is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

In general, PCR and other methods of amplification use primers which anneal to either end of the DNA of interest. For example, nucleic acids encoding mutant PKD1 or fragments thereof may be amplified using isolated nucleic acid primer pairs having the following sequences: 5' primer: caggtagacgggatagacga (SEQ ID NO:19) and 3' primer: ttcttcctggtcaacgactg (SEQ ID NO:20) (exon 29); 5' primer: acctactcccacaggaaacc (SEQ ID NO:17) and 3' primer: ggaacgaggcaacagtga (SEQ ID NO:18) (exon 24); 5' primer: cagacacgggacaggaga (SEQ ID NO:23) and 3' primer: ctcaaggtgagtgggatgtt (SEQ ID NO:24) (exon 37); 5' primer: gacaagatcgagatgggatg (SEQ ID NO:21) and 3' primer: cacactgggattggctga (SEQ ID NO:26) (exon 38). Amplification of DNA encoding mutant PKD1 from a biological sample from a subject suspected of being a PKD carrier indicates that the subject is a carrier for PKD.

Target nucleic acid sequences may be double or single-stranded DNA or RNA from any biological sample from a subject suspected of being a PKD carrier. Preferably, the target template is an isolated DNA sequence. Target DNA sequences may be isolated using a variety of techniques. For example, methods are known for lysing organisms and preparing extracts or purifying DNA. See, Current Protocols in Molecular Biology Volumes 1–3, John Wiley & Sons, Inc. (Ausubel et al., eds., 1994–1998) (hereinafter "Ausubel et al."). Also, total RNA or polyA+ RNA can be reverse transcribed to produce cDNA that can serve as the target DNA.

B. Reaction Components

1. Oligonucleotides

The oligonucleotides that are used in the present invention as well as oligonucleotides designed to detect amplification products can be chemically synthesized, as described above. These oligonucleotides can be labeled with radioisotopes, chemiluminescent moieties, or fluorescent moieties. Such labels are useful for the characterization and detection of amplification products using the methods and compositions of the present invention.

The primer components may be present in the PCR reaction mixture at a concentration of, e.g., between 0.1 and 1.0 µM. The concentration of the target primers can be from about 0.1 to about 0.75 µM. The primer length can be between, e.g., 15–100 nucleotides in length and preferably have 40–60% G and C composition. In the choice of primer, it is preferable to have exactly matching bases at the 3' end of the primer but this requirement decreases to relatively insignificance at the 5' end. Preferably, the primers of the invention all have approximately the same melting temperature.

Typically, the primers have the following design. The most 3' portion anneals to the constant region flanking the target region to be amplified, this portion will normally have at least 6 bp of homology to the target region, preferably 9 or more bp. The region of homology is adjacent to the restriction enzyme sequence. If this recognition site is an interrupted sequence, the intervening portion of sequence between the two portions of the restriction enzyme site will normally contain bases which can anneal to the appropriate portion of the constant region flanking the target of interest. 5' to the restriction enzyme site are sufficient bases to allow the restriction enzyme to recognize its site and cleave the recognized sequence. Where the restriction enzyme site cleaves twice, once on either side of the recognition site, the primer should be sufficiently long to allow the enzyme to cleave at both of the cleavage sites. The extra nucleotides may or may not have further homology to the constant region flanking the target of interest.

2. Buffer

Buffers that may be employed are borate, phosphate, carbonate, barbital, Tris, etc. based buffers. (See, U.S. Pat. No. 5,508,178). The pH of the reaction should be maintained in the range of about 4.5 to about 9.5. (See, U.S. Pat. No. 5,508,178. The standard buffer used in amplification reactions is a Tris based buffer between 10 and 50 mM with a pH of around 8.3 to 8.8. (See Innis et al., supra.).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

3. Salt Concentration

The concentration of salt present in the reaction can affect the ability of primers to anneal to the target nucleic acid. (See, Innis et al.). Potassium chloride is added up to a concentration of about 50 mM to the reaction mixture to promote primer annealing. Sodium chloride can also be added to promote primer annealing. (See, Innis et al.).

4. Magnesium Ion Concentration

The concentration of magnesium ion in the reaction can affect amplification of the target sequence(s). (See, Innis et al.). Primer annealing, strand denaturation, amplification specificity, primer-dimer formation, and enzyme activity are all examples of parameters that are affected by magnesium concentration. (See, Innis et al.). Amplification reactions should contain about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

5. Deoxynucleotide Triphosphate Concentration

Deoxynucleotide triphosphates (dNTPs) are added to the reaction to a final concentration of about 20 µM to about 300 µM. Typically, each of the four dNTPs (G, A, C, T) are present at equivalent concentrations. (See, Innis et al.).

6. Nucleic Acid Polymerase

A variety of DNA dependent polymerases are commercially available that will function using the methods and compositions of the present invention. For example, Taq DNA Polymerase may be used to amplify target DNA sequences. The PCR assay may be carried out using as an enzyme component a source of then nostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1–5 units per reaction mixture. The reaction mixture is typically between 20 and 100 µl.

In some embodiments, a "hot start" polymerase can be used to prevent extension of mispriming events as the temperature of a reaction initially increases. Hot start polymerases can have, for example, heat labile adducts requiring a heat activation step (typically 95° C. for approximately 10–15 minutes) or can have an antibody associated with the polymerase to prevent activation.

7. Other Agents

Additional agents are sometime added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction. (See, Innis et al. supra). Stabilizing agents such as gelatin, bovine serum albumin, and non-ionic detergents (e.g. Tween-20) are commonly added to amplification reactions. (See, Innis et al. supra).

C. Detection of Amplified Products

Amplified products can be detected using any means known in the art, including, e.g., restriction fragment length polymorphism (RFLP) analysis; denaturing gel electrophoresis, direct sequencing, and HPLC-based analysis.

1. RFLP Analysis

In some embodiments, a mutant PKD1 gene is detected using restriction fragment length polymorphism (RFLP) analysis. For example, exon 29 of PKD1 is amplified from a biological sample from a cat. The amplification products of exon 29 of PKD1 are digested with a restriction enzyme (e.g., Mly 1) that digests the mutant PKD1, but not the wild type PKD1. The restriction fragments are then analyzed using gel electrophoresis. For example, cats carrying a PKD1 mutation associated with PKD have a 559 bp undigested wild type fragment and two digested fragments of 316 bp and 243 bp.

2. Denaturing Gradient Gel Electrophoresis

Amplification products generated using the polymerase chain reaction can be analyzed by the use of denaturing gradient gel electrophoresis. Different PKD1 mutations can be identified based on the different sequence-dependent melting properties and electrophoretic migration of DNA in solution (see, e.g., Erlich, ed., PCR TECHNOLOGY, PRINCIPLES AND APPLICATIONS FOR DNA AMPLIFICATION, W. H. Freeman and Co, New York, 1992, Chapter 7).

3. DNA Sequencing and Single Base Extensions

The mutant PKD1 genes can also be detected by direct sequencing, e.g., to detect the C to A transversion in exon 29 of PKD1 or the C to T transversion at position 127 of exon 38. Methods include e.g., dideoxy sequencing-based methods and Maxam and Gilbert sequence (see, e.g., Sambrook and Russell, supra).

Other detection methods include pyrosequencing of oligonucleotide-length products. Such methods often employ amplification techniques such as PCR.

Another similar method for characterizing single base changes does not require use of a complete PCR, but typically uses only the extension of a primer by a single, fluorescence-labeled dideoxyribonucleic acid molecule (ddNTP) that is complementary to the nucleotide to be investigated. The nucleotide at the site of the PKD1 mutation can be identified via detection of a primer that has been extended by one base and is fluorescently labeled (e.g., Kobayashi et al, *Mol. Cell. Probes*, 9:175–182, 1995).

4. HPLC

Target mutant PKD1 sequences can be differentiated using high performance liquid chromatography (HPLC) based methods including denaturing HPLC (dHPLC) as described in e.g., Premstaller and Oefner, *LC-GC Europe* 1–9 (July 2002); Bennet et al., *BMC Genetics* 2:17 (2001); Schrimi et al., *Biotechniques* 28(4):740 (2000); and Nairz et al., *PNAS USA* 99(16):10575–10580 (2002); and ion-pair reversed phase HPLC-electrospray ionization mass spectrometry (ICEMS) as described in e.g., Oberacher et al.; *Hum. Mutat.* 21(1):86 (2003).

Partially denaturing HPLC analysis compares two or more sets of amplified products (e.g., a wild-type PKD1 amplicon and a mutant PKD1 amplicon). The amplified products are denatured (e.g., at about 95° C.) and allowed to reanneal by gradually lowering the temperature from about 95° C. to about 30° C. In the presence of a PKD1 mutation the original homoduplex products are reformed along with heteroduplex products comprising the sense and anti-sense strands of either homoduplex. The homoduplexes and heteroduplexes are loaded onto an HPLC apparatus at a partially denaturing temperature of about 50° C. to about 70° C. and can be distinguished based on their elution profile. Completely denaturing HPLC analysis compares two or more sets of amplicons (e.g., primer extension products). The amplified products are loaded onto an HPLC apparatus at a completely denaturing temperature of about 70° C. to about 80° C. Specific sequence variants are eluted from the column by varying the temperature of the column and sequence variants are distinguished based on their order of elution from the column.

Ion-pair reversed phase HPLC-electrospray ionization mass spectrometry (ICEMS) uses a combination of HPLC under completely denaturing conditions and ICEMS to resolve differences between nucleic acid sequences.

5. Single-Strand Conformation Polymorphism Analysis

Target mutant PKD1 sequences can also be differentiated using single-strand conformation polymorphism analysis, which identifies base differences by alteration in electrophoretic migration of single stranded PCR products, as described, e.g, in Orita et al., *Proc. Nat. Acad. Sci.* 86, 2766–2770 (1989). Amplified PCR products can be generated using methods known in the art, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between wild type and mutant PKD1 sequences.

Methods for detecting single base changes often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., $^{32}P$, electron-dense reagents, enzyme, such as peroxidase or alkaline phsophatase, biotin, or haptens and proteins for which antisera or monoclonal antibodies are available. Labeling techniques are well known in the art (see, e.g., Current Protocols in Molecular Biology, supra; Sambrook & Russell, supra).

6. Sequence Specific Hybridization

A technique commonly referred to as allele specific oligonucleotide hybridization (ASO) (e.g., Stoneking et al., *Am. J. Hum. Genet.* 48:70–382, 1991; Saiki et al., *Nature* 324, 163–166, 1986; EP 235,726; and WO 89/11548) can used to detect mutant PKD1 genes. Two DNA molecules differing by one base are distinguished by hybridizing an oligonucleotide probe that is specific for one of the variants (e.g., wild type or mutant PKD1) to an amplified product obtained from amplifying the nucleic acid sample. The probes are designed to differentially hybridize to one variant versus another. Principles and guidance for designing such probes is available in the art (see, e.g., Jeffrys and Mays, *Genome Res.* 13(1): 2316–2324 (2003) and Howell et al., *Nature Biotech* 17(1): 87–88 (1999)). Hybridization conditions should be sufficiently stringent that there is a significant difference in hybridization intensity between alleles, and preferably an essentially binary response, whereby a probe hybridizes to only one of the sequences.

The presence of a PKD1 mutation is determined by measuring the amount of sequence-specific oligonucleotide that is hybridized to the sample. Typically, the oligonucleotide is labeled with a label such as a fluorescent label. For example, a mutant PKD1-specific oligonucleotide is applied to immobilized oligonucleotides representing PKD1 sequences. After stringent hybridization and washing conditions, fluorescence intensity is measured for each PKD1 oligonucleotide.

For example, the nucleotide present at the site of the PKD1 mutation is identified by hybridization under sequence-specific hybridization conditions with an oligonucleotide probe exactly complementary to a PKD1 mutation in a region encompassing the PKD1 mutation. The probe hybridizing sequence and sequence-specific hybridization conditions are selected such that a single mismatch at the mutation site destabilizes the hybridization duplex sufficiently so that it is effectively not formed. Thus, under sequence-specific hybridization conditions, stable duplexes will form only between the probe and the exactly complementary PKD1 sequence.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers.

One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism. Such a subarray can be used in detecting the presence of the mutant PKD1 gene described herein.

7. Sequence-Specific Amplification

Mutations are also commonly detected using sequence-specific amplification or primer extension methods. These reactions typically involve use of primers that are designed to specifically target a polymorphism via a mismatch at the 3' end of a primer. The presence of a mismatch effects the ability of a polymerase to extend a primer when the polymerase lacks error-correcting activity. For example, to detect a mutant PKD1 sequence using a PKD1-specific amplification- or extension-based method, a primer complementary to the wild type or mutant PKD1 gene is designed such that the 3' terminal nucleotide hybridizes at the mutation site. The presence of the PKD1 mutation can be determined by the ability of the primer to initiate extension. If the 3' terminus is mismatched, the extension is impeded. Thus, for example, if a primer matches the PKD1 mutation at the 3' end, the primer matches and will be efficiently extended.

Typically, the primer is used in conjunction with a second primer in an amplification reaction. The second primer hybridizes at a site unrelated to the polymorphic position. Amplification proceeds from the two primers leading to a detectable product signifying the particular allelic form is present. Sequence-specific amplification-or extension-based methods are described in, for example, WO 93/22456; U.S. Pat. Nos. 5,137,806; 5,595,890; 5,639,611; and U.S. Pat. No. 4,851,331.

Using sequence-specific amplification-based genotyping, identification of the mutations requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, sequence-specific amplification methods, can be performed in reaction that employ multiple sequence-specific primers to target particular mutations. Primers for such multiplex applications are generally labeled with distinguishable labels or are selected such that the amplification products produced from the target sequences are distinguishable by size. Thus, for example, the presence of both a wild type and mutant PKD1 gene in a single sample can be identified using a single amplification by gel analysis of the amplification product.

As in the case of sequence-specific probes, a sequence-specific oligonucleotide primer may be exactly complementary to one of the PKD1 mutants in the hybridizing region or may have some mismatches at positions other than the 3' terminus of the oligonucleotide, which mismatches occur away from the site of the PKD1 mutation.

8. 5'-Nuclease Assay

Genotyping can also be performed using a "TaqMan®" or "5'-nuclease assay", as described in U.S. Pat. Nos. 5,210,015; 5,487,972; and 5,804,375; and Holland et al., 1988, *Proc. Natl. Acad. Sci. USA* 88:7276–7280. In the TaqMan® assay, labeled detection probes that hybridize within the amplified region are added during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

The hybridization probe can be a sequence-specific probe that discriminates between wild type and mutant PKD1. Alternatively, the method can be performed using a sequence-specific primer and a labeled probe that binds to amplified product.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673 describe alternative methods for detecting the degradation of probe which occurs concomitant with amplification.

In some cases, mRNA can also be used to determine the whether a cat carries a PKD1 mutation associated with PKD. Such an analysis can be performed by first reverse-transcribing the target RNA from a biological sample from the cat using, for example, a viral reverse transcriptase, and then amplifying the resulting cDNA; or using a combined high-temperature reverse-transcription-polymerase chain reaction (RT-PCR), as described in U.S. Pat. Nos. 5,310,652; 5,322,770; 5,561,058; 5,641,864; and 5,693,517.

V. Immunological Detection of PKD1

In addition to the identification of PKD carriers by detection of PKD1 genes and gene expression using nucleic acid hybridization technology, one can also use immunoassays to identify carriers of PKD by detecting PKD1 or antibodies that specifically bind to them. Immunoassays can be used to qualitatively or quantitatively analyze PKD1. A general overview of the applicable technology can be found in Harlow & Lane, Antibodies: A Laboratory Manual (1988).

A. Antibodies to PKD1

Methods of producing polyclonal and monoclonal antibodies that react specifically with PKD1, or immunogenic fragments of PKD1, are known to those of skill in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275–1281 (1989); Ward et al., Nature 341:544–546 (1989)).

A number of immunogens comprising portions of mutant PKD1 may be used to produce antibodies specifically reactive with mutant PKD1 or homologues thereof. For example, recombinant PKD1 (encoded by a sequence comprising SEQ ID NO:1) or antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-PKD1 proteins, using a competitive binding immunoassay. Specific polyclonal antisera and monoclonal antibodies will usually bind with a Kd of at least about 0.1 mM, more usually at least about 1 µM, preferably at least about 0.1 µM or better, and most preferably, 0.01 µM or better. Antibodies specific only for a particular mutant PKD1 homologue, such as the feline mutant PKD1 encoded by a sequence comprising SEQ ID NO:1, can also be made, by subtracting out other cross-reacting homologues from a species such as a non-human mammal.

Once the specific antibodies against a mutant PKD1 are available, mutant PKD1 homologues can be detected by a variety of immunoassay methods. For a review of immunological and immunoassay procedures, see Basic and Clinical Immunology (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra. Additional assay configurations (i.e., using multiplex assays using microspheres) are described in, e.g., De Jager et al., *Clin. Diagn. Lab. Immunol.* 10(1): 13309 (2003); Earley et al., *Cytometry* 50(5):239–42 (2002); and Seidman and Peritt, *J. Immunol. Methods* 267(2):165–71 (2002).

In one exemplary embodiment, the immunoassays are performed using Luminex technology. With Luminex technology, molecular reactions take place on the surface of microscopic beads called microspheres (Literature from Luminex Corporation, Austin, Tex.). For each reaction in a Luminex profile, thousands of molecules are attached to the surface of internally color-coded microspheres. The assigned color-code identifies each reaction throughout the test. The magnitude of the biomolecular reaction is measured using a second molecule called a reporter which can be a secondary antibody labeled with color. The reporter molecule signals the extent of the reaction by attaching to the molecules on the microspheres. Because the reporter's signal is also a color, there are two sources of color, the color-code inside the microsphere and the reporter color on the surface of the microsphere. To perform a test, the color-coded microspheres, reporter molecules, and sample are combined. This mixture is then injected into an instrument that uses microfluidics to align the microspheres in single file where lasers illuminate the colors inside and on the surface of each microsphere. Next, advanced optics capture the color signals. Finally, digital signal processing translates the signals into real-time, quantitative data for each reaction. The advantages of this Luminex techniques are that multiplex antigens representing different pathogens can be tested with single serum sample, therefore, it saves on labor, reagents, time and samples: and that it makes high throughput (20,000 microsphere per second) possible and shortens analysis time. For example, one color coded beads can be coated with wild type PKD1, and a different color coded beads can be coated with mutant PKD1: and 2 sets of beads can be mixed and reacted with the same fluid sample to determine whether the sample has wild type PKD1, mutant PKD1, or both by a single test.

B. Immunological Binding Assays

The PKD1 polypeptides of the invention and antibodies that specifically bind to them can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice (in this case PKD1 or an immunogenic fragment thereof). The antibody (e.g., anti-PKD1) may be produced by any of a number of means well known to those of skill in the art and as described above. Alternatively, a protein or antigen of choice (in this case PKD1, or an immunogenic fragment thereof) may be used to bind antibodies that specifically bind to the protein or antigen. The protein or antigen may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled PKD1 polypeptide or a labeled anti-PKD1 antibody. Alternatively, the labeling agent may be a third moiety, such a secondary antibody, which specifically binds to the antibody/PKD1 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., J. Immunol. 111:1401–1406 (1973); Akerstrom et al., J. Immunol. 135:2589–2542 (1985)). The labeling agent can be modified with a detectable moiety, such as biotin, to which another molecule can specifically bind, such as streptavidin. The streptavidin may be bound to a label or detectable group as discussed below. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize PKD1, or secondary antibodies that recognize anti-PKD1 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting PKD1 or immunogenic fragments thereof in samples may be either competitive or noncompetitive. Noncompetitive immunoassays are assays in which the amount of antigen is directly measured. In one preferred "sandwich" assay, for example, the anti-PKD1 antibodies can be bound directly to a solid substrate on which they are immobilized. These immobilized antibodies then capture PKD1 present in the test sample. PKD1 are thus immobilized and then bound by a labeling agent, such as a second PKD1 antibody bearing a label. Alternatively, the second antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

Noncompetitive immunoassays may also be assays in which the amount of anti-PKD1 antibody is directly measured. PKD1 or an immunogenic fragment thereof can be bound directly to a solid substrate on which they are immobilized. The immobilized PKD1 then captures anti-PKD1 antibodies present in the test sample. Anti-PKD1 antibodies are thus immobilized and then bound by a labeling agent, such as an anti-Fc antibody bearing a label. The anti-Fc antibody may be, for example, an anti-mouse Fc antibody, an anti-rat Fc antibody, or an anti-rabbit Fc antibody. Those of skill in the art will appreciate that any suitable anti-Fc antibody may be selected for use in this type of assay. Alternatively, the anti-Fc antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

2. Competitive Assay Formats

In competitive assays, the amount of the PKD1 present in the sample is measured indirectly by measuring the amount of known, added (exogenous) PKD1 displaced (competed away) from an anti-PKD1 antibody by the unknown PKD1 present in a sample. In one competitive assay, a known amount of the PKD1 is added to a sample and the sample is then contacted with an antibody that specifically binds to the PKD1. The amount of exogenous PKD1 bound to the antibody is inversely proportional to the concentration of the PKD1 present in the sample. In a particularly preferred embodiment, the antibody is immobilized on a solid substrate. The amount of PKD1 bound to the antibody may be determined either by measuring the amount of PKD1 present in a PKD1/antibody complex, or alternatively by measuring the amount of remaining uncomplexed protein. The amount of PKD1 may be detected by providing a labeled PKD1 molecule.

A hapten inhibition assay is another preferred competitive assay. In this assay the known PKD1 is immobilized on a solid substrate. A known amount of anti-PKD1 antibody is added to the sample, and the sample is then contacted with the immobilized PKD1. The amount of anti-PKD1 antibody bound to the known immobilized PKD1 is inversely proportional to the amount of PKD1 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations for PKD1 homologues. For example, a PKD1 protein at least partially corresponding to a polypeptide sequence encoded by SEQ ID NO:1 or an immunogenic fragment thereof, (e.g., the polypeptide encoded by exon 29 of PKD1, can be immobilized to a solid support. Other proteins such as PKD1 homologues or other proteins from other cat species, are added to the assay so as to compete for binding of the antisera to the immobilized antigen. The ability of the added proteins to compete for binding of the antisera to the immobilized protein is compared to the ability of the PKD1 or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues. Antibodies that specifically bind only to PKD1, or only to particular homologues of PKD1 can also be made using this methodology.

The immunoabsorbed and pooled antisera are then used in a competitive binding immunoassay as described above to compare a second protein, thought to be perhaps a PKD1 homologue or an allele, or polymorphic variant of PKD1, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by PKD1 that is required to inhibit 50% of binding, then the second protein is said to specifically bind to the polyclonal antibodies generated to the respective PKD1 immunogen.

4. Other Assay Formats

Western blot (immunoblot) analysis is used to detect and quantify the presence of the PKD1 polypeptides in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind PKD1 polypeptides. The anti-PKD1 antibodies specifically bind to PKD1 on the solid support, thereby forming an antibody-polypeptide complex. These antibodies may be directly labeled or alternatively may be subsequently detected using labeled antibodies (e.g., labeled sheep anti-mouse antibodies) that specifically bind to the anti-PKD1 antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

5. Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

VI. IV. Kits

PKD1 and their homologues are a useful tool for more specific and sensitive identification of PKD carriers in, e.g., cats. PKD1 specific reagents that specifically hybridize to PKD1 nucleic acid, such as PKD1 probes and primers, PKD1, and PKD1 specific reagents that specifically bind to the PKD1 protein, e.g., PKD1 antibodies are used to identify PKD carriers.

Nucleic acid assays for the presence of PKD1 DNA and RNA in a sample include numerous techniques are known to those skilled in the art, such as Southern analysis, northern analysis, dot blots, RNase protection, S 1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques 4:230–250 (1986); Haase et al., Methods in Virology, vol. VII, pp. 189–226 (1984); and Nucleic Acid Hybridization: A Practical Approach (Hames et al., eds. 1987). In addition, PKD1 protein can be detected with the various immunoassay techniques described above, e.g., ELISA, western blots, etc. The test sample is typically compared to both a positive control (e.g., a sample expressing recombinant PKD1) and a negative control. A wide variety of kits and components can be prepared according to the present invention, depending upon the intended user of the kit and the particular needs of the user. For example, the kit can be tailored for in vitro or in vivo assays.

The invention also provides kits and solutions for carrying out the amplification methods of the invention. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a target sample.

Kits can include, for instance, amplification reagents comprising primers sufficient to amplify at least two different target sequences, a polynucleotide sequence comprising the sequences of the primers or subsequences of the primers s described herein; and at least one probe for amplifying and detecting the polynucleotide sequence. In addition, the kit can include nucleotides (e.g., A, C, G and T), a DNA polymerase and appropriate buffers, salts and other reagents to facilitate amplification reactions.

In some embodiments, the kits comprise vessels such as sample processing cartridges useful for rapid amplification of a sample as described in Belgrader, P., et al., *Biosensors and Bioelectronics* 14:849–852 (2000); Belgrader, P., et al., *Science*, 284:449–450 (1999); and Northrup, M. A., et al. "A New Generation of PCR Instruments and Nucleic Acid Concentration Systems" in PCR Protocols (Sninsky, J. J. et al (eds.)) Academic, San Diego, Chapter 8 (1998).

EXAMPLES

The following examples are offered to illustrate, but not to limit the claimed invention.

Example 1

Materials and Methods

Sample Identification: Samples from cats representing families segregating with PKD were collected from five feline PKD ultrasound screening clinics that were held at the University of California, Davis (UC Davis), School of Veterinary Medicine between June 2000 and September 2002. Details regarding the disease criteria and the pedigrees developed from these clinics have been previously described (Young et al., *Mammal Genome* (2004)). Representatives from each pedigree were genotyped for the PKD mutation including 36 affected and 20 unaffected Persians and 33 individuals in feline PKD family 7. PKD cases from other breeds including Siamese, Exotic Shorthair, Domestic Shorthair (N=1 each), Selkirk Rexes (N=3), Scottish Folds (N=2), and Ragdolls (N=3) were identified by the authors (DJB) and from the UC Davis ultrasound screening clinics.

BAC clone Sequencing: The sequence of the feline BAC clone (GenBank Accession: AC145332.28) containing the feline PKD1 homolog was obtained using standard BAC isolation, shotgun sequencing, and finishing strategies as described previously (Roe: *Shotgun Library Construction for DNA Sequencing*. Totowa, N.J., Humana Press (2004); Bodenteich et al., *Shotgun Cloning as the Strategy of Choice to Generate Templates for High-throughput Dideoxynucleotide Sequencing*, London, Academic Press (1993); Chissoe et al., *Genomics* 27:67–82 (1995); Sambrook, T et al.: *Molecular Cloning: A Laboratory Manual*, New York, Cold Spring Harbor Laboratory Press (1989)). Briefly, 50 µg of purified BAC DNA was randomly sheared and made blunt-ended. After kinase treatment and gel purification, fragments in the 1–3 Kb range were ligated into SmaI-cut, bacterial alkaline phosphatase (BAP)-treated pUC18 (Pharmacia) and transformed by electroporation into *E. coli*, strain XL1BlueMRF' (Stratagene). A random library of approximately 2,500 colonies were picked from the transformation, grown in Terrific Broth (TB) medium supplemented with 100 µg of ampicillin for 14 hrs at 37° C. with shaking at 250 rpm, and the sequencing templates were isolated by a cleared lysate-based protocol. Sequencing reactions were performed as previously described using Taq DNA polymerase with the Amersham ET Fluorescent-labeled terminators (Roe: *Shotgun Library Construction for DNA Sequencing*. Totowa, N.J., Humana Press (2004); Bodenteich et al., *Shotgun Cloning as the Strategy of Choice to Generate Templates for High-throughput Dideoxynucleotide Sequencing*, London, Academic Press (1993); Chissoe et al., *Genomics* 27:67–82 (1995); Sambrook, T et al.:*Molecular Cloning: A Laboratory Manual*, New York, Cold Spring Harbor Laboratory Press (1989)). The reactions were incubated for 60 cycles in a Perkin-Elmer Cetus DNA Thermocycler 9600 and after removal of unincorporated dye terminators by ethanol precipitation, the fluorescent-labeled nested fragment sets were resolved by electrophoresis on an ABI 3700 Capillary DNA Sequencer. The resulting sequence data was transferred to a Sun Workstation Cluster, where it was base-called and assembled using the Phred and Phrap programs (Ewing and Green, *Genome Res.* 8:186–194 (1998); Ewing et al., *Genome Res.* 8:175–185 (1998)). Overlapping sequences and contigs were analyzed using Consed (Gordon et al., *Genome Res.* 8:195–202 (1998)).

PKDJ Sequence analysis: Isolation of the BAC clone containing the feline PKD1 homolog has been previously described (Grahn et al., R, Biller D, Young A, Roe B, Qin B; Lyons L: *Genetic testing for feline polycystic kidney disease*, submitted, 2004). Sequence of the PKD1 containing BAC clone (GenBank Accession: AC145332.28) was aligned to the human (GenBank Accession: AC009065.8), dog (GenBank Accession: AY102170.1), and mouse (GenBank Accession: AC132367.3) PKD1 sequences to identify potential intron/exon boundaries for the cat using the software PIPMAKER (Schwartz et al., *Genome Res.* 10:577–586 (2000)). Primers were developed in intronic regions for amplification of complete exons using the software Primer3 (Rozen and Skaletsky: *Primer3 on the WWW for general users and for biologist programmers*. Totowa, N.J., Human Press (2000)) and NetPrimer. Primers and the GenBank accession numbers for the exons analyzed are presented in Table 1. Primers (MWG Biotech, High Point, NC) were used to amplify PKD negative control cat DNA. Each primer was tested in the cat as previously described (Lyons et al., *Nat. Genet.* 15:47–56 (1997)) on a Stratagene 96-well temperature gradient Robocycler (Stratagene, La Jolla, Calif.). The amplified products were separated on 1.8% agarose gels at 100 Vhr. Gels were visualized by UV exposure after ethidium bromide staining and photo-documented using the Alpha Imaging System (Alpha Lnnotech Corp, San Leandro, Calif.). A positive optimization of the primers produced a single PCR product that was excised from the gel and purified using the Qiagen gel extraction column (Qiagen Inc., Valencia Calif.), or PCR products were directly purified using the Qiagen PCR clean up kit (Qiagen Inc., Valencia Calif.). Purified products were directly sequenced in both directions using the ABI Dye Terminator Sequencing chemistry v3.1 (Applied Biosystems, Foster City, Calif.). Sequencing reactions were separated on an ABI 377 DNA Analyzer and the DNA contig sequence was assembled using the Sequencer Software package (Gene Codes Corp, Ann Arbor, Mich.). Integrity of the sequence contig was confirmed by visual inspection and verified to be the correct gene by comparison to sequences in GenBank using BLAST (Altschul et al., *J. Mol. Biol.* 215:403–410 (1990)).

Genotyping: DNA from affected and normal cats was isolated from white cells by standard phenol/chloroform techniques. EDTA anti-coagulated blood was collected by venipuncture at the PKD clinics or sent by private clinicians. PKD exon products were amplified by PCR from genomic DNA of normal and affected cats using the optimized primers (Table 1). Individual exons were amplified independently in feline DNA samples using optimal PCR conditions on a Stratagene 96-well temperature gradient Robocycler. Approximately 12.5 ng DNA was used per PCR reaction. Reaction conditions for each primer pair were as follows: approximately 1 pmol of each forward and reverse primer, 1.25 mM dNTP, 1.75 mM MgCl2, 1×PCR buffer II and 0.375 U of Amplitaq (Applied Biosystems) polymerase in 10 µl reaction volumes. Cycling parameters included an initial 3 min denaturation at 94° C. followed by 35 cycles of: 1 min denaturation at 94° C., annealing for 1 min at 58° C. and a 72° C. extension for 1 min. The cycling parameters were followed by a final extension at 72° C. for 10 min. Products were generated, visualized, gel extracted, purified, and sequenced as described above and analyzed for mutations associated with PKD. Sequences generated from each exon were aligned (DNAStar, Madison, Wis.) with wild-type cat sequence to identify possible causative mutations for the observed phenotype. When polymorphisms were detected, sequence data was translated to determine if the mutation resulted in an amino acid change.

RFLP Analysis: Once the mutation was identified, additional cats were screened for the PKD mutation using RFLP typing on agarose gels. The amplification product for exon 29 is 559 bp. The identified mutation causes a restriction enzyme site alteration for Mly I, producing two fragments of 316 bp and 243 bp. Approximately 5 µl of amplification product was digested with 10 U of Mly I (New England Biolabs, Inc. Beverly, Mass.) in a 10 µl containing 1× NEBuffer 4 at 37° C. for 3 hrs followed by inactivation of the enzyme at 65° C. for 10 min. The complete digestion reaction was analyzed on 1.8–2% agarose gels as described above.

Example 2

Identification of Mutation in PKD1

A linkage analysis for feline PKD was performed by genotyping forty-three feline-derived microsatellites in seven extended feline pedigrees segregating for PKD (Young et al., *Mammal Genome* (2004)). The results showed a significant linkage and no recombinants (Z=5.83, θ=0) between feline PKD and the microsatellite marker, FCA476, that is within 10 cR to the PKD1 gene on cat chromosome E3 (Young et al., *Mammal Genome* (2004)). This data suggested an analysis of PKD1 for a causative mutation for the domestic cat. Additional microsatellites were identified from a BAC clone containing the feline PKD1 gene, which had been identified from the RPCI-86 cat library (Grahn et al., R, Biller D, Young A, Roe B, Qin B, Lyons L: *Genetic testing for feline polycystic kidney disease*, submitted, 2004). These analyses showed no recombinants between these markers and the disease and exclusion to markers associated with PKD2, further supporting that the feline PKD1 homolog may cause feline PKD.

Feline PKD1 was scanned for causative mutations and a C>A transversion was identified at c.10063 (human ref NM_000296) in exon 29 resulting in a stop mutation at positon 3284, which causes a loss of approximately 25% of the C-terminus of the protein. The same mutation has not been identified in humans, although similar regions of the protein are truncated. The C>A transversion was identified in the heterozygous state in forty-four affected cats examined, including three dozen Persians, a Siamese, and several other breeds that have been known to outcross to Persians, such as Exotic Shorthair, Selkirk Rex and Scottish Folds. Additionally, the mutation is segregating concordantly in all available PKD families. The causative mutation has not been observed in over two dozen unaffected cats and no homozygous affected cats have been identified, suggesting the mutation is embryonic lethal and is consistent with previous data (Young et al., *Mammal Genome* (2004); Grahn et al., R, Biller D, Young A, Roe B, Qin B, Lyons L: *Genetic testing for feline polycystic kidney disease*, submitted, 2004). This data suggests that the stop mutation causes feline PKD and that a carrier test is now possible for cats. Along with the similar clinical presentation, this data supports the use of the domestic cat as a model for human polycystic kidney disease, since the cat additionally has the same mode of inheritance, a mutation in the PKD1 gene and the affected cats have only the heterozygous state.

The sequenced BAC clone (GenBank Accession: AC145332.28) is in 8 contigs covering 167 Kb. The region containing the PKD1 gene is represented by 2 contigs that are separated in intron 4. The 5' region of exon 1 is not complete with an estimated 278 bp not represented in the assembled sequence. A schematic of the feline PKD1 gene in presented in FIG. 1. Intron and exon sizes as well as estimates of sequence and protein identity to human, mouse and dog are presented in Table 2. Over all exons, the cat sequence is most similar to dog, 83.66% (Range: 75.0–94.4%), the least similar to mouse, 73.44% (Range: 45.3–89.6%), and 80.02% similar to humans (Range: 64.9–94.4%). Exon 10 has the lowest similarity with the cat as compared to each species. The similarity of cat to a second species varied between exons, thus, the cat and dog were not always the most similar, identity was exon dependent.

Nine of 46 PKD1 exons were scanned for mutations by direct sequencing. A C>A transversion at c.10063 (human ref NM_000296) in exon 29 resulting in a C3284X protein change was identified, which is an OPA stop codon that causes a loss of approximately 25% of the protein (FIG. 2). The mutation causes a unique Mly I RFLP site in the amplification product of exon 29. A total of 20 affected and 25 unaffected cats were scanned for this stop mutation. Ten cats were confirmed by sequence analyses and the remaining by RFLP. All cats had the same mutation including the non-Persian cats. No unaffected cats were identified with the mutation. Pedigree analysis of feline PKD family 5 (Young et al., *Mammal Genome* (2004)) showed complete co-segregation of the stop mutation with the disease phenotype. No affected cats were found to be homozygous for the mutation.

Four of the nine exons and several intron regions had nucleotide variants as identified between two sequenced Persian cats and the PKD1 sequence from the BAC clone. One Persian was affected with PKD, thus the sequence comparison represents three normal alleles. Each identified variant was homozygote in the two Persian cats. Thirty variants were identified but only three were in translated regions of the exons. None were identified at exon/intron splice sites. Two of the three variants produced silent mutations. One mutation, a C>T transition at position 127 of exon 38, caused an amino acid change but both amino acids are hydrophobic and it is not anticipated that this substitution alters the protein conformation.

Our previous linkage analyses strongly implicated PKD1 as the causative gene for feline PKD (Young et al., *Mammal Genome* (2004); Grahn et al., R, Biller D, Young A, Roe B, Qin B, Lyons L: *Genetic testing for feline polycystic kidney disease*, submitted, 2004). Each newly identified family for human PKD has generally been found to be a novel mutation in the PKD1 gene. Mutations are found throughout the gene, with no single mutation being highly prevalent in the population. Since no particular mutation or region of the PKD1 gene in humans is highly prevalent for mutations, identification of the feline PKD mutation could have entailed the complete sequencing of the feline homolog from an affected cat. Once the draft sequence of the feline BAC clone containing PKD1 was obtained, we began a systematic scan for mutations. A nucleotide transversion causing a stop codon was identified in exon 29 that results in a truncated protein with a loss of 25% of its C-terminus. Thus, this feature is a very strong candidate for the causative mutation resulting in the PKD phenotype.

Additionally, concordant segregation of the mutation with the disease in a large cat family segregating for PKD supports the stop mutation as causative for feline PKD. A different mutation still possibly could cause feline PKD, but would have to be in strong linkage disequilibrium with this stop codon. Additionally, the stop codon mutation is consistent with the microsatellite haplotype that shows complete linkage to the PKD phenotype (14).

The feline PKD1 gene is represented by two contigs with the 5' region of exon 1 and intron 4 not yet represented by sequence. In humans, exon 1 has 424 bp, thus approximately 141 amino acids can not be compared to the cat. Intron 4 is 213 bp in humans, and this entire intron may not yet be represented in the cat sequence. Over all exons, the cat sequence is most similar to dog, followed by human, and least similar to mouse, which is consistent with the evolutionary relationship of the species. Exon 10 is the least similar for all species, as compared to the cat.

Only the Persian breed of cat and breeds derived from Persians, such as Exotic Shorthairs and Himalayans, have been recognized to have a high frequency of PKD. Other breeds, such as, Ragdolls, Scottish Folds, and Selkirk Rexes, have either purposely or accidentally used Persian lines to modify body conformation or to maintain or acquire coat length. While PKD has been identified in these breeds, we hypothesize it to be identical by descent with the Persian disease. All affected cats from the other breeds analyzed have the identical mutation as the Persians. Since a majority of human cases are de novo, more extensive sequence analyses are required to differentiate de novo, identical by state mutations from mutations that are identical by descent within various cat breeds. This disease is occurring within a closed breed implying identity by descent and disease homogeneity is expected. Persians, however, are one of the oldest and most popular breeds, having a large population that is dispersed throughout the world. All cases analyzed here represent cats from the United States, thus, more extensive surveys should be conducted to validate the causative mutation in different world regions of the world.

One Siamese cat was identified with the stop mutation and had severe PKD, as determined by ultrasound imaging. Siamese cats are short-haired, slender and tubular, while Persians are long-haired, stocky and broad. These two breeds represent the two extremes of body conformation in the cat fancy, thus it was surprising that the Siamese cat had the same mutation as the Persians. Pointed Persians are called Himalayans and share the albinism phenotype that signifies the Siamese. Some Siamese varieties have long fur (Balinese and Javanese), but, unlike Persians, only the top coats are longer, thus these breeds are not as full-coated as Persians. Therefore, due to the sharing of phenotypic traits, it is conceivable that Persian could have been intentionally bred in a Siamese line, producing the Siamese with PKD. The Siamese cat analyzed was not a "purebred", hence the mutation could be a result of accidental mating with a Persian. A photograph of this "Siamese" cat supports this hypothesis as the "Siamese" cat does not meet the current standards for the cat fancy. Otherwise, the Siamese cat represents a mutation that is identical by state.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method for detecting a mutation associated with polycystic kidney disease in a cat, said method comprising detecting a nucleic acid sequence comprising a C to A substitution at position 138 of exon 29 of a gene encoding polycystic kidney disease type 1 protein (PKD1) in a biological sample from the cat.

2. The method of claim 1, wherein said cat is a domestic cat.

3. The method of claim 1, wherein the nucleic acid sequence comprises a sequence set forth in SEQ ID NO:1 or a sequence fully complementary thereto.

4. The method of claim 1, wherein the nucleic acid sequence is detected by:
   (a) specifically amplifying a subsequence of a gene encoding PKD1 comprising position 138 of exon 29 of PKD1, thereby amplifying nucleic acids comprising the mutation; and
   (b) detecting the amplified nucleic acids, thereby detecting the mutation.

5. The method of claim 4, wherein the subsequence comprises SEQ ID NO:1 or a sequence fully complementary thereto.

6. The method of claim 4, wherein the subsequence is specifically amplified using primers comprising the sequences set forth in SEQ ID NOS:19 and 20.

7. The method of claim 4, wherein the mutation is detected by contacting the amplified nucleic acids with a restriction enzyme.

8. The method of claim 7, wherein the restriction enzyme is Mly J.

9. The method of claim 4, wherein the amplified nucleic acids are detected by sequencing.

* * * * *